US009527848B2

(12) United States Patent
Li et al.

(10) Patent No.: US 9,527,848 B2
(45) Date of Patent: *Dec. 27, 2016

(54) N-(1-(SUBSTITUTED-PHENYL)ETHYL)-9H-PURIN-6-AMINES AS PI3K INHIBITORS

(71) Applicants: Incyte Corporation, Wilmington, DE (US); Incyte Holdings Corporation, Wilmington, DE (US)

(72) Inventors: Yun-Long Li, Chadds Ford, PA (US); Andrew P. Combs, Kennett Square, PA (US); Eddy W. Yue, Landenberg, PA (US); Thomas P. Maduskuie, Wilmington, DE (US); Richard B. Sparks, Wilmington, DE (US)

(73) Assignees: Incyte Holdings Corporation, Wilmington, DE (US); Incyte Corporation, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/740,808

(22) Filed: Jun. 16, 2015

(65) Prior Publication Data

US 2015/0284390 A1 Oct. 8, 2015

Related U.S. Application Data

(63) Continuation of application No. 13/329,532, filed on Dec. 19, 2011, now Pat. No. 9,096,600.

(60) Provisional application No. 61/425,107, filed on Dec. 20, 2010.

(51) Int. Cl.
| | | |
|---|---|---|
| *C07D 473/32* | (2006.01) |
| *C07D 473/34* | (2006.01) |
| *A61K 31/5377* | (2006.01) |
| *A61K 31/52* | (2006.01) |
| *A61K 31/06* | (2006.01) |
| *A61K 45/06* | (2006.01) |

(52) U.S. Cl.
CPC ............ *C07D 473/34* (2013.01); *A61K 31/52* (2013.01); *A61K 31/5377* (2013.01); *A61K 45/06* (2013.01); *C07D 473/32* (2013.01)

(58) Field of Classification Search
CPC . C07D 473/34; C07D 473/32; A61K 31/5377; A61K 45/06; A61K 31/52
See application file for complete search history.

(56) References Cited

U.S. PATENT DOCUMENTS

| | | | |
|---|---|---|---|
| 3,037,980 A | 6/1962 | Hitchings et al. |
| 3,169,967 A | 2/1965 | Schittler |
| 3,506,643 A | 4/1970 | Thiel et al. |
| 3,862,189 A | 1/1975 | Schwender et al. |
| 3,936,454 A | 2/1976 | Schwender et al. |
| 3,962,443 A | 6/1976 | Minami et al. |
| 4,482,629 A | 11/1984 | Nakagawa et al. |
| 4,840,951 A | 6/1989 | Iwasaki et al. |
| 4,845,020 A | 7/1989 | Itoh et al. |
| 4,861,701 A | 8/1989 | Burns et al. |
| 5,124,331 A | 6/1992 | Arita et al. |
| 5,208,250 A | 5/1993 | Cetenko et al. |
| 5,252,580 A | 10/1993 | Takahashi et al. |
| 5,294,620 A | 3/1994 | Ratcliffe et al. |
| 5,314,883 A | 5/1994 | Tanikawa et al. |
| 5,459,132 A | 10/1995 | Bru-Magniez et al. |
| 5,521,184 A | 5/1996 | Zimmermann |
| 5,646,153 A | 7/1997 | Spada et al. |
| 5,811,439 A | 9/1998 | Ogawa et al. |
| 5,866,702 A | 2/1999 | Mackman et al. |
| 6,028,076 A | 2/2000 | Hirota et al. |
| 6,342,501 B1 | 1/2002 | Townsend et al. |
| 6,376,501 B1 | 4/2002 | Isobe et al. |
| 6,392,047 B1 | 5/2002 | Geissler et al. |
| 6,479,487 B1 | 11/2002 | Dumont et al. |
| 6,630,496 B1 | 10/2003 | Seehra et al. |
| 6,734,187 B1 | 5/2004 | Tanaka et al. |
| 6,828,344 B1 | 12/2004 | Seehra et al. |
| 7,129,264 B2 | 10/2006 | Smallheer et al. |
| 7,494,987 B2 | 2/2009 | Akada et al. |
| 7,495,002 B2 | 2/2009 | Langkopt et al. |
| 7,528,143 B2 | 5/2009 | Noronha et al. |
| 7,612,114 B2 | 11/2009 | Hamaoka et al. |
| 8,680,108 B2 | 3/2014 | Li et al. |
| 8,759,359 B2 | 6/2014 | Combs et al. |
| 8,940,752 B2 | 1/2015 | Li et al. |
| 2003/0008898 A1 | 1/2003 | Mahboobi et al. |
| 2003/0157052 A1 | 8/2003 | Choe et al. |
| 2004/0058930 A1 | 3/2004 | Belema et al. |

(Continued)

FOREIGN PATENT DOCUMENTS

| | | |
|---|---|---|
| AT | 388372 | 6/1989 |
| CA | 1066701 | 11/1979 |

(Continued)

OTHER PUBLICATIONS

"A to Z List of Cancers," National Cancer Institute (http://www.cancer.gov/) (Downloaded May 29, 2014), 22 pages.
"Angiogenesis" Merriam-Webster.com. Merriam-Webster, n.d. Web Jun. 16, 2014, www.merriam-webster.com/dictionary/angiogenesis, 3 pages.
"Arthritis: MedlinePlus Medical Encyclopedica," 2014, p. 1-5, accessed online Oct. 7, 2014; http://www.nlm.nih.gove/medlineplus/ency/article/001243.htm.

(Continued)

*Primary Examiner* — Samantha Shterengarts
*Assistant Examiner* — Matt Mauro
(74) *Attorney, Agent, or Firm* — Fish & Richardson P.C.

(57) ABSTRACT

The present invention provides N-(1-(substituted-phenyl) ethyl)-9H-purin-6-amines derivatives that modulate the activity of phosphoinositide 3-kinases (PI3Ks) and are useful in the treatment of diseases related to the activity of PI3Ks including, for example, inflammatory disorders, immune-based disorders, cancer, and other diseases.

12 Claims, No Drawings

(56) References Cited

U.S. PATENT DOCUMENTS

| | | |
|---|---|---|
| 2004/0063658 A1 | 4/2004 | Roberts et al. |
| 2004/0067964 A1 | 4/2004 | Matsuoka et al. |
| 2004/0142941 A1 | 7/2004 | Gudmundsson et al. |
| 2004/0209866 A1 | 10/2004 | Wang et al. |
| 2004/0242615 A1 | 12/2004 | Yamamori et al. |
| 2005/0043328 A1 | 2/2005 | Dolezal |
| 2005/0059677 A1 | 3/2005 | Alberti et al. |
| 2005/0107343 A1 | 5/2005 | Kasibhatla et al. |
| 2005/0165030 A1 | 7/2005 | Liu et al. |
| 2005/0261317 A1 | 11/2005 | Sadhu et al. |
| 2005/0267110 A1 | 12/2005 | Hirano et al. |
| 2005/0282831 A1 | 12/2005 | Beauglehole et al. |
| 2006/0025383 A1 | 2/2006 | Wishart et al. |
| 2006/0052403 A1 | 3/2006 | Isobe et al. |
| 2006/0074102 A1 | 4/2006 | Cusack et al. |
| 2006/0084687 A1 | 4/2006 | Boyce et al. |
| 2006/0166925 A1 | 7/2006 | Dolezal et al. |
| 2006/0247245 A1 | 11/2006 | Xu |
| 2006/0293334 A1 | 12/2006 | Fuji et al. |
| 2007/0060577 A1 | 3/2007 | Player et al. |
| 2007/0066624 A1 | 3/2007 | Zhou et al. |
| 2007/0167443 A1 | 7/2007 | Melikian et al. |
| 2007/0191395 A1 | 8/2007 | Kawakami et al. |
| 2007/0225303 A1 | 9/2007 | Ogita et al. |
| 2007/0275984 A1 | 11/2007 | Imogai et al. |
| 2008/0004269 A1 | 1/2008 | Xu et al. |
| 2008/0009508 A1 | 1/2008 | Szucova et al. |
| 2008/0014227 A1 | 1/2008 | Popa et al. |
| 2008/0114007 A1 | 5/2008 | Player |
| 2008/0161332 A1 | 7/2008 | Bissantz et al. |
| 2008/0194616 A1 | 8/2008 | Liu et al. |
| 2008/0249155 A1 | 10/2008 | Gong et al. |
| 2008/0287469 A1 | 11/2008 | Diacovo et al. |
| 2008/0293739 A1 | 11/2008 | Trede |
| 2008/0306093 A1 | 12/2008 | Servant et al. |
| 2009/0023729 A1 | 1/2009 | Nakamura et al. |
| 2009/0047249 A1 | 2/2009 | Graupe et al. |
| 2009/0053192 A1 | 2/2009 | Millan et al. |
| 2009/0074884 A1 | 3/2009 | Chesney et al. |
| 2009/0118263 A1 | 5/2009 | Hashimoto |
| 2009/0137581 A1 | 5/2009 | Chen et al. |
| 2009/0163545 A1 | 6/2009 | Goldfarb |
| 2009/0170879 A1 | 7/2009 | Szucova et al. |
| 2009/0253717 A1 | 10/2009 | Brown et al. |
| 2009/0325930 A1 | 12/2009 | Hamaoka et al. |
| 2010/0010059 A1 | 1/2010 | Yeh et al. |
| 2010/0035756 A1 | 2/2010 | Luthy et al. |
| 2010/0105683 A1 | 4/2010 | Keegan et al. |
| 2010/0190819 A1 | 7/2010 | Kanner |
| 2010/0240537 A1 | 9/2010 | Spichal et al. |
| 2010/0256118 A1 | 10/2010 | Isobe et al. |
| 2010/0298351 A1 | 11/2010 | Konakanchi et al. |
| 2011/0015212 A1 | 1/2011 | Li et al. |
| 2011/0028715 A1 | 2/2011 | Isobe et al. |
| 2011/0098248 A1 | 4/2011 | Halcomb et al. |
| 2011/0105508 A1 | 5/2011 | Allen et al. |
| 2011/0183985 A1 | 7/2011 | Li et al. |
| 2011/0190319 A1 | 8/2011 | Combs et al. |
| 2011/0224155 A1 | 9/2011 | Tachdjian et al. |
| 2011/0281884 A1 | 11/2011 | Combs et al. |
| 2011/0312979 A1 | 12/2011 | Li et al. |
| 2012/0157430 A1 | 6/2012 | Li et al. |
| 2013/0029982 A1 | 1/2013 | Castro et al. |
| 2013/0059835 A1 | 3/2013 | Li et al. |
| 2013/0261101 A1 | 10/2013 | Combs et al. |
| 2014/0031355 A1 | 1/2014 | Fisher et al. |
| 2014/0057912 A1 | 2/2014 | Combs et al. |
| 2014/0066448 A1 | 3/2014 | Combs et al. |
| 2014/0121222 A1 | 5/2014 | Li et al. |
| 2014/0275127 A1 | 9/2014 | Combs et al. |

FOREIGN PATENT DOCUMENTS

| | | |
|---|---|---|
| DE | 1770420 | 11/1971 |
| DE | 2139107 | 2/1973 |
| EP | 255085 | 2/1988 |
| EP | 464612 | 1/1992 |
| EP | 481614 | 4/1992 |
| EP | 1138328 | 11/2001 |
| EP | 1109805 | 12/2003 |
| EP | 1783114 | 5/2007 |
| EP | 1972631 | 9/2008 |
| EP | 2031037 | 3/2009 |
| EP | 2050749 | 4/2009 |
| EP | 934307 | 4/2011 |
| GB | 1440478 | 6/1976 |
| GB | 1472342 | 5/1977 |
| JP | 50111080 | 9/1975 |
| JP | 53059663 | 5/1978 |
| JP | 53092767 | 8/1978 |
| JP | 56025234 | 6/1981 |
| JP | 56123981 | 9/1981 |
| JP | 58083698 | 5/1983 |
| JP | 62103640 | 5/1987 |
| JP | 62245252 | 10/1987 |
| JP | 1250316 | 10/1989 |
| JP | 4190232 | 7/1992 |
| JP | 9087282 | 3/1997 |
| JP | 9176116 | 7/1997 |
| JP | 10025294 | 1/1998 |
| JP | 10231297 | 9/1998 |
| JP | 2000080295 | 3/2000 |
| JP | 2000281654 | 10/2000 |
| JP | 2001151771 | 6/2001 |
| JP | 2005035924 | 2/2005 |
| JP | 2009080233 | 4/2009 |
| JP | 2009120686 | 6/2009 |
| JP | 2011511761 | 4/2011 |
| JP | 2011136925 | 7/2011 |
| RU | 2233842 | 8/2004 |
| SU | 1712359 | 2/1992 |
| WO | WO 93/16076 | 8/1993 |
| WO | WO 93/22291 | 11/1993 |
| WO | WO 93/25524 | 12/1993 |
| WO | WO 99/43651 | 9/1999 |
| WO | WO 99/43672 | 9/1999 |
| WO | WO 00/09495 | 2/2000 |
| WO | WO 00/44750 | 8/2000 |
| WO | WO 00/53595 | 9/2000 |
| WO | WO 01/14402 | 3/2001 |
| WO | WO 01/64639 | 9/2001 |
| WO | WO 01/64655 | 9/2001 |
| WO | WO 01/72709 | 10/2001 |
| WO | WO 02/00196 | 1/2002 |
| WO | WO 02/06477 | 1/2002 |
| WO | WO 02/24685 | 3/2002 |
| WO | WO 02/064599 | 8/2002 |
| WO | WO 02/066478 | 8/2002 |
| WO | WO 02/078701 | 10/2002 |
| WO | WO 03/020721 | 3/2003 |
| WO | WO 03/024967 | 3/2003 |
| WO | WO 03/029209 | 4/2003 |
| WO | WO 03/037347 | 5/2003 |
| WO | WO 03/044014 | 5/2003 |
| WO | WO 03/049678 | 6/2003 |
| WO | WO 03/050064 | 6/2003 |
| WO | WO 03/068750 | 8/2003 |
| WO | WO 03/074497 | 9/2003 |
| WO | WO 03/099771 | 12/2003 |
| WO | WO 2004/005281 | 1/2004 |
| WO | WO 2004/024693 | 3/2004 |
| WO | WO 2004/046120 | 6/2004 |
| WO | WO 2004/048365 | 6/2004 |
| WO | WO 2004/056786 | 7/2004 |
| WO | WO 2004/069256 | 8/2004 |
| WO | WO 2004/076455 | 9/2004 |
| WO | WO 2004/080980 | 9/2004 |
| WO | WO 2004/087704 | 10/2004 |
| WO | WO 2004/107863 | 12/2004 |
| WO | WO 2004/113335 | 12/2004 |
| WO | WO 2005/000309 | 1/2005 |
| WO | WO 2005/016528 | 2/2005 |
| WO | WO 2005/028444 | 3/2005 |
| WO | WO 2005/046578 | 5/2005 |

(56) References Cited

FOREIGN PATENT DOCUMENTS

| | | |
|---|---|---|
| WO | WO 2005/091857 | 10/2005 |
| WO | WO 2005/113556 | 12/2005 |
| WO | WO 2006/008523 | 1/2006 |
| WO | WO 2006/030031 | 3/2006 |
| WO | WO 2006/056399 | 6/2006 |
| WO | WO 2006/068760 | 6/2006 |
| WO | WO 2006/089106 | 8/2006 |
| WO | WO 2007/002701 | 1/2007 |
| WO | WO 2007/012724 | 2/2007 |
| WO | WO 2007/042806 | 4/2007 |
| WO | WO 2007/076092 | 7/2007 |
| WO | WO 2007/087548 | 8/2007 |
| WO | WO 2007/095588 | 8/2007 |
| WO | WO 2007/102392 | 9/2007 |
| WO | WO 2007/114926 | 10/2007 |
| WO | WO 2007/126841 | 11/2007 |
| WO | WO 2008/002490 | 1/2008 |
| WO | WO 2008/005303 | 1/2008 |
| WO | WO 2008/025821 | 3/2008 |
| WO | WO 2008/032033 | 3/2008 |
| WO | WO 2008/064018 | 5/2008 |
| WO | WO 2008/064157 | 5/2008 |
| WO | WO 2008/082490 | 7/2008 |
| WO | WO 2008/097991 | 8/2008 |
| WO | WO 2008/100867 | 8/2008 |
| WO | WO 2008/116129 | 9/2008 |
| WO | WO 2008/118454 | 10/2008 |
| WO | WO 2008/118468 | 10/2008 |
| WO | WO 2009/034386 | 3/2009 |
| WO | WO 2009/062118 | 5/2009 |
| WO | WO 2009/063235 | 5/2009 |
| WO | WO 2009/081105 | 7/2009 |
| WO | WO 2009/085230 | 7/2009 |
| WO | WO 2009/086123 | 7/2009 |
| WO | WO 2009/097446 | 8/2009 |
| WO | WO 2009/128520 | 10/2009 |
| WO | WO 2009/130560 | 10/2009 |
| WO | WO 2009/140215 | 11/2009 |
| WO | WO 2009/151972 | 12/2009 |
| WO | WO 2010/006234 | 1/2010 |
| WO | WO 2010/008739 | 1/2010 |
| WO | WO 2010/018458 | 2/2010 |
| WO | WO 2010/036380 | 4/2010 |
| WO | WO 2010/057048 | 5/2010 |
| WO | WO 2010/074588 | 7/2010 |
| WO | WO 2010/075068 | 7/2010 |
| WO | WO 2010/092340 | 8/2010 |
| WO | WO 2010/114900 | 10/2010 |
| WO | WO 2010/118367 | 10/2010 |
| WO | WO 2010/123931 | 10/2010 |
| WO | WO 2010/127208 | 11/2010 |
| WO | WO 2010/129816 | 11/2010 |
| WO | WO 2010/151735 | 12/2010 |
| WO | WO 2010/151740 | 12/2010 |
| WO | WO 2011/001052 | 1/2011 |
| WO | WO 2011/002708 | 1/2011 |
| WO | WO 2011/002817 | 1/2011 |
| WO | WO 2011/008302 | 1/2011 |
| WO | WO 2011/008487 | 1/2011 |
| WO | WO 2011/011550 | 1/2011 |
| WO | WO 2011/025889 | 3/2011 |
| WO | WO 2011/048082 | 4/2011 |
| WO | WO 2011/055215 | 5/2011 |
| WO | WO 2011/058111 | 5/2011 |
| WO | WO 2011/058113 | 5/2011 |
| WO | WO 2011/058474 | 5/2011 |
| WO | WO 2011/069294 | 6/2011 |
| WO | WO 2011/075628 | 6/2011 |
| WO | WO 2011/075630 | 6/2011 |
| WO | WO 2011/075643 | 6/2011 |
| WO | WO 2011/092198 | 8/2011 |
| WO | WO 2011/117711 | 9/2011 |
| WO | WO 2011/123751 | 10/2011 |
| WO | WO 2011/130342 | 10/2011 |
| WO | WO 2011/146882 | 11/2011 |
| WO | WO 2011/156759 | 12/2011 |
| WO | WO 2011/163195 | 12/2011 |
| WO | WO 2012/003262 | 1/2012 |
| WO | WO 2012/003271 | 1/2012 |
| WO | WO 2012/003274 | 1/2012 |
| WO | WO 2012/040634 | 3/2012 |
| WO | WO 2012/061696 | 5/2012 |
| WO | WO 2012/064973 | 5/2012 |
| WO | WO 2012/068343 | 5/2012 |
| WO | WO 2012/080729 | 6/2012 |
| WO | WO 2012/087784 | 6/2012 |
| WO | WO 2012/087881 | 6/2012 |
| WO | WO 2012/097000 | 7/2012 |
| WO | WO 2012/125629 | 9/2012 |
| WO | WO 2012/135009 | 10/2012 |
| WO | WO 2013/033569 | 3/2013 |
| WO | WO 2013/151930 | 10/2013 |

OTHER PUBLICATIONS

"Autoimmune disorders: MedlinePlus Medical Encyclopedia," 2013, p. 1-4, accessed online Oct. 7, 2014; http://www.nlm.nih.gov/medlineplus/ency/article/000816.htm.

"Adult Acute Myeloid Leukemia Treatment (PDQ®)—Patient Version, Last Modified Jul. 30, 2012," National Cancer Institute, [retrieved from the internet on Nov. 26, 2012] at http://www.cancer.gov/cancertopics/pdq/treatment/adultAML/Patient/page1, 5 pgs.

Ali, et al., "Essential role for the p110δ phosphoinositide 3-kinase in the allergic response," Nature. 2004, 431(7011):1007-11.

Allen, et al., "Synthesis of C-6 substituted pymzolo[1,5-a]pyridines with potent activity against herpesviruses," *Bioorganic & Medicinal Chemistry* (2006), 14(4), 944-954.

Apsel et al., "Targeted polypharmacology: discovery of dual inhibitors of tyrosine and phosphoinositide kinases," Nat. Chem. Biol., 2008, 4(11): 691-699.

Bader, et al., "Cancer-specific mutations in PIK3CA are oncogenic in vivo," Proc Natl Acad Sci U S A. 2006, 103(5):1475-9.

Baek et al., "Complete remission induced by rituximab in refractory, seronegative, muscle-specific, kinase-positive myasthenia gravis," J Neurol Neurosurg Psychiatry, 2007, 78(7):771.

Ball, "PI3K inhibitors as potential therapeutics for autoimmune disease," Drug Discovery Today, 2014, pp. 1195-119.

Barber, et al., "PI3Kγ inhibition blocks glomerulonephritis and extends lifespan in a mouse model of systemic lupus," Nat Med. 2005, 11(9):933-5.

Barragan et al., "Protein Kinases in the Regulation of Apoptosis in B-cell Chronic Lymphocytic Leukemia," *Leukemia and Lymphoma*, 2003, 44(11):1865-1870.

Belema, et al., "Synthesis and structure-activity relationship of imidazo(1,2-a)thieno(3,2-e)pyrazines as IKK-β inhibitors," *Bioorganic & Medicinal Chemistry Letters* (2007), 17(15), 4284-4289.

Bendell, J.C., "Phase I, dose-escalation study of BKM120, an oral pan-Class I PI3K inhibitor, in patients with advanced solid tumors," Journal of Clincial Oncology (2011): JCO-2011.

Benistant, et al., "A specific function for phosphatidylinositol 3-kinase α (p85α-p110α) in cell survival and for phosphatidylinositol 3-kinase β (p85α-p110β) in de novo DNA synthesis of human colon carcinoma cells," Oncogene, 2000, 19(44):5083-90.

Bennasar, et al., "Generation and Intermolecular Reactions of 2-Indolylacyl Radicals," *Organic Letters* (2001), 3(11), 1697-1700, CODEN: ORLEF7; ISSN: 1523-7060.

Berge et al., "Pharmaceutical Salts," J Pharma Sci, 1977, 66(1):1-19.

Bergman, et al., "Synthesis of indolocarbazole quinones; potent aryl hydrocarbon receptor ligands," *Tetrahedron* (2002), 58(7), 1443-1452.

Bhatia and Rose, "Autoimmunity and autoimmune disease," Principles of Med Biol., 1996, 6:239-263, 244.

Bhovi, et al., "1,3-dipolar cycloaddition reaction: Synthesis and antimicrobial activity of some new3-ethoxycarbonyl-5-methoxy-6-bromo-2-triazolylmethylindoles," *Indian Journal of Heterocyclic Chemistry* (2004), 14(1), 15-18 CODEN: IJCHEI; ISSN: 0971-1627.

(56) References Cited

OTHER PUBLICATIONS

Billottet, et al., "A selective inhibitor of the p110δ isoform of PI 3-kinase inhibits AML cell proliferation and survival and increases the cytotoic effects of VP16," Oncogene. 2006, 25(50):6648-59.
Biswas, et al., "Synthesis of a trifluoromethylindolocarbazole, novel cyclic 27- and 36-membered N-benzyltri- and -tetraindoles, and an N-benzyltetraindolyltrimethane," *Monatshefte fuer Chemie* (1999), 130(10), 1227-1239, CODEN: MOCMB7; ISSN: 0026-9247.
Blom et al., Preparative LC-MS Purification: Improved Compound Specific Method Optimization, J. Combi. Chem. 2004, 6(6), 874-883.
Boger, et al., "First and Second Generation Total Synthesis of the Teicoplanin Aglycon," JACS, 123(9), 1862-1871, 2001.
Brachmann et al., "PI3K and mTOR inhibitors—a new generation of targeted anticancer agents," Current Opinion Cell Biol., 2009, 21:194-198.
Bringmann, et al., "Novel concepts in directed biaryl synthesis. Part 65. Synthesis and structure of a novel twofold lactone-bridged ternaphthyl," *Tetrahedron Letters* (1998), 39(12), 1545-1548 CODEN: TELEAY; ISSN: 0040-4039.
Brock et al., "Roles of Gβγ in membrane recruitment and activation of p110γ/p101 phosphoinositide 3-kinaseγ," J Cell Biol., 2003, 160(1):89-99.
Brown, et al., "Small molecule inhibitors of IgE synthesis," *Bioorganic & Medicinal Chemistry Letters* (2006), 16(17), 4697-4699.
Camps, et al., "Blockade of PI3Kγ suppresses joint inflammation and damage in mouse models of rheumatoid arthritis," Nat Med. 2005, 11(9):936-43.
Cannon, Burger's Medicinal Chemistry and Drug Discovery, Fifth Edition, vol. 1 Principles and Practice, Wiley-Interscience 1995, Ch. 19, pp, 783-803, 784.
Cantley, "The Phosphoinositide 3-Kinase Pathway," Science, (2002) 296 (5573):1655-7.
Castillo-Trivino, et al., "Rituximab in relapsing and progressive forms of multiple sclerosis: a systematic review," The PLoS One. Jul. 2013; 8(7):e66308. doi: 10.1371/journal.pone.0066308. Print 2013.
Chai, et al., "Synthesis and in vitro anti-hepatitis B virus activities of some ethyl 6-bromo-5-hydroxy-1H-indole-3-carboxylates," *Bioorganic & Medicinal Chemistry* (2006), 14(4), 911-917.
Chang, K-Y., "Novel phosphoinositide 3-kinase/mTOR dual inhibitor, NVP-BGT226, displays potent growth-inhibitory activity against human head and neck cancer cells in vitro and in vivo," Clinical Cancer Research 17.22 (2011): 7116-7126.
Chen, X., "Targeting oxidative stress in embryonal rhabdomyosarcoma," Cancer cell 24.6 (2013): 710-724.
Clayton, et al., "A Crucial Role for the p110δ Subunit of Phosphatidylinositol 3-Kinase in B Cell Development and Activation," J Exp Med. 2002, 196(6):753-63.
Collins et al., "Rituximab treatment of fibrillary glomerulonephritis," Am J Kidney Dis., 2008, 52(6):1158-62.
Coughlin et al., Approaches and limitations of phosphatidylinositol-3-kinase pathway activation status as a predictive biomarker in the clinical development of targeted theraphy, Breast Cancer Res Treatment, 2010, 124:1-11.
Courtney et al., "The PI3K Pathway as Drug Target in Human Cancer," J Clinc Oncol., 2010, 29:1075-1083.
Crabbe, "The PI3K inhibitor arsenal: choose your weapon!" Trends Biochem Sci., 2007, 32(10):450-56.
Dagia et al., A preferential p110α/γ PI3K inhibitor attenuates experimental inflammation by suppressing the production of proinflammatory mediators in a NF-κB-dependent manner, Am J Physiol—Cell Physiol., 2010, 298:929-941
DeBerardinis et al., "The Biology of Cancer: Metabolic Reprogramming Fuels Cell Growth and Proliferation," Cell Metabolism, Jan. 2008, 7:11-20.
Delmas and Meunier, "The Management of Paget's Disease of Bone," N Engl J Med., 1997, 336:558-566.

Devauchelle-Pensec, "Treatment of Primary Sjogren Syndrome with Rituximab," Annal Internal Med., 2014, 160:233-242.
Dolezal et al., "Preparation and biological activity of 6-benzylaminopurine derivatives in plants and human cancer cells," *Bioorganic & Medicinal Chemistry* (2006), 14(3), 875-884.
Dolezal et al., "Preparation, biological activity and endogenous occurrence of N6-benzyladenosines," *Bioorganic & Medicinal Chemistry* (2007), 15(11), 3737-3747.
Dorokhov, et al., "Synthesis of functionalized pyrimidine-4-thiones and pyrido[2,3-d]pyrimidin-5-one derivatives from aminals of monoacylketenes", Izvestiya Akademii Nauk, Seriya Khimicheskaya (1993), (11), 1932-7.
Doukas et al., "Aerosolized Phosphoinositide 3-Kinase γ/δ Inhibitor TG100-115 [3-[2,4-Diamino-6-(3-hydroxyphenyl)pteridin-7-yl]phenol] as a Therapeutic Candidate for Asthma and Chronic Obstructive Pulmonary Disease," The Journal of Pharmacology and Experimental Therapeutics, 328(3):758-765, 2009.
Dushianthan et al., "Acute respiratory distress syndrome and acute lung injury," Post Graduate Med J., 2011, 87:612-622.
Engelman, "Targeting PI3K signalling in cancer: opportunities, challenges and limitations," Nature Rev: Cancer, 2009, 9:550-562.
Fadeyeva, et al , "Inhibitors of early virus-cell interaction stages among 3-ethoxycarbony1-5-hydroxy-bromoindole derivatives," *Khimiko-Farmatsevticheskii Zhurnal* (1992), 26(9-10), 17-20 (with English abstract).
Fine et al., "Neoplasms of the Central Nervous System," Cancer Principles Practice Oncol., 2005, 2:1834-1887.
Flinn et al., "Preliminary evidence of clinical activity in a phase I study of CAL-101, a selective inhibitor of the p110δ isoform of phosphatidylinositol 3-kinase (PI3K), in patients with select hematologic malignancies," Journal of Clinical Oncology, (abstract), 27(15S):3543, 2009.
Floberg et al., "Extractive alkylation of 6-mercaptopurine and determination in plasma by gas chromatography-mass spectrometry," *Journal of Chromatography, Biomedical Applications*, (1981), 225(1), 73-81.
Froman and Bismuth, "Fine Tuning the Immune Response with PI3K," *Immunological Revs.*, 2006, 228:253-272.
Gati et al., "(125I)Iodohydroxynitrobenzylthioinosine: a new high-affinity nucleoside transporter probe," *Biochemistry and Cell Biology* (1987), 65(5), 467-73.
Geng, et al., "Exploring 9-benzyl purines as inhibitors of glutamate racemase (MurI) in Gram-positive bacteria", Bioorganic & Medicinal Chemistry Letters (2008),18(15), 4368-4372.
Ghigo et al., "PI3K inhibition in inflammation. Toward tailored therapies for specific diseases," BioEssays, 2010, 32:185-196.
Golantsov, et al., "Chirally N-substituted indole-2-carbaldehydes. Preparation and use in asymmetric synthesis," *Chemistry of Heterocyclic Compounds* (New York, NY, United States) (2005), 41(10), 1290-1299.
Granik, "Acetals of lactams and amides of acids. 40. Synthesis and hydrolytic splitting of mono- and bicyclic derivatives of 4-pyrimidinone", Khimiya Geterotsiklicheskikh Soedinenii (1984), (4),532-7 (with English abstract).
Greene and P. G. M. Wuts, Protective Groups in Organic Synthesis, 3rd Ed., Wiley & Sons, Inc., New York (1999)*Too Voluminous to Provide.
Harley, "Medical Management of Actue Renal Failure," Renal Failure Replacement Therapies, 2008, pp. 26-32.
Harris et al., "Alkyl 4-Chlorobenzoyloxycarbamates as Highly Effective Nitrogen Source Reagents for the Base-Free, Intermolecular Aminohydroxylation Reaction," J. Org. Chem., 76, 358-372, 2011.
Hauser et al., "B-Cell Depletion with Rituximab in Relapsing—Remitting Multiple Sclerosis," The New England Journal of Medicine, 358(7):676-688, 2008.
Hayter and Cook, "Updated assessment of the prevalence, spectrum and case definition of autoimmune disease," Autoimmunity Reviews, 2012, 11:754-765.
Hickey, et al., "BCR-ABL Regulates Phosphatidylinositol 3-Kinase-p110γ Transcription and Activation and is Required for Proliferation and Drug Resistance," J Biol Chem. 2006, 281(5):2441-50.

(56) References Cited

OTHER PUBLICATIONS

Hirose, et al., "Pyridone-carboxylic acids as antibacterial agents. I. Synthesis and antibacterial activity of 1-alkyl-1,4-dihydro-4-oxo-1,8- and -1,6-naphthyridine-3-carboxylic acids", Chemical & Pharmaceutical Bulletin (1982), 30(7), 2399-409.
Hirota, "Efficient synthesis of 2,9-disubstituted 8-hydroxyadenine derivatives", Organic & Biomolecular Chemistry (2003), 1(8), 1354-1365.
Hirsch et al., "Taming the PI3K team to hold inflammation and cancer at bay," Pharmacology & Therapeutics, 2008, 118: 192-205.
Hosalkar et al., "Skeletal Trauma and Common Orthopedic Problems," Chpt 10, Khurana (ed.) Bone Pathology, 2009, 93 pages.
Huang et al., "Design and synthesis of a pyrido[2,3-d]pyrimidin-5-one class of anti-inflammatory FMS inhibitors,", Bioorganic & Medicinal Chemistry Letters (2008), 18(7), 2355-2361.
Huang et al., "Synthesis and bioassay of a fluorine-containing cytokinin, N6-pentafluoro-benzyladenosine," Youji Huaxue (1988), 8(2), 147-8 (with English abstract).
Ihle et al, "Inhibitors of phosphatidylinositol-3-kinase in cancer therapy", Molecular Aspects of Medicine, 31(2):135-144, 2010.
Irie, et al., "Discovery of selective and nonpeptidic cathepsin Sinhibitors," Bioorganic & Medicinal Chemistry Letters (2008), 18(14), 3959-3962.
Isobe, et al., "Synthesis and Biological Evaluation of Novel 9-Substituted-8-Hydroxyadenine Derivatives as Potent Interferon Inducers", Journal of Medicinal Chemistry (2006), 49(6),2088-2095.
Itaya, et al., "Syntheses of the marine ascidian purine aplidiamine and its 9-β-D-ribofuranoside," Tetrahedron Letters (1998), 39(26), 4695-4696.
Itaya, et al., "Synthesis and structure of the marine ascidian 8-oxoadenine aplidiamine," Chemical & Pharmaceutical Bulletin (1999), 47(9), 1297-1300.
Jager et al., "Molecular recognition. II Discrimination of specific and non-specific intermolecular interactions by means of magnetic resonance spectroscopy," Magnetic Resonance in Chemistry (1998), 36(3), 205-210, CODEN: MRCHEG; ISSN: 0749-1581.
Jager, et al., "Molecular recognition analyzed by EPR, ENDOR, and NMR spectroscopy," Angewandte Chemie, International Edition in English (1996), 35(16), 1815-1818.
Japanese Office Action in Japanese Application No. 2014-528654, dated Mar. 29, 2016, 5 pages (English Translation).
Jimenez, et al, "The p85 Regulator Subunit Controls Sequential Activation of Phosphoinositide 3-Kinase by Tyr Kinases and Ras," J Biol Chem., 2002, 277(44):41556-62.
Jou, et al., "Essential, Nonredundant Role for the Phosphoinositide 3-Kinase p110δ in Signaling by the B-Cell Receptor Complex," Mol Cell Biol. 2002, 22(24):8580-91.
Kang et al., "Aplidiamine, a unique zwitterionic benzyl hydroxyadenine from the Western Australian marine ascidian Aplidiopsis sp.," Tetrahedron Letters (1997), 38(6), 941-944.
Kang, et al., "Phosphtidylinositol 3-kinase mutations identified in human cancer are oncogenic," Proc Natl Acad Sci U S A. 2005, 102(3):802-7.
Karpouzas, et al., "Rituximab Therapy Induces Durable Remissions in Hispanic and African American Patients with Refractory Systemic Lupus Erythematosus (SLE)," Presented at 73th Annual Scientific Meeting of the American College of Rheumatology, Oct. 2009; Philadelphia, PA.
Kasibhatla, "Rationally Designed High-Affinity 2-Amino-6-halopurine Heat Shock Protein 90 Inhibitors That Exhibit Potent Antitumor Activity",Journal of Medicinal Chemistry (2007), 50(12),2767-2778.
Katritzky, et al., "Facile Synthesis of 2-Substituted Indoles and Indolo[3,2-b]carbazoles from 2- (Benzotriazol-1-ylmethyl)indole," Journal of Organic Chemistry (1995), 60(11), 3401-4.
Kim et al., "A signaling network in Phenylephrine-Induced Benign Prostatic Hyperplasia," Endocrinology, 2009, 150:3576-3583.
Kim, et al., "A new structural class of S-adenosylhomocysteine hydrolase inhibitors", Bioorganic & Medicinal Chemistry (2009), 17(18), 6707-6714.
Kim, et al., "Synthesis and evaluation of antitumor activity of novel 1,4-naphthoquinone derivatives," Archives of Pharmacal Research (2006), 29(2), 123-130 CODEN: APHRDQ; ISSN: 0253-6269.
Knobbe, et al., "Genetic alteration and expression of the phosphoinositol-3-kinase/Akt pathway genes PIK3CA and PIKE in human glioblastomas," Neuropathol Appl Neurobiol. 2005, 31(5):486-90.
Kolasa, et al., "Synthesis of indolylalkoxyiminoalkylcarboxylates as leukotriene biosynthesis inhibitors," Bioorganic & Medicinal Chemistry (1997), 5(3), 507-514.
Kolliputi and Waxman, "IL-6 cytoprotection in hyperoxic acute lung injury occurs via PI3K/Akt-mediated Bax phosphorylation," Am J Physiol Lung Cellular Mole Physiol., 2009, 297:L6-L16.
Kong and Yamori, "Phosphatidylinositol 3-kinase inhibitors: promising drug candidates for cancer theraphy," Cancer Sci., 2008, 9:1734-1740.
Kong and Yamori, "Advances in Development of Phosphatidylinositol 3-Kinase Inhibitors," Current Medicinal Chemistry, 16:2839-2854, 2009.
Kuduk et al., "Heterocyclic fused pyridone carboxylic acid M1 positive allosteric modulators," Bioorganic & Medicinal Chemistry Letters (2010), 20(8), 2533-2537.
Kung et al., "Characterization of a Murine Model of Allergic Pulmonary Inflammation," Int. Arch. Allergy Immunol., (abstract), 105(1):83-90, 1994.
Kurimoto, et al., "Synthesis and Biological Evaluation of 8-Oxoadenine Derivatives as Toll-like Receptor 7 Agonists Introducing the Antedrug Concept", Journal of Medicinal Chemistry (2010), 53 (7),2964-2972.
Kuster (ed), Kinase Inhibitors: Methods and Protocols Methods in Molecular Biology, 2012, 795:1-44.
Kutney, et al., "Dihydropyridines in synthesis and biosynthesis. IV. Dehydrosecodine, in vitro precursor of indole alkaloids," Canadian Journal of Chemistry (1982), 60(11), 1269-78.
Lee, et al , "Inhibition of phosphoinositide 3-kinase δ attenuates allergic airway inflammation and hyperresponsiveness in murine asthma model," FASEB J. 2006, 20(3):455-65.
Li et al., "Design, synthesis and antitumor activities of novel 4-anilino-5H-pyridazino [4,5- b]indoles," Zhongnan Yaoxue (2008), 6(2), 144-148, CODEN: ZYHAC6; ISSN: 1672-2981, Publisher: Zhongnan Yaoxue Zazhishe (with English abstract within the article).
Li et al., "Synthesis and antitumor activities of novel 1-anilino 5H-pyridazino[4,5-b]indoles," Zhongguo Yaowu Huaxue Zazhi (2007), 17(6), 339-343, CODEN: ZYHZEF; ISSN: 1005-0108 (with English abstract within the article).
Li, et al., "Optimization of the heterocyclic core of the quinazolinone-derived CXCR3 antagonists," Bioorganic & Medicinal Chemistry Letters (2008), 18(2), 688-693.
Li, et al., "Synthesis and anti-tumor activities of a novel series of tricyclic 1-anilino-5H-pyridazino[4,5-b]indoles," Archiv der Pharmazie (Weinheim, Germany) (2007), 340(8), 424-428, CODEN: ARPMAS; ISSN: 0365-6233.
Lindsay, et al., "SmI2-Promoted Radical Addition Reactions with N-(2-Indolylacyl)oxazolidinones: Synthesis of Bisindole Compounds," Journal of Organic Chemistry (2007), 72(11), 4181-4188, CODEN: JOCEAH; ISSN: 0022-3263.
Link, J. T., "The intramolecular Heck reaction," Organic Reactions (Hoboken, NJ, United States) (2002), 60, No pp. given CODEN: ORHNBA URL: http://www3.interscience.wiley.com/cgi-bin/mrwhome/107610747/HOME.
Lipsky, "Systemic lupus erythematosus: an autoimmune disease of B cell hyperactivity," Nat Immunol., 2001, 2(9):764-6.
Liu et al , "Inhibition of the mitotic kinesin Eg5 up-regulates Hsp70 through the phosphatidylinositol 3-kinase/Akt pathway in multiple myeloma cells," J Biol Chem., 2006, 281(26):18090-18097.
Liu et al., "mTOR mediated anti-cancer drug discovery," Drug Discovery Today: Therapeutic Strategies, 2009, 6:47-55.
Lucas, et al., "Rauwolfia alkaloids. XXXI. The synthesis and activity of some reserpine analogs," Journal of the American Chemical Society (1959), 81, 1928-32.
Luo et al., "Principles of Cancer Therapy: Oncogene and Non-oncogene Addiction," Cell, 2009, 36:823-837.

(56) References Cited

OTHER PUBLICATIONS

Ma, et al., "Bromophenols Coupled with Nucleoside Bases and Brominated Tetrahydroisoquinolines from the Red Alga Rhodomela confervoides", Journal of Natural Products (2007), 70(3), 337-341.

Ma, et al., "Two new constituents from Artemisia capillaris Thunb", Molecules (2008), 13(2), 267-271.

Mahboobi, et al., "Bis(1H-2-indolyl)methanones as a Novel Class of Inhibitors of the Platelet-Derived Derived Growth Factor Receptor Kinase," Journal of Medicinal Chemistry (2002), 45(5):1002-1018.

Martelli et al., "Targeting the PI3K/AKT/mTOR signaling network in acute myelogenous leukemia," Expert Opin Investig Drugs. Sep. 2009;18(9):1333-49.

Matsumoto, et al., "Pyrido[2,3-d]pyrimidine antibacterial agents. 3. 8-Alkyl- and 8-vinyl-5,8-dihydro-5-oxo-2-(1-piperazinyl)pyrido[2,3-d]pyrimidine-6-carboxylic acids and their derivatives", J Medicinal Chem (1975), 18(1), 74-9.

McDermott and Settleman, "Personalized Cancer Theraphy with Selective Kinase Inhibitors: An Emerging Paradigm in Medical Oncology," J Clinical Oncol., 2009, 27:5650-5659.

McLean, et al., "Discovery of covalent inhibitors for MIF tautomerase via cocrystal structures with phantom hits from virtual screening," Bioorganic & Medicinal Chemistry Letters (2009), 19(23), 6717-6720.

McMahon, G., "VEGF Receptor Signaling in Tumor Angiogenesis," The Oncologist, 5(1):3-10, 2000.

Meade, et al., "Anxiolytic activity of analogs of 4-benzylamino-2-methyl-7H-pyrrolo[2,3- d]pyrimidines," European Journal of Medicinal Chemistry (1998), 33(5), 363-374.

MedicineNet.com' [online]. "Definition of Cancer," Sep. 18, 2004, retrieved on Sep. 16, 2005. Retrieved from the Internet: http://www.medterms.com, 1 page.

medpagetoday.com' [online] "Current Role of Rituximab in Systematic Lupus," Jan. 2015, [retrieved Apr. 23, 2015]. Retrieved from the Internet: URL <http://www.medpagetoday.com/Rheumatology/Lupus/49398#./49398?&_suid=14297429843880910545130428964>. 10 pages.

Meijer et al., "Treatment of primary Sjögren syndrome with rituximab: extended follow-up, safety and efficacy of retreatment," Ann. Rheum. Dis., 68(2):284-285, 2009.

Merrill, "Efficacy and safety of rituximab in moderately-to-severely active systemic lupus erythematosus: The randomized, double-blind, phase ii/iii systemic lupus erythematosus evaluation of rituximab trial," Arthritis & Rheumatism, 2010, 61(1):222-233.

Miki, et al., "Reaction of 1-benzylindole-2,3-dicarboxylic anhydride with 3-bromo-4-lithiopyridine: formal synthesis of ellipticine," Heterocycles (1998), 48(8), 1593-1597.

Miki, et al., "Reaction of indole-2,3-dicarboxylic anhydride with (3-bromo-4-pyridyl)triisopropoxytitanium: synthesis of ellipticine," Tetrahedron Letters (1996), 37(43), 7753-7754.

Miki, et al., "Synthesis of caulersin and its isomers by reaction of indole-2,3-dicarboxylic anhydrides with methyl indoleacetates," Tetrahedron Letters (2006), 47(29), 5215-5218, CODEN: TELEAY; ISSN: 0040-4039.

Miki, et al., "Synthesis of ellipticine by reaction of 1-(4-methoxybenzyl)indole-2,3-dicarboxylic anhydride with (3-bromo-4-pyridyl)triisopropoxytitanium," Journal of the Chemical Society, Perkin Transactions 1 (2001), (18), 2213-2216.

Mishra et al., "Decanuclear Copper Framework Supported by a Tripodal Adenine Ligand," Inorganic Chemistry (Washington, DC, United States), (2010), 49(8), 3691-3693.

Mizoguchi, et al., "Genetic Alterations of Phosphoinositide 3-kinase Subunit Genes in Human Glioblastomas," Brain Pathol. 2004, 14(4):372-7.

Moffett, "Antiulcer agents. p-Aminobenzamido aromatic compounds", Journal of Medicinal Chemistry (1971), 14(10), 963-8.

Mohammadizadeh, et al., "A novel and expedient synthesis of 7-pyrimidinylpyrimido[4,5- d]pyrimidinones," Helvetica Chimica Acta (2010), 93(1), 153-157.

Morrison, et al., "Pyrimido[4,5-c]pyridazines. 1. Cyclizations with α-keto esters", Journal of Organic Chemistry (1978), 43(25), 4844-9.

Mukhopadhyay, et al., "An ionic liquid {[secbmim]+ Br−} as a "dual reagent catalyst" for the multicomponent synthesis of (quinolinyl- and isoquinolinyl-amino) alkylnaphthols, their bis-analogs and a facile route to naphthoxazines," ARKIVOK (Gainesville, FL, United States) (2010), (10), 291-304.

Musmuca, et al., "Small-Molecule Interferon Inducers. Toward the Comprehension of the Molecular Determinants through Ligand-Based Approaches", Journal of Chemical Information and Modeling (2009),49(7), 1777-1786.

Najiwara, et al., "Behavior of naphthoyloxyl and methoxynaphthoyloxyl radicals generated from the photocleavage of dinaphthoyl peroxides and 1-(naphthoyloxy)-2-pyridones," Bulletin of the Chemical Society of Japan (2003), 76(3), 575-585.

Najiwara, et al., "Generation and behavior of naphthoyloxyl radicals in photocleavage of 1-(naphthoyloxy)-2-pyridones, Chemistry Letters (2001), (10), 1064-1065.

Nettekoven, M., "A combinatorial approach towards 2-acyl-3-amino-indole derivatives," Tetrahedron Letters (2000), 41(43), 8251-8254.

Norman, P., "Selective PI3Kδ inhibitors, a review of the patent literature", Expert Opinion on Therapeutic Patents, Informa Healthcare, 21(11):1773-1790, 2011.

Oki, et al., "Reactivities of Stable Rotamers. XLII. Generation and Fates of Rotameric [1-(9-Fluorenyl)-2-naphthyl]methyl Radicals," Bulletin of the Chemical Society of Japan (1999), 72(10), 2327-2336.

Okkenhaug, et al., "Impaired B and T Cell Antigen Receptor Signaling in p110δ PI 3-Kinase Mutant Mice," Science, 2002, 297(5583):1031-4).

Park et al., "Phosphoinositide 3-kinase δ inhibitor as a novel therapeutic agent in asthma," Respirology, 13:764-771, 2008.

Phillips, et al., "The reaction of anils with 8-quinolinol," Journal of Organic Chemistry (1954), 19, 907-9 CODEN: JOCEAH; ISSN: 0022-3263.

Pinedo and Slamon, "Translational Research: The Role of VEGF in Tumor Angiogenesis," The Oncologist, 5(1):1-2, 2000.

Platts, et al., "A concise synthesis of HIV integrase inhibitors bearing the dipyridone acid motif," Tetrahedron Letters (2011), 52(4), 512-514.

Portnaya, et al., "Azomethine dyes. IV. Indoaniline dyes derived from heterocyclic N-substituted 1-hydroxy-2-naphthamides," Ts. Vses. Nauchn.-Issled. Kinofotoinst. (1960), (No. 40), 106-18 (with English abstract).

Prezent, et al., STN Abstract, Accession No. 2004:358794, "Boron chelates as intermediates in the synthesis of new functionalized pyridines and pyrimidines from α,α-dioxoketene aminals," Boron Chemistry at the Beginning of the 21st Century, [Proceedings of the International Conference on the Chemistry of Boron], 11th, Moscow, Russian Federation, Jul. 28-Aug. 1, 2002 (2003), Meeting Date 2002, 91-93. Editor(s): Bubnov, Yu. N. A. N. Nesmeyanov Institute of Organoelement Compounds, Russian Academy of Sciences: Moscow, Russia.

Puri and Gold, "Selective inhibitors of phosphoinositide 3-kinase delta: modulators of B-cell function with potential for treating autoimmune inflammatory diseases and B-cell malignancies," Frontiers in Immunology, 3(256):1-16, 2012.

Ramos-Casals et al., "Rituximab in systemic lupus erythematosus; A systematic review of off-label use in 188 cases," Lupus, 18:767-776, 2009.

Randis, et al., "Role of PI3Kδ and PI3Kγ in inflammatory arthritis and tissue localization of neutrophils," Eur. J. Immunol., 2008, 38(5):1215-24.

Reich, et al., "Preparation of a,b-unsaturated carbonyl compounds and nitriles by selenoxide elimination," Organic Reactions (Hoboken, NJ, United States) (1993), 44, No pp. given.

Remington's Pharmaceutical Sciences, 17th ed., Mack Publishing Company, Easton, Pa., 1985, p. 1418* Too Voluminous to Provide.

Ringshausen et al., "Constitutively Actived phosphatidylinositol-3-kinase (PI-3K) is involved in the defect of apoptosis is B-CLL: assocaite with protein kinase C delta," Blood, 2002, 100:3741-3748.

(56) References Cited

OTHER PUBLICATIONS

Roxas-Duncan, et al., "Identification and biochemical characterization of small-molecule inhibitors of Clostridium botulinum neurotoxin serotype A," *Antimicrobial Agents and Chemotherapy* (2009), 53(8), 3478-3486.
Sahoo, et al., "Antispasmodic compounds IV," Journal of the Indian Chemical Society (1959), 36, 421-4.
Sako, M., "Product class 19: pyridopyrimidines," *Science of Synthesis* (2004), 16, 1155-1267.
Samuels and Ericson, "Oncogenic PI3K and its role in cancer," Curr Opin Oncol., 2006, 18(1):77-82.
Samuels, et al., "High Frequency of Mutations of the PIK3CA Gene in Human Cancers," Science, 2004, 304(5670):554.
Sasaki, et al., "Function of PI3Kγ in Thymocyte Development, T Cell Activation, and Neutrophil Migration," Science, 2000, 287(5455):1040-6.
Sawyers, "The cancer biomarker problem," Nature, 2008, 452:548-552.
Saxena, et al., "Pharmacophore-based virtual screening and docking studies on Hsp90 inhibitors", SAR and QSAR in Environmental Research (2010), 21(5-6), 445-462.
Schafer and Kolkhof, "Failure is an option: learning from unsuccessful proof-of-concept trials," Drug Discovery Today, Nov. 2008, 13(21/22):913-916.
Schell, et al., "Versatile Solid-Phase Synthesis of Trisubstituted 1H-Pyrido[2,3-d]pyrimidin-4-ones and Related Heterocycles," *Journal of Combinatorial Chemistry* (2005), 7(1), 96-98.
Segarra et al., "Successful treatment of membranous glomerulonephritis with rituximab in calcineurin inhibitor-dependent patients," Clin J Am Soc Nephrol., 2009, 4(6):1083-8.
Sen, et al., "Reaction of aldehydes and amines with 8-hydroxyquinaldine and 8-quinolinol. II," *Journal of the Indian Chemical Society* (1960), 37, 640-2.
Shi, et al., "Synthesis and preliminary cytotoxic evaluation of substituted indoles as potential anticancer agents," *Chinese Chemical Letters* (2007), 18(8), 899-901, CODEN: CCLEE7; ISSN: 1001-8417.
Shuttleworth et al., "Progress in the Preclinical Discovery and Clinical Development of Class 1 and Dual Class I/IV Phosphoinositide 3-Kinase (PI3K) Inhibitors", Current Medicinal Chemistry, 18(1):2686-2714, 2011.
Silverman, R. B., "The organic Chemistry of Drugs Design and Drug Action." Elsevier. Northwestern University. Second Edition. Evanston Illinois. 2004. p. 29 and table 2.2 *Too Voluminous to Provide.
Singh et al., "Application of Nazarov cyclization to access [6-5-6] and [6-5-5]tricyclic core embedded new heterocycles: an easy entry to structures related to Taiwaniaquinoids," *Organic & Biomolecular Chemistry* (2009), 7(9), 1858-1867, CODEN: OBCRAK; ISSN: 1477-0520.
Steliou, et al., "Does diatomic sulfur(S2) react as a free species?", *Journal of the American Chemical Society* (1992), 114(4), 1456-62.
Stüve et al., "Long-term B-Lymphocyte Depletion With Rituximab in Patients With Relapsing-Remitting Multiple Sclerosis," Arch Neurol., 66(2):259-261, 2009.
Sujobert, et al., "Essential role for the p110δ isoform in phosphoinositide 3-kinase activation and cell proliferation in acute myeloid leukemia," Blood, 2005, 106(3):1063-6.
Szuecova, et al., "Synthesis, characterization and biological activity of ring-substituted 6-benzylamino-9-tetrahydropyran-2-yl and 9-tetrahydrofuran-2-ylpurine derivatives," *Bioorganic & Medicinal Chemistry* (2009), 17(5), 1938-1947.
Terrier, et al., "Tolerance and Efficacy of Rituximab (RTX) in Systemic Lupus Erythematosus (SLE): Data of 104 Patients From the AIR (Auto-immunity and Rituximab) Registry," Presented at 73th Annual Scientific Meeting of the American College of Rheumatology, Oct. 2009; Philadelphia, PA.
Thomas, et al., "Airway inflammation. chemokine-induced neutrophilia and the class I phosphoinositide 3-kinases," Eur J Immunol. 2005, 35(4):1283-91.

Travnickek, et al., "2-Chloro-6-[(4-hydroxy-3,5-dimethoxybenzyl)amino]-9-isopropylpurine," *Acta Crystallographica*, Section E: Structure Reports Online (2007), E63(2), o728-o730 CODEN: ACSEBH; ISSN: 1600-5368 URL: http://journals.iucr.org/e/issues/2007/02/00/lh2285/lh2285.pdf.
Umar, A., "Future directions in cancer prevention," Nature Reviews Cancer, 12.12 (2012): 835-848.
Uddin et al., "Role of phosphatidylinositol 3'-kinase/AKT pathway in diffuse large B-cell lymphomas survival," Blood, 2006, 108:4178-4186.
Vanhaesebroeck et al., "Signalling by PI3K isoforms: insights from gene-targeted mice," Trends Biochem Sci., 2005, 30(4):194-204.
Vasil'ev, et al al., "Chelate synthesis of 1-alkyl-5-(trifluoromethyl)-1,6-naphthyridin-4(1H)-ones", Izvestiya Akademii Nauk, Seriya Khimicheskaya (1994),(8), 1510-11 (with English abstract).
Venet et al., "Lymphocytes in the Development of Lung Inflammation. A role of Regulatory CD4+ T Cells in Indirect Pulmonary Lung Injury," *J Immunol.*, 2009, 183:6472-3480.
Wallin, J J , "GDC-0980 is a novel class I PI3K/mTOR kinase inhibitor with robust activity in cancer models driven by the PI3K pathway," Molecular cancer therapeutics 10.12 (2011): 2426-2436.
Wang et al., "Anticancer drugs of phosphatidylinositol 3 kinase inhibitors," World Notes on Antibiotics, Dec. 2008, 29(5): 206-212.
WebMD. Arthritis Health Center: What is Inflammation? Jun. 7, 2012, www.webmd.com/arthritis/about-inflammation?page=2, 4 pages.
WebMD. Bladder Cancer Health Center: Bladder Cancer-Prevention, Apr. 30, 2013, www.webmd.com/cancer/bladder-cancer/bladder-cancer-prevention, 1 page.
WebMD. Lung Disease & Respiratory Health Center: ARDS, May 21, 2014, www.webmd.com/lung/ards-acute-respiratory-distress-syndrome?p.=2, 4 pages.
WebMD. Lung Disease & Respiratory Health Center: Lung Disease Overview, May 23, 2014, www.webmd.com/lung/lung-diseases-overview, 3 pages.
WebMD. Osteoarthritis Health Center: Osteoarthritis-prevention, Apr. 9, 2013, www.webmd.com/osteoarthritis/tc/osteoarthritis-prevention, 2 pages.
WebMD. Psoriasis Health Center: Psoriasis—prevention, Jan. 9, 2012, www.webmd.com/skin-problems-and-treatments/psoriasis/psoriasis-prevention, 1 page.
Xu et al., "Activation of the PI3K/Akt/mTOR pathway in diffuse large B cell lymphoma: clinical significance and inhibitory effect of rituximab," Ann Hematol., 2013, 92:1351-1358.
Yaguchi et al., "Antitumor Activity of ZSTK474, a new Phosphatidinylinositol 3-Kinase Inhibitor," J Natl. Cancer Inst., 2006, 98(8):545-556.
Yahay-Zadeh, "Synthesis of 9-Aryl-6-aminopurines from 5-Amino-1-aryl-1H-imidazole-4-carbonitriles", Russian Journal of Organic Chemistry (Translation of Zhurnal Organicheskoi Khimii) (2003), 39(11),1649-1651.
Yahyazadeh, et al., "Synthesis of 9-benzyl-6-aminopurines from 5-amino-l-benzyl-4-cyanoimidazoles", Bulletin of the Korean Chemical Society (2003), 24(12), 1723-1724.
Yamada et al., "Alpha-1 Adrenoceptors in Human Prostate: Characterization and Alteration in Benign Prostatic Hypertrophy," J Pharmacol Experimental Therapeutics, 1987, 242(1):326-330.
Yanni, A. S., "Synthesis of some new 5-iodo-7-substituted-aminomethy1-8-hydroxyquinoline," *Revue Roumaine de Chimie* (1994), 39(7), 833-6 CODEN: RRCHAX; ISSN: 0035-3930.
Yanni, et al., "Synthesis and biological activity of some 7-substituted aminomethy1-8-hydroxyquinoline-5- sulfonic acids," *Indian Journal of Chemistry, Section B: Organic Chemistry Including Medicinal Chemistry* (1982), 21B(7), 705-6.
Yoo, et al., "Synthesis and evaluation of antitumor activity of novel 2-[N-methyl-N-(4-methyl-1,3-benzothiazol-2-yl)aminomethyl]-5,8-diacyloxy-1,4-naphthoquinones," *Archives of Pharmacal Research* (2008), 31(2), 142-147 CODEN: APHRDQ; ISSN: 0253-6269.
Yoon et al., "Impact of fluoroquinolones on the diagnosis of pulmonary tuberculosis initially treated as bacterial pneumonia," Int'l J Tuberculosis and Lung Dis, 2005, 9:1215-1219.

(56) References Cited

OTHER PUBLICATIONS

Yoshida, et al., "MexAB-OprM specific efflux pump inhibitors in Pseudomonas aeruginosa. Part 5: Carbon-substituted analogues at the C-2 position," *Bioorganic & Medicinal Chemistry* (2006), 14(6), 1993-2004.
Yuan, T.L., "PI3K pathway alterations in cancer: variations on a theme," Oncogene, 2008, 27.41: 5497-551.
Zhang et al., "Advances in preclinical small molecules for the treatment of NSCLC", Expert Opinion on Therapeutic Patents, 19(6):731-751, 2009.
Zhao and Vogt, "Class I PI3K in oncogenic cellular transformation," Oncogene, 2008, 27:5486-5496.
Zhao, et al., "Synthesis and in vitro anti-hepatitis B virus activities of some ethyl 5-hydroxy-1H-indole-3-carboxylates," *Bioorganic & Medicinal Chemistry* (2006), 14(8), 2552-2558.
International Preliminary Report on Patentability dated Dec. 28, 2012 for International Appln. No. PCT/US2011/041202 (8 pgs.).
International Preliminary Report on Patentability dated Jul. 4, 2013 for International Appln. No. PCT/US2011/065743 (8 pgs).
International Preliminary Report on Patentability dated Jun. 19, 2012 for International Appln. No. PCT/US2010/061023 (6 pgs.).
International Preliminary Report on Patentability dated Jun. 19, 2012 for International Appln. No. PCT/US2010/060980 (8 pgs.).
International Preliminary Report on Patentability dated Oct. 16, 2012 for International Appln. No. PCT/US2011/032213 (6 pgs.).
International Preliminary Report on Patentability for PCT/US2010/040150 dated Jul. 5, 2011 (24pgs.).
International Preliminary Report on Patentability for PCT/US2012/030310 dated Oct. 1, 2013 (7pgs.).
International Preliminary Report on Patentability for PCT/US2012/028915 dated Sep. 17, 2013 (6pgs.).
International Preliminary Report on Patentability for PCT/US2012/053398, issued Mar. 4, 2014 (6 pgs.).
International Search Report dated Jul. 11, 2013 for International Appln. No. PCT/US2013/034803 (15 pgs.).
International Search Report dated Dec. 21, 2012 for International Appln. No. PCT/US2012/053398 (11 pgs.).
International Search Report dated Feb. 28, 2012 for International Appln. No. PCT/US2011/065743 (13 pgs.).
International Search Report dated May 11, 2012 for International Appln. No. PCT/US2012/030310 (11 pgs.).
International Search Report dated May 31, 2012 for International Appln. No. PCT/US2012/028915 (11 pgs.).
International Search Report dated Sep. 23, 2011 for International Appln. No. PCT/US2011/041202 (12 pgs.).
International Search Report for PCT/US2010/040150 dated Nov. 8, 2010 (19 pgs.).
International Search Report for PCT/US2010/060980 dated Mar. 15, 2011 (12 pgs.).
International Search Report for PCT/US2010/061023 dated Feb. 16, 2011 (10 pgs.).
International Search Report for PCT/US2011/032213 dated Jun. 14, 2011 (11 pgs.).
STN Search Report, conducted Dec. 1, 2010, 132 pages.
STN Search Report, conducted Dec. 16, 2009, 72 pages.
STN Search Report, conducted prior to Jun. 21, 2011, 224 pages.
STN Search Report, conducted Apr. 5, 2010, 513 pages.
STN Search Report, conducted Apr. 24, 2009, 43 pages.
STN Search Report, conducted Dec. 7, 2010, 213 pages.
STN Search Report, conducted Aug. 29, 2011, 181 pages.
STN Search Report, conducted May 27, 2009, 2 pages.
STN Search Report, conducted May 28, 2009, 81 pages.
STN Search Report, conducted Apr. 2, 2010, 141 pages.
STN Search Report, conducted Aug. 30, 2011, 61 pages.
Office Action in CO Application No. 11-179.464, received on Mar. 14, 2014, 17 pages.
Office Action in JP Application No. 2012-518563, dated Jul. 8, 2014, 6 pages (with English translation).
Office Action in JP Application No. 2013-546274, dated Sep. 15, 2015, 7 pages (with English Translation).
Office Action in JP Application No. 2014-223540, dated Jul. 21, 2015, 5 pages (with English Translation).

N-(1-(SUBSTITUTED-PHENYL)ETHYL)-9H-PURIN-6-AMINES AS PI3K INHIBITORS

This application is a continuation of U.S. Ser. No. 13/329,532, filed Dec. 19, 2011, which claims the benefit of priority of U.S. Provisional Appl. No. 61/425,107, filed Dec. 20, 2010, which is incorporated herein by reference in its entirety.

FIELD OF THE INVENTION

The present invention provides N-(1-(substituted-phenyl)ethyl)-9H-purin-6-amine derivatives that modulate the activity of phosphoinositide 3-kinases (PI3Ks) and are useful in the treatment of diseases related to the activity of PI3Ks including, for example, inflammatory disorders, immune-based disorders, cancer, and other diseases.

BACKGROUND OF THE INVENTION

The phosphoinositide 3-kinases (PI3Ks) belong to a large family of lipid signaling kinases that phosphorylate phosphoinositides at the D3 position of the inositol ring (Cantley, Science, 2002, 296(5573):1655-7). PI3Ks are divided into three classes (class I, II, and III) according to their structure, regulation and substrate specificity. Class I PI3Ks, which include PI3Kα, PI3Kβ, PI3Kγ, and PI3Kδ, are a family of dual specificity lipid and protein kinases that catalyze the phosphorylation of phosphatidylinosito-4,5-bisphosphate ($PIP_2$) giving rise to phosphatidylinosito-3,4,5-trisphosphate ($PIP_3$). $PIP_3$ functions as a second messenger that controls a number of cellular processes, including growth, survival, adhesion and migration. All four class I PI3K isoforms exist as heterodimers composed of a catalytic subunit (p110) and a tightly associated regulatory subunit that controls their expression, activation, and subcellular localization. PI3Kα, PI3Kβ, and PI3Kδ associate with a regulatory subunit known as p85 and are activated by growth factors and cytokines through a tyrosine kinase-dependent mechanism (Jimenez, et al., J Biol Chem., 2002, 277(44):41556-62) whereas PI3Kγ associates with two regulatory subunits (p101 and p84) and its activation is driven by the activation of G-protein-coupled receptors (Brock, et al., J Cell Biol., 2003, 160(1):89-99). PI3Kα and PI3Kβ are ubiquitously expressed. In contrast, PI3Kγ and PI3Kδ are predominantly expressed in leukocytes (Vanhaesebroeck, et al., Trends Biochem Sci., 2005, 30(4):194-204).

The differential tissue distribution of the PI3K isoforms factors in their distinct biological functions. Genetic ablation of either PI3Kα or PI3Kβ results in embryonic lethality, indicating that PI3Kα and PI3Kβ have essential and non-redundant functions, at least during development (Vanhaesebroeck, et al., 2005). In contrast, mice which lack PI3Kγ and PI3Kδ are viable, fertile and have a normal life span although they show an altered immune system. PI3Kγ deficiency leads to impaired recruitment of macrophages and neutrophils to sites of inflammation as well as impaired T cell activation (Sasaki, et al., Science, 2000, 287(5455):1040-6). PI3Kδ-mutant mice have specific defects in B cell signaling that lead to impaired B cell development and reduced antibody responses after antigen stimulation (Clayton, et al., J Exp Med. 2002, 196(6):753-63; Jou, et al., Mol Cell Biol. 2002, 22(24):8580-91; Okkenhaug, et al., Science, 2002, 297(5583): 1031-4).

The phenotypes of the PI3Kγ and PI3Kδ-mutant mice suggest that these enzymes may play a role in inflammation and other immune-based diseases and this is borne out in preclinical models. PI3Kγ-mutant mice are largely protected from disease in mouse models of rheumatoid arthritis (RA) and asthma (Camps, et al., Nat Med. 2005, 11(9):936-43; Thomas, et al., Eur J Immunol. 2005, 35(4):1283-91). In addition, treatment of wild-type mice with a selective inhibitor of PI3Kγ was shown to reduce glomerulonephritis and prolong survival in the MRL-1pr model of systemic lupus nephritis (SLE) and to suppress joint inflammation and damage in models of RA (Barber, et al., Nat Med. 2005, 11(9):933-5; Camps, et al., 2005). Similarly, both PI3Kδ-mutant mice and wild-type mice treated with a selective inhibitor of PI3Kδ have been shown to have attenuated allergic airway inflammation and hyper-responsiveness in a mouse model of asthma (Ali, et al., Nature. 2004, 431(7011):1007-11; Lee, et al., FASEB J. 2006, 20(3):455-65) and to have attenuated disease in a model of RA (Randis, et al., Eur. J. Immunol., 2008, 38(5):1215-24).

In addition to their potential role in inflammatory diseases, all four class I PI3K isoforms may play a role in cancer. The gene encoding p110α is mutated frequently in common cancers, including breast, prostate, colon and endometrial (Samuels, et al., Science, 2004, 304(5670):554; Samuels, et al., Curr Opin Oncol. 2006, 18(1):77-82). Eighty percent of these mutations are represented by one of three amino acid substitutions in the helical or kinase domains of the enzyme and lead to a significant upregulation of kinase activity resulting in oncogenic transformation in cell culture and in animal models (Kang, et al., Proc Natl Acad Sci USA. 2005, 102(3):802-7; Bader, et al., Proc Natl Acad Sci USA. 2006, 103(5):1475-9). No such mutations have been identified in the other PI3K isoforms although there is evidence that they can contribute to the development and progression of malignancies. Consistent overexpression of PI3Kδ is observed in acute myeloblastic leukemia (Sujobert, et al., Blood, 2005, 106(3):1063-6) and inhibitors of PI3Kδ can prevent the growth of leukemic cells (Billottet, et al., Oncogene. 2006, 25(50):6648-59). Elevated expression of PI3Kγ is seen in chronic myeloid leukemia (Hickey, et al., J Biol Chem. 2006, 281(5):2441-50). Alterations in expression of PI3Kβ, PI3Kγ and PI3Kδ have also been observed in cancers of the brain, colon and bladder (Benistant, et al., Oncogene, 2000, 19(44):5083-90; Mizoguchi, et al., Brain Pathol. 2004, 14(4):372-7; Knobbe, et al., Neuropathol Appl Neurobiol. 2005, 31(5):486-90). Further, these isoforms have all been shown to be oncogenic in cell culture (Kang, et al., 2006).

Thus, new or improved agents which inhibit kinases such as PI3K are continually needed for developing new and more effective pharmaceuticals that are aimed at augmentation or suppression of the immune and inflammatory pathways (such as immunosuppressive agents for organ transplants), as well as agents for the prevention and treatment of autoimmune diseases (e.g., multiple sclerosis, rheumatoid arthritis, asthma, type I diabetes, inflammatory bowel disease, Crohn's disease, autoimmune thyroid disorders, Alzheimer's disease, nephritis), diseases involving a hyperactive inflammatory response (e.g., eczema), allergies, lung diseases, cancer (e.g., prostate, breast, leukemia, multiple myeloma), and some immune reactions (e.g., skin rash or contact dermatitis or diarrhea) caused by other therapeutics. The compounds, compositions, and methods described herein are directed toward these needs and others.

SUMMARY

The present invention provides, inter alia, compounds of Formula I:

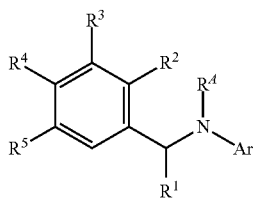

and pharmaceutically acceptable salts thereof; wherein the variables are defined infra.

The present invention further provides compositions comprising a compound of the invention, or a pharmaceutically acceptable salt thereof, and at least one pharmaceutically acceptable carrier.

The present invention also provides methods of modulating an activity of a PI3K kinase, comprising contacting the kinase with a compound of the invention, or a pharmaceutically acceptable salt thereof.

The present invention further provides methods of treating a disease in a patient, wherein said disease is associated with abnormal expression or activity of a PI3K kinase, comprising administering to said patient a therapeutically effective amount of a compound of the invention, or a pharmaceutically acceptable salt thereof.

The present invention further provides methods of treating an immune-based disease in a patient, comprising administering to said patient a therapeutically effective amount of a compound of the invention, or a pharmaceutically acceptable salt thereof.

The present invention also provides methods of treating a cancer in a patient, comprising administering to said patient a therapeutically effective amount of a compound of the invention, or a pharmaceutically acceptable salt thereof.

The present invention further provides methods of treating a lung disease in a patient, comprising administering to said patient a therapeutically effective amount of a compound of the invention, or a pharmaceutically acceptable salt thereof.

The present invention also provides a compound of invention, or a pharmaceutically acceptable salt thereof, for use in any of the methods described herein.

The present invention further provides use of a compound, or a pharmaceutically acceptable salt thereof, for the manufacture of a medicament for use in any of the methods described herein.

DETAILED DESCRIPTION

The present invention provides, inter alia, a compound of Formula I:

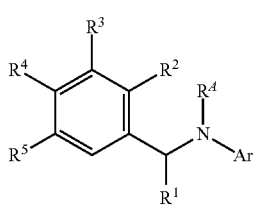

or a pharmaceutically acceptable salt thereof; wherein:

Ar is

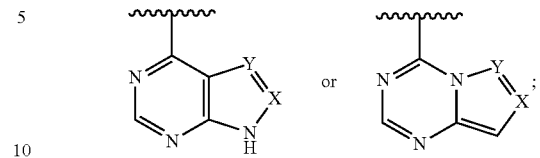

X is CH or N;

Y is CH or N;

$R^1$ is selected from $C_{1-6}$ alkyl, $C_{2-6}$ alkenyl, $C_{2-6}$ alkynyl, and $C_{1-6}$ haloalkyl; wherein said $C_{1-6}$ alkyl, $C_{2-6}$ alkenyl, and $C_{2-6}$ alkynyl are each optionally substituted by 1, 2, 3, or 4 groups independently selected from halo, OH, CN, $NR^{1a}R^{2b}$, $C_{1-6}$ alkoxy, and $C_{1-6}$ haloalkoxy;

each $R^{1a}$ and $R^{2b}$ is independently selected from H and $C_{1-6}$ alkyl;

or any $R^{1a}$ and $R^{2b}$ together with the N atom to which they are attached form a 4-, 5-, 6-, or 7-membered heterocycloalkyl group, which is optionally substituted with 1, 2, 3, or 4 substituents independently selected from $C_{1-6}$ alkyl;

$R^2$ is selected from halo, CN, $C_{1-6}$ alkyl, $C_{1-6}$ haloalkyl, -L-($C_{1-6}$ alkyl), -L-($C_{1-6}$ haloalkyl), and -L-($C_{1-4}$ alkylene)$_n$-$Cy^2$ and —($C_{1-4}$ alkylene)$_n$-$Cy^2$; wherein said $C_{1-6}$ alkyl in said $C_{1-6}$ alkyl and -L-($C_{1-6}$ alkyl) is optionally substituted by 1, 2, 3, or 4 independently selected $R^{2a}$ groups;

L is O, $NR^B$, S, S(O), S(O)$_2$, C(O), C(O)$NR^B$, S(O)$NR^B$, S(O)$_2NR^B$, $NR^BC(O)$, $NR^BS(O)$, and $NR^BS(O)_2$;

$R^A$ and $R^B$ are each independently selected from H and $C_{1-6}$ alkyl;

$Cy^2$ is selected from $C_{3-7}$ cycloalkyl, 4-7 membered heterocycloalkyl, phenyl, and 5-6 membered heteroaryl; each of which is substituted with p independently selected $R^{2a}$ groups; wherein p is 0, 1, 2, 3, or 4;

each $R^{2a}$ is independently selected from OH, NO$_2$, CN, halo, $C_{1-6}$ alkyl, $C_{2-6}$ alkenyl, $C_{2-6}$ alkynyl, $C_{3-7}$ cycloalkyl, $C_{1-6}$ haloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

$R^3$ is halo, CN, NO$_2$, $C_{1-6}$ alkyl, $C_{2-6}$ alkenyl, $C_{2-6}$ alkynyl, $C_{1-6}$ haloalkyl, —($C_{1-4}$ alkylene)$_r$-$Cy^3$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^b$, $NR^fC(O)R^b$, $NR^fC(O)OR^b$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^fS(O)_2R^b$, $NR^cS(O)_2NR^cR^d$, $S(O)R^b$, $S(O)NR^cR^d$, $S(O)_2R^b$, or $S(O)_2NR^cR^d$; wherein said $C_{1-6}$ alkyl, $C_{2-6}$ alkenyl, and $C_{2-6}$ alkynyl are each optionally substituted by 1, 2, 3, or 4 independently selected $R^{3a}$ groups;

$Cy^3$ is selected from $C_{3-7}$ cycloalkyl, 4-7 membered heterocycloalkyl, phenyl, and 5-6 membered heteroaryl; each of which is optionally substituted with 1, 2, 3, or 4 independently selected $R^{3a}$ groups;

provided that one of the following is true:
(1) $R^3$ is —($C_{1-4}$ alkylene)$_r$-$Cy^3$; or
(2) $R^2$ is selected from -L-($C_{1-4}$ alkylene)$_n$-$Cy^2$ and —($C_{1-4}$ alkylene)$_n$-$Cy^2$; or
(3) $R^3$ is —($C_{1-4}$ alkylene)$_r$-$Cy^3$; and $R^2$ is selected from -L-($C_{1-4}$ alkylene)$_n$-$Cy^2$ and —($C_{1-4}$ alkylene)$_n$-$Cy^2$;

each $R^{3a}$ is independently selected from halo, CN, $NO_2$, $C_{1-6}$ alkyl, $C_{2-6}$ alkenyl, $C_{2-6}$ alkynyl, $C_{1-6}$ haloalkyl, $C_{3-7}$ cycloalkyl, 4-7 membered heterocycloalkyl, phenyl, 5-6 membered heteroaryl, (4-7 membered heterocycloalkyl)-$C_{1-4}$ alkyl, phenyl-$C_{1-4}$ alkyl, (5-6 membered heteroaryl)-$C_{1-4}$ alkyl, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^b$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$; wherein said $C_{1-6}$ alkyl, $C_{2-6}$ alkenyl, $C_{2-6}$ alkynyl, $C_{3-7}$ cycloalkyl, 4-7 membered heterocycloalkyl, phenyl, 5-6 membered heteroaryl, (4-7 membered heterocycloalkyl)-$C_{1-4}$ alkyl, phenyl-$C_{1-4}$ alkyl, and (5-6 membered heteroaryl)-$C_{1-4}$ alkyl are each optionally substituted by 1, 2, 3, or 4 groups independently selected from OH, $NO_2$, CN, halo, $C_{1-6}$ alkyl, cyano-$C_{1-6}$ alkyl, HO—$C_{1-6}$ alkyl, $C_{1-4}$ alkoxy-$C_{1-6}$ alkyl, $C_{1-6}$ haloalkyl, $C_{2-6}$ alkenyl, $C_{2-6}$ alkynyl, $C_{3-7}$ cycloalkyl, $C_{1-6}$ haloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, amino carbonylamino, $C_{1-6}$ alkylaminocarbonylamino, and di($C_{1-6}$ alkyl)aminocarbonylamino;

$R^4$ is selected from H, OH, $NO_2$, CN, halo, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-4}$ alkoxy-$C_{1-6}$ alkyl, $C_{3-7}$ cycloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, amino sulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)amino carbonylamino;

$R^5$ is selected from halo, OH, CN, $C_{1-4}$ alkyl, $C_{1-4}$ alkoxy, and $C_{1-4}$ haloalkoxy;

each $R^a$, $R^c$, and $R^d$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, 4-7 membered heterocycloalkyl, phenyl, 5-6 membered heteroaryl, (4-7 membered heterocycloalkyl)-$C_{1-4}$ alkyl, phenyl-$C_{1-4}$ alkyl, and (5-6 membered heteroaryl)-$C_{1-4}$ alkyl; wherein said $C_{1-6}$ alkyl, $C_{2-6}$ alkenyl, $C_{2-6}$ alkynyl, $C_{3-7}$ cycloalkyl, 4-7 membered heterocycloalkyl, phenyl, 5-6 membered heteroaryl, (4-7 membered heterocycloalkyl)-$C_{1-4}$ alkyl, phenyl-$C_{1-4}$ alkyl, and (5-6 membered heteroaryl)-$C_{1-4}$ alkyl are each optionally substituted with 1, 2, 3, 4, or 5 substituents independently selected from OH, $NO_2$, CN, halo, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-4}$ alkoxy-$C_{1-6}$ alkyl, $C_{3-7}$ cycloalkyl, $C_{1-6}$ haloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

each $R^b$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, 4-7 membered heterocycloalkyl, phenyl, 5-6 membered heteroaryl, (4-7 membered heterocycloalkyl)-$C_{1-4}$ alkyl, phenyl-$C_{1-4}$ alkyl, and (5-6 membered heteroaryl)-$C_{1-4}$ alkyl; each optionally substituted with 1, 2, 3, 4, or 5 substituents independently selected from OH, $NO_2$, CN, halo, $C_{1-6}$ alkyl, $C_{2-6}$ alkenyl, $C_{2-6}$ alkynyl, $C_{1-6}$ haloalkyl, cyano-$C_{_-6}$ alkyl, HO—$C_1$-6 alkyl, $C_{1-4}$ alkoxy-$C_{1-6}$ alkyl, $C_{3-7}$ cycloalkyl, $C_{1-6}$ haloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

each $R^e$ is independently selected from H, $C_{1-4}$ alkyl, CN, OH, $C_{1-4}$ alkoxy, $C_{1-4}$ alkylsulfonyl, carbamyl, $C_{1-4}$ alkylcarbamyl, di($C_{1-4}$ alkyl)carbamyl, and $C_{1-4}$ alkylcarbonyl;

each $R^f$ is independently selected from $C_{1-4}$ alkylsulfonyl, $C_{1-4}$ alkylcarbonyl and $C_{1-4}$ alkoxycarbonyl;

n is 0 or 1; and r is 0 or 1.

In some embodiments, Ar is

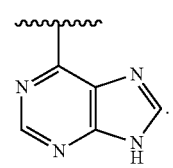 [SMILES: *c1ncnc2[nH]cnc12]

In some embodiments, Ar is

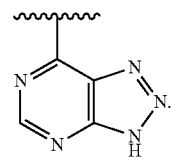 [SMILES: *c1ncnc2[nH]nnc12]

In some embodiments, Ar is

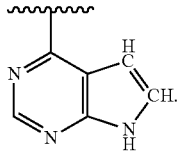 [SMILES: *c1ncnc2[nH]ccc12]

In some embodiments, Ar is

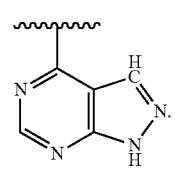 [SMILES: *c1ncnc2[nH]ncc12]

In some embodiments, Ar is

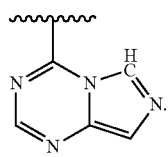 [SMILES: *c1ncnc2cncn12]

In some embodiments, X is N and Y is CH; or X is CH and Y is N.

In some embodiments, $R^4$ is selected from OH, $NO_2$, CN, halo, $C_{1-6}$ alkyl, $C_{2-6}$ alkenyl, $C_{2-6}$ alkynyl, $C_{1-6}$ haloalkyl, cyano-$C_{1-6}$ alkyl, HO—$C_{1-6}$ alkyl, $C_{1-4}$ alkoxy-$C_{1-6}$ alkyl, $C_{3-7}$ cycloalkyl, $C_{1-6}$ alkoxy, $C_{1-6}$ haloalkoxy, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino In some embodiments, $R^4$ is selected from H, halo, CN, $C_{1-6}$ alkyl, cyano-$C_{1-6}$ alkyl, and $C_{1-6}$ haloalkyl.

In some embodiments, $R^4$ is selected from $C_{1-6}$ alkyl, cyano-$C_{1-6}$ alkyl, and $C_{1-6}$ haloalkyl.

In some embodiments, $R^4$ is $C_{1-6}$ alkyl.

In some embodiments, $R^4$ is H.

In some embodiments, $R^4$ is methyl.

In some embodiments, $R^4$ is F.

In some embodiments, $R^4$ is Cl.

In some embodiments, $R^4$ is CN.

In some embodiments, $R^1$ is $C_{1-3}$ alkyl.

In some embodiments, $R^1$ is methyl.

In some embodiments, $R^1$ is ethyl.

In some embodiments, $R^1$ is methyl or ethyl

In some embodiments, $R^2$ is —($C_{1-6}$ alkyl), —O—($C_{1-6}$ alkyl), —O—($C_{1-4}$ alkylene)$_n$-$Cy^2$, or -$Cy^2$; wherein $C_{1-6}$ alkyl is optionally substituted by 1, 2, 3, or 4 independently selected $R^{2a}$ groups.

In some embodiments, $R^2$ is $C_{1-6}$ alkyl, —O—($C_{1-6}$ alkyl), —O—($C_{1-4}$ alkylene)$_n$-(4-7 membered heterocycloalkyl), or phenyl; wherein said phenyl is optionally substituted by 1, 2, 3, or 4 independently selected $R^{2a}$ groups.

In some embodiments, $R^2$ is methyl.

In some embodiments, $R^2$ is methoxy.

In some embodiments, $R^2$ is ethoxy.

In some embodiments, $R^2$ is methoxy or ethoxy.

In some embodiments, $R^2$ is $Cy^2$.

In some embodiments, $R^2$ is phenyl; wherein phenyl is optionally substituted by 1, 2, 3, or 4 groups independently selected from halo.

In some embodiments, each $R^{2a}$ is independently selected from OH, $NO_2$, CN, halo, $C_{1-6}$ alkyl, $C_{1-6}$ haloalkyl, $C_{1-6}$ alkoxy, $C_{1-6}$ haloalkoxy, amino, $C_{1-6}$ alkylamino, and di($C_{1-6}$ alkyl)amino.

In some embodiments, each $R^{2a}$ is independently halo.

In some embodiments, $R^4$ is H.

In some embodiments, $R^5$ is halo.

In some embodiments, $R^5$ is Cl.

In some embodiments, $R^5$ is Cl, F, methyl or CN.

In some embodiments, $R^3$ is CN, $NO_2$, $Cy^3$, C(O)NR$^c$R$^d$, NR$^f$C(O)OR$^b$, NR$^f$S(O)$_2$R$^b$, and NR$^c$C(O)R$^b$.

In some embodiments, $R^3$ is $Cy^3$.

In some embodiments, $Cy^3$ is selected from 4-7 membered heterocycloalkyl, phenyl, and 5-6 membered heteroaryl; each of which is optionally substituted with 1, 2, 3, or 4 independently selected $R^{3a}$ groups.

In some embodiments, $Cy^3$ is selected from phenyl, a piperidine ring, a 1,3-oxazolidin-2-one ring, an isoxazole ring, a pyrazole ring, a tetrazole ring, a triazole ring, a pyridine ring, and a pyrimidine ring; each of which is optionally substituted with 1, 2, 3, or 4 independently selected $R^{3a}$ groups.

In some embodiments, $Cy^3$ is selected from phenyl, a piperidine ring, a pyrrolidon-2-one ring, a 1,3-oxazolidin-2-one ring, an isoxazole ring, a pyrazole ring, a tetrazole ring, a triazole ring, a pyridine ring, a pyrimidine ring, an azetidine ring, a pyrrole ring, a tetrahydrofuran ring, and a morpholin-2-one ring; each of which is optionally substituted with 1, 2, 3, or 4 independently selected $R^{3a}$ groups;

In some embodiments, each $R^{3a}$ is independently selected from halo, CN, $NO_2$, $C_{1-6}$ alkyl, $C_{1-6}$ haloalkyl, $C_{3-7}$ cycloalkyl, 4-7 membered heterocycloalkyl, phenyl, 5-6 membered heteroaryl, (4-7 membered heterocycloalkyl)-$C_{1-4}$ alkyl, phenyl-$C_{1-4}$ alkyl, (5-6 membered heteroaryl)-$C_{1-4}$ alkyl, OR$^a$, C(O)R$^b$, C(O)NR$^c$R$^d$, C(O)OR$^a$, NR$^c$R$^d$, NR$^c$C(O)R$^b$, S(O)$_2$R$^b$, and S(O)$_2$NR$^c$R$^d$; wherein said $C_{1-6}$ alkyl, $C_{3-7}$ cycloalkyl, 4-7 membered heterocycloalkyl, phenyl, 5-6 membered heteroaryl, (4-7 membered heterocycloalkyl)-$C_{1-4}$ alkyl, phenyl-$C_{1-4}$ alkyl, and (5-6 membered heteroaryl)-$C_{1-4}$ alkyl are each optionally substituted by 1, 2, 3, or 4 groups independently selected from OH, CN, halo, $C_{1-6}$ alkyl, $C_{1-6}$ haloalkyl, cyano-$C_{1-6}$ alkyl, HO—$C_{1-6}$ alkyl, $C_{1-4}$ alkoxy-$C_{1-6}$ alkyl, $C_{1-6}$ alkoxy, $C_{1-6}$ haloalkoxy, amino, $C_{1-6}$ alkylamino, and di($C_{1-6}$ alkyl)amino.

In some embodiments, each $R^{3a}$ is independently selected from halo, CN, $NO_2$, $C_{1-6}$ alkyl, $C_{1-6}$ haloalkyl, $C_{3-7}$ cycloalkyl, 4-7 membered heterocycloalkyl, OR$^a$, C(O)R$^b$, C(O)NR$^c$R$^d$, NR$^c$R$^d$, NR$^c$C(O)R$^b$, and S(O)$_2$R$^b$; wherein said $C_{1-6}$ alkyl, $C_{3-7}$ cycloalkyl, and 4-7 membered heterocycloalkyl are each optionally substituted by 1, 2, 3, or 4 groups independently selected from OH, CN, halo, $C_{1-6}$ alkyl, $C_{1-6}$ haloalkyl, cyano-$C_{1-6}$ alkyl, HO—$C_{1-6}$ alkyl, $C_{1-4}$ alkoxy-$C_{1-6}$ alkyl, $C_{1-6}$ alkoxy, $C_{1-6}$ haloalkoxy, amino, $C_{1-6}$ alkylamino, and di($C_{1-6}$ alkyl)amino.

In some embodiments:
each $R^a$, $R^c$, and $R^d$ is independently selected from H, $C_{1-6}$ alkyl, $C_{3-7}$ cycloalkyl, 4-7 membered heterocycloalkyl; wherein said $C_{1-6}$ alkyl, $C_{3-7}$ cycloalkyl, and 4-7 membered heterocycloalkyl are each optionally substituted with 1, 2, 3, 4, or 5 substituents independently selected from OH, CN, halo, $C_{1-6}$ alkyl, $C_{1-6}$ haloalkyl, $C_{1-6}$ alkoxy, and $C_{1-6}$ haloalkoxy; and
each $R^b$ is independently selected from $C_{1-6}$ alkyl, $C_{3-7}$ cycloalkyl, and 4-7 membered heterocycloalkyl; each of which is optionally substituted with 1, 2, 3, 4, or 5 substituents independently selected from OH, CN, halo, $C_{1-6}$ alkyl, $C_{1-6}$ haloalkyl, $C_{1-6}$ alkoxy, and $C_{1-6}$ haloalkoxy.

In some embodiments:
each $R^{3a}$ is independently selected from halo, CN, $NO_2$, $C_{1-6}$ alkyl, $C_{1-6}$ haloalkyl, $C_{3-7}$ cycloalkyl, 4-7 membered heterocycloalkyl, (4-7 membered heterocycloalkyl)-$C_{1-3}$ alkyl, (5-6 membered heteroaryl)-$C_{1-3}$ alkyl, OR$^a$, C(O)R$^b$, C(O)OR$^a$, C(O)NR$^c$R$^d$, NR$^c$R$^d$, NR$^c$C(O)R$^b$, and S(O)$_2$R$^b$; wherein said $C_{1-6}$ alkyl, $C_{3-7}$ cycloalkyl, and 4-7 membered heterocycloalkyl are each optionally substituted by 1, 2, 3, or 4 groups independently selected from OH, CN, halo, $C_{1-6}$ alkyl, $C_{1-6}$ haloalkyl, cyano-$C_{1-6}$ alkyl, HO—$C_{1-6}$ alkyl, $C_{1-4}$ alkoxy-$C_{1-6}$ alkyl, $C_{1-6}$ alkoxy, $C_{1-6}$ haloalkoxy, amino, $C_{1-6}$ alkylamino, di($C_{1-6}$ alkyl)amino, and $C_{3-7}$ cycloalkyl;

each $R^a$, $R^c$, and $R^d$ is independently selected from H, $C_{1-6}$ alkyl, $C_{1-6}$ haloalkyl, $C_{3-7}$ cycloalkyl, 4-7 membered heterocycloalkyl; wherein said $C_{1-6}$ alkyl, $C_{3-7}$ cycloalkyl, and $C_{2-7}$ heterocycloalkyl are each optionally substituted with 1, 2, 3, 4, or 5 substituents independently selected from OH, CN, halo, $C_{1-6}$ alkyl, $C_{1-6}$ haloalkyl, $C_{1-6}$ alkoxy, $C_{1-6}$ haloalkoxy, and amino; and each $R^b$ is independently selected from $C_{1-6}$ alkyl, $C_{1-6}$ haloalkyl, $C_{3-7}$ cycloalkyl, 4-7 membered heterocycloalkyl; each of which is optionally substituted with 1, 2, 3, 4, or 5 substituents independently selected from OH, CN, halo, $C_{1-6}$ alkyl, $C_{1-6}$ haloalkyl, $C_{1-6}$ alkoxy, $C_{1-6}$ haloalkoxy, and amino.

In some embodiments:

$Cy^3$ is selected from phenyl, a piperidine ring, a pyrrolidon-2-one ring, a 1,3-oxazolidin-2-one ring, an isoxazole ring, a pyrazole ring, a tetrazole ring, a triazole ring, a pyridine ring, a pyrimidine ring, an azetidine ring, a pyrrole ring, a tetrahydrofuran ring, and a morpholin-2-one ring; each of which is optionally substituted with 1, 2, 3, or 4 independently selected $R^{3a}$ groups; each $R^a$, $R^c$, and $R^d$ is independently selected from H, $C_{1-6}$ alkyl, $C_{1-6}$ haloalkyl, $C_{3-7}$ cycloalkyl, 4-7 membered heterocycloalkyl; wherein said $C_{1-6}$ alkyl, $C_{3-7}$ cycloalkyl, and $C_{2-7}$ heterocycloalkyl are each optionally substituted with 1, 2, 3, 4, or 5 substituents independently selected from OH, CN, halo, $C_{1-6}$ alkyl, $C_{1-6}$ haloalkyl, $C_{1-6}$ alkoxy, $C_{1-6}$ haloalkoxy, and amino; and each $R^b$ is independently selected from $C_{1-6}$ alkyl, $C_{1-6}$ haloalkyl, $C_{3-7}$ cycloalkyl, 4-7 membered heterocycloalkyl; each of which is optionally substituted with 1, 2, 3, 4, or 5 substituents independently selected from OH, CN, halo, $C_{1-6}$ alkyl, $C_{1-6}$ haloalkyl, $C_{1-6}$ alkoxy, $C_{1-6}$ haloalkoxy, and amino.

In some embodiments:
Ar is

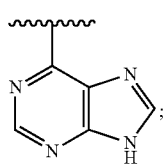

$R^1$ is $C_{1-6}$ alkyl;
$R^4$ is H;
$R^2$ is —($C_{1-6}$ alkyl), —O—($C_{1-6}$ alkyl), —O—($C_{1-4}$ alkylene)$_n$-$Cy^2$, or -$Cy^2$; wherein $C_{1-6}$ alkyl is optionally substituted by 1, 2, 3, or 4 independently selected $R^{2a}$ groups;

$Cy^2$ is selected from $C_{3-7}$ cycloalkyl, 4-7 membered heterocycloalkyl, phenyl, and 5-6 membered heteroaryl; each of which is optionally substituted with 1, 2, 3, or 4 independently selected $R^{2a}$ groups;

$R^3$ is CN, NO$_2$, Cy$^3$, C(O)NR$^c$R$^d$, NR$^c$C(O)OR$^b$, NR$^c$S(O)$_2$R$^b$, and NR$^c$C(O)R$^b$;

$Cy^3$ is selected from $C_{3-7}$ cycloalkyl, 4-7 membered heterocycloalkyl, phenyl, and 5-6 membered heteroaryl; each of which is optionally substituted with 1, 2, 3, or 4 independently selected $R^{3a}$ groups;

$R^4$ is selected from H, $C_{1-6}$ alkyl, cyano-$C_{1-6}$ alkyl, and $C_{1-6}$ haloalkyl; and $R^5$ is halo.

In some embodiments:
Ar is

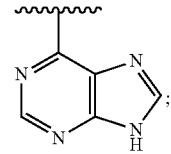

$R^1$ is $C_{1-6}$ alkyl;
$R^4$ is H;
$R^2$ is —($C_{1-6}$ alkyl), —O—($C_{1-6}$ alkyl), —O—($C_{1-4}$ alkylene)$_n$-$Cy^2$, or -$Cy^2$; wherein $C_{1-6}$ alkyl is optionally substituted by 1, 2, 3, or 4 independently selected $R^{2a}$ groups;

$Cy^2$ is selected from $C_{3-7}$ cycloalkyl, 4-7 membered heterocycloalkyl, phenyl, and 5-6 membered heteroaryl; each of which is optionally substituted with 1, 2, 3, or 4 independently selected $R^{2a}$ groups;

$R^3$ is CN, NO$_2$, Cy$^3$, C(O)NR$^c$R$^d$, NR$^c$C(O)OR$^b$, NR$^c$S(O)$_2$R$^b$, and NR$^c$C(O)R$^b$;

$Cy^3$ is selected from $C_{3-7}$ cycloalkyl, 4-7 membered heterocycloalkyl, phenyl, and 5-6 membered heteroaryl; each of which is optionally substituted with 1, 2, 3, or 4 independently selected $R^{3a}$ groups;

$R^4$ is selected from H, $C_{1-6}$ alkyl, cyano-$C_{1-6}$ alkyl, and $C_{1-6}$ haloalkyl; and $R^5$ is halo;

each $R^{2a}$ is independently selected from OH, NO$_2$, CN, halo, $C_{1-6}$ alkyl, $C_{1-6}$ haloalkyl, $C_{1-6}$ alkoxy, $C_{1-6}$ haloalkoxy, amino, $C_{1-6}$ alkylamino, and di($C_{1-6}$ alkyl)amino;

each $R^{3a}$ is independently selected from halo, CN, NO$_2$, $C_{1-6}$ alkyl, $C_{1-6}$ haloalkyl, $C_{3-7}$ cycloalkyl, 4-7 membered heterocycloalkyl, OR$^a$, C(O)R$^b$, C(O)NR$^c$R$^d$, NR$^c$R$^d$, NR$^c$C(O)R$^b$, and S(O)$_2$R$^b$; wherein said $C_{1-6}$ alkyl, $C_{3-7}$ cycloalkyl, and 4-7 membered heterocycloalkyl are each optionally substituted by 1, 2, 3, or 4 groups independently selected from OH, CN, halo, $C_{1-6}$ alkyl, $C_{1-6}$ haloalkyl, cyano-$C_{1-6}$ alkyl, HO—$C_{1-6}$ alkyl, $C_{1-4}$ alkoxy-$C_{1-6}$ alkyl, $C_{1-6}$ alkoxy, $C_{1-6}$ haloalkoxy, amino, $C_{1-6}$ alkylamino, and di($C_{1-6}$ alkyl)amino;

each $R^a$, $R^c$, and $R^d$ is independently selected from H, $C_{1-6}$ alkyl, $C_{1-6}$ haloalkyl, $C_{3-7}$ cycloalkyl, 4-7 membered heterocycloalkyl; wherein said $C_{1-6}$ alkyl, $C_{3-7}$ cycloalkyl, and $C_{2-7}$ heterocycloalkyl are each optionally substituted with 1, 2, 3, 4, or 5 substituents independently selected from OH, CN, halo, $C_{1-6}$ alkyl, $C_{1-6}$ haloalkyl, $C_{1-6}$ alkoxy, and $C_{1-6}$ haloalkoxy; and each $R^b$ is independently selected from $C_{1-6}$ alkyl, $C_{1-6}$ haloalkyl, $C_{3-7}$ cycloalkyl, 4-7 membered heterocycloalkyl; each of which is optionally substituted with 1, 2, 3, 4, or 5 substituents independently selected from OH, CN, halo, $C_{1-6}$ alkyl, $C_{1-6}$ haloalkyl, $C_{1-6}$ alkoxy, and $C_{1-6}$ haloalkoxy.

In some embodiments:
Ar is

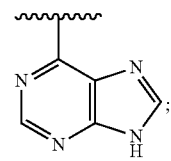 [SMILES: *c1ncnc2[nH]cnc12]

$R^1$ is $C_{1-6}$ alkyl;
$R^4$ is H;

$R^2$ is $C_{1-6}$ alkyl, —O—($C_{1-6}$ alkyl), —O—($C_{1-4}$ alkylene)$_n$-(4-7 membered heterocycloalkyl), or phenyl; wherein said phenyl is optionally substituted by 1, 2, 3, or 4 independently selected $R^{2a}$ groups;

$Cy^2$ is selected from $C_{3-7}$ cycloalkyl, 4-7 membered heterocycloalkyl, phenyl, and 5-6 membered heteroaryl; each of which is optionally substituted with 1, 2, 3, or 4 independently selected $R^{2a}$ groups;

$R^3$ is CN, $NO_2$, $Cy^3$, $C(O)NR^cR^d$, $NR^fC(O)OR^b$, $NR^fS(O)_2R^b$, and $NR^cC(O)R^b$;

$Cy^3$ is selected from $C_{3-7}$ cycloalkyl, 4-7 membered heterocycloalkyl, phenyl, and 5-6 membered heteroaryl; each of which is optionally substituted with 1, 2, 3, or 4 independently selected $R^{3a}$ groups;

$R^4$ is selected from $C_{1-6}$ alkyl, cyano-$C_{1-6}$ alkyl, and $C_{1-6}$ haloalkyl; and $R^5$ is halo;

each $R^{2a}$ is independently selected from OH, $NO_2$, CN, halo, $C_{1-6}$ alkyl, $C_{1-6}$ haloalkyl, $C_{1-6}$ alkoxy, $C_{1-6}$ haloalkoxy, amino, $C_{1-6}$ alkylamino, and di($C_{1-6}$ alkyl)amino;

each $R^{3a}$ is independently selected from halo, CN, $NO_2$, $C_{1-6}$ alkyl, $C_{1-6}$ haloalkyl, $C_{3-7}$ cycloalkyl, 4-7 membered heterocycloalkyl, $OR^a$, $C(O)R^b$, $C(O)NR^cR^d$, $NR^cR^d$, $NR^cC(O)R^b$, and $S(O)_2R^b$; wherein said $C_{1-6}$ alkyl, $C_{3-7}$ cycloalkyl, and 4-7 membered heterocycloalkyl are each optionally substituted by 1, 2, 3, or 4 groups independently selected from OH, CN, halo, $C_{1-6}$ alkyl, $C_{1-6}$ haloalkyl, cyano-$C_{1-6}$ alkyl, HO—$C_{1-6}$ alkyl, $C_{1-4}$ alkoxy-$C_{1-6}$ alkyl, $C_{1-6}$ alkoxy, $C_{1-6}$ haloalkoxy, amino, $C_{1-6}$ alkylamino, and di($C_{1-6}$ alkyl)amino;

each $R^a$, $R^c$, and $R^d$ is independently selected from H, $C_{1-6}$ alkyl, $C_{1-6}$ haloalkyl, $C_{3-7}$ cycloalkyl, 4-7 membered heterocycloalkyl; wherein said $C_{1-6}$ alkyl, $C_{3-7}$ cycloalkyl, and $C_{2-7}$ heterocycloalkyl are each optionally substituted with 1, 2, 3, 4, or 5 substituents independently selected from OH, CN, halo, $C_{1-6}$ alkyl, $C_{1-6}$ haloalkyl, $C_{1-6}$ alkoxy, and $C_{1-6}$ haloalkoxy; and each $R^b$ is independently selected from $C_{1-6}$ alkyl, $C_{1-6}$ haloalkyl, $C_{3-7}$ cycloalkyl, 4-7 membered heterocycloalkyl; each of which is optionally substituted with 1, 2, 3, 4, or 5 substituents independently selected from OH, CN, halo, $C_{1-6}$ alkyl, $C_{1-6}$ haloalkyl, $C_{1-6}$ alkoxy, and $C_{1-6}$ haloalkoxy.

In some embodiments:

Ar is

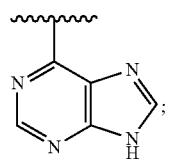 [SMILES: *c1ncnc2[nH]cnc12]

$R^1$ is methyl or ethyl;

$R^4$ is H;

$R^2$ is selected from $C_{1-6}$ alkyl, —O—($C_{1-6}$ alkyl), —O—($C_{1-4}$ alkylene)$_n$-(4-7 membered heterocycloalkyl), and phenyl; wherein said phenyl is optionally substituted by 1, 2, 3, or 4 independently selected halo groups;

$R^3$ is selected from CN, $NO_2$, $Cy^3$, $C(O)NR^cR^d$, $NR^fC(O)OR^b$, $NR^fS(O)_2R^b$, and $NR^cC(O)R^b$;

$Cy^3$ is selected from phenyl, a piperidine ring, a pyrrolidon-2-one ring, a 1,3-oxazolidin-2-one ring, an isoxazole ring, a pyrazole ring, a tetrazole ring, a triazole ring, a pyridine ring, a pyrimidine ring, an azetidine ring, a pyrrole ring, a tetrahydrofuran ring, and a morpholin-2-one ring; each of which is optionally substituted with 1, 2, 3, or 4 independently selected $R^{3a}$ groups;

$R^4$ is selected from H, halo, $C_1$-3 alkyl, CN, cyano-$C_{1-6}$ alkyl, and $C_{1-6}$ haloalkyl;

$R^5$ is selected from $C_1$-3 alkyl, halo, and CN;

each $R^{3a}$ is independently selected from halo, CN, $NO_2$, $C_{1-6}$ alkyl, $C_{1-6}$ haloalkyl, $C_{3-7}$ cycloalkyl, 4-7 membered heterocycloalkyl, (4-7 membered heterocycloalkyl)-$C_{1-3}$ alkyl, (5-6 membered heteroaryl)-$C_1$-3 alkyl, $OR^a$, $C(O)R^b$, $C(O)OR^a$, $C(O)NR^cR^d$, $NR^cR^d$, $NR^cC(O)R^b$, and $S(O)_2R^b$; wherein said $C_{1-6}$ alkyl, $C_{3-7}$ cycloalkyl, and 4-7 membered heterocycloalkyl are each optionally substituted by 1, 2, 3, or 4 groups independently selected from OH, CN, halo, $C_{1-6}$ alkyl, $C_{1-6}$ haloalkyl, cyano-$C_{1-6}$ alkyl, HO—$C_{1-6}$ alkyl, $C_{1-4}$ alkoxy-$C_{1-6}$ alkyl, $C_{1-6}$ alkoxy, $C_{1-6}$ haloalkoxy, amino, $C_{1-6}$ alkylamino, di($C_{1-6}$ alkyl)amino, and $C_{3-7}$ cycloalkyl;

each $R^a$, $R^c$, and $R^d$ is independently selected from H, $C_{1-6}$ alkyl, $C_{1-6}$ haloalkyl, $C_{3-7}$ cycloalkyl, 4-7 membered heterocycloalkyl; wherein said $C_{1-6}$ alkyl, $C_{3-7}$ cycloalkyl, and $C_{2-7}$ heterocycloalkyl are each optionally substituted with 1, 2, 3, 4, or 5 substituents independently selected from OH, CN, halo, $C_{1-6}$ alkyl, $C_{1-6}$ haloalkyl, $C_{1-6}$ alkoxy, $C_{1-6}$ haloalkoxy, and amino;

each $R^b$ is independently selected from $C_{1-6}$ alkyl, $C_{1-6}$ haloalkyl, $C_{3-7}$ cycloalkyl, 4-7 membered heterocycloalkyl; each of which is optionally substituted with 1, 2, 3, 4, or 5 substituents independently selected from OH, CN, halo, $C_{1-6}$ alkyl, $C_{1-6}$ haloalkyl, $C_{1-6}$ alkoxy, $C_{1-6}$ haloalkoxy, and amino; and each $R^f$ is independently selected from $C_{1-4}$ alkylcarbonyl and $C_{1-4}$ alkoxycarbonyl.

In some embodiments, the compound is a compound of Formula II:

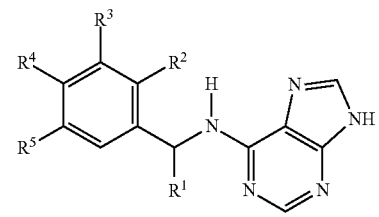

or a pharmaceutically acceptable salt thereof.

In some embodiments, the compound is a compound of Formula IIa:

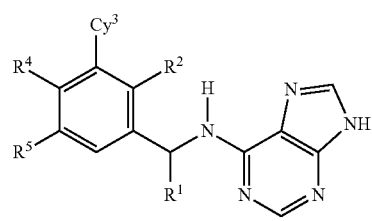

or a pharmaceutically acceptable salt thereof.

In some embodiments, the compound is a compound of Formula III or IV:

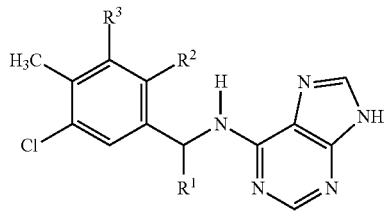

III

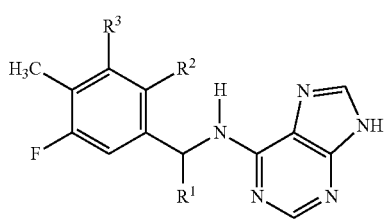

IV or a pharmaceutically acceptable salt thereof.

In some embodiments, the compound is a compound of Formula V or VI:

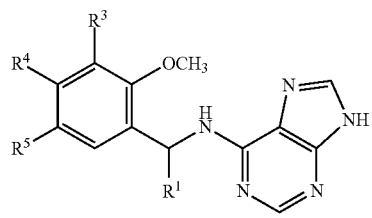

V

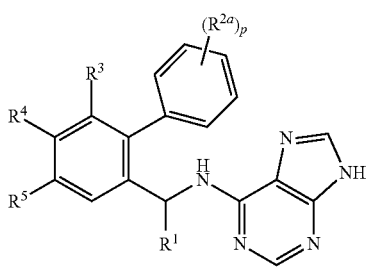

VI or a pharmaceutically acceptable salt thereof.

In some embodiments, the compound is a compound of Formula VII or VIII:

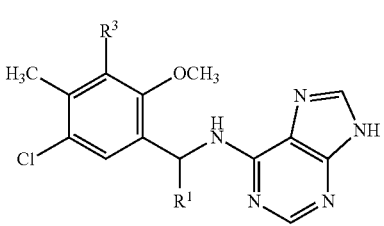

VII

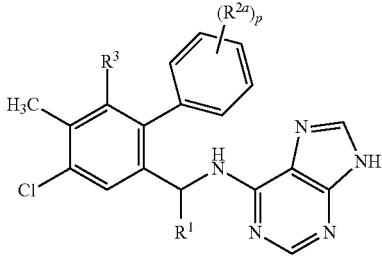

VIII or a pharmaceutically acceptable salt thereof.

In some embodiments, the compound is a compound of Formula III or IV:

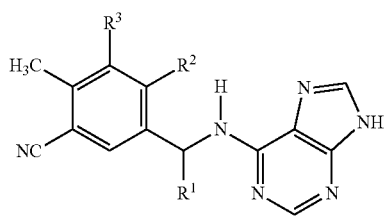

IIIa

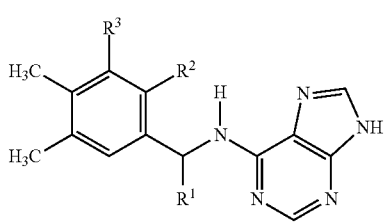

IVa or a pharmaceutically acceptable salt thereof.

In some embodiments, the compound is a compound of Formula IXa, Formula IXb, Formula IXc, Formula IXd, Formula IXe, or Formula IXf:

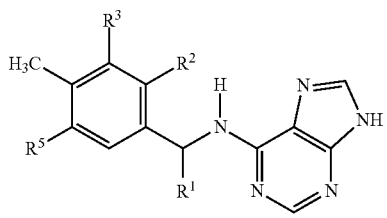

IXa

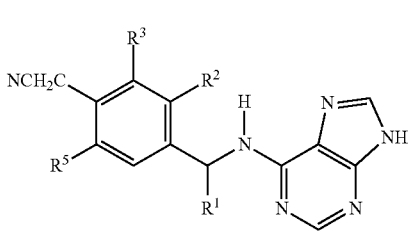

IXb

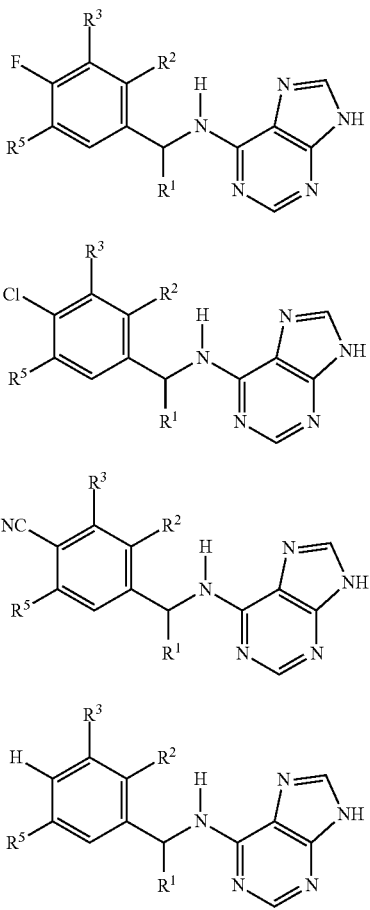

or a pharmaceutically acceptable salt thereof.

In some embodiments, the compound is selected from:
4-Chloro-3'-fluoro-3-methyl-6-[1-(9H-purin-6-ylamino)ethyl]biphenyl-2-carbonitrile;
4-Chloro-3'-fluoro-3-methyl-6-[1-(9H-purin-6-ylamino)ethyl]biphenyl-2-carboxamide;
N-[1-(4-chloro-3'-fluoro-5-methyl-6-nitrobiphenyl-2-yl)ethyl]-9H-purin-6-amine;
4-Chloro-3-(cyanomethyl)-3'-fluoro-6-[1-(9H-purin-6-ylamino)ethyl]biphenyl-2-carbonitrile;
1-{4-Chloro-3'-fluoro-3-methyl-6-[1-(9H-purin-6-ylamino)ethyl]biphenyl-2-yl}pyrrolidin-2-one;
1-{4-Chloro-3',5'-difluoro-3-methyl-6-[1-(9H-purin-6-ylamino)ethyl]biphenyl-2-yl}pyrrolidin-2-one;
3-{4-Chloro-3'-fluoro-3-methyl-6-[1-(9H-purin-6-ylamino)ethyl]biphenyl-2-yl}-1,3-oxazolidin-2-one;
N-{1-[4-chloro-3'-fluoro-5-methyl-6-(1H-tetrazol-5-yl)biphenyl-2-yl]ethyl}-9H-purin-6-amine;
N-{4-chloro-3'-fluoro-3-methyl-6-[1-(9H-purin-6-ylamino)ethyl]biphenyl-2-yl}acetamide;
Dimethyl {4-chloro-3'-fluoro-3-methyl-6-[1-(9H-purin-6-ylamino)ethyl]biphenyl-2-yl}imidodicarbonate;
N-{1-[4-chloro-3'-fluoro-5-methyl-6-(4H-1,2,4-triazol-4-yl)biphenyl-2-yl]ethyl}-9H-purin-6-amine;
N-{4-chloro-3'-fluoro-3-methyl-6-[1-(9H-purin-6-ylamino)ethyl]biphenyl-2-yl}-N-(methylsulfonyl)methanesulfonamide;
N-{1-[4-chloro-6-(2,6-difluoropyridin-4-yl)-5-methylbiphenyl-2-yl]ethyl}-9H-purin-6-amine;
1-{3-Chloro-6-methoxy-2-methyl-5-[1-(9H-purin-6-ylamino)ethyl]phenyl}pyrrolidin-2-one;
4-Chloro-3',5'-difluoro-3-methyl-6-[1-(9H-purin-6-ylamino)ethyl]biphenyl-2-carboxamide;
N-(1-{5-chloro-3-[2-(dimethylamino)pyrimidin-5-yl]-2-methoxy-4-methylphenyl}ethyl)-9H-purin-6-amine;
1-{3-Chloro-6-methoxy-2-methyl-5-[1-(9H-purin-6-ylamino)ethyl]phenyl}piperidin-4-ol;
3'-Chloro-4-fluoro-6'-methoxy-2'-methyl-5'-[1-(9H-purin-6-ylamino)ethyl]biphenyl-3-carboxamide;
3'-Chloro-3-fluoro-6'-methoxy-2'-methyl-5'-[1-(9H-purin-6-ylamino)ethyl]biphenyl-4-carboxamide;
1-({3'-Chloro-3-fluoro-6'-methoxy-2'-methyl-5'-[1-(9H-purin-6-ylamino)ethyl]biphenyl-4-yl}carbonyl)azetidine-3-carbonitrile;
N-{1-[4-chloro-6-(3,5-dimethylisoxazol-4-yl)-3'-fluoro-5-methylbiphenyl-2-yl]ethyl}-9H-purin-6-amine;
N-{1-[4-Chloro-3'-fluoro-5-methyl-6-(1H-pyrazol-4-yl)biphenyl-2-yl]ethyl}-9H-purin-6-amine;
N-[1-(4-Chloro-3',5'-difluoro-5-methyl-6-pyridin-4-ylbiphenyl-2-yl)ethyl]-9H-purin-6-amine;
N-{1-[4-Chloro-3',5'-difluoro-5-methyl-6-(1H-pyrazol-4-yl)biphenyl-2-yl]ethyl}-9H-purin-6-amine;
N-{1-[5-Chloro-3-(5-fluoropyridin-3-yl)-2-methoxy-4-methylphenyl]ethyl}-9H-purin-6-amine;
N-{1-[5-Chloro-2-methoxy-3-(5-methoxypyridin-3-yl)-4-methylphenyl]ethyl}-9H-purin-6-amine;
(4-{3-Chloro-6-methoxy-2-methyl-5-[1-(9H-purin-6-ylamino)ethyl]phenyl}-1H-pyrazol-1-yl)acetonitrile;
N-{1-[5-chloro-2-methoxy-4-methyl-3-(1-methyl-1H-pyrazol-5-yl)phenyl]ethyl}-9H-purin-6-amine;
N-{1-[5-chloro-3-(3,5-dimethylisoxazol-4-yl)-2-methoxy-4-methylphenyl]ethyl}-9H-purin-6-amine;
N-{1-[5-chloro-2-methoxy-3-(2-methoxypyrimidin-5-yl)-4-methylphenyl]ethyl}-9H-purin-6-amine;
N-{3'-chloro-6'-methoxy-2'-methyl-5'-[1-(9H-purin-6-ylamino)ethyl]biphenyl-4-yl}acetamide;
N-[1-(5-chloro-3'-fluoro-2-methoxy-6-methylbiphenyl-3-yl)ethyl]-9H-purin-6-amine;
N-[1-(5-chloro-3',5'-difluoro-2-methoxy-6-methylbiphenyl-3-yl)ethyl]-9H-purin-6-amine;
3'-chloro-6'-methoxy-2'-methyl-5'-[1-(9H-purin-6-ylamino)ethyl]biphenyl-4-carbonitrile;
3'-chloro-N-cyclopropyl-6'-methoxy-2'-methyl-5'-[1-(9H-purin-6-ylamino)ethyl]biphenyl-4-carboxamide;
N-{1-[5-chloro-2-methoxy-6-methyl-4'-(methylsulfonyl)biphenyl-3-yl]ethyl}-9H-purin-6-amine;
N-{1-[3-(2-aminopyrimidin-5-yl)-5-chloro-2-methoxy-4-methylphenyl]ethyl}-9H-purin-6-amine;
N-{1-[5-chloro-2-methoxy-3-(5-methoxypyridin-3-yl)-4-methylphenyl]ethyl}-9H-purin-6-amine;
N-[1-(3',5-dichloro-2-methoxy-6-methylbiphenyl-3-yl)ethyl]-9H-purin-6-amine;
N-{1-[5-chloro-3-(5-chloropyridin-3-yl)-2-methoxy-4-methylphenyl]ethyl}-9H-purin-6-amine;
3,3'-dichloro-6'-methoxy-N,2'-dimethyl-5'-[1-(9H-purin-6-ylamino)ethyl]biphenyl-4-carboxamide;
N-{1-[5-chloro-2-methoxy-6-methyl-4'-(trifluoromethyl)biphenyl-3-yl]ethyl}-9H-purin-6-amine;
N-[1-(5-chloro-4'-ethoxy-3'-fluoro-2-methoxy-6-methylbiphenyl-3-yl)ethyl]-9H-purin-6-amine;
3'-chloro-6'-methoxy-2'-methyl-5'-[1-(9H-purin-6-ylamino)ethyl]biphenyl-3-carbonitrile;
{3'-chloro-6'-methoxy-2'-methyl-5'-[1-(9H-purin-6-ylamino)ethyl]biphenyl-4-yl}acetonitrile;
N-{1-[5-chloro-2-methoxy-4'-(methoxymethyl)-6-methylbiphenyl-3-yl]ethyl}-9H-purin-6-amine;

N-{1-[5-chloro-2-methoxy-6-methyl-4'-(1H-pyrazol-1-yl)
biphenyl-3-yl]ethyl}-9H-purin-6-amine;
N-{1-[5-chloro-2-methoxy-3'-(methoxymethyl)-6-methyl-
biphenyl-3-yl]ethyl}-9H-purin-6-amine;
N-(1-{5-chloro-2-methoxy-4-methyl-3-[6-(tetrahydro-2H-
pyran-4-yloxy)pyridin-3-yl]phenyl}ethyl)-9H-purin-6-
amine;
{3'-chloro-6'-methoxy-2'-methyl-5'-[1-(9H-purin-6-
ylamino)ethyl]biphenyl-3-yl}acetonitrile;
N-[1-(3',5,5'-trichloro-2-methoxy-6-methylbiphenyl-3-yl)
ethyl]-9H-purin-6-amine;
N-{1-[5-chloro-2-methoxy-4-methyl-3-(6-morpholin-4-
ylpyridin-3-yl)phenyl]ethyl}-9H-purin-6-amine;
N-{1-[5-chloro-3-(3-fluoro-2-morpholin-4-ylpyridin-4-yl)-
2-methoxy-4-methylphenyl]ethyl}-9H-purin-6-amine;
N-[1-(5-chloro-2',5'-difluoro-2-methoxy-6-methylbiphenyl-
3-yl)ethyl]-9H-purin-6-amine;
N-{1-[5-chloro-3-(6-fluoropyridin-3-yl)-2-methoxy-4-
methylphenyl]ethyl}-9H-purin-6-amine;
N-{1-[5-chloro-2-methoxy-3-(6-methoxypyridin-3-yl)-4-
methylphenyl]ethyl}-9H-purin-6-amine;
5-{3-chloro-6-methoxy-2-methyl-5-[1-(9H-purin-6-
ylamino)ethyl]phenyl}nicotinonitrile;
3-(4-{3-chloro-6-methoxy-2-methyl-5-[1-(9H-purin-6-
ylamino)ethyl]phenyl}-1H-pyrazol-1-yl)-3-(cyanom-
ethyl)cyclobutanecarbonitrile;
N-{1-[5-chloro-2-methoxy-4-methyl-3-(5-methylpyridin-3-
yl)phenyl]ethyl}-9H-purin-6-amine;
N-(1-{5-chloro-2-methoxy-4-methyl-3-[5-(methylsulfonyl)
pyridin-3-yl]phenyl}ethyl)-9H-purin-6-amine;
N-{1-[3-(6-aminopyridin-3-yl)-5-chloro-2-methoxy-4-
methylphenyl]ethyl}-9H-purin-6-amine;
5-{3-chloro-6-methoxy-2-methyl-5-[1-(9H-purin-6-
ylamino)ethyl]phenyl}pyridine-2-carbonitrile;
N-{1-[5-chloro-3-(6-isopropoxypyridin-3-yl)-2-methoxy-4-
methylphenyl]ethyl}-9H-purin-6-amine;
3'-chloro-N-ethyl-3-fluoro-6'-methoxy-2'-methyl-5'-[1-(9H-
purin-6-ylamino)ethyl]biphenyl-4-carboxamide;
3'-chloro-3-fluoro-6'-methoxy-N,N,2'-trimethyl-5'-[1-(9H-
purin-6-ylamino)ethyl]biphenyl-4-carboxamide;
N-{1-[5-chloro-3'-fluoro-2-methoxy-6-methyl-4'-(pyrroli-
din-1-ylcarbonyl)biphenyl-3-yl]ethyl}-9H-purin-6-
amine;
N-{1-[5-chloro-3'-fluoro-2-methoxy-6-methyl-4'-(morpho-
lin-4-ylcarbonyl)biphenyl-3-yl]ethyl}-9H-purin-6-amine;
3'-chloro-3-fluoro-6'-methoxy-N,2'-dimethyl-5'-[1-(9H-pu-
rin-6-ylamino)ethyl]biphenyl-4-carboxamide;
1-({3'-chloro-3-fluoro-6'-methoxy-2'-methyl-5'-[1-(9H-pu-
rin-6-ylamino)ethyl]biphenyl-4-yl}carbonyl)piperidin-4-
ol;
3'-chloro-N-cyclobutyl-3-fluoro-6'-methoxy-2'-methyl-5'-
[1-(9H-purin-6-ylamino)ethyl]biphenyl-4-carboxamide;
N-{1-[5-chloro-3-(2-fluoropyridin-4-yl)-2-methoxy-4-
methylphenyl]ethyl}-9H-purin-6-amine;
N-[1-(3',5-dichloro-5'-fluoro-2-methoxy-6-methylbiphenyl-
3-yl)ethyl]-9H-purin-6-amine;
N-{1-[5-chloro-2'-fluoro-2-methoxy-6-methyl-5'-(trifluo-
romethyl)biphenyl-3-yl]ethyl}-9H-purin-6-amine;
N-{1-[5-chloro-3-(6-fluoro-5-methylpyridin-3-yl)-2-
methoxy-4-methylphenyl]ethyl}-9H-purin-6-amine;
N-[1-(5-chloro-2-methoxy-6-methyl-4'-morpholin-4-ylbi-
phenyl-3-yl)ethyl]-9H-purin-6-amine;
N-[1-(3',5-dichloro-4'-fluoro-2-methoxy-6-methylbiphenyl-
3-yl)ethyl]-9H-purin-6-amine;
N-{1-[5-chloro-2-methoxy-6-methyl-4'-(trifluoromethoxy)
biphenyl-3-yl]ethyl}-9H-purin-6-amine;
N-[1-(5-chloro-3'-ethoxy-2-methoxy-6-methylbiphenyl-3-
yl)ethyl]-9H-purin-6-amine;
N-[1-(4',5-dichloro-3'-fluoro-2-methoxy-6-methylbiphenyl-
3-yl)ethyl]-9H-purin-6-amine;
N-{1-[5-chloro-4'-fluoro-2-methoxy-6-methyl-3'-(trifluo-
romethyl)biphenyl-3-yl]ethyl}-9H-purin-6-amine;
3'-chloro-4-fluoro-6'-methoxy-N,N,2'-trimethyl-5'-[1-(9H-
purin-6-ylamino)ethyl]biphenyl-3-carboxamide;
N-[1-(5-chloro-4'-fluoro-2,3'-dimethoxy-6-methylbiphenyl-
3-yl)ethyl]-9H-purin-6-amine;
N-[1-(5-chloro-2,3',4'-trimethoxy-6-methylbiphenyl-3-yl)
ethyl]-9H-purin-6-amine;
N-[1-(3',5-dichloro-2,4'-dimethoxy-6-methylbiphenyl-3-yl)
ethyl]-9H-purin-6-amine;
N-{1-[5-chloro-3-(2-chloropyridin-4-yl)-2-methoxy-4-
methylphenyl]ethyl}-9H-purin-6-amine;
N-[1-(4',5-dichloro-2-methoxy-6-methylbiphenyl-3-yl)
ethyl]-9H-purin-6-amine;
N-{1-[5-chloro-3'-(dimethylamino)-2-methoxy-6-methylbi-
phenyl-3-yl]ethyl}-9H-purin-6-amine;
N-[1-(5-chloro-2,4'-dimethoxy-6-methylbiphenyl-3-yl)
ethyl]-9H-purin-6-amine;
N-[1-(5-chloro-2,4'-dimethoxy-3',6-dimethylbiphenyl-3-yl)
ethyl]-9H-purin-6-amine;
N-[1-(5-chloro-2,3'-dimethoxy-6-methylbiphenyl-3-yl)
ethyl]-9H-purin-6-amine;
N-{3'-chloro-6'-methoxy-2'-methyl-5'-[1-(9H-purin-6-
ylamino)ethyl]biphenyl-3-yl}acetamide;
N-[1-(5-chloro-3',4'-difluoro-2-methoxy-6-methylbiphenyl-
3-yl)ethyl]-9H-purin-6-amine;
N-{1-[5-chloro-3-(5-fluoro-6-methoxypyridin-3-yl)-2-
methoxy-4-methylphenyl]ethyl}-9H-purin-6-amine;
3'-chloro-5-fluoro-6'-methoxy-2'-methyl-5'-[1-(9H-purin-6-
ylamino)ethyl]biphenyl-3-carboxamide;
N-(1-{5-chloro-2-methoxy-4-methyl-3-[5-(morpholin-4-yl-
carbonyl)pyridin-3-yl]phenyl}ethyl)-9H-purin-6-amine;
N-(5-{3-chloro-6-methoxy-2-methyl-5-[1-(9H-purin-6-
ylamino)ethyl]phenyl}pyridin-2-yl)acetamide;
5-{3-chloro-6-methoxy-2-methyl-5-[1-(9H-purin-6-
ylamino)ethyl]phenyl}nicotinonitrile;
N-{1-[3-(2-aminopyrimidin-5-yl)-5-chloro-2-methoxy-4-
methylphenyl]ethyl}-9H-purin-6-amine;
N-{1-[5-chloro-2-methoxy-6-methyl-4'-(methylsulfonyl)bi-
phenyl-3-yl]ethyl}-9H-purin-6-amine;
N-{1-[5'-chloro-6'-methyl-4-(methylsulfonyl)-1,1':2',1"-ter-
phenyl-3'-yl]ethyl}-9H-purin-6-amine;
N-(1-{4-chloro-6-[2-(dimethylamino)pyrimidin-5-yl]-5-
methylbiphenyl-2-yl}ethyl)-9H-purin-6-amine;
5'-chloro-N-cyclopropyl-6'-methyl-3'-[1-(9H-purin-6-
ylamino)ethyl]-1,1':2',1"-terphenyl-4-carboxamide;
N-{1-[6-(2-aminopyrimidin-5-yl)-4-chloro-5-methylbiphe-
nyl-2-yl]ethyl}-9H-purin-6-amine;
5'-chloro-6'-methyl-3'-[1-(9H-purin-6-ylamino)ethyl]-1,1':
2',1"-terphenyl-4-carbonitrile;
N-{1-[4-chloro-6-(2-methoxypyrimidin-5-yl)-5-methylbi-
phenyl-2-yl]ethyl}-9H-purin-6-amine;
N-{5'-chloro-6'-methyl-3'-[1-(9H-purin-6-ylamino)ethyl]-1,
1':2',1"-terphenyl-4-yl}acetamide;
N-{1-[4-chloro-3'-fluoro-5-methyl-6-(1-methyl-1H-pyra-
zol-4-yl)biphenyl-2-yl]ethyl}-9H-purin-6-amine;
N-{1-[4-chloro-3'-fluoro-5-methyl-6-(1-methyl-1H-pyra-
zol-5-yl)biphenyl-2-yl]ethyl}-9H-purin-6-amine;
N-{1-[4-chloro-3'-fluoro-5-methyl-6-(1,3,5-trimethyl-1H-
pyrazol-4-yl)biphenyl-2-yl]ethyl}-9H-purin-6-amine;
N-{1-[4-chloro-6-(3,5-dimethylisoxazol-4-yl)-3',5'-dif-
luoro-5-methylbiphenyl-2-yl]ethyl}-9H-purin-6-amine;

N-[1-(4-chloro-3',5'-difluoro-5-methyl-6-pyridin-3-ylbiphenyl-2-yl)ethyl]-9H-purin-6-amine;
5'-chloro-3'',5''-difluoro-6'-methyl-3'-[1-(9H-purin-6-ylamino)ethyl]-1,1':2',1''-terphenyl-4-carbonitrile;
N-{1-[4-chloro-6-(2,6-difluoropyridin-4-yl)-3',5'-difluoro-5-methylbiphenyl-2-yl]ethyl}-9H-purin-6-amine;
N-[1-(4-chloro-3',5'-difluoro-5-methyl-6-pyrimidin-5-ylbiphenyl-2-yl)ethyl]-9H-purin-6-amine;
N-{1-[4-chloro-3',5'-difluoro-6-(2-methoxypyrimidin-5-yl)-5-methylbiphenyl-2-yl]ethyl}-9H-purin-6-amine;
N-{5'-chloro-3'',5''-difluoro-6'-methyl-3'-[1-(9H-purin-6-ylamino)ethyl]-1,1':2',1''-terphenyl-4-yl}acetamide;
N-{1-[4-chloro-6-(3,5-dimethyl-1H-pyrazol-4-yl)-3',5'-difluoro-5-methylbiphenyl-2-yl]ethyl}-9H-purin-6-amine;
N-{1-[5-fluoro-2-methoxy-6-methyl-4'-(methylsulfonyl)biphenyl-3-yl]ethyl}-9H-purin-6-amine;
N-[1-(3'-ethoxy-5-fluoro-2-methoxy-6-methylbiphenyl-3-yl)ethyl]-9H-purin-6-amine;
N-cyclopropyl-3'-fluoro-6'-methoxy-2'-methyl-5'-[1-(9H-purin-6-ylamino)ethyl]biphenyl-4-carboxamide;
N-{1-[5-fluoro-2-methoxy-4-methyl-3-(1-methyl-1H-pyrazol-4-yl)phenyl]ethyl}-9H-purin-6-amine;
N-{1-[5-fluoro-2-methoxy-4-methyl-3-(1-methyl-1H-pyrazol-5-yl)phenyl]ethyl}-9H-purin-6-amine;
N-{1-[3-(2-aminopyrimidin-5-yl)-5-fluoro-2-methoxy-4-methylphenyl]ethyl}-9H-purin-6-amine;
N-{1-[4-Chloro-3',5'-difluoro-6-(1H-pyrazol-4-yl)biphenyl-2-yl]ethyl}-9H-purin-6-amine;
N-{1-[5-Chloro-3-(5-chloropyridin-3-yl)-2-methoxyphenyl]ethyl}-9H-purin-6-amine;
N-{1-[5-Chloro-4-methyl-2-(2-morpholin-4-ylethoxy)-3-pyridin-4-ylphenyl]ethyl}-9H-purin-6-amine;
N-[1-(5-Chloro-2,4-dimethyl-3-pyridin-4-ylphenyl)ethyl]-9H-purin-6-amine;
N-{1-[5-Chloro-6-methyl-4'-(methylsulfonyl)-2-(2-morpholin-4-ylethoxy)biphenyl-3-yl]ethyl}-9H-purin-6-amine;
N-{1-[4-chloro-3',5'-difluoro-6-(2-methoxypyrimidin-5-yl)biphenyl-2-yl]ethyl}-9H-purin-6-amine;
N-{5'-chloro-3'',5''-difluoro-3'-[1-(9H-purin-6-ylamino)ethyl]-1,1':2',1''-terphenyl-4-yl}acetamide;
N-[1-(4-chloro-3',5'-difluoro-6-pyridin-4-ylbiphenyl-2-yl)ethyl]-9H-purin-6-amine;
N-[1-(4-chloro-3',5'-difluoro-6-pyrimidin-5-ylbiphenyl-2-yl)ethyl]-9H-purin-6-amine;
N-{1-[4-chloro-6-(2,6-difluoropyridin-4-yl)-3',5'-difluorobiphenyl-2-yl]ethyl}-9H-purin-6-amine;
N-{1-[5'-chloro-3'',5''-difluoro-4-(methylsulfonyl)-1,1':2',1''-terphenyl-3'-yl]ethyl}-9H-purin-6-amine;
N-{1-[6-(2-aminopyrimidin-5-yl)-4-chloro-3',5'-difluorobiphenyl-2-yl]ethyl}-9H-purin-6-amine;
N-{1-[5-chloro-2-methoxy-3-(2-methoxypyrimidin-5-yl)phenyl]ethyl}-9H-purin-6-amine;
N-{5'-chloro-2'-methoxy-3'-[1-(9H-purin-6-ylamino)ethyl]biphenyl-4-yl}acetamide;
N-{1-[5-chloro-2-methoxy-3-(1-methyl-1H-pyrazol-5-yl)phenyl]ethyl}-9H-purin-6-amine;
N-[1-(5-chloro-2-methoxy-3-pyridin-4-ylphenyl)ethyl]-9H-purin-6-amine;
N-[1-(5-chloro-2-methoxy-3-pyrimidin-5-ylphenyl)ethyl]-9H-purin-6-amine;
N-{1-[5-chloro-3-(2,6-difluoropyridin-4-yl)-2-methoxyphenyl]ethyl}-9H-purin-6-amine;
N-{1-[5-chloro-2-methoxy-4'-(methylsulfonyl)biphenyl-3-yl]ethyl}-9H-purin-6-amine;
N-{1-[3-(2-aminopyrimidin-5-yl)-5-chloro-2-methoxyphenyl]ethyl}-9H-purin-6-amine;

3,5'-dichloro-2'-methoxy-N-methyl-3'-[1-(9H-purin-6-ylamino)ethyl]biphenyl-4-carboxamide;
N-{1-[5-chloro-3-(2-fluoropyridin-4-yl)-2-methoxyphenyl]ethyl}-9H-purin-6-amine;
N-{1-[5-chloro-2-methoxy-3-(5-methoxypyridin-3-yl)phenyl]ethyl}-9H-purin-6-amine;
N-{1-[5-chloro-3-(6-fluoropyridin-3-yl)-2-methoxyphenyl]ethyl}-9H-purin-6-amine;
N-{1-[5-chloro-2-methoxy-3-(6-methoxypyridin-3-yl)phenyl]ethyl}-9H-purin-6-amine;
N-{1-[3-(2-aminopyrimidin-5-yl)-5-chloro-4-methyl-2-(2-morpholin-4-ylethoxy)phenyl]ethyl}-9H-purin-6-amine;
N-{1-[5-chloro-3'-methoxy-6-methyl-2-(2-morpholin-4-ylethoxy)biphenyl-3-yl]ethyl}-9H-purin-6-amine;
N-{1-[5-chloro-3-(5-chloropyridin-3-yl)-4-methyl-2-(2-morpholin-4-ylethoxy)phenyl]ethyl}-9H-purin-6-amine;
N-{1-[5-chloro-4-methyl-3-(1-methyl-1H-pyrazol-5-yl)-2-(2-morpholin-4-ylethoxy)phenyl]ethyl}-9H-purin-6-amine;
N-{1-[5-chloro-3',4'-dimethoxy-6-methyl-2-(2-morpholin-4-ylethoxy)biphenyl-3-yl]ethyl}-9H-purin-6-amine;
3,3'-dichloro-N,2'-dimethyl-6'-(2-morpholin-4-ylethoxy)-5'-[1-(9H-purin-6-ylamino)ethyl]biphenyl-4-carboxamide;
N-{1-[5-chloro-4-methyl-3-[5-(morpholin-4-ylcarbonyl)pyridin-3-yl]-2-(2-morpholin-4-ylethoxy)phenyl]ethyl}-9H-purin-6-amine;
N-{1-[5-chloro-4-methyl-3-[5-(methylsulfonyl)pyridin-3-yl]-2-(2-morpholin-4-ylethoxy)phenyl]ethyl}-9H-purin-6-amine;
N-{1-[5-chloro-3-(5-methoxypyridin-3-yl)-4-methyl-2-(2-morpholin-4-ylethoxy)phenyl]ethyl}-9H-purin-6-amine;
N-(5-{3-chloro-2-methyl-6-(2-morpholin-4-ylethoxy)-5-[1-(9H-purin-6-ylamino)ethyl]phenyl}pyridin-2-yl)acetamide;
3'-chloro-5-fluoro-2'-methyl-6'-(2-morpholin-4-ylethoxy)-5'-[1-(9H-purin-6-ylamino)ethyl]biphenyl-3-carboxamide;
N-{1-[5-chloro-3-(5-fluoro-6-methoxypyridin-3-yl)-4-methyl-2-(2-morpholin-4-ylethoxy)phenyl]ethyl}-9H-purin-6-amine;
N-{1-[5-chloro-3-(2-methoxypyrimidin-5-yl)-4-methyl-2-(2-morpholin-4-ylethoxy)phenyl]ethyl}-9H-purin-6-amine; and
N-{1-[5-chloro-3-(5-fluoropyridin-3-yl)-4-methyl-2-(2-morpholin-4-ylethoxy)phenyl]ethyl}-9H-purin-6-amine;
1. or a pharmaceutically acceptable salt of any of the aforementioned.

In some embodiment, the compound is selected from:
N-[1-(5-chloro-2-methoxy-4-methyl-3-pyridazin-4-ylphenyl)ethyl]-9H-purin-6-amine;
N-{1-[5-chloro-2-methoxy-4-methyl-3-(1,3-thiazol-4-yl)phenyl]ethyl}-9H-purin-6-amine;
N-[1-(3-azetidin-3-yl-5-chloro-2-methoxy-4-methylphenyl)ethyl]-9H-purin-6-amine;
N-{1-[3-(1-acetylazetidin-3-yl)-5-chloro-2-methoxy-4-methylphenyl]ethyl}-9H-purin-6-amine;
methyl 3-{3-chloro-6-methoxy-2-methyl-5-[1-(9H-purin-6-ylamino)ethyl]phenyl}azetidine-1-carboxylate;
3-{3-chloro-6-methoxy-2-methyl-5-[1-(9H-purin-6-ylamino)ethyl]phenyl}-N-methylazetidine-1-carboxamide;
N-(1-{5-chloro-2-methoxy-4-methyl-3-[1-(methylsulfonyl)azetidin-3-yl]phenyl}ethyl)-9H-purin-6-amine;
N-{1-[5-chloro-3-(1-isopropylazetidin-3-yl)-2-methoxy-4-methylphenyl]ethyl}-9H-purin-6-amine;
N-{1-[5-chloro-2-methoxy-4-methyl-3-(1-methylazetidin-3-yl)phenyl]ethyl}-9H-purin-6-amine;

N-{1-[5-chloro-4-fluoro-3-(1-isopropylazetidin-3-yl)-2-methoxyphenyl]ethyl}-9H-purin-6-amine;
N-{1-[5-chloro-2-ethoxy-4-methyl-3-(1-methylazetidin-3-yl)phenyl]ethyl}-9H-purin-6-amine;
N-{1-[5-chloro-2-methoxy-4-methyl-3-(1-piperidin-4-yl-1H-pyrazol-4-yl)phenyl]ethyl}-9H-purin-6-amine;
4-{3-chloro-6-methoxy-2-methyl-5-[1-(9H-purin-6-ylamino)ethyl]phenyl}-N, 1-dimethyl-1H-pyrrole-2-carboxamide;
N-{1-[5-chloro-2-methoxy-4-methyl-3-(1-methylpiperidin-4-yl)phenyl]ethyl}-9H-purin-6-amine;
6-{3-chloro-6-methoxy-2-methyl-5-[1-(9H-purin-6-ylamino)ethyl]phenyl}-N,N-dimethylpyridine-2-carboxamide;
6-{3-chloro-6-methoxy-2-methyl-5-[1-(9H-purin-6-ylamino)ethyl]phenyl}-N,N-dimethylpyridazine-4-carboxamide;
5-{3-chloro-2-cyano-6-ethoxy-5-[1-(9H-purin-6-ylamino)ethyl]phenyl}-N,N-dimethylpyridine-2-carboxamide;
6-chloro-3-ethoxy-2-[6-(1-hydroxyethyl)pyridin-3-yl]-4-[1-(9H-purin-6-ylamino)ethyl]benzonitrile;
N-{1-[5-chloro-3-(5-fluoropyridin-3-yl)-2-methoxy-4-methylphenyl]propyl}-9H-purin-6-amine;
N-(1-{5-chloro-2-methoxy-4-methyl-3-[5-(methylsulfonyl)pyridin-3-yl]phenyl}propyl)-9H-purin-6-amine;
(5-{3-chloro-6-methoxy-2-methyl-5-[1-(9H-purin-6-ylamino)ethyl]phenyl}pyridin-2-yl)methanol;
2-(5-{3-chloro-6-methoxy-2-methyl-5-[1-(9H-purin-6-ylamino)ethyl]phenyl}pyridin-2-yl)propan-2-ol;
N-(1-{5-chloro-2-methoxy-3-[6-(1-methoxy-1-methylethyl)pyridin-3-yl]-4-methylphenyl}ethyl)-9H-purin-6-amine;
3-ethoxy-6-methyl-2-[5-(methylsulfonyl)pyridin-3-yl]-4-[1-(9H-purin-6-ylamino)ethyl]benzonitrile;
N-{1-[5-chloro-4-fluoro-2-methoxy-3-(1,2,3,6-tetrahydropyridin-4-yl)phenyl]ethyl}-9H-purin-6-amine hydrochloride;
N-{1-[5-chloro-4-fluoro-2-methoxy-3-(morpholin-4-ylmethyl)phenyl]ethyl}-9H-purin-6-amine;
5-{3-chloro-6-methoxy-2-methyl-5-[1-(9H-purin-6-ylamino)ethyl]phenyl}-3-isopropyl-1,3-oxazolidin-2-one;
1-{3-chloro-6-methoxy-2-methyl-5-[1-(9H-purin-6-ylamino)ethyl]phenyl}-2-morpholin-4-ylethanol;
6-{3-chloro-6-methoxy-2-methyl-5-[1-(9H-purin-6-ylamino)ethyl]phenyl}-4-isopropylmorpholin-3-one;
4-{3-chloro-6-methoxy-2-methyl-5-[1-(9H-purin-6-ylamino)ethyl]phenyl}pyrrolidin-2-one;
4-{3-chloro-6-methoxy-2-methyl-5-[1-(9H-purin-6-ylamino)ethyl]phenyl}-1-methylpyrrolidin-2-one;
N-{1-[4,5-dichloro-3-(1-isopropylazetidin-3-yl)-2-methoxyphenyl]ethyl}-9H-purin-6-amine;
N-{1-[3-(1-acetylazetidin-3-yl)-4,5-dichloro-2-methoxyphenyl]ethyl}-9H-purin-6-amine;
2-(3-{2,3-dichloro-6-methoxy-5-[1-(9H-purin-6-ylamino)ethyl]phenyl}azetidin-1-yl)ethanol;
N-(1-{4,5-dichloro-2-methoxy-3-[1-(tetrahydrofuran-3-yl)azetidin-3-yl]phenyl}ethyl)-9H-purin-6-amine;
N-{1-{4,5-dichloro-2-methoxy-3-[1-(2,2,2-trifluoro-1-methylethyl)azetidin-3-yl]phenyl}ethyl)-9H-purin-6-amine;
N-{1-[4,5-dichloro-2-methoxy-3-(1-methylazetidin-3-yl)phenyl]ethyl}-9H-purin-6-amine;
N-(1-{4,5-dichloro-2-methoxy-3-[1-(2-methoxyethyl)azetidin-3-yl]phenyl}ethyl)-9H-purin-6-amine;
N-(1-{4,5-dichloro-3-[1-(cyclopropylmethyl)azetidin-3-yl]-2-methoxyphenyl}ethyl)-9H-purin-6-amine;
N-(1-{4,5-dichloro-2-methoxy-3-[1-(tetrahydrofuran-3-ylmethyl)azetidin-3-yl]phenyl}ethyl)-9H-purin-6-amine;
N-(1-{4,5-dichloro-2-methoxy-3-[1-(4,4,4-trifluorobutyl)azetidin-3-yl]phenyl}ethyl)-9H-purin-6-amine;
N-(1-{4,5-dichloro-2-methoxy-3-[1-(1,3-thiazol-4-ylmethyl)azetidin-3-yl]phenyl}ethyl)-9H-purin-6-amine;
N-(1-{4,5-dichloro-2-methoxy-3-[1-(3,3,3-trifluoropropyl)azetidin-3-yl]phenyl}ethyl)-9H-purin-6-amine;
(3-{2,3-dichloro-6-methoxy-5-[1-(9H-purin-6-ylamino)ethyl]phenyl}azetidin-1-yl)acetonitrile;
N-(1-{4,5-dichloro-2-methoxy-3-[1-(2,2,2-trifluoroethyl)azetidin-3-yl]phenyl}ethyl)-9H-purin-6-amine;
2-(3-{2,3-dichloro-6-methoxy-5-[1-(9H-purin-6-ylamino)ethyl]phenyl}azetidin-1-yl)propan-1-ol;
N-{1-[4,5-dichloro-3-(1-cyclobutylazetidin-3-yl)-2-methoxyphenyl]ethyl}-9H-purin-6-amine;
N-(1-{4,5-dichloro-3-[1-(2,2-difluoroethyl)azetidin-3-yl]-2-methoxyphenyl}ethyl)-9H-purin-6-amine;
5-{3-cyano-6-ethoxy-2-fluoro-5-[1-(9H-purin-6-ylamino)ethyl]phenyl}-N,N-dimethylpyridine-2-carboxamide;
4-ethoxy-2-fluoro-3-[5-(methylsulfonyl)pyridin-3-yl]-5-[1-(9H-purin-6-ylamino)ethyl]benzonitrile;
6-chloro-3-ethoxy-2-(1-ethylazetidin-3-yl)-4-[1-(9H-purin-6-ylamino)ethyl]benzonitrile;
and
6-chloro-3-ethoxy-2-(1-isopropylazetidin-3-yl)-4-[1-(9H-purin-6-ylamino)ethyl]benzonitrile;
or a pharmaceutically acceptable salt of any of the aforementioned.

In some embodiments for each of the aforementioned species, the compound has the (R)-configuration at the carbon atom in Formula I to which $R^1$ is attached.

In some embodiments for each of the aforementioned species, the compound has the (S)-configuration at the carbon atom in Formula I to which $R^1$ is attached.

It is appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

At various places in the present specification, divalent linking substituents are described. It is specifically intended that each divalent linking substituent include both the forward and backward forms of the linking substituent. For example, —NR(CR'R")$_n$— includes both —NR(CR'R")$_n$— and —(CR'R")$_n$NR—. Where the structure clearly requires a linking group, the Markush variables listed for that group are understood to be linking groups.

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

Throughout the definitions, the term "$C_{n-m}$" is referred to indicate $C_{1-4}$, $C_{1-6}$, and the like, wherein n and m are integers and indicate the number of carbons, wherein n-m indicates a range which includes the endpoints.

As used herein, the term "$C_{n-m}$ alkyl", employed alone or in combination with other terms, refers to a saturated hydrocarbon group that may be straight-chain or branched, having n to m carbons. In some embodiments, the alkyl group contains from 1 to 6 carbon atoms, from 1 to 4 carbon atoms, from 1 to 3 carbon atoms, or 1 to 2 carbon atoms. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, and the like.

As used herein, the term "alkylene" refers to a divalent alkyl linking group. Examples of alkylene groups include, but are not limited to, ethan-1,2-diyl, propan-1,3-diyl, propan-1,2-diyl, butan-1,4-diyl, butan-1,3-diyl, butan-1,2-diyl, 2-methyl-propan-1,3-diyl, and the like.

As used herein, "$C_{n-m}$ alkenyl" refers to an alkyl group having one or more double carbon-carbon bonds and having n to m carbons. In some embodiments, the alkenyl moiety contains 2 to 6 or to 2 to 4 carbon atoms. Example alkenyl groups include, but are not limited to, ethenyl, n-propenyl, isopropenyl, n-butenyl, sec-butenyl, and the like.

As used herein, "$C_{n-m}$ alkynyl" refers to an alkyl group having one or more triple carbon-carbon bonds and having n to m carbons. Example alkynyl groups include, but are not limited to, ethynyl, propyn-1-yl, propyn-2-yl, and the like. In some embodiments, the alkynyl moiety contains 2 to 6 or 2 to 4 carbon atoms.

As used herein, the term "$C_{n-m}$ alkoxy", employed alone or in combination with other terms, refers to a group of formula —O-alkyl, wherein the alkyl group has n to m carbons. Example alkoxy groups include methoxy, ethoxy, propoxy (e.g., n-propoxy and isopropoxy), t-butoxy, and the like. In some embodiments, the alkyl group has 1 to 6 or 1 to 4 carbon atoms.

As used herein, the term "$C_{n-m}$ alkylamino" refers to a group of formula —NH(alkyl), wherein the alkyl group has n to m carbon atoms. In some embodiments, the alkyl group has 1 to 6 or 1 to 4 carbon atoms.

As used herein, the term "$C_{n-m}$ alkoxycarbonyl" refers to a group of formula —C(O)O— alkyl, wherein the alkyl group has n to m carbon atoms. In some embodiments, the alkyl group has 1 to 6 or 1 to 4 carbon atoms.

As used herein, the term "$C_{n-m}$ alkylcarbonyl" refers to a group of formula —C(O)-alkyl, wherein the alkyl group has n to m carbon atoms. In some embodiments, the alkyl group has 1 to 6 or 1 to 4 carbon atoms.

As used herein, the term "$C_{n-m}$ alkylcarbonylamino" refers to a group of formula —NHC(O)-alkyl, wherein the alkyl group has n to m carbon atoms. In some embodiments, the alkyl group has 1 to 6 or 1 to 4 carbon atoms.

As used herein, the term "$C_{n-m}$ alkylsulfonylamino" refers to a group of formula —NHS(O)$_2$-alkyl, wherein the alkyl group has n to m carbon atoms. In some embodiments, the alkyl group has 1 to 6 or 1 to 4 carbon atoms.

As used herein, the term "aminosulfonyl" refers to a group of formula —S(O)$_2$NH$_2$, wherein the alkyl group has n to m carbon atoms.

As used herein, the term "$C_{n-m}$ alkylaminosulfonyl" refers to a group of formula —S(O)$_2$NH(alkyl), wherein the alkyl group has n to m carbon atoms. In some embodiments, the alkyl group has 1 to 6 or 1 to 4 carbon atoms.

As used herein, the term "di($C_{n-m}$ alkyl)aminosulfonyl" refers to a group of formula —S(O)$_2$N(alkyl)$_2$, wherein each alkyl group independently has n to m carbon atoms. In some embodiments, each alkyl group has, independently, 1 to 6 or 1 to 4 carbon atoms.

As used herein, the term "aminosulfonylamino" refers to a group of formula —NHS(O)$_2$NH$_2$.

As used herein, the term "$C_{n-m}$ alkylaminosulfonylamino" refers to a group of formula —NHS(O)$_2$NH(alkyl), wherein the alkyl group has n to m carbon atoms. In some embodiments, the alkyl group has 1 to 6 or 1 to 4 carbon atoms.

As used herein, the term "di($C_{n-m}$ alkyl)aminosulfonylamino" refers to a group of formula —NHS(O)$_2$N(alkyl)$_2$, wherein each alkyl group independently has n to m carbon atoms. In some embodiments, each alkyl group has, independently, 1 to 6 or 1 to 4 carbon atoms.

As used herein, the term "aminocarbonylamino", employed alone or in combination with other terms, refers to a group of formula —NHC(O)NH$_2$.

As used herein, the term "$C_{n-m}$ alkylaminocarbonylamino" refers to a group of formula —NHC(O)NH(alkyl), wherein the alkyl group has n to m carbon atoms. In some embodiments, the alkyl group has 1 to 6 or 1 to 4 carbon atoms.

As used herein, the term "di($C_{n-m}$ alkyl)aminocarbonylamino" refers to a group of formula —NHC(O)N(alkyl)$_2$, wherein each alkyl group independently has n to m carbon atoms. In some embodiments, each alkyl group has, independently, 1 to 6 or 1 to 4 carbon atoms.

As used herein, the term "$C_{n-m}$ alkylcarbamyl" refers to a group of formula —C(O)—NH(alkyl), wherein the alkyl group has n to m carbon atoms. In some embodiments, the alkyl group has 1 to 6 or 1 to 4 carbon atoms.

As used herein, the term "thio" refers to a group of formula —S—H.

As used herein, the term "$C_{n-m}$ alkylthio" refers to a group of formula —S-alkyl, wherein the alkyl group has n to m carbon atoms. In some embodiments, the alkyl group has 1 to 6 or 1 to 4 carbon atoms.

As used herein, the term "$C_{n-m}$ alkylsulfinyl" refers to a group of formula —S(O)-alkyl, wherein the alkyl group has n to m carbon atoms. In some embodiments, the alkyl group has 1 to 6 or 1 to 4 carbon atoms.

As used herein, the term "$C_{n-m}$ alkylsulfonyl" refers to a group of formula —S(O)$_2$-alkyl, wherein the alkyl group has n to m carbon atoms. In some embodiments, the alkyl group has 1 to 6 or 1 to 4 carbon atoms.

As used herein, the term "amino" refers to a group of formula —NH$_2$.

As used herein, the term "carbamyl" to a group of formula —C(O)NH$_2$.

As used herein, the term "carbonyl", employed alone or in combination with other terms, refers to a —C(O)— group.

As used herein, the term "carboxy" refers to a group of formula —C(O)OH.

As used herein, the term "di($C_{n-m}$-alkyl)amino" refers to a group of formula —N(alkyl)$_2$, wherein the two alkyl groups each has, independently, n to m carbon atoms. In some embodiments, each alkyl group independently has 1 to 6 or 1 to 4 carbon atoms.

As used herein, the term "di($C_{n-m}$-alkyl)carbamyl" refers to a group of formula —C(O)N(alkyl)$_2$, wherein the two alkyl groups each has, independently, n to m carbon atoms. In some embodiments, each alkyl group independently has 1 to 6 or 1 to 4 carbon atoms.

As used herein, "$C_{n-m}$ haloalkoxy" refers to a group of formula —O-haloalkyl having n to m carbon atoms. An example haloalkoxy group is OCF$_3$. In some embodiments, the haloalkoxy group is fluorinated only. In some embodiments, the alkyl group has 1 to 6 or 1 to 4 carbon atoms.

As used herein, the term "$C_{n-m}$ haloalkyl", employed alone or in combination with other terms, refers to an alkyl group having from one halogen atom to 2s+1 halogen atoms which may be the same or different, where "s" is the number of carbon atoms in the alkyl group, wherein the alkyl group has n to m carbon atoms. In some embodiments, the haloalkyl group is fluorinated only. In some embodiments, the alkyl group has 1 to 6 or 1 to 4 carbon atoms.

As used herein, the term "phenyl-$C_{1-4}$ alkyl" refers to a group of formula —$C_{1-4}$ alkylene-phenyl.

As used herein, "cycloalkyl" refers to non-aromatic cyclic hydrocarbons including cyclized alkyl and/or alkenyl groups. Cycloalkyl groups can include mono- or polycyclic (e.g., having 2, 3 or 4 fused rings) groups and spirocycles. Ring-forming carbon atoms of a cycloalkyl group can be optionally substituted by oxo or sulfido. Cycloalkyl groups also include cycloalkylidenes. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, and the like. In some embodiments, cycloalkyl is cyclopropyl, cyclobutyl, cyclopentyl, or cyclohexyl. Also included in the definition of cycloalkyl are moieties that have one or more aromatic rings fused (i.e., having a bond in common with) to the cycloalkyl ring, for example, benzo or thienyl derivatives of cyclopentane, cyclopentene, cyclohexane, and the like. A cycloalkyl group containing a fused aromatic ring can be attached through any ring-forming atom including a ring-forming atom of the fused aromatic ring.

As used herein, "5-6 membered heteroaryl" refers to a monocyclic aromatic heterocycle having at least one heteroatom ring member such as sulfur, oxygen, or nitrogen and 5-6 ring members. In some embodiments, the heteroaryl ring has 1, 2, or 3 heteroatom ring members independently selected from nitrogen, sulfur and oxygen. In some embodiments, the heteroaryl ring has 1, 2, 3 or 4 N heteroatom ring members. In some embodiments, any ring-forming N in a heteroaryl moiety can be an N-oxide.

A five-membered ring heteroaryl is a heteroaryl with a ring having five ring atoms wherein one or more (e.g., 1, 2, or 3) ring atoms are independently selected from N, O, and S. Exemplary five-membered ring heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl.

A six-membered ring heteroaryl is a heteroaryl with a ring having six ring atoms wherein one or more (e.g., 1, 2, or 3) ring atoms are independently selected from N, O, and S. Exemplary six-membered ring heteroaryls are pyridyl, pyrazinyl, pyrimidinyl, triazinyl and pyridazinyl.

As used herein, the term "heteroarylalkyl" refers to a group of formula -alkylene-heteroaryl. In some embodiments, heteroarylalkyl is 5-6 membered heteroaryl ring, wherein the heteroaryl ring is monocyclic and has 1, 2, or 3 heteroatom ring members independently selected from nitrogen, sulfur and oxygen.

As used herein, "4-7 membered heterocycloalkyl" refers to non-aromatic heterocycles having one or more ring-forming heteroatoms selected from O, N, or S and having 4-7 ring members. Heterocycloalkyl groups include spirocycles. Example "4-7 membered heterocycloalkyl" groups include pyrrolidin2-one, 1,3-isoxazolidin-2-one, pyranyl, azetidinyl, morpholino, thiomorpholino, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, azepanyl, and the like. Ring-forming carbon atoms and heteroatoms of a heterocycloalkyl group can be optionally substituted by oxo or sulfido (e.g., C(O), S(O), C(S), or S(O)$_2$, etc.). The heterocycloalkyl group can be attached through a ring-forming carbon atom or a ring-forming heteroatom. In some embodiments, the heterocycloalkyl group contains 0 to 3 double or triple bonds. In some embodiments, the heterocycloalkyl group contains 0 to 2 double bonds.

As used herein, the term "heterocycloalkylalkyl" refers to a group of formula alkylene-heterocycloalkyl. In some embodiments, heterocycloalkylalkyl is 4-7 membered heterocycloalkyl ring, wherein the heterocycloalkyl portion is monocyclic and has 1, 2, or 3 heteroatom ring members independently selected from nitrogen, sulfur and oxygen.

As used herein, the term "cyano-$C_{1-6}$ alkyl" refers to a group of formula —$C_{1-6}$ alkylene-CN.

As used herein, the term "HO—$C_{1-6}$ alkyl" refers to a group of formula —$C_{1-6}$ alkylene-OH.

As used herein, the term "$C_{1-4}$ alkoxy-$C_{1-6}$ alkyl" refers to a group of formula —$C_{1-6}$ alkylene-($C_{1-4}$ alkoxy).

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms.

In some embodiments, the compound has the (R)-configuration at the carbon attached to $R^1$. In some embodiments, the compound has the (S)-configuration at the carbon attached to $R^1$.

Resolution of racemic mixtures of compounds can be carried out by any of numerous methods known in the art. An example method includes fractional recrystallizaion using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution. For example, purine includes the 9H and a 7H tautomeric forms:

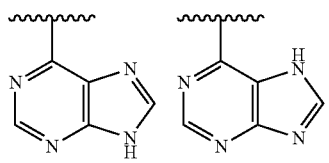

Compounds of the invention can include both the 9H and 7H tautomeric forms.

Compounds of the invention can also include all isotopes of atoms occurring in the intermediates or final compounds. Isotopes include those atoms having the same atomic number but different mass numbers. For example, isotopes of hydrogen include tritium and deuterium.

The term, "compound," as used herein is meant to include all stereoisomers, geometric isomers, tautomers, and isotopes of the structures depicted. Compounds herein identified by name or structure as one particular tautomeric form are intended to include other tautomeric forms unless otherwise specified.

All compounds, and pharmaceutically acceptable salts thereof, can be found together with other substances such as water and solvents (e.g. hydrates and solvates) or can be isolated.

In some embodiments, the compounds of the invention, or salts thereof, are substantially isolated. By "substantially isolated" is meant that the compound is at least partially or substantially separated from the environment in which it was formed or detected. Partial separation can include, for example, a composition enriched in the compounds of the invention. Substantial separation can include compositions containing at least about 50%, at least about 60%, at least about 70%, at least about 80%, at least about 90%, at least about 95%, at least about 97%, or at least about 99% by weight of the compounds of the invention, or salt thereof. Methods for isolating compounds and their salts are routine in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expressions, "ambient temperature" and "room temperature," as used herein, are understood in the art, and refer generally to a temperature, e.g. a reaction temperature, that is about the temperature of the room in which the reaction is carried out, for example, a temperature from about 20° C. to about 30° C.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (ACN) are preferred. Lists of suitable salts are found in *Remington's Pharmaceutical Sciences*, 17th ed., Mack Publishing Company, Easton, Pa., 1985, p. 1418 and *Journal of Pharmaceutical Science*, 66, 2 (1977), each of which is incorporated herein by reference in its entirety.

Synthesis

Compounds of the invention, including salts thereof, can be prepared using known organic synthesis techniques and can be synthesized according to any of numerous possible synthetic routes.

The reactions for preparing compounds of the invention can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis*, 3$^{rd}$ Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC), liquid chromatography-mass spectroscopy (LCMS) or thin layer chromatography (TLC). Compounds can be purified by those skilled in the art by a variety of methods, including high performance liquid chromatography (HPLC) ("*Preparative LC-MS Purification: Improved Compound Specific Method Optimization*" Karl F. Blom, Brian Glass, Richard Sparks, Andrew P. Combs *J. Combi. Chem.* 2004, 6(6), 874-883, which is incorporated herein by reference in its entirety) and normal phase silica chromatography.

Compounds of Formula I can be formed as shown in Scheme I. The compound (i) can be halogenated with N-chlorosuccinamide, N-bromosuccinamide or N-iodosuccinamide to give compound (ii) where X=Cl, Br, or I. The halo group of (ii) can be coupled to $R^3$-M, where M is a boronic acid, boronic ester or an appropriately substituted metal (e.g., $R^3$-M is $R^3$—B(OH)$_2$ or $R^3$—Sn(Bu)$_4$), under standard Suzuki conditions or standard Stille conditions (e.g., in the presence of a palladium(0) catalyst, such as tetrakis(triphenylphosphine)palladium(0) and a base (e.g., a bicarbonate or carbonate base) to give a derivative of formula (iii). Alternatively, $R^3$-M can be a cyclic amine (where M is H and attached to the amine nitrogen) with coupling to compound (ii) being performed by heating in base or under Buchwald conditions (e.g., in the presence of a palladium(0) catalyst, such as tetrakis(triphenylphosphine) palladium(0) and a base (e.g., an alkoxide base)) to afford ketone (iii). Reductive amination of the ketone (iii) can furnish the amine intermediate (v). Alternatively, ketone (iii) can be reduced to give an alcohol which can be converted to the mesylate and reacted with sodium azide to give an azide derivative (iv). The azide of compound (iv) can be converted to an amine (v) under appropriate reducing conditions, such as trimethylphosphine or TMSI. The amine (v) can be reacted with an appropriate alkylating agent $R^4X$ (e.g., MeI) or reacted under reductive amination conditions to give compound (vi). Finally compound (vi) can be reacted with a heteroaryl halide compound (e.g., Ar—X) to give a compound of Formula I. The reaction of amine (v) with $R^4$—X can be eliminated to give compounds of Formula I, wherein $R^4$ is H.

(e.g., TFA when P=Boc) and reacted with an appropriate alkylating agent $R^4X$ (e.g., MeI) and the resulting secondary amine can be reacted with a heteroaryl halide compound (e.g., Ar—X) to give a compound (vi). The reaction of amine (v) with $R^4$—X can be eliminated to give compounds (vi), wherein $R^4$ is H. Finally, the halo group of (vi) can be coupled to $R^3$-M, where M is a boronic acid, boronic ester or an appropriately substituted metal (e.g., $R^3$-M is $R^3$—B(OH)$_2$ or $R^3$—Sn(Bu)$_4$), under standard Suzuki conditions or standard Stille conditions (e.g., in the presence of a palladium(0) catalyst, such as tetrakis(triphenylphosphine) palladium(0) and a base (e.g., a bicarbonate or carbonate base)) to give a derivative of formula (vii). Alternatively, $R^3$-M can be a cyclic amine (where M is H and attached to the amine nitrogen) with coupling to compound (vi) being performed by heating in base or under Buchwald conditions (e.g., in the presence of a palladium(0) catalyst, such as tetrakis(triphenylphosphine)palladium(0) and a base (e.g., an alkoxide base)) to afford compounds of Formula I (vii).

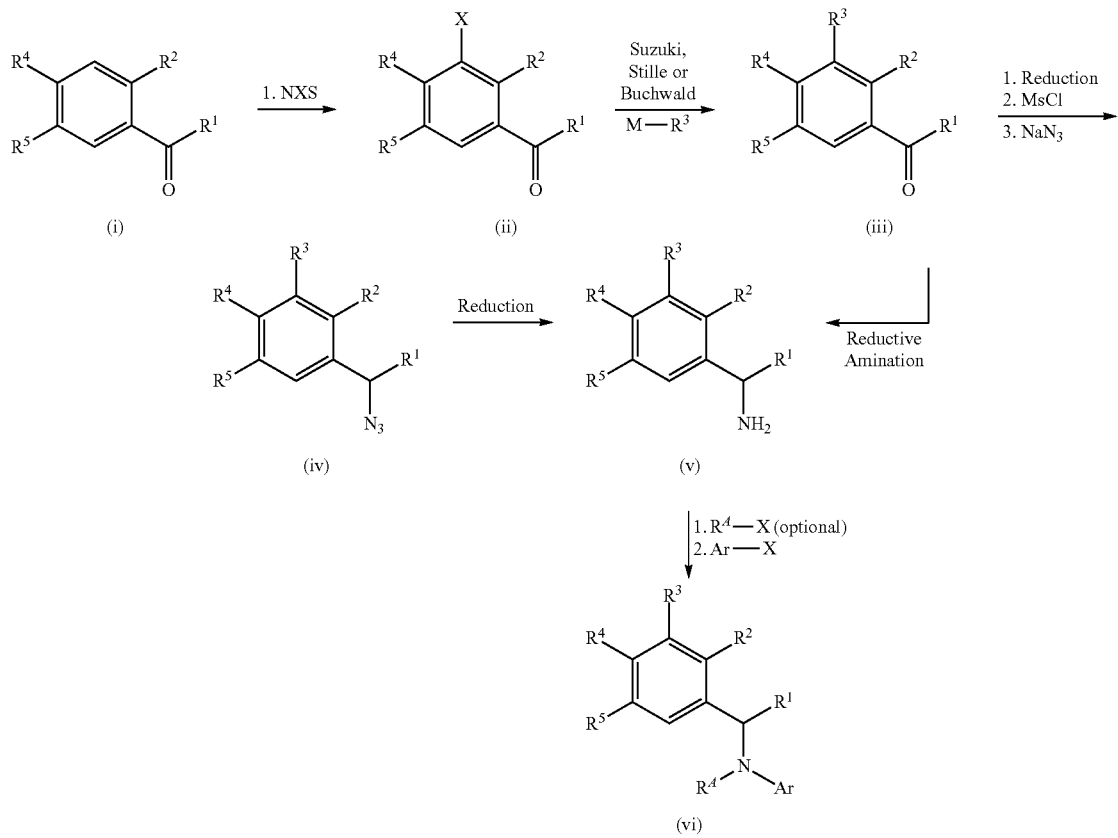

Scheme I

Alternatively, compounds of Formula I can also be formed as shown in Scheme II. The ketone compound (i) can be halogenated with N-chlorosuccinamide, N-bromosuccinamide or N-iodosuccinamide to give compound (ii) where X=Cl, Br, or I. Ketone (ii) can be reduced to give an alcohol (iii) which can be converted to the mesylate and reacted with sodium azide to give an azide derivative (iv). The azide of compound (iv) can be converted to an amine (v) under appropriate reducing conditions, such as trimethylphosphine or TMSI. The amine (v) can be protected with a suitable protecting group (e.g., by reacting with Boc$_2$O) and purified by chiral chromatography to afford a single enantiomer of amine compound (v). The amino group can be deprotected

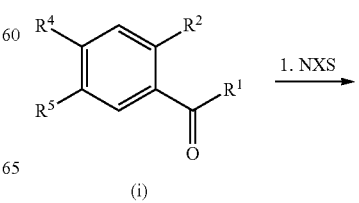

Scheme II

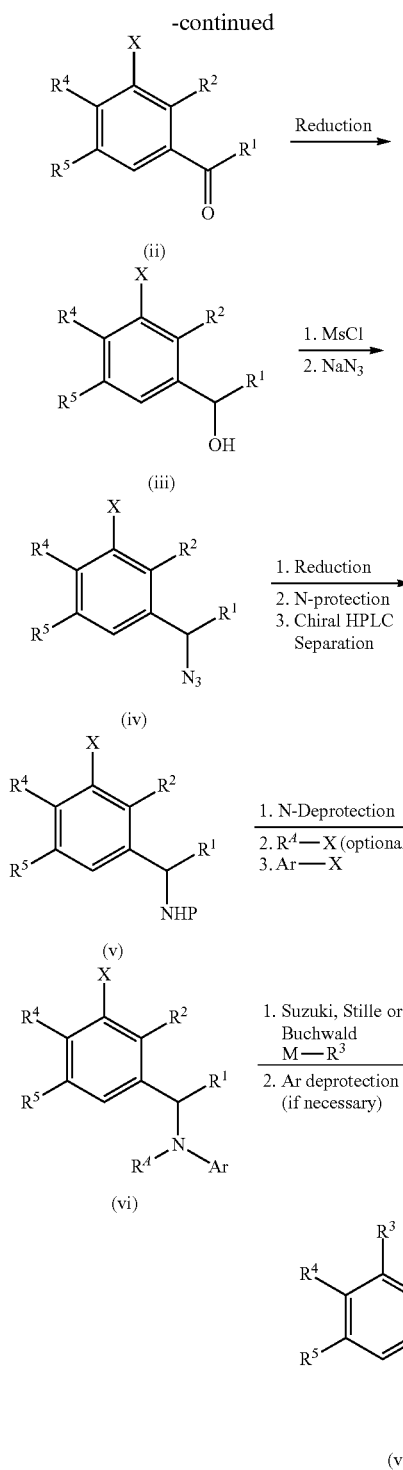

(e.g., in the presence of a palladium(0) catalyst, such as tetrakis(triphenylphosphine)-palladium(0) and a base (e.g., a bicarbonate or carbonate base)) to give a derivative of formula (iii). Alternatively, $R^3$-M can be a cyclic amine (where M is H and attached to the amine nitrogen) with coupling to compound (ii) being performed by heating in base or under Buchwald conditions (e.g., in the presence of a palladium(0) catalyst, such as tetrakis(triphenylphosphine)-palladium(0) and a base (e.g., an alkoxide base)) to afford compounds of formula (iii). The ketone (iii) can be transformed using similar methods as shown in Scheme I and II to afford compounds of Formula I (iv). Alternatively, the halo-ketone (ii) can be transformed using similar methods as shown in Scheme I and II to afford halo intermediate (v). Suzuki, Stille, Negishi or Buchwald coupling of $R^3$-M with halo intermediate (v) by similar methods described in Schemes I and II can also afford compounds of Formula I (iv).

Scheme III

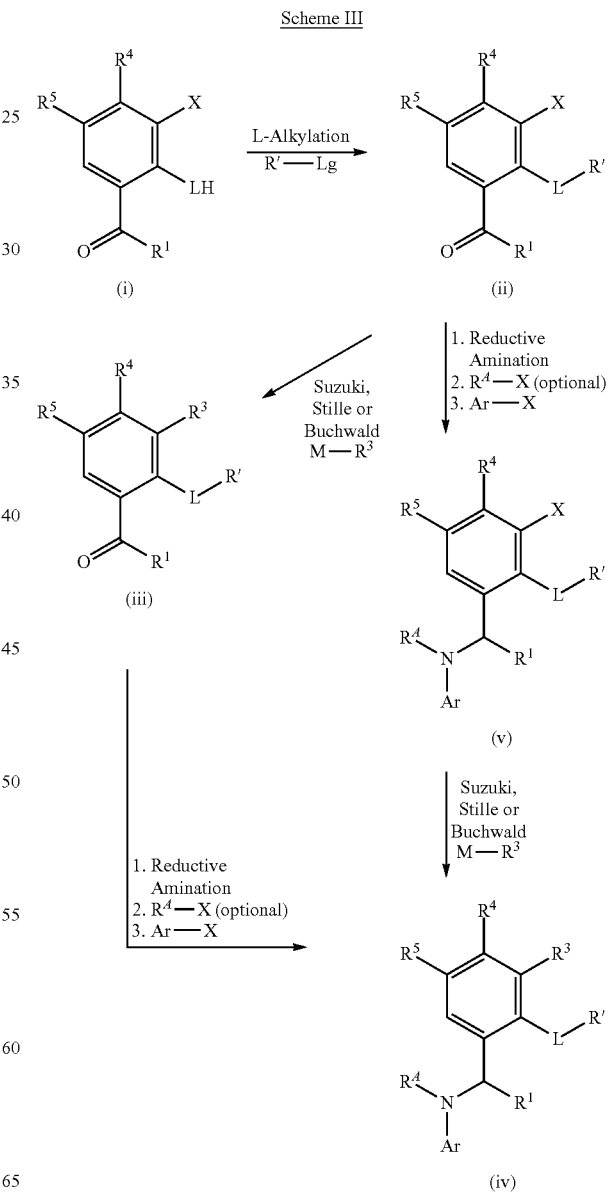

Compounds of Formula I, wherein L is O, N, or S, can be formed as shown in Scheme III. The thiols, phenols or amines (i) can be alkylated using Mitsunobu conditions (e.g., R'OH, DEAD, $Ph_3P$) or standard alkylating conditions (R'-Lg, Lg=leaving group) to afford thioether, ether, or alkylamine derivatives (ii), respectively. The halo group (e.g., X=Br, I) of (ii) can be coupled to $R^3$-M, where M is a boronic acid, boronic ester or an appropriately substituted metal (e.g., $R^3$-M is $R^3$—$B(OH)_2$ or $R^3$—$Sn(Bu)_4$), under standard Suzuki conditions or standard Stille conditions Compounds of Formula I can be formed as shown in Scheme IV. Compound (i) can be acylated with a suitable acylating reagent (e.g., $R^1$—COCl) to form an ester which can be rearranged under Lewis acid conditions e.g., $BF_3$/HOAc complex) to afford ketone (ii). Halogenation of ketone (ii) using NXS (e.g., NXS=N-chlorosuccinamide, N-bromosuccinamide or N-iodosuccinamide) can give compound (iii) where X=Cl, Br, or I. The phenol can be converted to the triflate (iv) using standard conditions (e.g., $Tf_2O$). The triflate group of (iv) can be coupled to $R^2$-M, where M is a boronic acid, boronic ester or an appropriately substituted metal (e.g., $R^2$-M is $R^2$—$B(OH)_2$ or $R^2$—$Sn(Bu)_4$), under standard Suzuki conditions or standard Stille conditions (e.g., in the presence of a palladium(0) catalyst, such as tetrakis(triphenylphosphine)palladium(0) and a base (e.g., a bicarbonate or carbonate base)) to give a derivative of formula (v). Alternatively, $R^2$-M can be a cyclic amine (where M is H and attached to the amine nitrogen) with coupling to compound (iv) being performed by heating in base or under Buchwald conditions (e.g., in the presence of a palladium(0) catalyst, such as tetrakis(triphenylphosphine)palladium(0) and a base (e.g., an alkoxide base)) to afford ketone (v). The halo group of (v) can be coupled to $R^3$-M, where M is a boronic acid, boronic ester or an appropriately substituted metal (e.g., $R^3$-M is $R^3$—$B(OH)_2$ or $R^3$—$Sn(Bu)_4$), under standard Suzuki conditions or standard Stille conditions (e.g., in the presence of a palladium(0) catalyst, such as tetrakis(triphenylphosphine) palladium(0) and a base (e.g., a bicarbonate or carbonate base)) to give a derivative of formula (vi). Alternatively, $R^3$-M can be a cyclic amine (where M is H and attached to the amine nitrogen) with coupling to compound (iv) being performed by heating in base or under Buchwald conditions (e.g., in the presence of a palladium(0) catalyst, such as tetrakis(triphenylphosphine)palladium(0) and a base (e.g., an alkoxide base)) to afford ketone (vi). The ketone (vi) can be transformed using similar methods as shown in Scheme I and II to afford compounds of Formula I (viii).

Alternatively, the halo-ketone (v) can be transformed using similar methods as shown in Scheme I and II to afford halo intermediate (viii). Suzuki, Stille, Negishi or Buchwald coupling of M-$R^3$ with compound (viii) by similar methods described in Schemes I and II can also afford compounds of Formula I (vii).

Ketones which can be used in the processes of Scheme I, II and III can be formed as shown in Scheme V below. The carboxylic acid (i) can be activated with a coupling agent (e.g., HBTU, HATU or EDC) and then reacted with N,O-dimethylhydroxylamine to give a N-methoxy-N-methylcarboxamide derivative (ii). Amide (ii) may then be reacted with a Grignard reagent of formula $R^1$—MgX (X=halo) to give a ketone (iii). The ketone (iii) can be transformed using similar methods as shown in Scheme I, II and III to afford compounds of Formula I.

Scheme IV

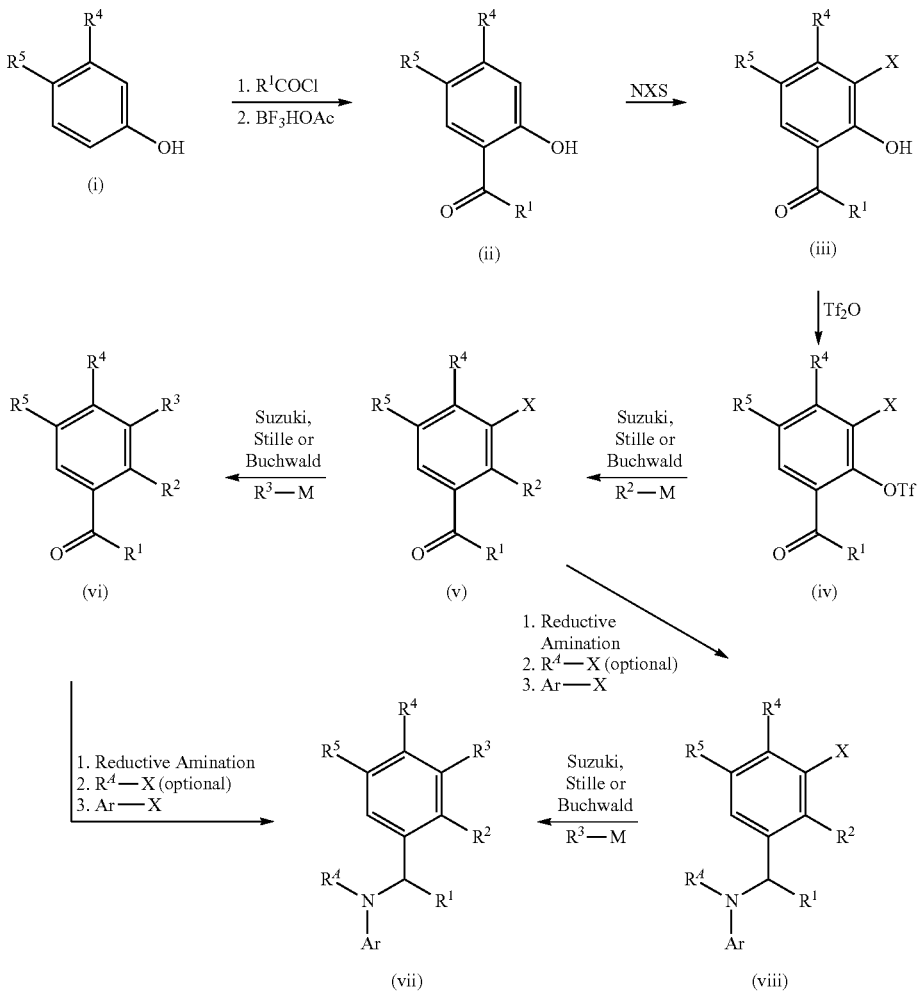

Scheme V

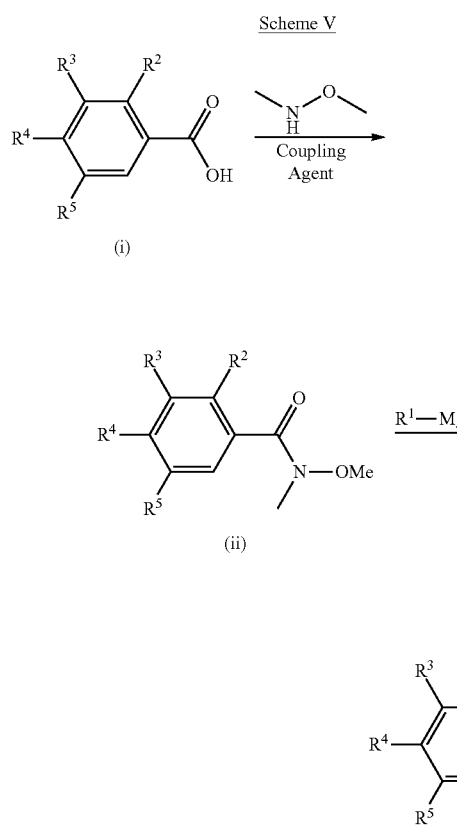

Scheme VI

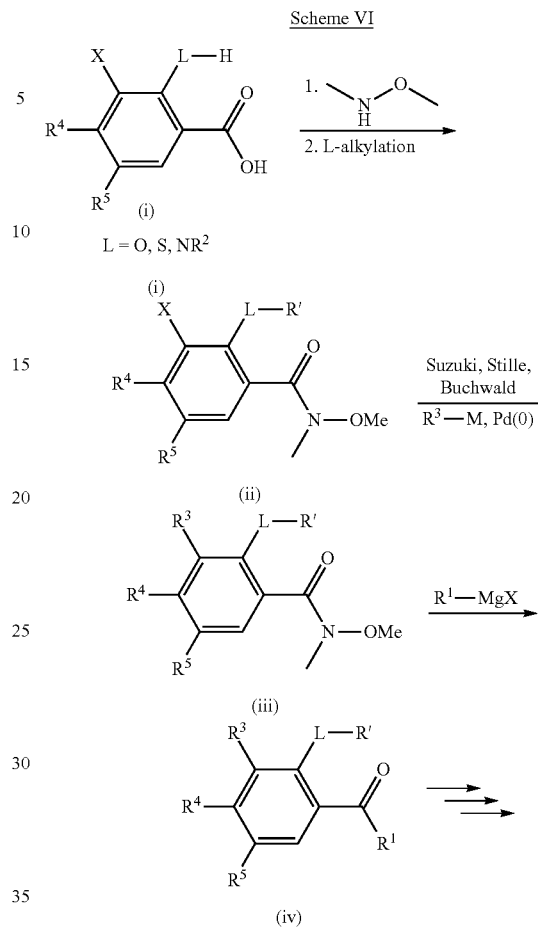

Ketones which can be used in the processes of Scheme I, II and III, can also be formed as shown in Scheme VI below. The carboxylic acid (i) can be activated with a coupling agent (e.g. HBTU or HATU) and then reacted with N,O-dimethylhydroxylamine to give a N-methoxy-N-methyl-carboxamide. The thiols, phenols or amines can be alkylated using Mitsunobu conditions (e.g., R'OH, DEAD, Ph$_3$P) or standard alkylating conditions (R'-Lg, Lg=leaving group) to afford thioether, ether or alkylamine derivatives (ii), respectively. The halo group (e.g., X=Br, or I) of (ii) can be coupled to R$^3$-M, where M is a boronic acid, boronic ester or an appropriately substituted metal (e.g., R$^3$-M is R$^3$—B(OH)$_2$ or R$^3$—Sn(Bu)$_4$), under standard Suzuki conditions or standard Stille conditions (e.g., in the presence of a palladium(0) catalyst, such as tetrakis(triphenylphosphine)palladium(0) and a base (e.g., a bicarbonate or carbonate base)) to give a derivative of formula (iii). Alternatively, R$^3$-M can be a cyclic amine (where M is H and attached to the amine nitrogen) with coupling to compound (ii) being performed by heating in base or under Buchwald conditions (e.g., in the presence of a palladium(0) catalyst, such as tetrakis(triphenylphosphine)palladium(0) and a base (e.g., an alkoxide base)) to afford amides (iii) of Formula I. Reaction of compound (iii) with a Grignard reagent of formula R$^1$—MgX (X=halo) can give ketone (iv). The ketone (iv) can be transformed using similar methods as shown in Scheme I, II and III to afford compounds of Formula I.

Compounds which can be used in the processes of Schemes I-III can also be formed as shown in Scheme VII. The halo-ketone (i) can be converted to the cyano-ketone (ii) using standard cyanation conditions (e.g., Pd(0) and Zn(CN)$_2$). Hydrolysis of the cyano group of (ii) under acid or base conditions can give the carboxylic acid which can be coupled to amines using a coupling agent (e.g., HATU, HBTU, EDC) and appropriate amines (HNR$^c$R$^d$) to give amide (iii). In some embodiments, R and R$^d$, along with the nitrogen atom to which they are attached can optionally cyclize to form a 4-7 membered heterocycloalkyl group (thereby providing compounds wherein R$^3$ is C(O)R$^b$, wherein R$^b$ is 4-7 membered heterocycloalkyl). The ketone of amide (iii) can be transformed using similar methods as shown in Scheme I, II and III to afford compounds of Formula I.

Scheme VII

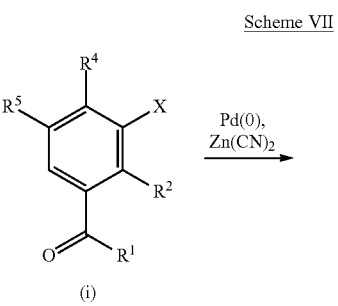

Scheme VIII

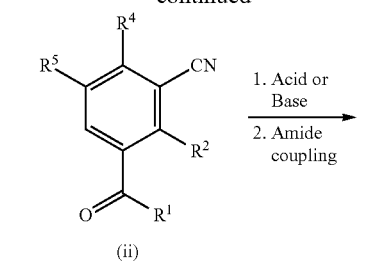
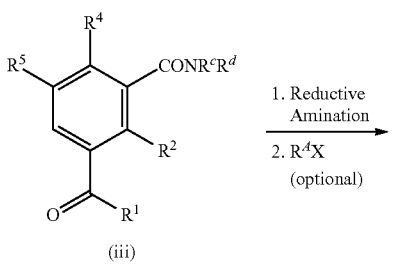
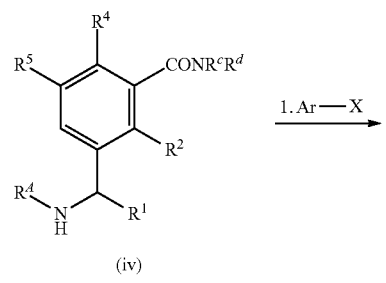
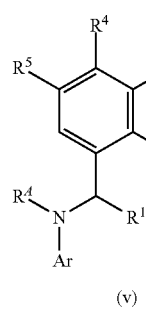
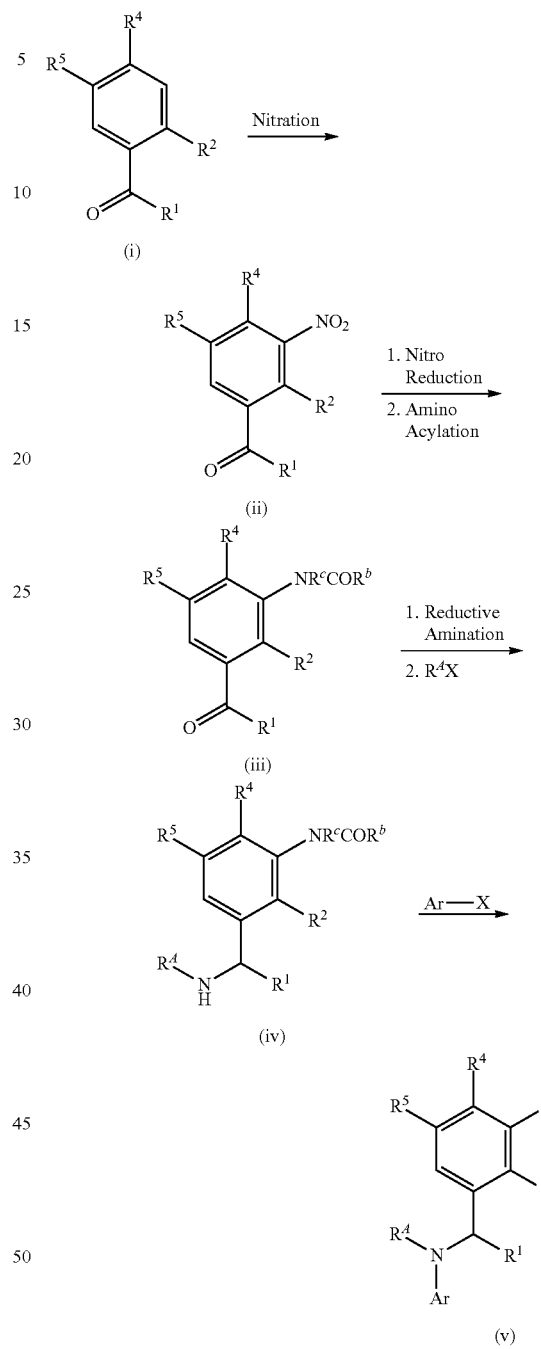

Additional compounds which can be used in the processes of Schemes I-III can be formed as shown in Scheme VIII. The ketone (i) can be converted to the nitro-ketone (ii) using standard nitration conditions (e.g., $HNO_3$). Reduction of the nitro group of (ii) under standard conditions (e.g., Fe, Zn, $H_2$ over Pd/C) can give the amino compound which can be acylated with appropriate acylating agents (e.g., RC=OCl, ROC=OCl, $SO_2Cl$, RRNC=O) to give ketone (iii). The ketone (iii) can be transformed using similar methods as shown in Scheme I, II and III to afford compounds of Formula I. In some embodiments, R and $R^d$, along with the nitrogen atom to which they are attached can optionally cyclize to form a 4-7 membered heterocycloalkyl group (thereby providing compounds wherein $R^3$ is $C(O)R^b$, wherein $R^b$ is 4-7 membered heterocycloalkyl).

Further compounds which can be used in the processes of Schemes I-III can be formed as shown in Scheme IX. The ether (i) can be converted to a phenol (ii) using standard nitration conditions (e.g., $BBr_3$). The halo-phenol (ii) can be converted to the cyano-phenol (iii) using standard cyanation conditions (e.g., CuCN or Pd(0) and $Zn(CN)_2$). The phenol (iii) can be converted to the triflate (iv) using $Tf_2O$. The triflate group of (iv) can be coupled to $R^2$-M, where M is a boronic acid, boronic ester or an appropriately substituted metal (e.g., $R^2$-M is $R^2$—$B(OH)_2$ or $R^2$—$Sn(Bu)_4$), under standard Suzuki conditions or standard Stille conditions (e.g., in the presence of a palladium(0) catalyst, such as tetrakis(triphenylphosphine)palladium(0) and a base (e.g., a bicarbonate or carbonate base)) to give a derivative of formula (v). Alternatively, R²-M can be a cyclic amine (where M is H and attached to the amine nitrogen) with coupling to compound (iv) being performed by heating in base or under Buchwald conditions (e.g., in the presence of a palladium(0) catalyst, such as tetrakis(triphenylphosphine) palladium(0) and a base (e.g., an alkoxide base)) to afford ketone (v). Hydrolysis of the cyano group of (v) under acid or base conditions can give the carboxylic acid which can be coupled to amines using a coupling agent (e.g., HATU, HBTU, EDC) and an appropriate amine (HNRiR₂) to give amide (vi). The ketone of amide (vi) can be transformed using similar methods as shown in Scheme I, II and III to afford compounds of Formula I.

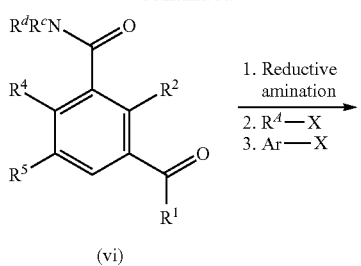

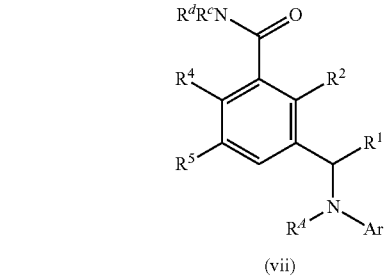

Compounds of Formula I can be formed as shown in Scheme X. The halo ($X^1$) group of (i) can be coupled to $R^3$-M, where M is an appropriately substituted metal (e.g., $R^3$-M is Zn(R³)₂); appropriate non-limiting starting materials for generating $R^3$-M are shown in Scheme X) under standard Negishi conditions (e.g., in the presence of a palladium(0) catalyst, such as Pd₂(dba)₃ or tetrakis(triphenylphosphine)palladium(0)) to give a protected amino derivative of formula (ii). The nitrogen protecting group Pg in formula (ii) (e.g., Boc or Cbz) can be removed under a variety of standard conditions (e.g., TFA or HCl for Boc and H₂ over Pd/C for Cbz) to afford the free amine which can be further reacted with a variety of alkylating, arylating, acylating, or sulfonylating conditions (e.g., $R^{3a}$—$X^2$; where $X^2$=halo or other leaving group and $R^{3a}$=alkyl, aryl, acyl, sulfonyl and a base, such as TEA) to give compounds of formula (iii). Compounds of formula (iii) can be converted to compounds of Formula I using conditions described in Scheme I.

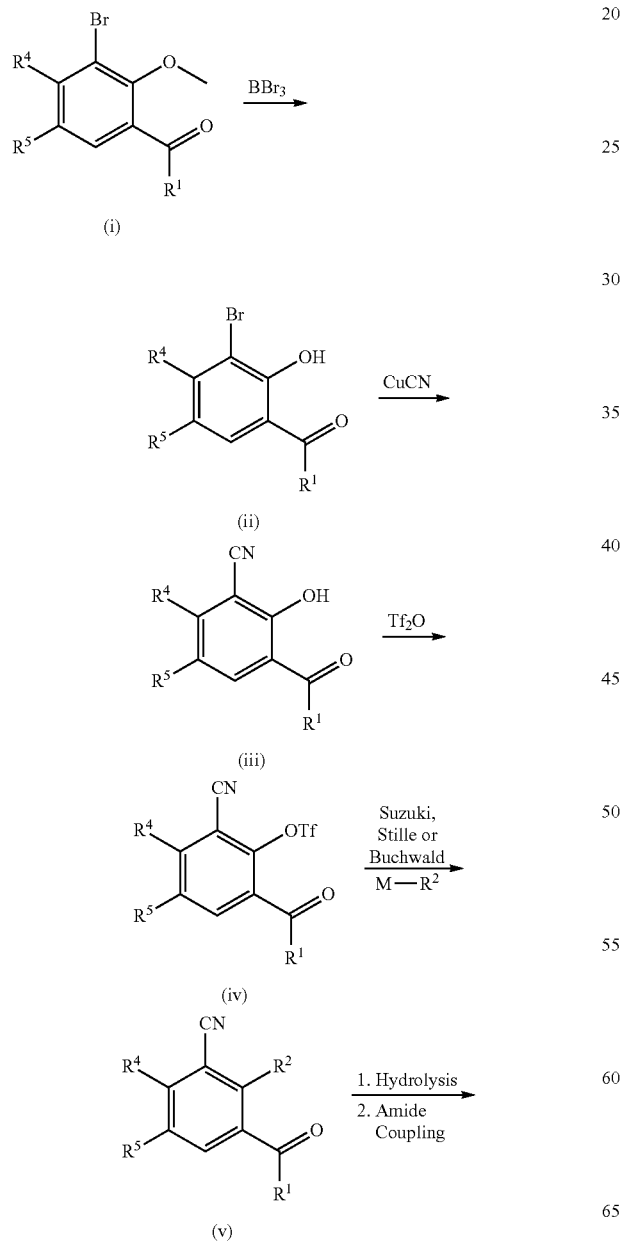

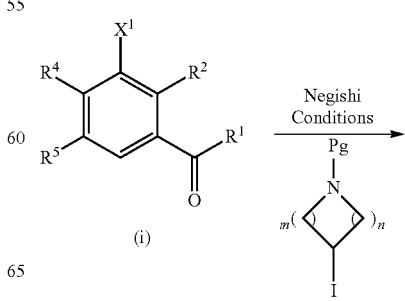

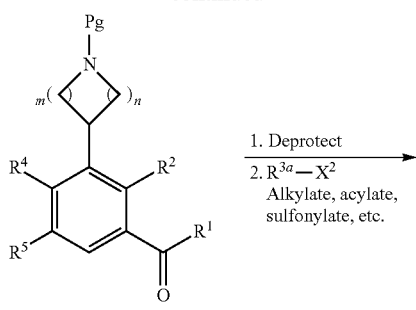

(ii)

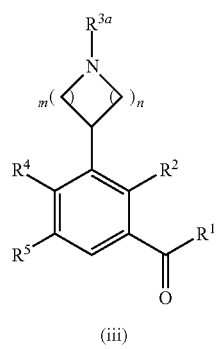

(iii)

Alternatively, compounds of Formula I can be formed as shown in Scheme Xa wherein the protected amino derivative (ii) can be reduced to the alcohol which can be converted to a leaving group (e.g., Lg=mesylate or halo, such as Cl or bromo) to give compounds of formula (iv). The leaving group of compound (iv) can be displaced with sodium azide to afford the azide derivative which can be reduced (e.g., trimethylphosphine or $H_2$ over Pd/C) to give the corresponding amino derivative (v). Purination of the amino derivative under standard conditions and subsequent removal of the nitrogen protecting group (e.g., Boc or Cbz) under a variety of standard conditions (e.g., TFA or HCl for Boc and $H_2$ over Pd/C for Cbz) can afford the free amine which can be further reacted under a variety of alkylating, arylating, acylating, sulfonylating conditions (e.g., $R^{3a}—X^1$; where $X^1$=halo and $R^{3a}$=alkyl, aryl, acyl, sulfonyl and a base, such as TEA) to give compounds of formula (vii). Removal of the purine protecting group, when present, can give compounds of Formula I.

Scheme Xa

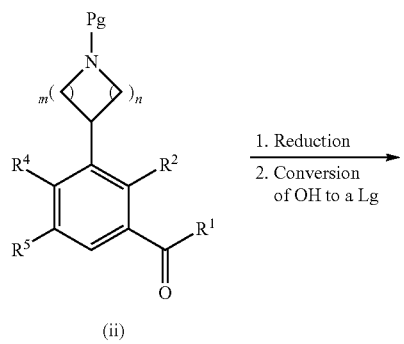

(ii)

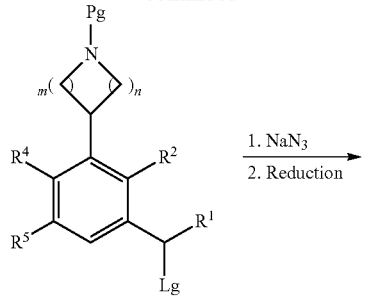

(iv)

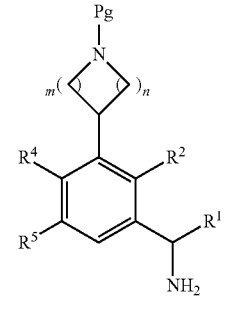

(v)

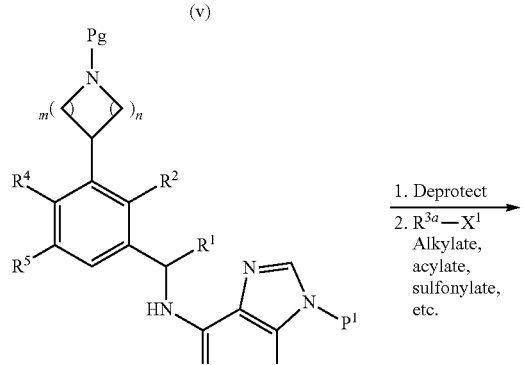

(vi)

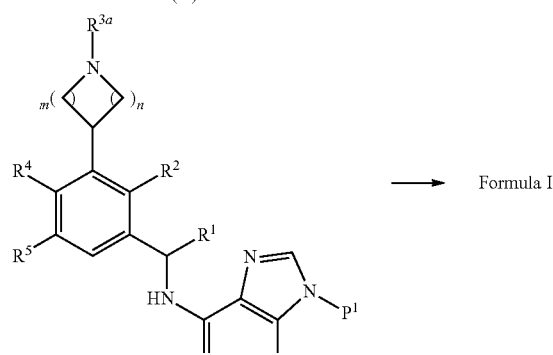

(vii)

Compounds of Formula I can be formed as shown in Scheme XI. The halo group, $X^1$, of (i) can be coupled to an alkene (e.g., acrylate or acrylamide) under standard Heck conditions (e.g., in the presence of a palladium(II) catalyst, such as palladium acetate)) to give an alkene of formula (ii). Reaction of alkene (ii) with nitromethane in the presence of DBU can afford the nitro derivative (iii) which can be reduced under standard conditions (e.g., $NiCl_2/NaBH_4$) to give the free amine that closes to form the lactam (iv). The lactam can be alkylated under standard conditions ($R^{3a}$—$X^2$; $X^2$=halo in the presence of a base, such as TEA or NaH) to give an N-alkyl-lactam (v). Compounds of formula (v) and pyrrolidines derived from the reduction of the lactam (v) with suitable reducing agents, such as $LiAlH_4$, can be converted to compounds of Formula I using conditions described in Scheme I.

Scheme XI

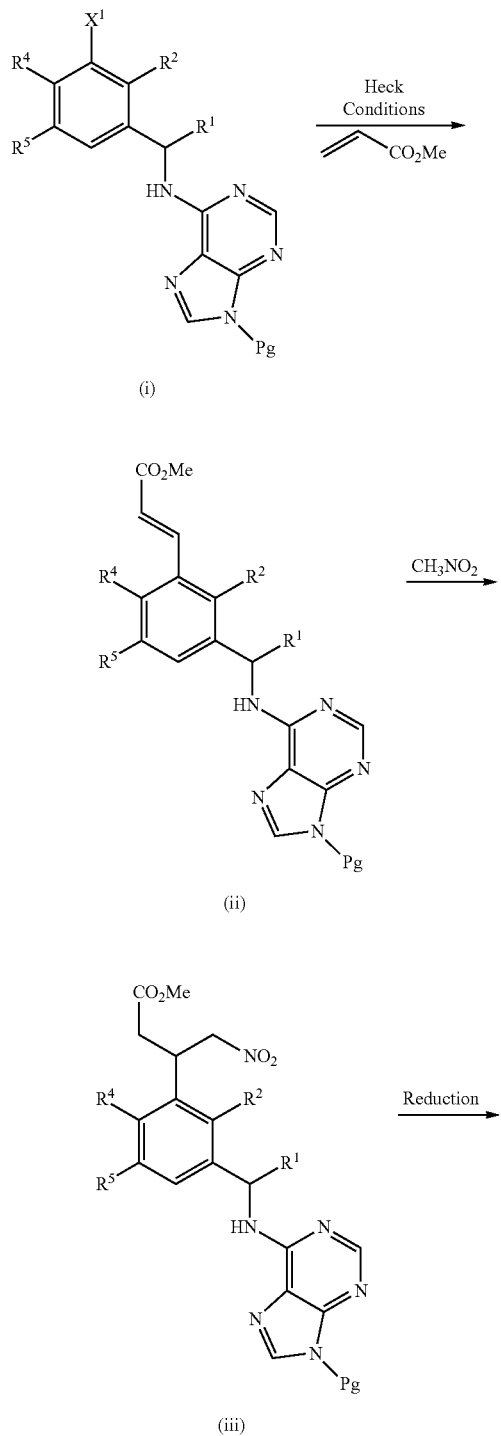

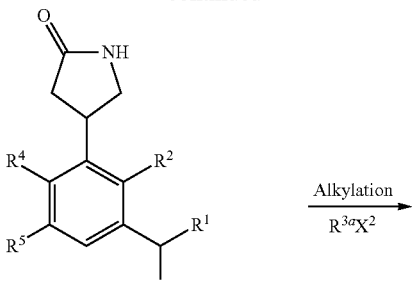

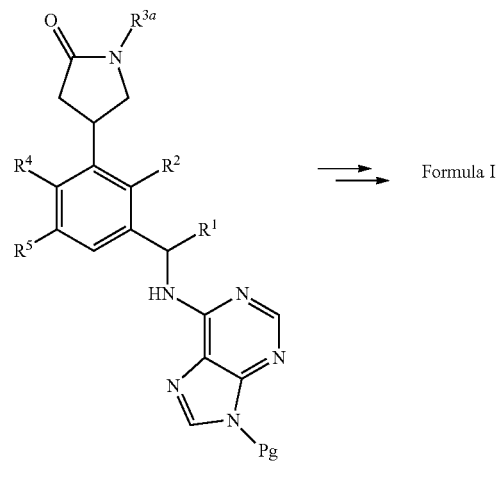

Compounds of Formula I can be formed as shown in Scheme XII. The halo group $X^1$ of (i) can be coupled to $R^3$-M, where M is an appropriately substituted metal (e.g., $R^3$-M is $R^3B(OH)_2$; appropriate non-limiting starting materials for generating $R^3$-M are shown in Scheme XII) under standard Suzuki conditions (e.g., in the presence of a palladium(0) catalyst, such as tetrakis(triphenylphosphine)palladium(0)) to give an alkene of formula (ii). Epoxidation of alkene (ii) with mCPBA can afford the epoxide (iii) which can be reacted with a secondary or primary amine (amine=NHR$^c$R$^d$; R$^c$=H for primary amine) to give amino compounds of formula (iv). Secondary or tertiary amine derivatives (iv) can be further reacted with carbonyldiamidazole or phosgene to form an oxazolidinone (v) or an acetyl-halide (e.g., chloro-acetylchloride in the presence of base, such as TEA) to give the N-acyl derivative which can be converted to the morpholinone derivative (vi) upon treatment with a base (e.g., NaH). Compounds of formula (iv, v, and vi) can be deprotected using standard conditions (e.g., Pg=THP then treat with an acid, such as TFA or HCl) to give compounds of Formula I.

Scheme XII
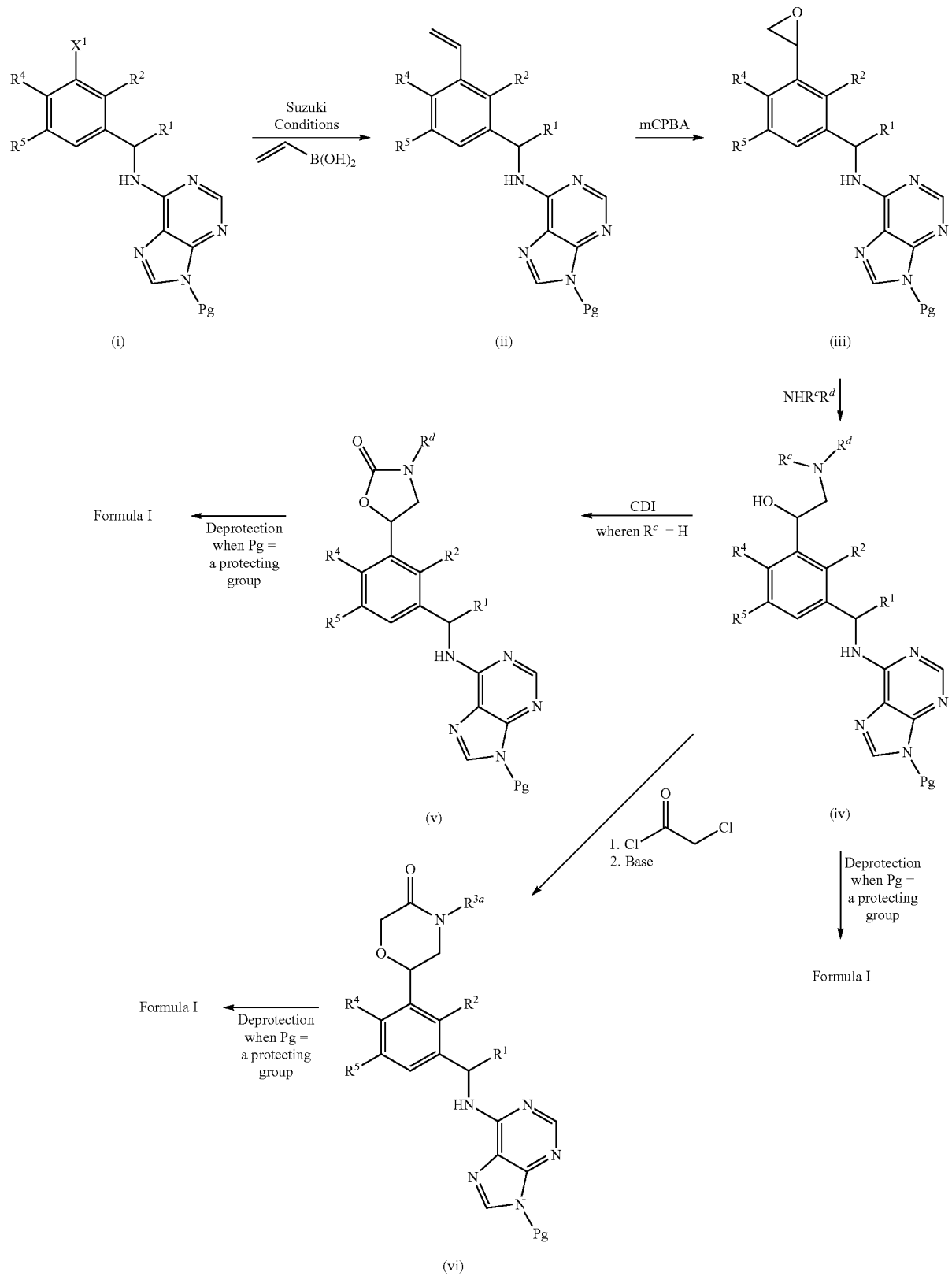

Compounds of Formula I can be synthesized as shown in Scheme XIII. The halo group (e.g., $X^1$=Cl, Br, I) of (i) can be converted to the boronic ester (ii) under standard conditions (e.g., pinnacle boronate ester in the presence of a palladium(0) catalyst, such as tetrakis(triphenylphosphine) palladium(0)) The boronate (ii) can be reacted with an arylhalide or heteroarylhalide (e.g., $R^3$—$X^2$) under Suzuki conditions (e.g., in the presence of a palladium(0) catalyst, such as tetrakis(triphenylphosphine)palladium(0) and a base, such as $Na_2CO_3$) to give compounds of formula (iii). Compounds of formula (iii) can be converted to compounds of Formula I using conditions described in Scheme I.

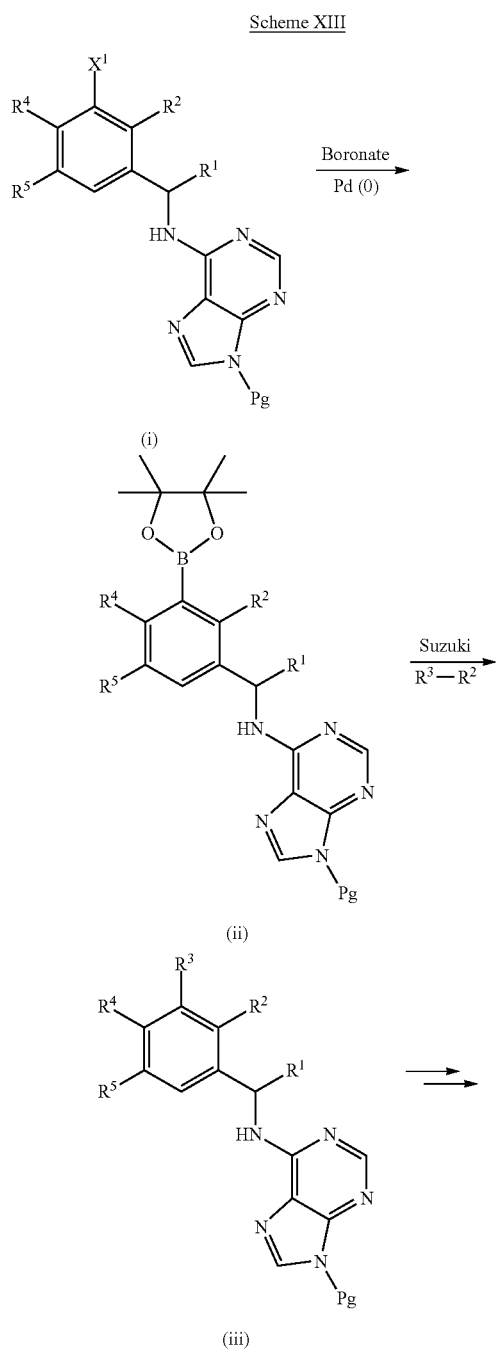

Scheme XIII

Methods

The compounds of the invention can modulate activity of one or more of various kinases including, for example, phosphoinositide 3-kinases (PI3Ks). The term "modulate" is meant to refer to an ability to increase or decrease the activity of one or more members of the PI3K family. Accordingly, the compounds of the invention can be used in methods of modulating a PI3K by contacting the PI3K with any one or more of the compounds or compositions described herein. In some embodiments, compounds of the present invention can act as inhibitors of one or more PI3Ks. In further embodiments, the compounds of the invention can be used to modulate activity of a PI3K in an individual in need of modulation of the receptor by administering a modulating amount of a compound of the invention, or a pharmaceutically acceptable salt thereof. In some embodiments, modulating is inhibiting.

Given that cancer cell growth and survival is impacted by multiple signaling pathways, the present invention is useful for treating disease states characterized by drug resistant kinase mutants. In addition, different kinase inhibitors, exhibiting different preferences in the kinases which they modulate the activities of, may be used in combination. This approach could prove highly efficient in treating disease states by targeting multiple signaling pathways, reduce the likelihood of drug-resistance arising in a cell, and reduce the toxicity of treatments for disease.

Kinases to which the present compounds bind and/or modulate (e.g., inhibit) include any member of the PI3K family. In some embodiments, the PI3K is PI3Kα, PI3Kβ, PI3Kγ, or PI3Kδ. In some embodiments, the PI3K is PI3Kγ or PI3Kδ. In some embodiments, the PI3K is PI3Kγ. In some embodiments, the PI3K is PI3Kδ. In some embodiments, the PI3K includes a mutation. A mutation can be a replacement of one amino acid for another, or a deletion of one or more amino acids. In such embodiments, the mutation can be present in the kinase domain of the PI3K.

In some embodiments, more than one compound of the invention is used to inhibit the activity of one kinase (e.g., PI3Kγ or PI3Kδ).

In some embodiments, more than one compound of the invention is used to inhibit more than one kinase, such as at least two kinases (e.g., PI3Kγ and PI3Kδ).

In some embodiments, one or more of the compounds is used in combination with another kinase inhibitor to inhibit the activity of one kinase (e.g., PI3Kγ or PI3Kδ).

In some embodiments, one or more of the compounds is used in combination with another kinase inhibitor to inhibit the activities of more than one kinase (e.g., PI3Kγ or PI3Kδ), such as at least two kinases.

The compounds of the invention can be selective. By "selective" is meant that the compound binds to or inhibits a kinase with greater affinity or potency, respectively, compared to at least one other kinase. In some embodiments, the compounds of the invention are selective inhibitors of PI3Kγ or PI3Kδ over PI3Kα and/or PI3Kβ. In some embodiments, the compounds of the invention are selective inhibitors of PI3Kδ (e.g., over PI3Kα, PI3Kβ and PI3Kγ). In some embodiments, the compounds of the invention are selective inhibitors of PI3Kγ (e.g., over PI3Kα, PI3Kβ and PI3Kδ). In some embodiments, selectivity can be at least about 2-fold, 5-fold, 10-fold, at least about 20-fold, at least about 50-fold, at least about 100-fold, at least about 200-fold, at least about 500-fold or at least about 1000-fold. Selectivity can be measured by methods routine in the art. In some embodiments, selectivity can be tested at the $K_m$ ATP concentration of each enzyme. In some embodiments, the selectivity of compounds of the invention can be determined by cellular assays associated with particular PI3K kinase activity.

Another aspect of the present invention pertains to methods of treating a kinase (such as PI3K)-associated disease or disorder in an individual (e.g., patient) by administering to the individual in need of such treatment a therapeutically effective amount or dose of one or more compounds of the present invention or a pharmaceutical composition thereof. A PI3K-associated disease can include any disease, disorder or condition that is directly or indirectly linked to expression or activity of the PI3K, including overexpression and/or abnormal activity levels. In some embodiments, the disease can be linked to Akt (protein kinase B), mammalian target of rapamycin (mTOR), or phosphoinositide-dependent kinase 1 (PDK1). In some embodiments, the mTOR-related disease can be inflammation, atherosclerosis, psoriasis, restenosis, benign prostatic hypertrophy, bone disorders, pancreatitis, angiogenesis, diabetic retinopathy, atherosclerosis, arthritis, immunological disorders, kidney disease, or cancer. A PI3K-associated disease can also include any disease, disorder or condition that can be prevented, ameliorated, or cured by modulating PI3K activity. In some embodiments, the disease is characterized by the abnormal activity of PI3K. In some embodiments, the disease is characterized by mutant PI3K. In such embodiments, the mutation can be present in the kinase domain of the PI3K.

Examples of PI3K-associated diseases include immune-based diseases involving the system including, for example, rheumatoid arthritis, allergy, asthma, glomerulonephritis, lupus, or inflammation related to any of the above.

Further examples of PI3K-associated diseases include cancers such as breast, prostate, colon, endometrial, brain, bladder, skin, uterus, ovary, lung, pancreatic, renal, gastric, or hematological cancer.

In some embodiments, the hematological cancer is acute myeloblastic leukemia (AML) or chronic myeloid leukemia (CML), or B cell lymphoma.

Further examples of PI3K-associated diseases include lung diseases such as acute lung injury (ALI) and adult respiratory distress syndrome (ARDS).

Further examples of PI3K-associated diseases include osteoarthritis, restenosis, atherosclerosis, bone disorders, arthritis, diabetic retinopathy, psoriasis, benign prostatic hypertrophy, inflammation, angiogenesis, pancreatitis, kidney disease, inflammatory bowel disease, myasthenia gravis, multiple sclerosis, or Sjögren's syndrome, and the like.

As used herein, the term "contacting" refers to the bringing together of indicated moieties in an in vitro system or an in vivo system. For example, "contacting" a PI3K with a compound of the invention includes the administration of a compound of the present invention to an individual or patient, such as a human, having a PI3K, as well as, for example, introducing a compound of the invention into a sample containing a cellular or purified preparation containing the PI3K.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician. In some embodiments, the dosage of the compound, or a pharmaceutically acceptable salt thereof, administered to a patient or individual is about 1 mg to about 2 g, or about 50 mg to about 500 mg.

As used herein, the term "treating" or "treatment" refers to one or more of (1) preventing the disease; for example, preventing a disease, condition or disorder in an individual who may be predisposed to the disease, condition or disorder but does not yet experience or display the pathology or symptomatology of the disease; (2) inhibiting the disease; for example, inhibiting a disease, condition or disorder in an individual who is experiencing or displaying the pathology or symptomatology of the disease, condition or disorder (i.e., arresting further development of the pathology and/or symptomatology); and (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

Combination Therapies

One or more additional pharmaceutical agents such as, for example, chemotherapeutics, anti-inflammatory agents, steroids, immunosuppressants, as well as Bcr-Abl, Flt-3, EGFR, HER2, JAK, c-MET, VEGFR, PDGFR, cKit, IGF-1R, RAF and FAK kinase inhibitors such as, for example, those described in WO 2006/056399, or other agents such as, therapeutic antibodies can be used in combination with the compounds of the present invention for treatment of PI3K-associated diseases, disorders or conditions. The one or more additional pharmaceutical agents can be administered to a patient simultaneously or sequentially.

Example antibodies for use in combination therapy include but are not limited to Trastuzumab (e.g. anti-HER2), Ranibizumab (e.g. anti-VEGF-A), Bevacizumab (trade name Avastin, e.g. anti-VEGF, Panitumumab (e.g. anti-EGFR), Cetuximab (e.g. anti-EGFR), Rituxan (anti-CD20) and antibodies directed to c-MET.

One or more of the following agents may be used in combination with the compounds of the present invention and are presented as a non limiting list: a cytostatic agent, cisplatin, doxorubicin, taxotere, taxol, etoposide, irinotecan, camptostar, topotecan, paclitaxel, docetaxel, epothilones, tamoxifen, 5-fluorouracil, methoxtrexate, temozolomide, cyclophosphamide, SCH 66336, R115777, L778,123, BMS 214662, Iressa, Tarceva, antibodies to EGFR, Gleevec™, intron, ara-C, adriamycin, cytoxan, gemcitabine, Uracil mustard, Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, oxaliplatin, leucovirin, ELOXATIN™, Pentostatine, Vinblastine, Vincristine, Vindesine, Bleomycin, Dactinomycin, Daunorubicin, Doxorubicin, Epirubicin, Idarubicin, Mithramycin, Deoxycoformycin, Mitomycin-C, L-Asparaginase, Teniposide 17.alpha.-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Cisplatin, Carboplatin, Hydroxyurea, Amsacrine, Procarbazine, Mitotane, Mitoxantrone, Levamisole, Navelbene, Anastrazole, Letrazole, Capecitabine, Reloxafine, Droloxafine, Hexamethylmelamine, Avastin, herceptin, Bexxar, Velcade, Zevalin, Trisenox, Xeloda, Vinorelbine, Porfimer, Erbitux, Liposomal, Thiotepa, Altretamine, Melphalan, Trastuzumab, Lerozole, Fulvestrant, Exemestane, Fulvestrant, Ifosfomide, Rituximab, C225, Campath, Clofarabine, cladribine, aphidicolon, rituxan, sunitinib, dasatinib, tezacitabine, Sml1, fludarabine, pentostatin, triapine, didox, trimidox, amidox, 3-AP, MDL-101,731, and bendamustine (Treanda).

Example chemotherapeutics include proteosome inhibitors (e.g., bortezomib), thalidomide, revlimid, and DNA-damaging agents such as melphalan, doxorubicin, cyclophosphamide, vincristine, etoposide, carmustine, and the like.

Example steroids include coriticosteroids such as dexamethasone or prednisone.

Example Bcr-Abl inhibitors include the compounds, and pharmaceutically acceptable salts thereof, of the genera and species disclosed in U.S. Pat. No. 5,521,184, WO 04/005281, and U.S. Ser. No. 60/578,491.

Example suitable Flt-3 inhibitors include compounds, and their pharmaceutically acceptable salts, as disclosed in WO 03/037347, WO 03/099771, and WO 04/046120.

Example suitable RAF inhibitors include compounds, and their pharmaceutically acceptable salts, as disclosed in WO 00/09495 and WO 05/028444.

Example suitable FAK inhibitors include compounds, and their pharmaceutically acceptable salts, as disclosed in WO 04/080980, WO 04/056786, WO 03/024967, WO 01/064655, WO 00/053595, and WO 01/014402.

In some embodiments, the compounds of the invention can be used in combination with one or more other kinase inhibitors including imatinib, particularly for treating patients resistant to imatinib or other kinase inhibitors.

In some embodiments, the compounds of the invention can be used in combination with a chemotherapeutic in the treatment of cancer, such as multiple myeloma, and may improve the treatment response as compared to the response to the chemotherapeutic agent alone, without exacerbation of its toxic effects. Examples of additional pharmaceutical agents used in the treatment of multiple myeloma, for example, can include, without limitation, melphalan, melphalan plus prednisone [MP], doxorubicin, dexamethasone, and Velcade (bortezomib). Further additional agents used in the treatment of multiple myeloma include Bcr-Abl, Flt-3, RAF and FAK kinase inhibitors. Additive or synergistic effects are desirable outcomes of combining a PI3K inhibitor of the present invention with an additional agent. Furthermore, resistance of multiple myeloma cells to agents such as dexamethasone may be reversible upon treatment with the PI3K inhibitor of the present invention. The agents can be combined with the present compound in a single or continuous dosage form, or the agents can be administered simultaneously or sequentially as separate dosage forms.

In some embodiments, a corticosteroid such as dexamethasone is administered to a patient in combination with the compounds of the invention where the dexamethasone is administered intermittently as opposed to continuously.

In some further embodiments, combinations of the compounds of the invention with other therapeutic agents can be administered to a patient prior to, during, and/or after a bone marrow transplant or stem cell transplant.

Pharmaceutical Formulations and Dosage Forms

When employed as pharmaceuticals, the compounds of the invention can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, the compound of the invention or a pharmaceutically acceptable salt thereof, in combination with one or more pharmaceutically acceptable carriers (excipients). In some embodiments, the composition is suitable for topical administration. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

The compounds of the invention may be milled using known milling procedures such as wet milling to obtain a particle size appropriate for tablet formation and for other formulation types. Finely divided (nanoparticulate) preparations of the compounds of the invention can be prepared by processes known in the art, e.g., see International App. No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 1000 mg (1 g), more usually about 100 to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

In some embodiments, the compositions of the invention contain from about 5 to about 50 mg of the active ingredient. One having ordinary skill in the art will appreciate that this embodies compositions containing about 5 to about 10, about 10 to about 15, about 15 to about 20, about 20 to about 25, about 25 to about 30, about 30 to about 35, about 35 to about 40, about 40 to about 45, or about 45 to about 50 mg of the active ingredient.

In some embodiments, the compositions of the invention contain from about 50 to about 500 mg of the active ingredient. One having ordinary skill in the art will appreciate that this embodies compositions containing about 50 to about 100, about 100 to about 150, about 150 to about 200, about 200 to about 250, about 250 to about 300, about 350 to about 400, or about 450 to about 500 mg of the active ingredient.

In some embodiments, the compositions of the invention contain from about 500 to about 1000 mg of the active ingredient. One having ordinary skill in the art will appreciate that this embodies compositions containing about 500 to about 550, about 550 to about 600, about 600 to about 650, about 650 to about 700, about 700 to about 750, about 750 to about 800, about 800 to about 850, about 850 to about 900, about 900 to about 950, or about 950 to about 1000 mg of the active ingredient.

Similar dosages may be used of the compounds described herein in the methods and uses of the invention.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, for example, liquid paraffin, polyoxyethylene alkyl ether, propylene glycol, white Vaseline, and the like. Carrier compositions of creams can be based on water in combination with glycerol and one or more other components, e.g. glycerinemonostearate, PEG-glycerinemonostearate and cetylstearyl alcohol. Gels can be formulated using isopropyl alcohol and water, suitably in combination with other components such as, for example, glycerol, hydroxyethyl cellulose, and the like. In some embodiments, topical formulations contain at least about 0.1, at least about 0.25, at least about 0.5, at least about 1, at least about 2, or at least about 5 wt % of the compound of the invention. The topical formulations can be suitably packaged in tubes of, for example, 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of a compound of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 g/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compositions of the invention can further include one or more additional pharmaceutical agents such as a chemotherapeutic, steroid, anti-inflammatory compound, or immunosuppressant, examples of which are listed herein.

Labeled Compounds and Assay Methods

Another aspect of the present invention relates to labeled compounds of the invention (radio-labeled, fluorescent-labeled, etc.) that would be useful not only in imaging techniques but also in assays, both in vitro and in vivo, for localizing and quantitating PI3K in tissue samples, including human, and for identifying PI3K ligands by inhibition binding of a labeled compound. Accordingly, the present invention includes PI3K assays that contain such labeled compounds.

The present invention further includes isotopically-labeled compounds of the invention. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^{3}H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$ and $^{131}I$. The radionuclide that is incorporated in the instant radio-labeled compounds will depend on the specific application of that radio-labeled compound. For example, for in vitro PI3K labeling and competition assays, compounds that incorporate $^{3}H$, $^{14}C$, $^{82}Br$, $^{125}I$, $^{131}I$, $^{35}S$ or will generally be most useful. For radio-imaging applications $^{11}C$, $^{18}F$, $^{125}I$, $^{123}I$, $^{124}I$, $^{131}I$, $^{75}Br$, $^{76}Br$ or $^{77}Br$ will generally be most useful.

It is understood that a "radio-labeled" or "labeled compound" is a compound that has incorporated at least one radionuclide. In some embodiments the radionuclide is selected from the group consisting of $^{3}H$, $^{14}C$, $^{125}I$, $^{35}S$ and $^{82}Br$. In some embodiments, one or more H atoms for any compound described herein is each replaced by a deuterium atom.

The present invention can further include synthetic methods for incorporating radio-isotopes into compounds of the invention. Synthetic methods for incorporating radio-isotopes into organic compounds are well known in the art, and an ordinary skill in the art will readily recognize the methods applicable for the compounds of invention.

A labeled compound of the invention can be used in a screening assay to identify/evaluate compounds. For example, a newly synthesized or identified compound (i.e., test compound) which is labeled can be evaluated for its ability to bind a PI3K by monitoring its concentration variation when contacting with the PI3K, through tracking of the labeling. For example, a test compound (labeled) can be evaluated for its ability to reduce binding of another compound which is known to bind to a PI3K (i.e., standard compound). Accordingly, the ability of a test compound to compete with the standard compound for binding to the PI3K directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

Kits

The present invention also includes pharmaceutical kits useful, for example, in the treatment or prevention of PI3K-associated diseases or disorders, such as cancer, which include one or more containers containing a pharmaceutical composition comprising a therapeutically effective amount of a compound of the invention. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples have been found to be PI3K inhibitors according to at least one assay described herein.

EXAMPLES

The example compounds below containing one or more chiral centers were obtained in racemate form or as isomeric mixtures, unless otherwise specified. At points throughout the Examples, the stereochemistry at the carbon attached to $R^1$ has been indicated, as currently understood.

Example 1

4-Chloro-3'-fluoro-3-methyl-6-[1-(9H-purin-6-ylamino)ethyl]biphenyl-2-carbonitrile

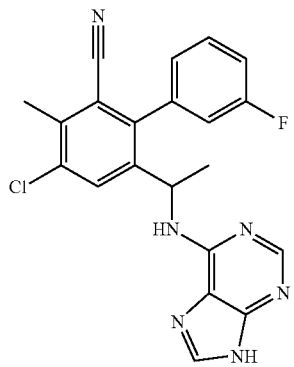 [SMILES: Cc1c(Cl)cc(C(C)Nc2ncnc3[nH]cnc23)c(-c2cccc(F)c2)c1C#N]

Step 1. 1-(3-Bromo-5-chloro-2-hydroxy-4-methyl-phenyl)ethanone

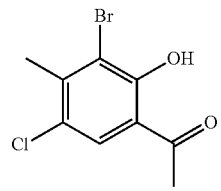

To a mixture of 1-(3-bromo-5-chloro-2-methoxy-4-methylphenyl)ethanone (1.0 g, 3.6 mmol) in methylene chloride (20 mL) was added 1.0 M boron tribromide in methylene chloride (3.8 mL, 3.8 mmol) at −78° C. After stirring at −78° C. for 10 minutes, the reaction was allowed to warm to 0° C. and was then quenched with water at 0° C. and extracted with dichloromethane. The combined organic layers were washed with brine and dried over sodium sulfate. The volatiles were removed under reduced pressure to afford 1-(3-Bromo-5-chloro-2-hydroxy-4-methylphenyl)ethanone (0.91 g, 96%). $^1$H NMR (CDCl$_3$, 300 MHz) δ 12.96 (1H, s), 7.72 (1H, s), 2.64 (3H, s), 2.59 (3H, s) ppm.

Step 2.
3-Acetyl-5-chloro-2-hydroxy-6-methylbenzonitrile

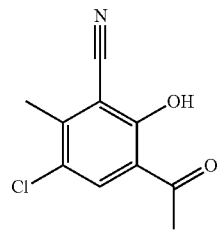

A mixture of 1-(3-bromo-5-chloro-2-hydroxy-4-methylphenyl)ethanone (4.9 g, 18 mmol) and copper cyanide (2.5 g, 28 mmol) in N-methylpyrrolidinone (15 mL) was heated at 200° C. for 1 hour. The resulting mixture was allowed to cool to room temperature and was then diluted with ethyl acetate and 1 N HCl. The organic and aqueous layers were separated and the aqueous layer was extracted with ethyl acetate. The combined organic layers were washed with water and brine, dried over magnesium sulfate and concentrated to dryness under reduced pressure to give 3-Acetyl-5-chloro-2-hydroxy-6-methylbenzonitrile (3.7 g, 96%). LCMS calculated for C$_{10}$H$_9$ClNO$_2$ (M+H)$^+$: m/z=210.0. found: 210.1.

Step 3. 6-Acetyl-4-chloro-2-cyano-3-methylphenyl trifluoromethanesulfonate

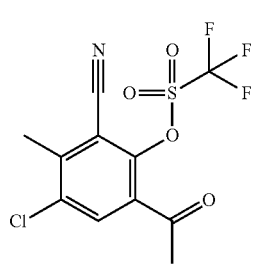 [SMILES: CC(=O)c1cc(Cl)c(C)c(C#N)c1OS(=O)(=O)C(F)(F)F]

To a mixture of 3-acetyl-5-chloro-2-hydroxy-6-methylbenzonitrile (3.7 g, 18 mmol) in methylene chloride (70 mL) was added triethylamine (7.4 mL, 53 mmol) and trifluoromethanesulfonic anhydride (4.4 mL, 26 mmol) at −78° C. The reaction mixture was allowed to warm to room temperature gradually and then stirred at room temperature for 30 minutes. The mixture was quenched with water and extracted with dichloromethane. The combined organic layers were washed with brine, dried over sodium sulfate, and concentrated to dryness. The resulting residue was purified on silica gel, eluting with 0 to 40% ethyl acetate in hexane, to give the desired product (2.54 g, 42% isolated yield for 3 steps). LCMS calculated for C$_{11}$H$_8$ClF$_3$NO$_4$S (M+H)$^+$: m/z=342.0. found: 342.1.

Step 4. 6-Acetyl-4-chloro-3'-fluoro-3-methylbiphenyl-2-carbonitrile

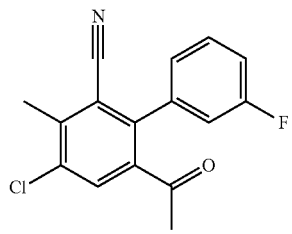 [SMILES: CC(=O)c1cc(Cl)c(C)c(C#N)c1-c1cccc(F)c1]

A biphasic solution of 6-acetyl-4-chloro-2-cyano-3-methylphenyl trifluoromethanesulfonate (2.54 g, 7.4 mmol) and (3-fluorophenyl)boronic acid (1.6 g, 11 mmol) in toluene (70 mL) and saturated sodium bicarbonate (70 mL) was bubbled with N$_2$ to degas. After tetrakis(triphenylphosphine)palladium(0) (0.43 g, 0.37 mmol) was added, the mixture was bubbled with N$_2$ for 5 min. more and then heated at 80° C. for 2 hours. After cool to room temperature, the mixture was diluted with ethyl acetate. The layers were separated and the aq. layer was extracted with more ethyl acetate. The combined extracts were washed with brine, dried over Na$_2$SO$_4$, filtered, and concentrated. The residue was purified on silica gel column, eluting with 0 to 40% ethyl acetate in hexane, to give the desired product (2.1 g, 99%). LCMS calculated for C$_{16}$H$_{12}$ClFNO (M+H)$^+$: m/z=288.1. found: 288.1.

Step 5. 6-(1-Aminoethyl)-4-chloro-3'-fluoro-3-methylbiphenyl-2-carbonitrile

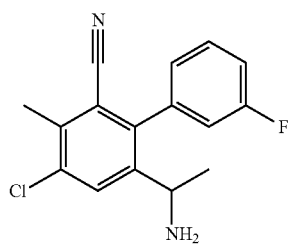 [SMILES: Cc1c(Cl)cc(C(C)N)c(-c2cccc(F)c2)c1C#N]

A mixture of 6-acetyl-4-chloro-3'-fluoro-3-methylbiphenyl-2-carbonitrile (50 mg, 0.2 mmol) and ammonium acetate (130 mg, 1.7 mmol) in methanol (0.98 mL) and acetonitrile (0.99 mL) was heated at 65° C. in a sealed tube for 30 min. After the mixture was cooled, sodium cyanoborohydride (22 mg, 0.35 mmol) was added. The reaction was heated at 65° C. for another 4 hours, then cooled to room temperature and quenched with saturated sodium bicarbonate and extracted with dichloromethane. The combined extracts were dried over magnesium sulfate and evaporated to dryness. The residue was used directly in next step. LCMS calculated for $C_{16}H_{15}ClFN_2$ (M+H)$^+$: m/z=289.1. found: 289.1.

Step 6. 4-Chloro-3'-fluoro-3-methyl-6-[1-(9H-purin-6-ylamino)ethyl]biphenyl-2-carbonitrile

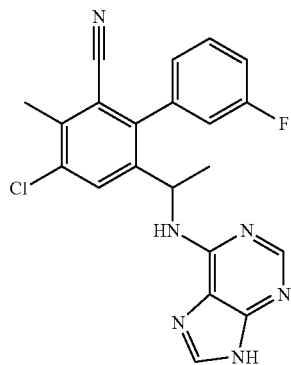 [SMILES: Cc1c(Cl)cc(C(C)Nc2ncnc3[nH]cnc23)c(-c2cccc(F)c2)c1C#N]

A mixture of 6-bromo-9H-purine (41 mg, 0.21 mmol), 6-(1-aminoethyl)-4-chloro-3'-fluoro-3-methylbiphenyl-2-carbonitrile (50 mg, 0.2 mmol), and N,N-diisopropylethylamine (0.060 mL, 0.35 mmol) in isopropyl alcohol (0.7 mL) was heated at 90° C. under nitrogen overnight. The mixture was evaporated and the resulting mixture was purified on RP-HPLC (XBridge C18 Column, eluting with a gradient of acetonitrile in water with 0.2% ammonium hydroxide, at flow rate of 30 mL/min) to give the desired product. LCMS calculated for $C_{21}H_{17}ClFN_6$ (M+H)$^+$: m/z=407.1. found: 407.1.

Example 2

4-Chloro-3'-fluoro-3-methyl-6-[1-(9H-purin-6-ylamino)ethyl]biphenyl-2-carboxamide

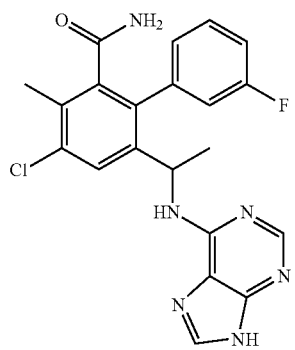 [SMILES: Cc1c(Cl)cc(C(C)Nc2ncnc3[nH]cnc23)c(-c2cccc(F)c2)c1C(N)=O]

Step 1. 6-Acetyl-4-chloro-3'-fluoro-3-methylbiphenyl-2-carboxamide

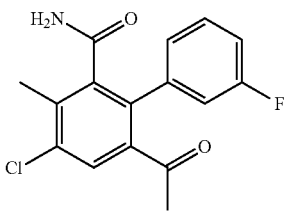 [SMILES: CC(=O)c1cc(Cl)c(C)c(C(N)=O)c1-c1cccc(F)c1]

A mixture of 6-acetyl-4-chloro-3'-fluoro-3-methylbiphenyl-2-carbonitrile (0.87 g, 3.0 mmol) and potassium hydroxide (0.34 g, 6.1 mmol) in ethanol (4 mL) was refluxed for 2 hours. The mixture was cooled, acidified with 1 N HCl, and extracted with ethyl acetate. The combined organic layers were washed with brine, dried over magnesium sulfate, and evaporated to dryness under reduced pressure to yield the crude product. LCMS calculated for $C_{16}H_{14}ClFNO_2$ (M+H)$^+$: m/z=306.1. found: 306.0.

Step 2. 6-(1-Aminoethyl)-4-chloro-3'-fluoro-3-methylbiphenyl-2-carboxamide

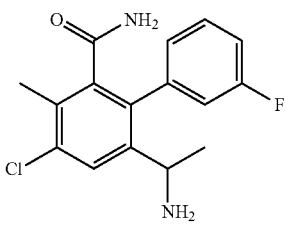 [SMILES: Cc1c(Cl)cc(C(C)N)c(-c2cccc(F)c2)c1C(N)=O]

A mixture of 6-acetyl-4-chloro-3'-fluoro-3-methylbiphenyl-2-carboxamide (110 mg, 0.34 mmol) and ammonium acetate (270 mg, 3.4 mmol) in methanol (1.9 mL) and acetonitrile (2.0 mL) was heated at 65° C. in a sealed tube for 30 min. The mixture was cooled and sodium cyanoborohydride (43 mg, 0.69 mmol) was added. The reaction was heated at 65° C. for another 4 hours. The mixture was cooled, quenched with saturated sodium bicarbonate, and extracted with dichloromethane. The combined extracts were dried over magnesium sulfate and evaporated to dryness. The residue was used directly in next step (98 mg, 93%). LCMS calculated for $C_{16}H_{17}ClFN_2O$ (M+H)$^+$: m/z=307.1. found: 306.9.

Step 3. 4-Chloro-3'-fluoro-3-methyl-6-[1-(9H-purin-6-ylamino)ethyl]biphenyl-2-carboxamide

A mixture of 6-bromo-9H-purine (110 mg, 0.56 mmol), 6-(1-aminoethyl)-4-chloro-3'-fluoro-3-methylbiphenyl-2-carboxamide (0.086 g, 0.28 mmol), and N,N-diisopropylethylamine (0.16 mL, 0.94 mmol) in isopropyl alcohol (2 mL) was heated at 90° C. under nitrogen overnight. The mixture was evaporated and the resulting mixture was purified on RP-HPLC (XBridge C18 Column, eluting with a gradient of acetonitrile in water with 0.2% ammonium hydroxide, at flow rate of 30 mL/min) to give the desired product (49 mg, 41%). LCMS calculated for $C_{21}H_{19}ClFN_6O$ (M+H)$^+$: m/z=425.1. found: 425.0.

Example 3

N-[1-(4-chloro-3'-fluoro-5-methyl-6-nitrobiphenyl-2-yl)ethyl]-9H-purin-6-amine

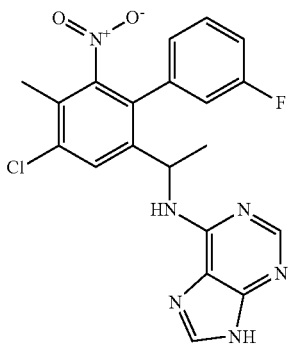 [SMILES: Cc1c(Cl)cc(C(C)Nc2ncnc3[nH]cnc23)c(-c2cccc(F)c2)c1[N+](=O)[O-]]

Step 1. 1-(5-Chloro-2-hydroxy-4-methyl-3-nitrophenyl)ethanone

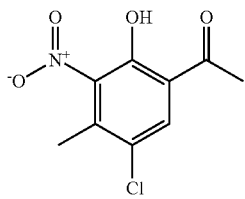

To a mixture of 1-(5-chloro-2-methoxy-4-methyl-3-nitrophenyl)ethanone (8.9 g, 37 mmol, from Oakwood) in methylene chloride (200 mL) was added 1.0 M boron tribromide in methylene chloride (38.4 mL, 38.4 mmol) at −78° C. After stirring at −78° C. for 10 minutes, the reaction was allowed to warm up to 0° C., quenched with water at 0° C., and extracted with dichloromethane. The combined organic layers were washed with brine, dried over sodium sulfate and filtered. After evaporating to dryness under reduced pressure, the residue was used directly in next step (8.2 g, 98%). LCMS calculated for $C_9H_9ClNO_4$ (M+H)$^+$: m/z=230.0. found: 230.1.

Step 2. 6-Acetyl-4-chloro-3-methyl-2-nitrophenyl trifluoromethanesulfonate

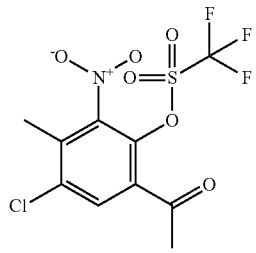

To a mixture of 1-(5-chloro-2-hydroxy-4-methyl-3-nitrophenyl)ethanone (8.6 g, 37 mmol) in methylene chloride (200 mL) was added triethylamine (16 mL, 110 mmol) followed by trifluoromethanesulfonic anhydride (9.4 mL, 56 mmol) at −78° C. The reaction was allowed to warm up to room temperature gradually and stirred at room temperature for 30 min. The mixture was quenched with water and extracted with dichloromethane. The combined organic layers were washed with brine, dried over sodium sulfate, and concentrated to dryness. The residue was purified on silica gel, eluting with 0 to 30% ethyl acetate in hexane, to give the desired product (11 g, 78% isolated yield for 2 steps). LCMS calculated for $C_{10}H_8ClF_3NO_6S$ (M+H)$^+$: m/z=362.0. found: 362.1.

Step 3. 1-(4-Chloro-3'-fluoro-5-methyl-6-nitrobiphenyl-2-yl)ethanone

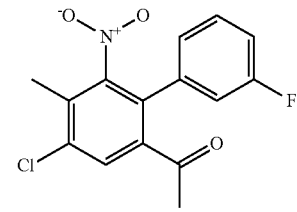

A biphasic solution of 6-acetyl-4-chloro-3-methyl-2-nitrophenyl trifluoromethanesulfonate (3.0 g, 8.3 mmol), (3-fluorophenyl)boronic acid (1.7 g, 12 mmol) in toluene (80 mL) and saturated sodium bicarbonate in water (80 mL) was bubbled with $N_2$ to degas. After tetrakis(triphenylphosphine)palladium(0) (0.48 g, 0.42 mmol) was added, the mixture was bubbled with $N_2$ for 5 min. more and heated at 80° C. for 2 hours. After cooling to r.t., the mixture was diluted with ethyl acetate. The layers were separated and the aq. layer was extracted with more ethyl acetate. The combined extracts were washed with brine, dried over $Na_2SO_4$, filtered, and concentrated. The residue was purified on silica gel column, eluting with 0 to 30% ethyl acetate in hexane, to give the desired product (2.35 g, 92%). LCMS calculated for $C_{15}H_{12}ClFNO_3$ (M+H)$^+$: m/z=308.0. found: 308.1.

Step 4. 1-(4-Chloro-3'-fluoro-5-methyl-6-nitrobiphenyl-2-yl)ethanamine

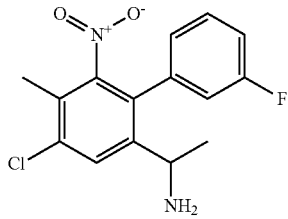 [SMILES: Cc1c(Cl)cc(C(C)N)c(-c2cccc(F)c2)c1[N+](=O)[O-]]

A mixture of 1-(4-chloro-3'-fluoro-5-methyl-6-nitrobiphenyl-2-yl)ethanone (50 mg, 0.2 mmol) and ammonium acetate (130 mg, 1.7 mmol) in methanol (1 mL) and acetonitrile (1 mL) was heated at 65° C., in a sealed tube, for 30 min. The mixture was cooled to room temperature and sodium cyanoborohydride (22 mg, 0.35 mmol) was added. The reaction was heated at 65° C. for another 4 hours, cooled to room temperature, quenched with saturated sodium bicarbonate, and extracted with dichloromethane. The combined extracts were dried over magnesium sulfate and evaporated to dryness. The residue was used directly in next step. LCMS calculated for $C_{15}H_{15}ClFN_2O_2$ (M+H)$^+$: m/z=309.1. found: 309.1.

Step 5. N-[1-(4-chloro-3'-fluoro-5-methyl-6-nitrobiphenyl-2-yl)ethyl]-9H-purin-6-amine

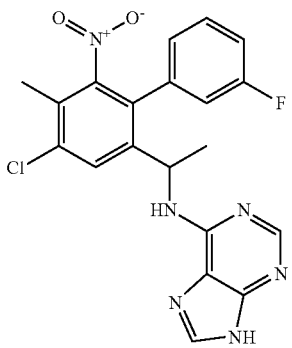 [SMILES: Cc1c(Cl)cc(C(C)Nc2ncnc3[nH]cnc23)c(-c2cccc(F)c2)c1[N+](=O)[O-]]

A mixture of 6-bromo-9H-purine (41 mg, 0.21 mmol), 1-(4-chloro-3'-fluoro-5-methyl-6-nitrobiphenyl-2-yl)ethanamine (54 mg, 0.17 mmol), and N,N-diisopropylethylamine (0.06 mL, 0.35 mmol) in isopropyl alcohol (0.7 mL) was heated at 90° C. under nitrogen overnight. The mixture was evaporated and the resulting mixture was purified on RP-HPLC (XBridge C18 Column, eluting with a gradient of acetonitrile in water with 0.2% ammonium hydroxide, at flow rate of 30 mL/min) to give the desired product. LCMS calculated for $C_{20}H_{17}ClFN_6O_2$ (M+H)$^+$: m/z=427.1. found: 427.1.

Example 4

4-Chloro-3-(cyanomethyl)-3'-fluoro-6-[1-(9H-purin-6-ylamino)ethyl]biphenyl-2-carbonitrile

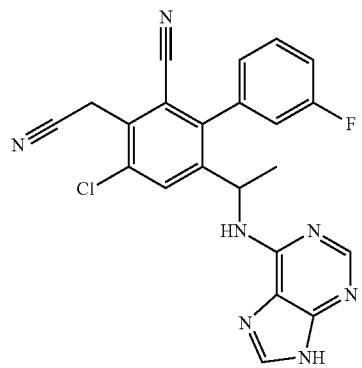 [SMILES: CC(Nc1ncnc2[nH]cnc12)c1cc(Cl)c(CC#N)c(C#N)c1-c1cccc(F)c1]

Step 1. 1-[3-Bromo-4-(bromomethyl)-5-chloro-2-methoxyphenyl]ethanone

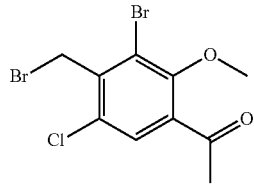

A mixture of 1-(3-bromo-5-chloro-2-methoxy-4-methylphenyl)ethanone (3.3 g, 12 mmol), N-bromosuccinimide (2.2 g, 13 mmol), and benzoyl peroxide (0.15 g, 0.60 mmol) in carbon tetrachloride (50 mL) was heated at reflux overnight. The mixture was cooled to room temperature and concentrated. The resulting residue was diluted with ethyl acetate and washed with water. The organic layers were dried over magnesium sulfate and evaporated to dryness. The crude product was used directly in next step. LCMS calculated for $C_{10}H_{10}Br_2ClO_2$ (M+H)$^+$: m/z=355.1. found: 355.1.

Step 2. 6-Acetyl-4-chloro-3-(cyanomethyl)-3'-fluorobiphenyl-2-carbonitrile

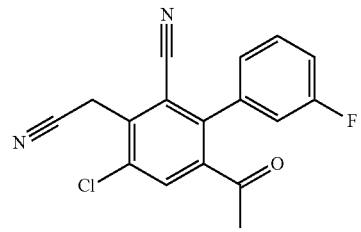 [SMILES: CC(=O)c1cc(Cl)c(CC#N)c(C#N)c1-c1cccc(F)c1]

To a mixture of sodium cyanide (100 mg, 2.0 mmol) in water (0.5 mL) was added sulfuric acid (0.95 g, 0.97 mmol) at 0° C. (the reaction generates hydrogen cyanide and must be run in a fume hood with good ventilation), followed by a solution of 6-acetyl-3-(bromomethyl)-4-chloro-3'-fluoro-biphenyl-2-carbonitrile (70 mg, 0.2 mmol) in acetonitrile (2 mL). The reaction was heated at 80° C. for 1 hour with pH adjustment to 9 by addition of solid sodium cyanide. The reaction mixture was cooled and extracted with ethyl acetate. The combined organic layers were washed with brine, dried over sodium sulfate and concentrated to dryness under reduced pressure. The residue was purified on silica gel, eluting with 0 to 40% ethyl acetate in hexane. LCMS calculated for $C_{17}H_{11}ClFN_2O$ (M+H)$^+$: m/z=313.1. found: 313.1.

Step 3. 6-(1-Aminoethyl)-4-chloro-3-(cyanomethyl)-3'-fluorobiphenyl-2-carbonitrile

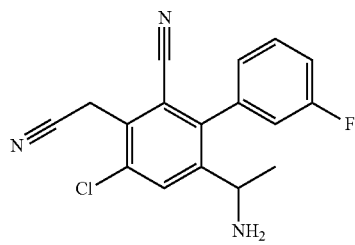 [SMILES: CC(N)c1cc(Cl)c(CC#N)c(C#N)c1-c1cccc(F)c1]

A mixture of 6-acetyl-4-chloro-3-(cyanomethyl)-3'-fluorobiphenyl-2-carbonitrile (0.020 g, 0.064 mmol) and ammonium acetate (49 mg, 0.64 mmol) in methanol (0.4 mL) and acetonitrile (0.4 mL) was heated at 65° C. in a sealed tube for 30 min. The mixture was cooled to room temperature and sodium cyanoborohydride (8 mg, 0.13 mmol) was added. The reaction was heated at 65° C. for another 4 hours, cooled to room temperature, quenched with saturated sodium bicarbonate and extracted with dichloromethane. The combined extracts were dried over magnesium sulfate and evaporated to dryness. The residue was used directly in next step (20 mg, 100%). LCMS calculated for $C_{17}H_{14}ClFN_3$ (M+H)$^+$: m/z=314.1. found: 313.9.

Step 4. 4-Chloro-3-(cyanomethyl)-3'-fluoro-6-[1-(9H-purin-6-ylamino)ethyl]biphenyl-2-carbonitrile

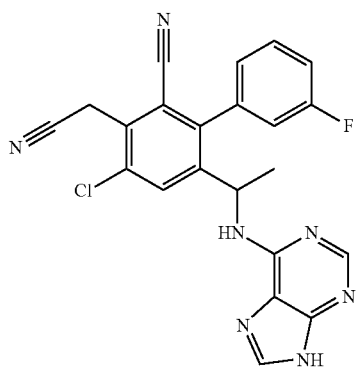 [SMILES: CC(Nc1ncnc2[nH]cnc12)c1cc(Cl)c(CC#N)c(C#N)c1-c1cccc(F)c1]

A mixture of 6-bromo-9H-purine (22 mg, 0.11 mmol), 6-(1-aminoethyl)-4-chloro-3-(cyanomethyl)-3'-fluorobiphenyl-2-carbonitrile (17 mg, 0.054 mmol), and N,N-diisopropylethylamine (0.032 mL, 0.18 mmol) in isopropyl alcohol (0.4 mL) was heated at 90° C. under nitrogen overnight. The mixture was evaporated and the resulting mixture was purified on RP-HPLC (XBridge C18 Column, eluting with a gradient of acetonitrile in water with 0.2% ammonium hydroxide, at flow rate of 30 mL/min) to give the desired product (8 mg, 30%). LCMS calculated for $C_{22}H_{16}ClFN_7$ (M+H)$^+$: m/z=432.1. found: 432.1.

Example 5

1-{4-Chloro-3'-fluoro-3-methyl-6-[1-(9H-purin-6-ylamino)ethyl]biphenyl-2-yl}pyrrolidin-2-one

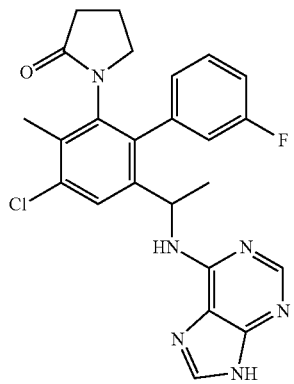 [SMILES: Cc1c(Cl)cc(C(C)Nc2ncnc3[nH]cnc23)c(-c2cccc(F)c2)c1N1CCCC1=O]

Step 1. 1-(6-Amino-4-chloro-3'-fluoro-5-methylbiphenyl-2-yl)ethanone

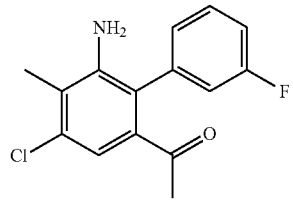 [SMILES: CC(=O)c1cc(Cl)c(C)c(N)c1-c1cccc(F)c1]

A mixture of 1-(4-chloro-3'-fluoro-5-methyl-6-nitrobiphenyl-2-yl)ethanone (4.4 g, 14 mmol) in methanol (80 mL) was hydrogenated in the presence of 5% Pt/C (443 mg) under balloon pressure of hydrogen overnight. The catalyst was filtered and the filtrate was concentrated under reduced pressure to give the desired product (4.0 g, 100%). LCMS calculated for $C_{15}H_{14}ClFNO$ (M+H)$^+$: m/z=278.1. found: 278.1.

Step 2. 1-(6-Acetyl-4-chloro-3'-fluoro-3-methylbiphenyl-2-yl)pyrrolidin-2-one

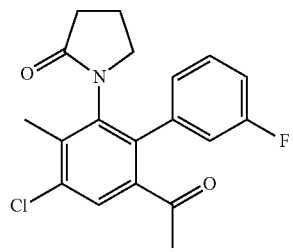 [SMILES: CC(=O)c1cc(Cl)c(C)c(N2CCCC2=O)c1-c1cccc(F)c1]

To a mixture of 1-(6-amino-4-chloro-3'-fluoro-5-methylbiphenyl-2-yl)ethanone (100 mg, 0.4 mmol) and 4-dimethylaminopyridine (52.8 mg, 0.432 mmol) in tetrahydrofuran (1 mL) was added 4-chlorobutanoyl chloride (0.044 mL, 0.40 mmol). The reaction was stirred at room temperature for 1 hour. Potassium tert-butoxide (1.0 M) in tetrahydrofuran (0.79 mL, 0.79 mmol) was added and the resulting mixture was stirred at room temperature for 2 hours, then quenched with aq. ammonium chloride and extracted with ethyl acetate. The combined organic layers were washed with water, brine, dried and evaporated. The resulting residue was purified on silica gel, eluting with 0 to 50% ethyl acetate in hexane, to give the product (40 mg, 30%). LCMS calculated for $C_{19}H_{18}ClFNO_2$ (M+H)$^+$: m/z=346.1. found: 346.1.

Step 3. 1-[6-(1-Aminoethyl)-4-chloro-3'-fluoro-3-methylbiphenyl-2-yl]pyrrolidin-2-one

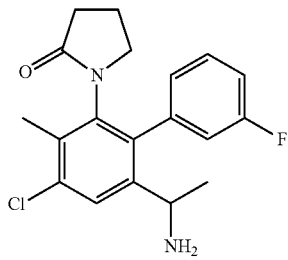 [SMILES: Cc1c(Cl)cc(C(C)N)c(-c2cccc(F)c2)c1N1CCCC1=O]

A mixture of 1-(6-acetyl-4-chloro-3'-fluoro-3-methylbiphenyl-2-yl)pyrrolidin-2-one (40 mg, 0.1 mmol) and ammonium acetate (89 mg, 1.2 mmol) and sodium cyanoborohydride (15 mg, 0.23 mmol) in methanol (0.4 mL) and acetonitrile (0.4 mL) was heated at 65° C. overnight in a sealed tube. The mixture was cooled to room temperature and quenched with saturated sodium bicarbonate and extracted with dichloromethane. The combined extracts were dried over magnesium sulfate and evaporated to dryness. The crude product was used directly in next step (34 mg, 80%). LCMS calculated for $C_{19}H_{18}ClFNO$ (M-NH$_2$)$^+$: m/z=330.1. found: 330.0.

Step 4. 1-{4-Chloro-3'-fluoro-3-methyl-6-[1-(9H-purin-6-ylamino)ethyl]biphenyl-2-yl}pyrrolidin-2-one

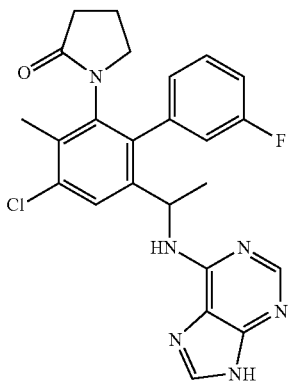 [SMILES: Cc1c(Cl)cc(C(C)Nc2ncnc3[nH]cnc23)c(-c2cccc(F)c2)c1N1CCCC1=O]

A mixture of 6-bromo-9H-purine (21 mg, 0.11 mmol), 1-[6-(1-aminoethyl)-4-chloro-3'-fluoro-3-methylbiphenyl-2-yl]pyrrolidin-2-one (34 mg, 0.098 mmol), and N,N-diisopropylethylamine (0.034 mL, 0.20 mmol) in isopropyl alcohol (0.4 mL) was heated at 90° C. under nitrogen overnight. The mixture was evaporated and the resulting mixture was purified on RP-HPLC (XBridge C18 Column, eluting with a gradient of acetonitrile in water with 0.2% ammonium hydroxide, at flow rate of 30 mL/min) to give the desired product. LCMS calculated for $C_{24}H_{23}ClFN_6O$ (M+H)$^+$: m/z=465.2. found: 465.1.

Example 6

1-{4-Chloro-3',5'-difluoro-3-methyl-6-[1-(9H-purin-6-ylamino)ethyl]biphenyl-2-yl}pyrrolidin-2-one trifluoroacetate

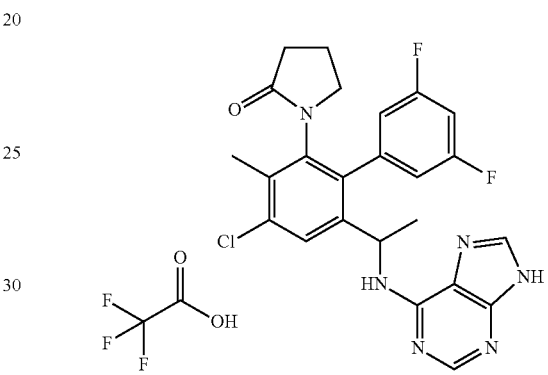

Step 1. 1-(4-Chloro-3',5'-difluoro-5-methyl-6-nitrobiphenyl-2-yl)ethanone

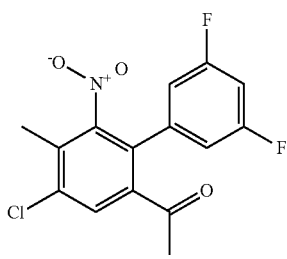

A biphasic solution of 6-acetyl-4-chloro-3-methyl-2-nitrophenyl trifluoromethanesulfonate (9.6 g, 26 mmol) and (3,5-difluorophenyl)boronic acid (5.0 g, 32 mmol) in toluene (100 mL) and saturated sodium bicarbonate in water (100 mL) was bubbled with N$_2$ to degas. After tetrakis(triphenylphosphine)palladium(0) (1.22 g, 1.06 mmol) was added, the mixture was bubbled with N$_2$ for 5 min. more and heated at 80° C. for 2 hours. The mixture was cooled to room temperature and diluted with ethyl acetate. The layers were separated and the aq. layer was extracted with more ethyl acetate. The combined extracts were washed with brine, dried over Na$_2$SO$_4$, filtered and concentrated. The residue was purified on silica gel column, eluting with 0-30% ethyl acetate in hexane, to give the desired product. LCMS calculated for $C_{15}H_{11}ClF_2NO_3$ (M+H)$^+$: m/z=326.0. found: 326.0.

Step 2. 1-(6-Amino-4-chloro-3',5'-difluoro-5-methylbiphenyl-2-yl) ethanone

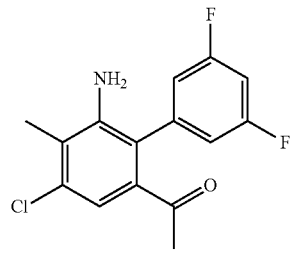 [SMILES: CC(=O)c1cc(Cl)c(C)c(N)c1-c1cc(F)cc(F)c1]

Into a flask was placed a suspension of iron (1.50 g, 26.9 mmol) (<10 m) in ethanol (22 mL). 6.0 M hydrogen chloride in water (0.374 mL, 2.24 mmol) was added and the suspension was stirred for 2 h at 60° C. A solution of 5.0 M ammonium chloride in water (3.86 mL, 19.3 mmol) was added followed by a solution of 1-[4-chloro-3',5'-difluoro-6-(hydroxyamino)-5-methylbiphenyl-2-yl]ethanone (1.4 g, 4.5 mmol) in ethanol (5.2 mL). The resulting suspension was stirred at 60° C. for 1 hour. The mixture was cooled, filtered and evaporated in vacuo. The residue was dissolved in a mixture of ethyl acetate and saturated sodium bicarbonate solution and stirred for a few minutes. The layers were separated and the ethyl acetate layer was washed with brine, dried over MgSO$_4$ and evaporated in vacuo to give the desired product (0.95 g, 72%). LCMS calculated for C$_{15}$H$_{13}$ClF$_2$NO (M+H)$^+$: m/z=296.1. found: 296.0.

Step 3. 1-(6-Acetyl-4-chloro-3',5'-difluoro-3-methylbiphenyl-2-yl)pyrrolidin-2-one

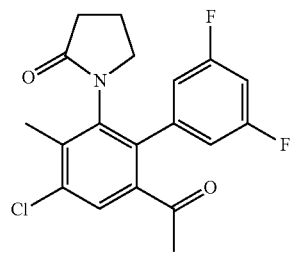 [SMILES: CC(=O)c1cc(Cl)c(C)c(N2CCCC2=O)c1-c1cc(F)cc(F)c1]

To a mixture of 1-(6-amino-4-chloro-3',5'-difluoro-5-methylbiphenyl-2-yl)ethanone (0.10 g, 0.34 mmol) and pyridine (0.041 mL, 0.51 mmol) in methylene chloride (2 mL) was added 4-chlorobutanoyl chloride (0.042 mL, 0.37 mmol). The reaction was stirred at room temperature for 1 hour, quenched with saturated sodium bicarbonate solution and extracted with ethyl acetate. The combined extracts were dried over MgSO$_4$ and concentrated to dryness under reduced pressure. The resulting residue was treated with 1.0 M potassium tert-butoxide in tetrahydrofuran (0.84 mL, 0.84 mmol) in tetrahydrofuran (2 mL) at room temperature for 2 hours. The reaction was quenched with aq. NH$_4$Cl, extracted with ethyl acetate. The combined organic layers were washed with water and brine, dried over MgSO$_4$ and evaporated. The residue was purified on silica gel (eluting with 0-40% of ethyl acetate in hexanes) to give the desired product (15 mg, 12%). LCMS calculated for C$_{19}$H$_{17}$ClF$_2$NO$_2$ (M+H)$^+$: m/z=364.1. found: 364.1.

Step 4. 1-[6-(1-Aminoethyl)-4-chloro-3',5'-difluoro-3-methylbiphenyl-2-yl]pyrrolidin-2-one

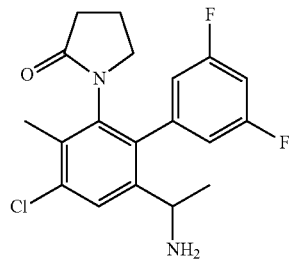 [SMILES: Cc1c(Cl)cc(C(C)N)c(-c2cc(F)cc(F)c2)c1N1CCCC1=O]

A mixture of 1-(6-acetyl-4-chloro-3',5'-difluoro-3-methylbiphenyl-2-yl)pyrrolidin-2-one (0.015 g, 0.041 mmol), ammonium acetate (0.032 g, 0.41 mmol), 1.0 M sodium cyanoborohydride in tetrahydrofuran (0.10 mL, 0.10 mmol) in methanol (0.1 mL) and acetonitrile (0.1 mL) was heated at 65° C. overnight. The mixture was cooled to room temperature, quenched with saturated sodium bicarbonate solution and extracted with dichloromethane. The combined organic layers were dried over MgSO$_4$ and concentrated to give the desired product. LCMS calculated for C$_{19}$H$_{17}$ClF$_2$NO (M-NH$_2$)$^+$: m/z=348.1. found: 348.0.

Step 5. 1-{4-Chloro-3',5'-difluoro-3-methyl-6-[1-(9H-purin-6-ylamino)ethyl]biphenyl-2-yl}pyrrolidin-2-one trifluoroacetate

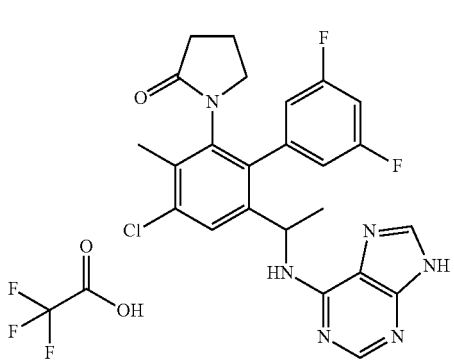

A mixture of 1-[6-(1-amino ethyl)-4-chloro-3',5'-difluoro-3-methylbiphenyl-2-yl]pyrrolidin-2-one (0.014 g, 0.038 mmol), 6-bromo-9H-purine (0.011 g, 0.058 mmol) and N,N-diisopropylethylamine (0.013 mL, 0.077 mmol) in ethanol (0.2 mL) was heated at 100° C. overnight. The mixture was purified on prep LCMS (XBridge C18 Column, eluting with a gradient of acetonitrile in water with 0.05% trifluoroacetic acid, at flow rate of 30 mL/min, to afford the desired product as TFA salt. LCMS calculated for C$_{24}$H$_{22}$ClF$_2$N$_6$O (M+H)$^+$: m/z=483.1. found: 483.1.

Example 7

3-{4-Chloro-3'-fluoro-3-methyl-6-[1-(9H-purin-6-ylamino)ethyl]biphenyl-2-yl}-1,3-oxazolidin-2-one

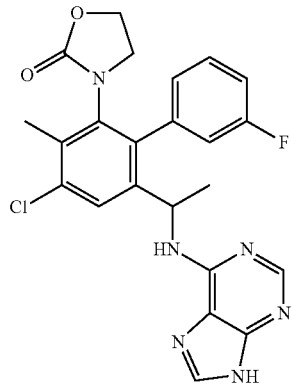 [SMILES: Cc1c(Cl)cc(C(C)Nc2ncnc3[nH]cnc23)c(-c2cccc(F)c2)c1N1CCOC1=O]

Step 1. 3-(6-Acetyl-4-chloro-3'-fluoro-3-methylbiphenyl-2-yl)-1,3-oxazolidin-2-one

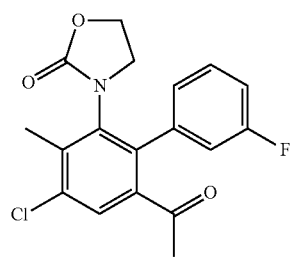 [SMILES: CC(=O)c1cc(Cl)c(C)c(N2CCOC2=O)c1-c1cccc(F)c1]

To a mixture of 1-(6-amino-4-chloro-3'-fluoro-5-methylbiphenyl-2-yl)ethanone (100 mg, 0.4 mmol) and 4-dimethylaminopyridine (53 mg, 0.43 mmol) in tetrahydrofuran (1 mL) was added 2-chloroethyl chloridocarbonate (0.041 mL, 0.40 mmol). The mixture was stirred at room temperature overnight. To the mixture was added 1.0 M potassium tert-butoxide in tetrahydrofuran (0.79 mL) at 0° C., and the resulting mixture stirred at room temperature for 2 hours, then quenched with aq. ammonium chloride, extracted with ethyl acetate. The combined organic layers were washed with brine, dried, and evaporated. The filtrate was applied on silica gel, eluting with 0 to 60% ethyl acetate in hexane, to give the desired product (14 mg, 10%). LCMS calculated for $C_{18}H_{16}ClFNO_3$ (M+H)$^+$: m/z=348.1. found: 348.0.

Step 2. 3-[6-(1-Aminoethyl)-4-chloro-3'-fluoro-3-methylbiphenyl-2-yl]-1,3-oxazolidin-2-one

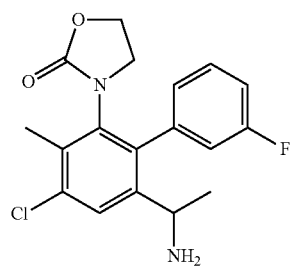 [SMILES: Cc1c(Cl)cc(C(C)N)c(-c2cccc(F)c2)c1N1CCOC1=O]

A mixture of 3-(6-acetyl-4-chloro-3'-fluoro-3-methylbiphenyl-2-yl)-1,3-oxazolidin-2-one (14 mg, 0.040 mmol) and ammonium acetate (31 mg, 0.40 mmol) and sodium cyanoborohydride (5 mg, 0.08 mmol) in methanol (0.1 mL) and acetonitrile (0.1 mL) was heated at 65° C. overnight in a sealed tube. The mixture was cooled to room temperature, quenched with saturated sodium bicarbonate and extracted with dichloromethane. The combined extracts were dried over magnesium sulfate and evaporated to dryness. The crude product was used directly in next step (10 mg, 70%). LCMS calculated for $C_{18}H_{16}ClFNO_2$ (M-NH$_2$)$^+$: m/z=332.1. found: 332.1.

Step 3. 3-{4-Chloro-3'-fluoro-3-methyl-6-[1-(9H-purin-6-ylamino)ethyl]biphenyl-2-yl}-1,3-oxazolidin-2-one

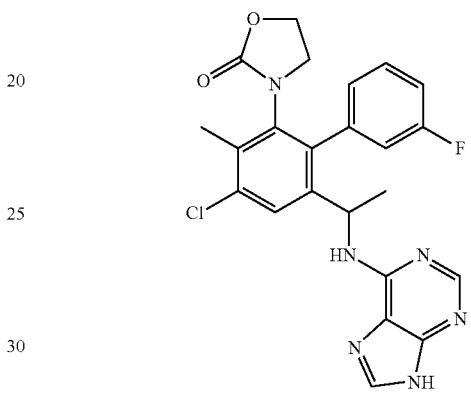

A mixture of 6-bromo-9H-purine (6.3 mg, 0.032 mmol), 3-[6-(1-aminoethyl)-4-chloro-3'-fluoro-3-methylbiphenyl-2-yl]-1,3-oxazolidin-2-one (10 mg, 0.03 mmol), and N,N-diisopropylethylamine (0.010 mL, 0.057 mmol) in isopropyl alcohol (0.1 mL) was heated at 90° C. under nitrogen overnight. The mixture was evaporated and the resulting mixture was purified on RP-HPLC (XBridge C18 Column, eluting with a gradient of acetonitrile in water with 0.2% ammonium hydroxide, at flow rate of 30 mL/min, to give the desired. LCMS calculated for $C_{23}H_{21}ClFN_6O_2$ (M+H)$^+$: m/z=467.1. found: 467.1.

Example 8

N-{1-[4-chloro-3'-fluoro-5-methyl-6-(1H-tetrazol-5-yl)biphenyl-2-yl]ethyl}-9H-purin-6-amine

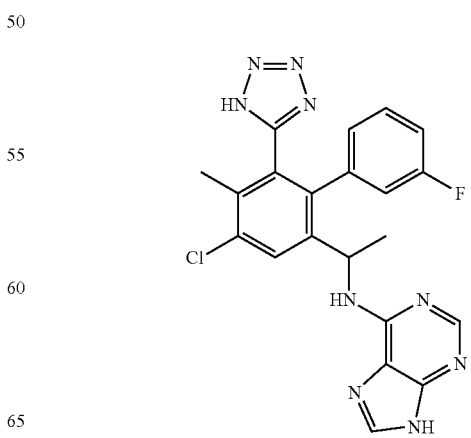

Step 1. 1-[4-Chloro-3'-fluoro-5-methyl-6-(1H-tetrazol-5-yl)biphenyl-2-yl]ethanone

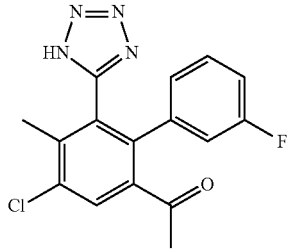 [SMILES: CC(=O)c1cc(Cl)c(C)c(-c2nnn[nH]2)c1-c1cccc(F)c1]

A mixture of 6-acetyl-4-chloro-3'-fluoro-3-methylbiphenyl-2-carbonitrile (100 mg, 0.3 mmol), azidotrimethylsilane (0.092 mL, 0.69 mmol), and dibutyloxostannane (13 mg, 0.052 mmol) in toluene (2.9 mL) was heated at reflux overnight. The mixture was evaporated to dryness and purified on silica gel, eluting with 0 to 50% ethyl acetate in hexane, to give the desired product (85 mg, 70%). LCMS calculated for $C_{16}H_{13}ClFN_4O$ (M+H)$^+$: m/z=331.1; found: 331.0.

Step 2. 1-[4-Chloro-3'-fluoro-5-methyl-6-(1H-tetrazol-5-yl)biphenyl-2-yl]ethanamine

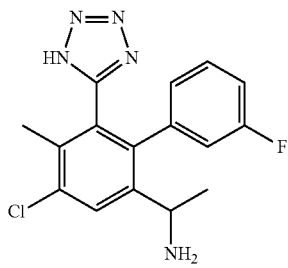 [SMILES: Cc1c(Cl)cc(C(C)N)c(-c2cccc(F)c2)c1-c1nnn[nH]1]

A mixture of 1-[4-chloro-3'-fluoro-5-methyl-6-(1H-tetrazol-5-yl)biphenyl-2-yl]ethanone (85 mg, 0.26 mmol), ammonium acetate (198 mg, 2.57 mmol) and sodium cyanoborohydride (32 mg, 0.51 mmol) in methanol (0.9 mL) and acetonitrile (0.9 mL) was heated at 65° C. overnight in a sealed tube. The mixture was cooled to room temperature and quenched with saturated sodium bicarbonate and extracted with ethyl acetate. The combined extracts were dried over magnesium sulfate and evaporated to dryness. The crude product was used directly in next step (45 mg, 53%). LCMS calculated for $C_{16}H_{13}ClFN_4$ (M-NH$_2$)$^+$: m/z=315.1. found: 315.1.

Step 3. N-{1-[4-chloro-3'-fluoro-5-methyl-6-(1H-tetrazol-5-yl) biphenyl-2-yl]ethyl}-9H-purin-6-amine

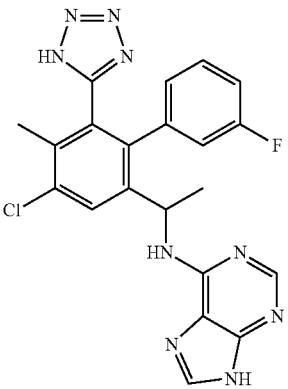 [SMILES: Cc1c(Cl)cc(C(C)Nc2ncnc3[nH]cnc23)c(-c2cccc(F)c2)c1-c1nnn[nH]1]

A mixture of 6-bromo-9H-purine (30 mg, 0.15 mmol), 1-[4-chloro-3'-fluoro-5-methyl-6-(1H-tetrazol-5-yl)biphenyl-2-yl]ethanamine (45 mg, 0.14 mmol), and N,N-diisopropylethylamine (0.047 mL, 0.27 mmol) in isopropyl alcohol (0.5 mL) was heated at 90° C. under nitrogen overnight. The mixture was evaporated and the resulting mixture was purified on RP-HPLC (XBridge C18 Column, eluting with a gradient of acetonitrile in water with 0.2% ammonium hydroxide, at flow rate of 30 mL/min) to give the desired product. LCMS calculated for $C_{21}H_{18}ClFN_9$ (M+H)$^+$: m/z=450.1. found: 450.1.

Example 9

N-{4-chloro-3'-fluoro-3-methyl-6-[1-(9H-purin-6-ylamino)ethyl]biphenyl-2-yl}acetamide

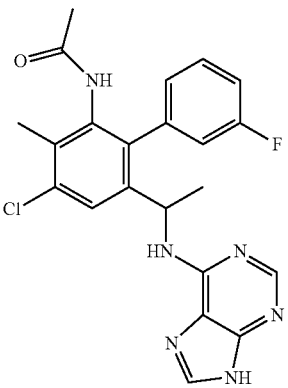 [SMILES: CC(=O)Nc1c(C)c(Cl)cc(C(C)Nc2ncnc3[nH]cnc23)c1-c1cccc(F)c1]

Step 1. N-acetyl-N-(6-acetyl-4-chloro-3'-fluoro-3-methylbiphenyl-2-yl) acetamide

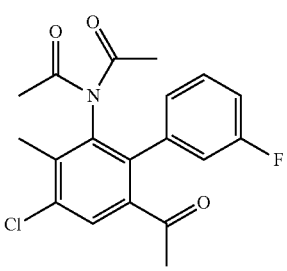 [SMILES: CC(=O)c1cc(Cl)c(C)c(N(C(C)=O)C(C)=O)c1-c1cccc(F)c1]

To a mixture of 1-(6-amino-4-chloro-3'-fluoro-5-methyl-biphenyl-2-yl)ethanone (100 mg, 0.4 mmol) in methylene chloride (2 mL) was added N,N-diisopropylethylamine (0.094 mL, 0.54 mmol) followed by acetyl chloride (0.038 mL, 0.53 mmol). The mixture was stirred at room temperature for 30 minutes, quenched with water and extracted with ethyl acetate. The combined organic layers were washed with brine and dried over sodium sulfate and concentrated. The residue was purified on silica gel, eluting with 0 to 60% ethyl acetate in hexane, to give the desired products (57 mg, 40%). LCMS calculated for $C_{19}H_{18}ClFNO_3$ $(M+H)^+$: m/z=362.1. found: 362.0.

Step 2. N-[6-(1-aminoethyl)-4-chloro-3'-fluoro-3-methylbiphenyl-2-yl]acetamide

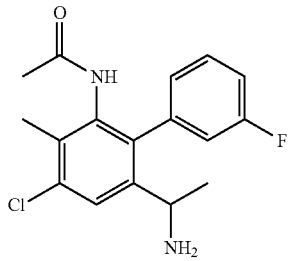 [SMILES: CC(=O)Nc1c(C)c(Cl)cc(C(C)N)c1-c1cccc(F)c1]

A mixture of N-acetyl-N-(6-acetyl-4-chloro-3'-fluoro-3-methylbiphenyl-2-yl)acetamide (57 mg, 0.16 mmol), ammonium acetate (120 mg, 1.6 mmol) and sodium cyanoborohydride (20 mg, 0.32 mmol) in methanol (0.6 mL) and acetonitrile (0.6 mL) was heated at 65° C. overnight in a sealed tube. The mixture was then cooled to room temperature and quenched with saturated sodium bicarbonate and extracted with ethyl acetate. The combined extracts were dried over magnesium sulfate and evaporated to dryness. The crude product was used directly in next step. LCMS calculated for $C_{17}H_{19}ClFN_2O$ $(M+H)^+$: m/z=321.1. found: 321.0.

Step 3. N-{4-chloro-3'-fluoro-3-methyl-6-[1-(9H-purin-6-ylamino)ethyl]biphenyl-2-yl}acetamide

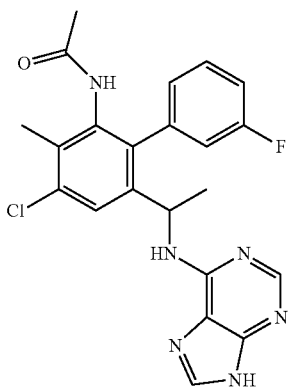 [SMILES: CC(=O)Nc1c(C)c(Cl)cc(C(C)Nc2ncnc3[nH]cnc23)c1-c1cccc(F)c1]

A mixture of 6-bromo-9H-purine (22 mg, 0.11 mmol), N-[6-(1-aminoethyl)-4-chloro-3'-fluoro-3-methylbiphenyl-2-yl]acetamide (32 mg, 0.10 mmol), and N,N-diisopropylethylamine (0.035 mL, 0.20 mmol) in isopropyl alcohol (0.4 mL) was heated at 90° C. under nitrogen overnight. The mixture was evaporated and the resulting mixture was purified on RP-HPLC (XBridge C18 Column, eluting with a gradient of acetonitrile in water with 0.2% ammonium hydroxide, at flow rate of 30 mL/min) to give the desired product. LCMS calculated for $C_{22}H_{21}ClFN_6O$ $(M+H)^+$: m/z=439.1. found: 439.3.

Example 10

Dimethyl {4-chloro-3'-fluoro-3-methyl-6-[1-(9H-purin-6-ylamino)ethyl]biphenyl-2-yl}imidodicarbonate

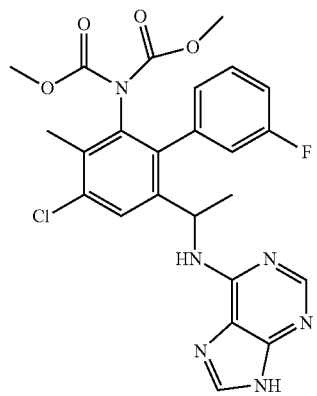 [SMILES: COC(=O)N(C(=O)OC)c1c(C)c(Cl)cc(C(C)Nc2ncnc3[nH]cnc23)c1-c1cccc(F)c1]

Step 1. Dimethyl (6-acetyl-4-chloro-3'-fluoro-3-methylbiphenyl-2-yl)imidodicarbonate

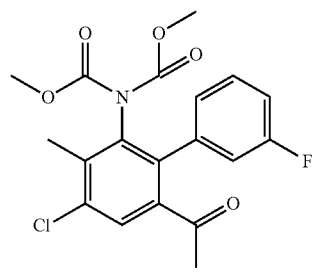 [SMILES: COC(=O)N(C(=O)OC)c1c(C)c(Cl)cc(C(C)=O)c1-c1cccc(F)c1]

To a mixture of 1-(6-amino-4-chloro-3'-fluoro-5-methyl-biphenyl-2-yl)ethanone (100 mg, 0.4 mmol) in methylene chloride (2 mL) was added N,N-diisopropylethylamine (0.094 mL, 0.54 mmol) followed by methyl chloroformate (0.033 mL, 0.43 mmol). The mixture was stirred at room temperature for 30 min. To the reaction mixture was added a catalytic amount of DMAP and another equivalent of methyl chloroformate. The reaction was stirred at room temperature over a weekend, quenched with water and extracted with ethyl acetate. The combined organic layers were washed with brine and dried over sodium sulfate, then concentrated. The residue was purified on silica gel, eluting with 0 to 50% ethyl acetate in hexane, to give the bis-acylated product (67 mg, 50%). LCMS calculated for $C_{19}H_{18}ClFNO_5$ $(M+H)^+$: m/z=394.1. found: 394.1.

Step 2. Dimethyl [6-(1-aminoethyl)-4-chloro-3'-fluoro-3-methylbiphenyl-2-yl]imidodicarbonate

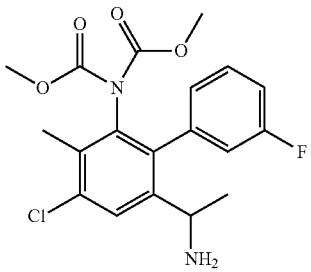 [SMILES: COC(=O)N(C(=O)OC)c1c(C)c(Cl)cc(C(C)N)c1-c1cccc(F)c1]

A mixture of dimethyl (6-acetyl-4-chloro-3'-fluoro-3-methylbiphenyl-2-yl)imidodicarbonate (67 mg, 0.17 mmol), ammonium acetate (131 mg, 1.70 mmol) and sodium cyanoborohydride (21 mg, 0.34 mmol) in methanol (0.6 mL) and acetonitrile (0.6 mL) was heated at 65° C. overnight in a sealed tube. The mixture was then cooled to room temperature and quenched with saturated sodium bicarbonate and extracted with dichloromethane. The combined extracts were dried over magnesium sulfate and evaporated to dryness. The crude product was used directly in next step (67 mg, 100%). LCMS calculated for $C_{19}H_{21}ClFN_2O_4$ (M+H)$^+$: m/z=395.1. found: 395.1.

Step 3. Dimethyl {4-chloro-3'-fluoro-3-methyl-6-[1-(9H-purin-6-ylamino)ethyl]biphenyl-2-yl}imidodicarbonate

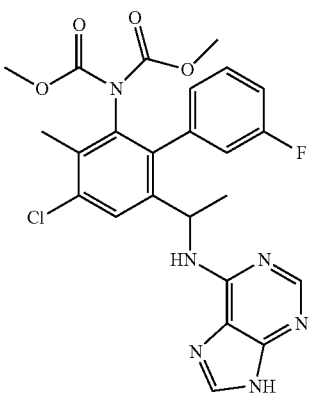 [SMILES: COC(=O)N(C(=O)OC)c1c(C)c(Cl)cc(C(C)Nc2ncnc3[nH]cnc23)c1-c1cccc(F)c1]

A mixture of 6-bromo-9H-purine (36 mg, 0.18 mmol), dimethyl [6-(1-aminoethyl)-4-chloro-3'-fluoro-3-methylbiphenyl-2-yl]imidodicarbonate (66 mg, 0.17 mmol), and N,N-diisopropylethylamine (0.058 mL, 0.33 mmol) in isopropyl alcohol (0.6 mL) was heated at 90° C. under nitrogen overnight. The mixture was evaporated and the resulting mixture was purified on RP-HPLC (XBridge C18 Column, eluting with a gradient of acetonitrile in water with 0.2% ammonium hydroxide, at flow rate of 30 mL/min) to give the desired. LCMS calculated for $C_{24}H_{23}ClFN_6O_4$ (M+H)$^+$: m/z=513.1. found: 513.2.

Example 11

N-{1-[4-chloro-3'-fluoro-5-methyl-6-(4H-1,2,4-triazol-4-yl)biphenyl-2-yl]ethyl}-9H-purin-6-amine

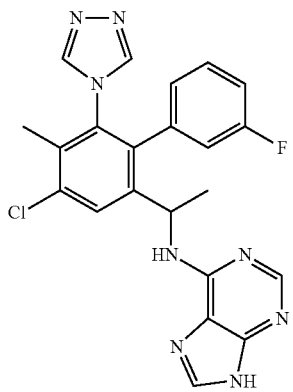 [SMILES: Cc1c(Cl)cc(C(C)Nc2ncnc3[nH]cnc23)c(-c2cccc(F)c2)c1-n1cnnc1]

Step 1. 1-[4-Chloro-3'-fluoro-5-methyl-6-(4H-1,2,4-triazol-4-yl)biphenyl-2-yl]ethanone

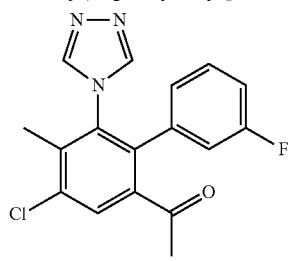

1,2-Hydrazinedicarboxaldehyde (0.095 g, 1.1 mmol) and then, drop by drop, chlorotrimethylsilane (0.69 mL, 5.4 mmol) and triethylamine (0.35 mL, 2.5 mmol) were added to a suspension of 1-(6-amino-4-chloro-3'-fluoro-5-methyl-biphenyl-2-yl)ethanone (0.10 g, 0.36 mmol) in pyridine (2 mL). The mixture was heated at 100° C. overnight. Evaporation at reduced pressure of the solvent yielded a solid that was treated with water and extracted with dichloromethane. The extracts were dried over sodium sulfate and concentrated. The reside was purified on silica gel, eluting with 0 to 50% ethyl acetate in hexane, then 0 to 10% methanol in dichloromethane, to give the desired product (44 mg, 37%). LCMS calculated for $C_{17}H_{14}ClFN_3O$ (M+H)$^+$: m/z=330.1. found: 330.0.

Step 2. 1-[4-Chloro-3'-fluoro-5-methyl-6-(4H-1,2,4-triazol-4-yl)biphenyl-2-yl]ethanamine

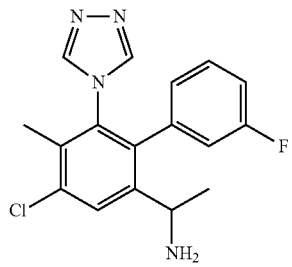 [SMILES: Cc1c(Cl)cc(C(C)N)c(-c2cccc(F)c2)c1-n1cnnc1]

A mixture of 1-[4-chloro-3'-fluoro-5-methyl-6-(4H-1,2,4-triazol-4-yl)biphenyl-2-yl]ethanone (44 mg, 0.13 mmol), ammonium acetate (103 mg, 1.33 mmol) and sodium cyanoborohydride (17 mg, 0.27 mmol) in methanol (0.5 mL) and acetonitrile (0.5 mL) was heated at 65° C. overnight in a sealed tube. The mixture was then cooled to room temperature and quenched with saturated sodium bicarbonate and extracted with dichloromethane. The combined extracts were dried over magnesium sulfate and evaporated to dryness. The crude product was used directly in next step (15 mg, 34%). LCMS calculated for $C_{17}H_{17}ClFN_4$ (M+H)$^+$: m/z=331.1. found: 331.1.

Step 3. N-{1-[4-chloro-3'-fluoro-5-methyl-6-(4H-1,2,4-triazol-4-yl)biphenyl-2-yl]ethyl}-9H-purin-6-amine

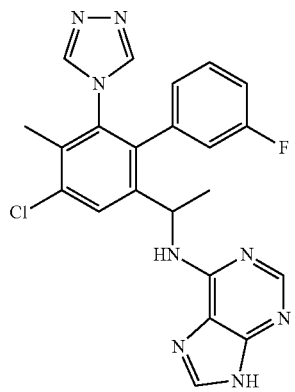

A mixture of 6-bromo-9H-purine (10 mg, 0.050 mmol), 1-[4-chloro-3'-fluoro-5-methyl-6-(4H-1,2,4-triazol-4-yl)biphenyl-2-yl]ethanamine (15 mg, 0.045 mmol), and N,N-diisopropylethylamine (0.016 mL, 0.091 mmol) in isopropyl alcohol (0.2 mL) was heated at 90° C. under nitrogen overnight. The mixture was evaporated and the resulting mixture was purified on RP-HPLC (XBridge C18 Column, eluting with a gradient of acetonitrile in water with 0.2% ammonium hydroxide, at flow rate of 30 mL/min) to give the desired product. LCMS calculated for $C_{22}H_{19}ClFN_8$ (M+H)$^+$: m/z=449.1. found: 449.1.

Example 12

N-{4-chloro-3'-fluoro-3-methyl-6-[1-(9H-purin-6-ylamino)ethyl]biphenyl-2-yl}-N-(methylsulfonyl)methanesulfonamide

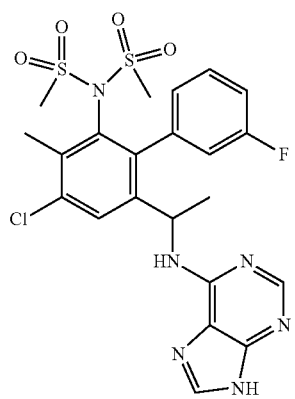 [SMILES: Cc1c(Cl)cc(C(C)Nc2ncnc3[nH]cnc23)c(-c2cccc(F)c2)c1N(S(C)(=O)=O)S(C)(=O)=O]

Step 1. N-(6-acetyl-4-chloro-3'-fluoro-3-methylbiphenyl-2-yl)-N-(methylsulfonyl)methanesulfonamide

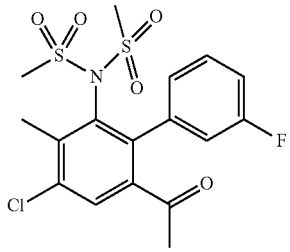 [SMILES: CC(=O)c1cc(Cl)c(C)c(N(S(C)(=O)=O)S(C)(=O)=O)c1-c1cccc(F)c1]

To a mixture of 1-(6-amino-4-chloro-3'-fluoro-5-methylbiphenyl-2-yl)ethanone (50 mg, 0.2 mmol) in methylene chloride (1 mL) was added 4-dimethylaminopyridine (33 mg, 0.27 mmol) followed by methanesulfonyl chloride (0.017 mL, 0.22 mmol). The mixture was stirred for 2 hours, quenched with water and extracted with ethyl acetate. The combined organic layers were washed with brine and dried over sodium sulfate and concentrated. The residue was purified on silica gel, eluting with 0 to 40% ethyl acetate in hexane, to give the desired product (25 mg, 30%). LCMS calculated for $C_{17}H_{18}ClFNO_5S_2$ (M+H)$^+$: m/z=434.0. found: 434.1.

Step 2. N-[6-(1-aminoethyl)-4-chloro-3'-fluoro-3-methylbiphenyl-2-yl]-N-(methylsulfonyl)methanesulfonamide

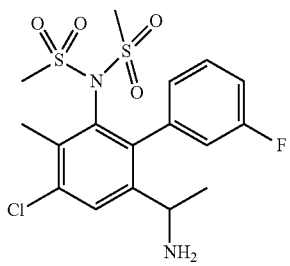 [SMILES: Cc1c(Cl)cc(C(C)N)c(-c2cccc(F)c2)c1N(S(C)(=O)=O)S(C)(=O)=O]

A mixture of N-(6-acetyl-4-chloro-3'-fluoro-3-methylbiphenyl-2-yl)-N-(methylsulfonyl)methanesulfonamide (25 mg, 0.058 mmol), ammonium acetate (44 mg, 0.58 mmol) and sodium cyanoborohydride (7 mg, 0.12 mmol) in methanol (0.2 mL) and acetonitrile (0.2 mL) was heated at 65° C. overnight in a sealed tube. The mixture was then cooled to room temperature and quenched with saturated sodium bicarbonate and extracted with dichloromethane. The combined extracts were dried over magnesium sulfate and evaporated to dryness. The crude product was used directly in next step (21 mg, 84%). LCMS calculated for $C_{17}H_{18}ClFNO_4S_2$ (M-NH$_2$)$^+$: m/z=418.0. found: 418.0.

Step 3. N-{4-chloro-3'-fluoro-3-methyl-6-[1-(9H-purin-6-ylamino)ethyl]biphenyl-2-yl}-N-(methylsulfonyl)methanesulfonamide

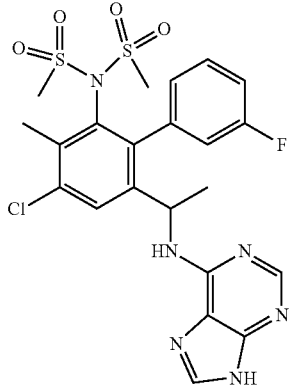 [SMILES: Cc1c(Cl)cc(C(C)Nc2ncnc3[nH]cnc23)c(-c2cccc(F)c2)c1N(S(C)(=O)=O)S(C)(=O)=O]

A mixture of 6-bromo-9H-purine (10 mg, 0.053 mmol), N-[6-(1-aminoethyl)-4-chloro-3'-fluoro-3-methylbiphenyl-2-yl]-N-(methylsulfonyl)methanesulfonamide (21 mg, 0.048 mmol), and N,N-diisopropylethylamine (0.017 mL, 0.096 mmol) in isopropyl alcohol (0.2 mL) was heated at 90° C. under nitrogen overnight. The mixture was evaporated and the resulting mixture was purified on RP-HPLC (XBridge C18 Column, eluting with a gradient of acetonitrile in water with 0.2% ammonium hydroxide, at flow rate of 30 mL/min) to give the desired product. LCMS calculated for $C_{22}H_{23}ClFN_6O_4S_2$ (M+H)$^+$: m/z=553.1. found: 553.1.

Example 13

N-{1-[4-chloro-6-(2,6-difluoropyridin-4-yl)-5-methylbiphenyl-2-yl]ethyl}-9H-purin-6-amine

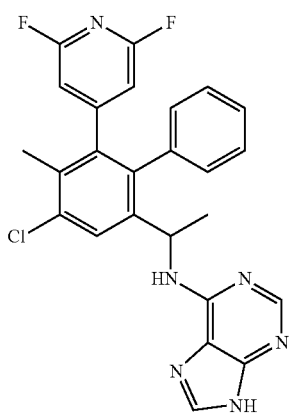 [SMILES: Cc1c(Cl)cc(C(C)Nc2ncnc3[nH]cnc23)c(-c2ccccc2)c1-c1cc(F)nc(F)c1]

Step 1. 1-(3-Bromo-5-chloro-2-hydroxy-4-methylphenyl)ethanone

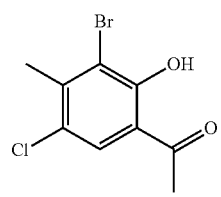

To a stirred solution of 1-(5-chloro-2-hydroxy-4-methylphenyl)ethanone (10 g, 54 mmol, from Aldrich) in acetic acid (100 mL) was added N-bromosuccinimide (12 g, 65 mmol) and the resulting mixture was stirred at room temperature for 18 hours. The reaction mixture was concentrated in vacuo, neutralized with saturated sodium bicarbonate and filtered to remove insoluble succinimide. The filtrate was extracted with ethyl acetate. The combined organic layers were washed with brine, dried over sodium sulfate, and then concentrated to dryness under reduced pressure. The crude product was recrystalized from a mixture of ethyl acetate and hexane (11.4 g, 80%).

Step 2. 6-Acetyl-2-bromo-4-chloro-3-methylphenyl trifluoromethanesulfonate

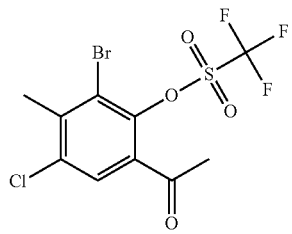 [SMILES: CC(=O)c1cc(Cl)c(C)c(Br)c1OS(=O)(=O)C(F)(F)F]

To a mixture of 1-(3-bromo-5-chloro-2-hydroxy-4-methylphenyl)ethanone (11 g, 40 mmol) in methylene chloride (200 mL) was added triethylamine (17 mL, 120 mmol) followed by trifluoromethanesulfonic anhydride (10 mL, 60 mmol) at −78° C. The reaction was allowed to warm up to room temperature gradually and stirred at room temperature for 30 min. After the mixture was evaporated under reduced pressure at room temperature, the residue was diluted with ethyl acetate and washed with water. The combined organic layers were washed with brine, dried over sodium sulfate, and concentrated to dryness. The residue was purified on silica gel, eluting with 0 to 30% ethyl acetate in hexane, to give the desired product (13.6 g, 86%). LCMS calculated for $C_{10}H_8BrClF_3O_4S$ (M+H)$^+$: m/z=394.9. found: 394.9.

Step 3.
1-(6-Bromo-4-chloro-5-methylbiphenyl-2-yl)ethanone

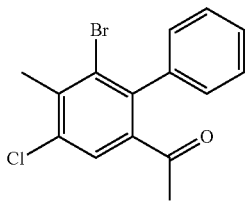 [SMILES: CC(=O)c1cc(Cl)c(C)c(Br)c1-c1ccccc1]

A biphasic solution of 6-acetyl-2-bromo-4-chloro-3-methylphenyl trifluoromethanesulfonate (3.3 g, 8.3 mmol) and phenylboronic acid (1.2 g, 10 mmol) in toluene (30 mL) and saturated sodium bicarbonate in water (30 mL) was bubbled with $N_2$ to degas. After tetrakis(triphenylphosphine)palladium(0) (0.385 g, 0.333 mmol) was added, the mixture was bubbled with $N_2$ for 5 min. more and heated at 80° C. for 2 hours. After cooling to r.t., the mixture was diluted with ethyl acetate. The layers were separated and the aq. layer was extracted with more ethyl acetate. The combined extracts were washed with brine, dried over Na$_2$SO$_4$, filtered, and concentrated. The residue was purified on silica gel column, eluting with 0-20% of ethyl acetate in hexane, to give the desired product (2.5 g, 93%). LCMS calculated for C$_{15}$H$_{13}$BrClO (M+H)$^+$: m/z=323.0. found: 323.0.

Step 4. 1-[4-Chloro-6-(2,6-difluoropyridin-4-yl)-5-methylbiphenyl-2-yl]ethanone

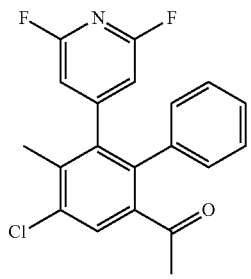 [SMILES: CC(=O)c1cc(Cl)c(C)c(-c2cc(F)nc(F)c2)c1-c1ccccc1]

A biphasic solution of 1-(6-bromo-4-chloro-5-methylbiphenyl-2-yl)ethanone (0.20 g, 0.62 mmol) and (2,6-difluoropyridin-4-yl)boronic acid (0.12 g, 0.74 mmol) in 1,4-dioxane (2.0 mL) and 10% Na$_2$CO$_3$ in water (0.98 mL, 0.93 mmol)) was bubbled with N$_2$ to degas. After tetrakis(triphenylphosphine)palladium(0) (29 mg, 0.025 mmol) was added the mixture was bubbled with N$_2$ for 5 min. and heated at 100° C. overnight. The mixture was cooled to room temperature and diluted with ethyl acetate. The layers were separated and the aq. layer was extracted with more ethyl acetate. The combined extracts were washed with brine, dried over Na$_2$SO$_4$, filtered and concentrated. The residue was purified on silica gel column, eluting with 0-30% of ethyl acetate in hexane, to give the desired product (60 mg, 30%). LCMS calculated for C$_{20}$H$_{15}$ClF$_2$NO (M+H)$^+$: m/z=358.1. found: 358.0.

Step 5. 1-[4-Chloro-6-(2,6-difluoropyridin-4-yl)-5-methylbiphenyl-2-yl]ethanamine

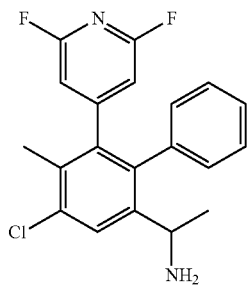 [SMILES: Cc1c(Cl)cc(C(C)N)c(-c2ccccc2)c1-c1cc(F)nc(F)c1]

A mixture of 1-[4-chloro-6-(2,6-difluoropyridin-4-yl)-5-methylbiphenyl-2-yl]ethanone (60 mg, 0.2 mmol), ammonium acetate (130 mg, 1.7 mmol) and sodium cyanoborohydride (21 mg, 0.34 mmol) in methanol (0.6 mL) and acetonitrile (0.6 mL) was heated at 65° C. overnight in a sealed tube. The mixture was then cooled to room temperature and quenched with saturated sodium bicarbonate and extracted with dichloromethane. The combined extracts were dried over magnesium sulfate and evaporated to dryness. The crude product was used directly in next step (60 mg, 100%). LCMS calculated for C$_{20}$H$_{15}$ClF$_2$N (M-NH$_2$)$^+$: m/z=342.1. found: 342.1.

Step 5. N-{1-[4-chloro-6-(2,6-difluoropyridin-4-yl)-5-methylbiphenyl-2-yl]ethyl}-9H-purin-6-amine

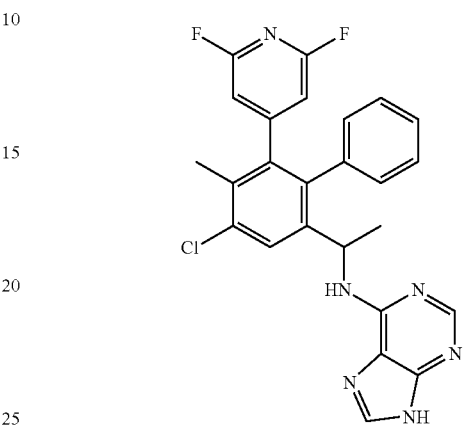

A mixture of 6-bromo-9H-purine (36 mg, 0.18 mmol), 1-[4-chloro-6-(2,6-difluoropyridin-4-yl)-5-methylbiphenyl-2-yl]ethanamine (60 mg, 0.17 mmol), and N,N-diisopropylethylamine (0.058 mL, 0.33 mmol) in isopropyl alcohol (0.6 mL) was heated at 90° C. under nitrogen overnight. The mixture was evaporated and the resulting mixture was purified on RP-HPLC (XBridge C18 Column, eluting with a gradient of acetonitrile in water with 0.2% ammonium hydroxide, at flow rate of 30 mL/min) to give the desired product. LCMS calculated for C$_{25}$H$_{20}$ClF$_2$N$_6$ (M+H)$^+$: m/z=477.1. found: 477.1.

Example 18

1-{3-Chloro-6-methoxy-2-methyl-5-[1-(9H-purin-6-ylamino)ethyl]phenyl}pyrrolidin-2-one

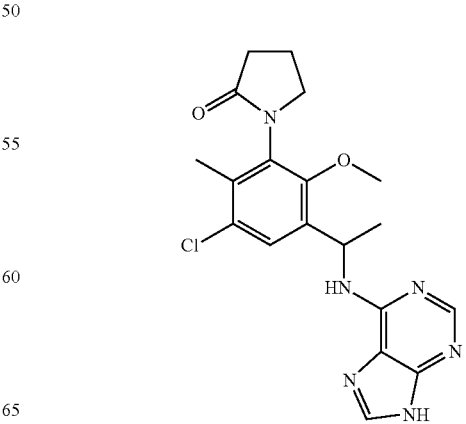

Step 1. 1-(3-Amino-5-chloro-2-methoxy-4-methyl-phenyl)ethanone

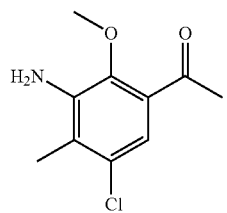

1-(5-Chloro-2-methoxy-4-methyl-3-nitrophenyl)ethanone (5.0 g, 20 mmol) was hydrogenated in 100 mL of methanol in the presence of 0.5 g of 10% Pt/C, under a balloon pressure of hydrogen overnight. The catalyst was filtered off and the filtrate was concentrated.

The residue was dissolved in dichloromethane and dried over sodium sulfate and then evaporated to dryness. The crude product was used directly in next step (4.4 g, 100%). LCMS calculated for $C_{10}H_{13}ClNO_2$ (M+H)$^+$: m/z=214.1. found: 214.1.

Step 2. 1-(3-Acetyl-5-chloro-2-methoxy-6-methyl-phenyl)pyrrolidin-2-one

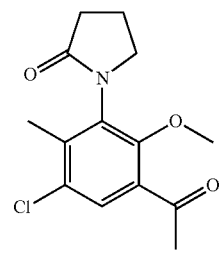 [SMILES: COc1c(C(C)=O)cc(Cl)c(C)c1N1CCCC1=O]

To a mixture of 1-(3-amino-5-chloro-2-methoxy-4-methylphenyl)ethanone (100 mg, 0.5 mmol) and 4-dimethylaminopyridine (69 mg, 0.56 mmol) in tetrahydrofuran (1 mL) was added 4-chlorobutanoyl chloride (0.058 mL, 0.52 mmol). The reaction was stirred at room temperature for 1 hour. To the reaction mixture was added 1.0 M potassium tert-butoxide in tetrahydrofuran (1.03 mL, 1.03 mmol). The resulting mixture was stirred at room temperature for 2 hours, quenched with aq. ammonium chloride and extracted with ethyl acetate. The combined organic layers were washed with water, brine, dried and evaporated. The residue was purified on silica gel, eluting with 0 to 50% ethyl acetate in hexane, to give the product (20 mg, 20%). LCMS calculated for $C_{14}H_{17}ClNO_3$ (M+H)$^+$: m/z=282.1. found: 282.1.

Step 3. 1-[3-(1-Aminoethyl)-5-chloro-2-methoxy-6-methylphenyl]pyrrolidin-2-one

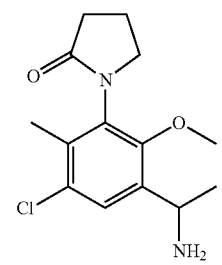 [SMILES: COc1c(C(C)N)cc(Cl)c(C)c1N1CCCC1=O]

A mixture of 1-(3-acetyl-5-chloro-2-methoxy-6-methylphenyl)pyrrolidin-2-one (20 mg, 0.07 mmol), ammonium acetate (55 mg, 0.71 mmol) and sodium cyanoborohydride (9.0 mg, 0.14 mmol) in methanol (0.2 mL) and acetonitrile (0.2 mL) was heated at 65° C. overnight in a sealed tube. The mixture was cooled to room temperature, quenched with saturated sodium bicarbonate and extracted with dichloromethane. The combined extracts were dried over magnesium sulfate and evaporated to dryness. The crude product was used directly in next step (11 mg, 50%). LCMS calculated for $C_{14}H_{20}ClN_2O_2$ (M+H)$^+$: m/z=283.1. found: 283.1.

Step 4. 1-{3-Chloro-6-methoxy-2-methyl-5-[1-(9H-purin-6-ylamino)ethyl]phenyl}pyrrolidin-2-one

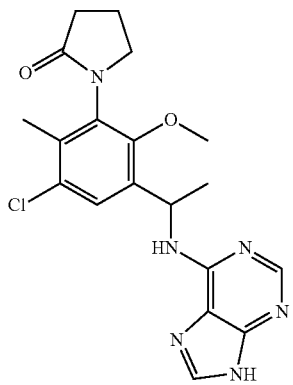 [SMILES: COc1c(C(C)Nc2ncnc3[nH]cnc23)cc(Cl)c(C)c1N1CCCC1=O]

A mixture of 6-bromo-9H-purine (8.5 mg, 0.043 mmol), 1-[3-(1-aminoethyl)-5-chloro-2-methoxy-6-methylphenyl]pyrrolidin-2-one (11 mg, 0.039 mmol), and N,N-diisopropylethylamine (0.014 mL, 0.078 mmol) in isopropyl alcohol (0.1 mL) was heated at 90° C. under nitrogen overnight. The mixture was evaporated and the resulting mixture was purified on RP-HPLC (XBridge C18 Column, eluting with a gradient of acetonitrile in water with 0.2% ammonium hydroxide, at flow rate of 30 mL/min) to give the desired product. LCMS calculated for $C_{19}H_{22}ClN_6O_2$ (M+H)$^+$: m/z=401.1. found: 401.1.

Example 19

4-Chloro-3',5'-difluoro-3-methyl-6-[1-(9H-purin-6-ylamino)ethyl]biphenyl-2-carboxamide

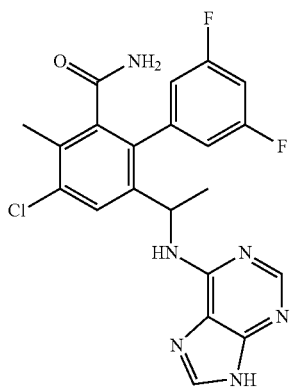 [SMILES: Cc1c(Cl)cc(C(C)Nc2ncnc3[nH]cnc23)c(-c2cc(F)cc(F)c2)c1C(N)=O]

Step 1. 6-Acetyl-4-chloro-3',5'-difluoro-3-methylbiphenyl-2-carbonitrile

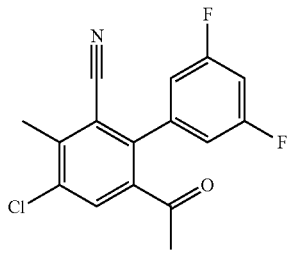 [SMILES: CC(=O)c1cc(Cl)c(C)c(C#N)c1-c1cc(F)cc(F)c1]

A biphasic solution of 6-acetyl-4-chloro-2-cyano-3-methylphenyl trifluoromethanesulfonate (4.5 g, 13 mmol) and (3,5-difluorophenyl)boronic acid (2.5 g, 16 mmol) in toluene (50 mL) and saturated sodium bicarbonate in water (50 mL) was bubbled with $N_2$ to degas. After tetrakis(triphenylphosphine)palladium(0) (0.61 g, 0.53 mmol) was added, the mixture was bubbled with $N_2$ for 5 min. and then heated at 80° C. for 2 hours. The mixture was cooled to room temperature and diluted with ethyl acetate. The layers were separated and the aq. layer was extracted with more ethyl acetate. The combined extracts were washed with brine, dried over $Na_2SO_4$, filtered and concentrated. The residue was purified on silica gel column, eluting with 0-30% of ethyl acetate in hexane, to give the desired product (1.94 g, 48%). LCMS calculated for $C_{16}H_{11}ClF_2NO$ $(M+H)^+$: m/z=306.0. found: 306.0.

Step 2. 6-Acetyl-4-chloro-3',5'-difluoro-3-methylbiphenyl-2-carboxamide

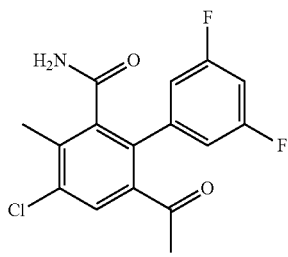 [SMILES: CC(=O)c1cc(Cl)c(C)c(C(N)=O)c1-c1cc(F)cc(F)c1]

A mixture of 6-acetyl-4-chloro-3',5'-difluoro-3-methylbiphenyl-2-carbonitrile (0.20 g, 0.65 mmol) and potassium hydroxide (0.074 g, 1.3 mmol) in ethanol (0.9 mL) was refluxed for 2 hours. After cooled, the mixture was acidified with 1 N HCl and extracted with ethyl acetate. The combined organic layers were washed with brine, dried over magnesium sulfate, and evaporated to dryness under reduced pressure. The crude mixture was purified on silica gel, eluting with 0 to 80% ethyl acetate in hexane, to yield the desired product (61 mg, 29%). LCMS calculated for $C_{16}H_{13}ClF_2NO_2$ $(M+H)^+$: m/z=324.1. found: 324.0.

Step 3. 6-(1-Aminoethyl)-4-chloro-3',5'-difluoro-3-methylbiphenyl-2-carboxamide

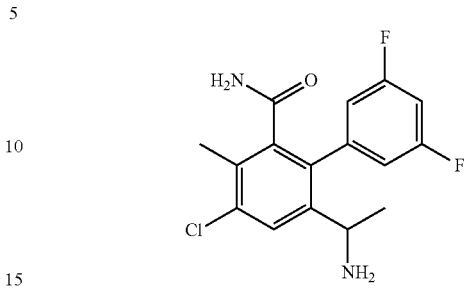

A mixture of 6-acetyl-4-chloro-3',5'-difluoro-3-methylbiphenyl-2-carboxamide (61 mg, 0.19 mmol), ammonium acetate (150 mg, 1.9 mmol) and sodium cyanoborohydride (24 mg, 0.38 mmol) in methanol (0.7 mL) and acetonitrile (0.7 mL) was heated at 65° C. overnight in a sealed tube. The mixture was then cooled to room temperature, quenched with saturated sodium bicarbonate and extracted with ethyl acetate. The combined extracts were dried over magnesium sulfate and evaporated to dryness. The crude product was used directly in next step (61 mg, 99%). LCMS calculated for $C_{16}H_{13}ClF_2NO$ $(M-NH_2)^+$: m/z=308.1. found: 308.0.

Step 4. 4-Chloro-3',5'-difluoro-3-methyl-6-[1-(9H-purin-6-ylamino)ethyl]biphenyl-2-carboxamide

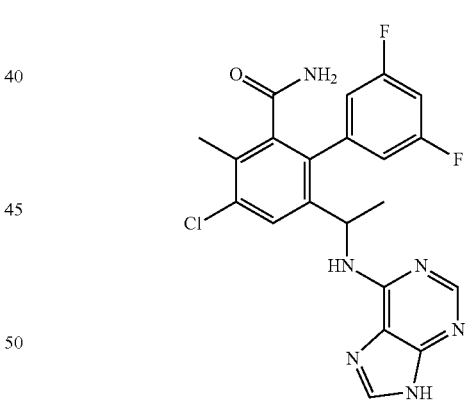

A mixture of 6-bromo-9H-purine (41 mg, 0.21 mmol), 6-(1-aminoethyl)-4-chloro-3',5'-difluoro-3-methylbiphenyl-2-carboxamide (61 mg, 0.19 mmol), and N,N-diisopropylethylamine (0.065 mL, 0.38 mmol) in isopropyl alcohol (0.7 mL) was heated at 90° C. under nitrogen overnight. The mixture was evaporated and the resulting mixture was purified on RP-HPLC (XBridge C18 Column, eluting with a gradient of acetonitrile in water with 0.2% ammonium hydroxide, at flow rate of 30 mL/min) to give the desired product. LCMS calculated for $C_{21}H_{18}ClF_2N_6O$ $(M+H)^+$: m/z=443.1. found: 443.1.

Example 20

N-(1-{5-chloro-3-[2-(dimethylamino)pyrimidin-5-yl]-2-methoxy-4-methylphenyl}ethyl)-9H-purin-6-amine

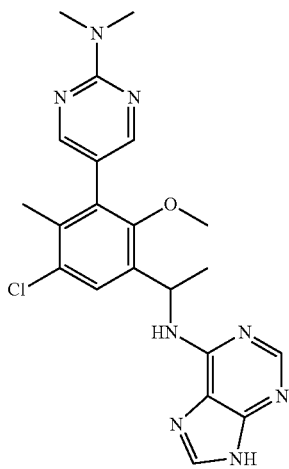 [SMILES: COc1c(C(C)Nc2ncnc3[nH]cnc23)cc(Cl)c(C)c1-c1cnc(N(C)C)nc1]

Step 1.
1-(3-Bromo-5-chloro-2-methoxy-4-methylphenyl)ethanone

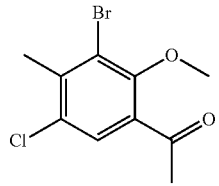

A mixture of 1-(3-bromo-5-chloro-2-hydroxy-4-methylphenyl)ethanone (10 g, 38 mmol), dimethyl sulfate (4.3 mL, 46 mmol) and potassium carbonate (11 g, 76 mmol) in acetone (200 mL) was heated at reflux overnight. After evaporation to dryness, the mixture was diluted with water and extracted with ethyl acetate. The combined organic layers were washed with brine, dried over sodium sulfate, and evaporated to dryness. The residue was purified on silica gel, eluting with 0 to 20% ethyl acetate in hexane, to yield the desired product (8.8 g, 84%). LCMS calculated for $C_{10}H_{11}BrClO_2$ (M+H)$^+$: m/z=277.0. found: 277.0.

Step 2. 1-{5-Chloro-3-[2-(dimethylamino)pyrimidin-5-yl]-2-methoxy-4-methylphenyl}ethanone

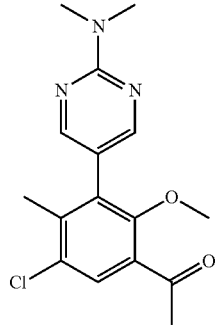 [SMILES: COc1c(C(C)=O)cc(Cl)c(C)c1-c1cnc(N(C)C)nc1]

A biphasic solution of 1-(3-bromo-5-chloro-2-methoxy-4-methylphenyl)ethanone (0.10 g, 0.36 mmol) and N,N-dimethyl-5-(4,4,5,5-tetramethyl-1,3,2-dioxaborolan-2-yl)pyrimidin-2-amine (0.11 g, 0.43 mmol) in 1,4-dioxane (1.2 mL) and 10% sodium carbonate in water (0.57 mL, 0.54 mmol) was bubbled with N$_2$ to degas. After tetrakis(triphenylphosphine)palladium(0) (17 mg, 0.014 mmol) was added, the mixture was bubbled with N$_2$ for 5 min. and heated at 100° C. overnight. The mixture was cooled to r.t. and diluted with ethyl acetate. The layers were separated and the aq. layer was extracted with more ethyl acetate. The combined extracts were washed with brine, dried over Na$_2$SO$_4$, filtered and concentrated. The residue was purified on silica gel column, eluting with 0-30% of ethyl acetate in hexane, to give the desired product (60 mg, 50%). LCMS calculated for $C_{16}H_{19}ClN_3O_2$ (M+H)$^+$: m/z=320.1. found: 320.1.

Step 3. 5-[3-(1-Aminoethyl)-5-chloro-2-methoxy-6-methylphenyl]-N,N-dimethylpyrimidin-2-amine

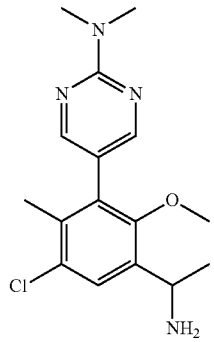 [SMILES: COc1c(C(C)N)cc(Cl)c(C)c1-c1cnc(N(C)C)nc1]

A mixture of 1-{5-chloro-3-[2-(dimethylamino)pyrimidin-5-yl]-2-methoxy-4-methylphenyl}ethanone (60 mg, 0.2 mmol), ammonium acetate (150 mg, 1.9 mmol) and sodium cyanoborohydride (24 mg, 0.38 mmol) in methanol (0.7 mL) and acetonitrile (0.7 mL) was heated at 65° C. overnight in a sealed tube. The mixture was cooled to room temperature, quenched with saturated sodium bicarbonate and extracted with ethyl acetate. The combined extracts were dried over magnesium sulfate and evaporated to dryness. The crude product was used directly in next step (60 mg, 100%). LCMS calculated for $C_{16}H_{22}ClN_4O$ (M+H)$^+$: m/z=321.1. found: 321.1.

Step 4. N-(1-{5-chloro-3-[2-(dimethylamino)pyrimidin-5-yl]-2-methoxy-4-methylphenyl}ethyl)-9H-purin-6-amine

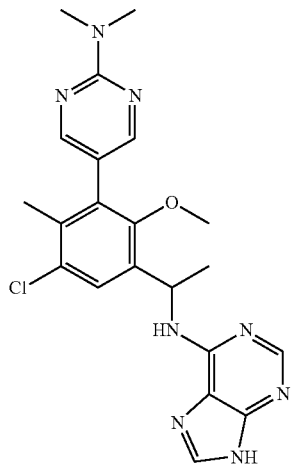 [SMILES: COc1c(C(C)Nc2ncnc3[nH]cnc23)cc(Cl)c(C)c1-c1cnc(N(C)C)nc1]

A mixture of 6-bromo-9H-purine (41 mg, 0.20 mmol), 5-[3-(1-aminoethyl)-5-chloro-2-methoxy-6-methylphenyl]-N,N-dimethylpyrimidin-2-amine (60 mg, 0.2 mmol), and N,N-diisopropylethylamine (0.065 mL, 0.37 mmol) in isopropyl alcohol (0.7 mL) was heated at 90° C. under nitrogen overnight. The mixture was evaporated and the resulting mixture was purified on RP-HPLC (XBridge C18 Column, eluting with a gradient of acetonitrile in water with 0.2% ammonium hydroxide, at flow rate of 30 mL/min) to give the desired product. LCMS calculated for $C_{21}H_{24}ClN_8O$ $(M+H)^+$: m/z=439.2. found: 439.1. $^1$H NMR (DMSO-d$_6$, 400 MHz) δ 12.91 (1H, br s), 8.29 (2H, s), 8.20 (1H, m), 8.13 (1H, s), 8.10 (1H, s), 7.61 (1H, s), 5.73 (1H, m), 3.46 (3H, s), 3.16 (6H, s), 2.06 (3H, s), 1.47 (3H, d, J=6.8 Hz) ppm.

Example 60

1-{3-Chloro-6-methoxy-2-methyl-5-[1-(9H-purin-6-ylamino)ethyl]phenyl}piperidin-4-ol

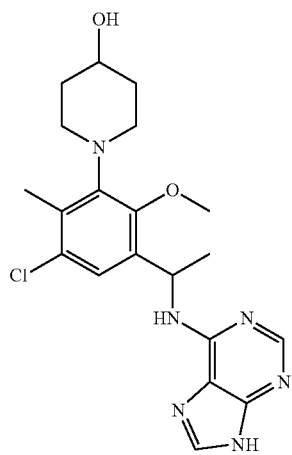 [SMILES: COc1c(C(C)Nc2ncnc3[nH]cnc23)cc(Cl)c(C)c1N1CCC(O)CC1]

Step 1.
1-(5-Chloro-2-hydroxy-3-iodo-4-methylphenyl)ethanone

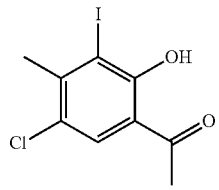

To a stirred solution of 1-(5-chloro-2-hydroxy-4-methylphenyl)ethanone (20 g, 110 mmol) in acetic acid (200 mL) was added N-iodosuccinimide (29 g, 130 mmol) and the resulting mixture was stirred at room temperature for 18 hours. The reaction mixture was concentrated in vacuo, neutralized with saturated sodium bicarbonate, filtered off insoluble succinimide and extracted with ethyl acetate. The combined organic layers were washed with brine, dried over sodium sulfate, filtered and concentrated to dryness under reduced pressure. The crude product was recrystalized from a mixture of ethyl acetate and hexane (25.8 mg, 77%). LCMS calculated for $C_9H_9ClIO_2$ $(M+H)^+$: m/z=311.0. found: 311.0.

Step 2.
1-(5-Chloro-3-iodo-2-methoxy-4-methylphenyl)ethanone

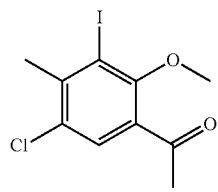

A mixture of 1-(5-chloro-2-hydroxy-3-iodo-4-methylphenyl)ethanone (10 g, 32 mmol), dimethyl sulfate (3.7 mL, 39 mmol) and potassium carbonate (8.9 g, 64 mmol) in acetone (200 mL) was heated at reflux overnight. After evaporation to dryness, the mixture was diluted with water and extracted with ethyl acetate. The combined organic layers were washed with brine, dried over sodium sulfate, filtered and evaporated to dryness. The residue was purified on silica gel, eluting with 0 to 20% ethyl acetate in hexane, to yield the desired product (8.99 g, 86%). LCMS calculated for $C_{10}H_{11}ClIO_2$ $(M+H)^+$: m/z=324.9. found: 324.9.

Step 3. 1-[5-Chloro-3-(4-hydroxypiperidin-1-yl)-2-methoxy-4-methylphenyl]ethanone

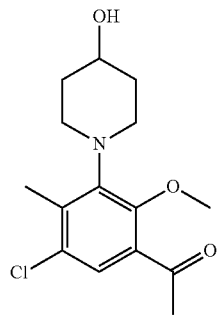

To a mixture of 1-(5-chloro-3-iodo-2-methoxy-4-methylphenyl)ethanone (150 mg, 0.46 mmol) and 4-hydroxypiperidine (56 mg, 0.56 mmol) in isopropyl alcohol (1 mL) was added 1,2-ethanediol (0.052 mL, 0.92 mmol), potassium phosphate (200 mg, 0.93 mmol), and copper(I) iodide (5 mg, 0.02 mmol). The reaction was heated at 80° C. overnight and then cooled to room temperature. Water was added, and the mixture was extracted with ethyl acetate. The combined organic phases were washed with brine and dried over sodium sulfate, filtered and concentrated to dryness. The residue was purified on silica gel, eluting with 0 to 50% ethyl acetate in hexanes, to give the desired product (15 mg, 11%). LCMS calculated for $C_{15}H_{21}ClNO_3$ $(M+H)^+$: m/z=298.1. found: 298.0.

Step 4. 1-[3-(1-Aminoethyl)-5-chloro-2-methoxy-6-methylphenyl]piperidin-4-ol

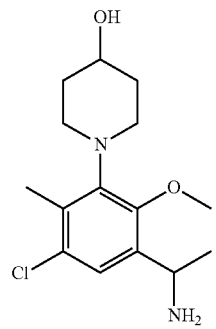

A mixture of 1-[5-chloro-3-(4-hydroxypiperidin-1-yl)-2-methoxy-4-methylphenyl]ethanone (15 mg, 0.050 mmol), ammonium acetate (39 mg, 0.50 mmol) and sodium cyanoborohydride (6 mg, 0.1 mmol) in methanol (0.2 mL) and acetonitrile (0.2 mL) was heated at 65° C. overnight in a sealed tube. The mixture was then cooled to room temperature, quenched with saturated sodium bicarbonate and extracted with dichloromethane. The combined extracts were dried over magnesium sulfate, filtered and concentrated to dryness. The resulting crude product was used directly in next step (7 mg, 50%). LCMS calculated for $C_{15}H_{24}ClN_2O_2$ (M+H)$^+$: m/z=299.1. found: 299.1.

Step 5. 1-{3-Chloro-6-methoxy-2-methyl-5-[1-(9H-purin-6-ylamino)ethyl]phenyl}piperidin-4-ol

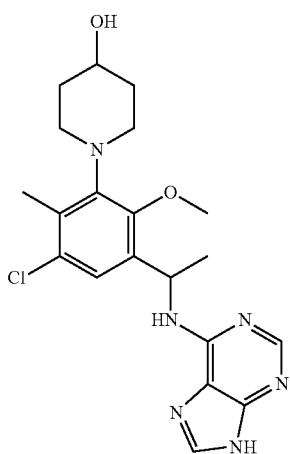 [SMILES: COc1c(C(C)Nc2ncnc3[nH]cnc23)cc(Cl)c(C)c1N1CCC(O)CC1]

A mixture of 6-bromo-9H-purine (5 mg, 0.03 mmol), 1-[3-(1-aminoethyl)-5-chloro-2-methoxy-6-methylphenyl]piperidin-4-ol (7 mg, 0.02 mmol), and N,N-diisopropylethylamine (0.0082 mL, 0.047 mmol) in isopropyl alcohol (0.1 mL) was heated at 90° C. under nitrogen overnight. The mixture was evaporated and the resulting mixture was purified on RP-HPLC (XBridge C18 Column, eluting with a gradient of acetonitrile in water with 0.2% ammonium hydroxide, at flow rate of 30 mL/min) to give the desired product. LCMS calculated for $C_{20}H_{26}ClN_6O_2$ (M+H)$^+$: m/z=417.2. found: 417.1.

Example 61

3'-Chloro-4-fluoro-6'-methoxy-2'-methyl-5'-[1-(9H-purin-6-ylamino)ethyl]biphenyl-3-carboxamide

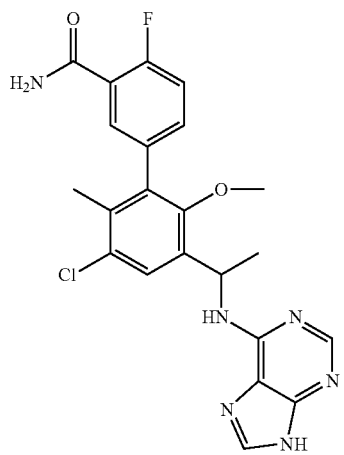 [SMILES: COc1c(C(C)Nc2ncnc3[nH]cnc23)cc(Cl)c(C)c1-c1ccc(F)c(C(N)=O)c1]

Step 1. Methyl 3'-acetyl-5'-chloro-4-fluoro-2'-methoxy-6'-methylbiphenyl-3-carboxylate

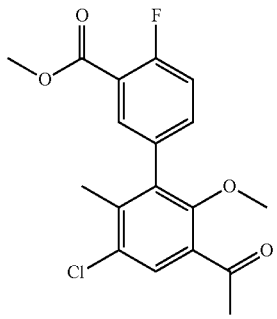

A biphasic solution of 1-(3-bromo-5-chloro-2-methoxy-4-methylphenyl)ethanone (0.800 g, 2.88 mmol) and [4-fluoro-3-(methoxycarbonyl)phenyl]boronic acid (0.684 g, 3.45 mmol) in 1,4-dioxane (9.3 mL) and 10% sodium carbonate in water (4.58 mL, 4.32 mmol) was bubbled with $N_2$ to degas. After tetrakis(triphenylphosphine)palladium(0) (133 mg, 0.115 mmol) was added, the mixture was bubbled with $N_2$ for 5 min. and heated at 100° C. overnight. The mixture was cooled to room temperature and diluted with ethyl acetate. The layers were separated and the aq. layer was extracted with more ethyl acetate. The combined extracts were washed with brine, dried over $Na_2SO_4$, filtered, and concentrated to crude product. LCMS calculated for $C_{18}H_{17}ClFO_4$ (M+H)$^+$: m/z=351.1. found: 351.1.

Step 2. 3'-Acetyl-5'-chloro-4-fluoro-2'-methoxy-6'-methylbiphenyl-3-carboxamide

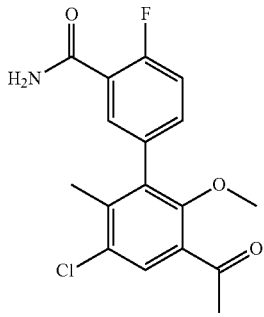 [SMILES: COc1c(C(C)=O)cc(Cl)c(C)c1-c1ccc(F)c(C(N)=O)c1]

A mixture of methyl 3'-acetyl-5'-chloro-4-fluoro-2'-methoxy-6'-methylbiphenyl-3-carboxylate (50 mg, 0.1 mmol) and 7.0 M ammonia in methanol (2.0 mL, 14 mmol) was heated at 90° C. in a sealed tube overnight. After evaporating the mixture to dryness, the residue was used directly in next step. LCMS calculated for $C_{17}H_{16}ClFNO_3$ $(M+H)^+$: m/z=336.1. found: 336.0.

Step 3. 3'-(1-Aminoethyl)-5'-chloro-4-fluoro-2'-methoxy-6'-methylbiphenyl-3-carboxamide

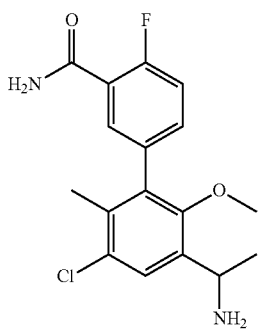 [SMILES: COc1c(C(C)N)cc(Cl)c(C)c1-c1ccc(F)c(C(N)=O)c1]

A mixture of 3'-acetyl-5'-chloro-4-fluoro-2'-methoxy-6'-methylbiphenyl-3-carboxamide (50 mg, 0.1 mmol), ammonium acetate (115 mg, 1.49 mmol) and sodium cyanoborohydride (19 mg, 0.30 mmol) in methanol (0.5 mL) and acetonitrile (0.5 mL) was heated at 65° C. overnight in a sealed tube. The mixture was then cooled to room temperature, quenched with saturated sodium bicarbonate and extracted with dichloromethane. The combined extracts were dried over magnesium sulfate, filtered and concentrated to dryness. The resulting crude product was used directly in next step (36 mg, 70%). LCMS calculated for $C_{17}H_{16}ClFNO_2$ $(M-NH_2)^+$: m/z=320.1. found: 320.1.

Step 4. 3'-Chloro-4-fluoro-6'-methoxy-2'-methyl-5'-[1-(9H-purin-6-ylamino)ethyl]biphenyl-3-carboxamide

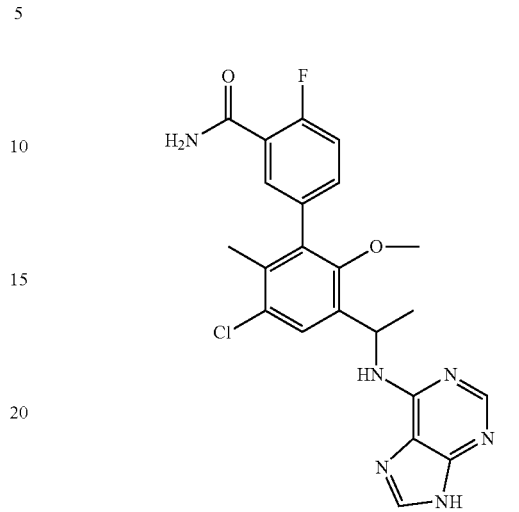

A mixture of 6-bromo-9H-purine (23 mg, 0.12 mmol), 3'-(1-aminoethyl)-5'-chloro-4-fluoro-2'-methoxy-6'-methylbiphenyl-3-carboxamide (36 mg, 0.11 mmol), and N,N-diisopropylethylamine (0.037 mL, 0.21 mmol) in isopropyl alcohol (0.4 mL) was heated at 90° C. under nitrogen overnight. The mixture was evaporated and the resulting mixture was purified on RP-HPLC (XBridge C18 Column, eluting with a gradient of acetonitrile in water with 0.2% ammonium hydroxide, at flow rate of 30 mL/min) to give the desired product. LCMS calculated for $C_{22}H_{21}ClFN_6O_2$ $(M+H)^+$: m/z=455.1. found: 455.1.

Example 62

3'-Chloro-3-fluoro-6'-methoxy-2'-methyl-5'-[1-(9H-purin-6-ylamino)ethyl]biphenyl-4-carboxamide

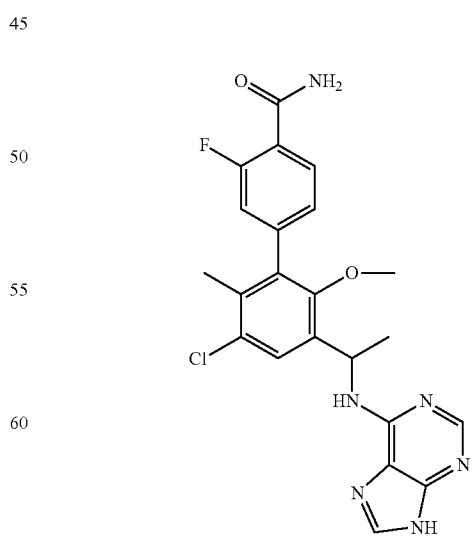

Step 1. Methyl 3'-acetyl-5'-chloro-3-fluoro-2'-methoxy-6'-methylbiphenyl-4-carboxylat

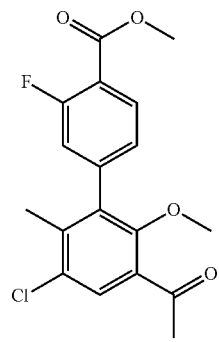

A mixture of 1-(3-bromo-5-chloro-2-methoxy-4-methylphenyl)ethanone (1.0 g, 3.6 mmol) and [3-fluoro-4-(methoxycarbonyl)phenyl]boronic acid (0.85 g, 4.3 mmol) in 1,4-dioxane (12 mL) and 10% sodium carbonate in water (5.73 mL, 5.40 mmol) was bubbled with $N_2$ to degas. After tetrakis(triphenylphosphine)palladium(0) (166 mg, 0.144 mmol) was added, the mixture was bubbled with $N_2$ for 5 min. more and heated at 100° C. overnight. The mixture was cooled to room temperature and diluted with ethyl acetate. The layers were separated and the aq. layer was extracted with more ethyl acetate. The combined extracts were washed with brine, dried over $Na_2SO_4$, filtered, and concentrated to give crude product.

Step 2. 3'-Acetyl-5'-chloro-3-fluoro-2'-methoxy-6'-methylbiphenyl-4-carboxamide

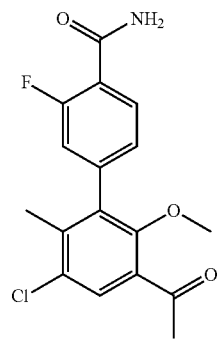

A mixture of methyl 3'-acetyl-5'-chloro-3-fluoro-2'-methoxy-6'-methylbiphenyl-4-carboxylate (25 mg, 0.071 mmol) and 7.0 M ammonia in methanol (2.0 mL, 14 mmol) was heated at 90° C. in a sealed tube overnight. After evaporating the mixture to dryness, the residue was used directly in next step.

Step 3. 3'-(1-Aminoethyl)-5'-chloro-3-fluoro-2'-methoxy-6'-methylbiphenyl-4-carboxamide

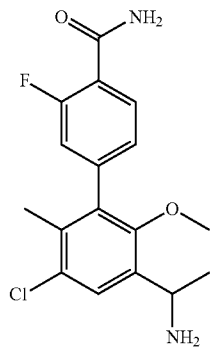 [SMILES: COc1c(C(C)N)cc(Cl)c(C)c1-c1ccc(C(N)=O)c(F)c1]

A mixture of 3'-acetyl-5'-chloro-3-fluoro-2'-methoxy-6'-methylbiphenyl-4-carboxamide (25 mg, 0.074 mmol), ammonium acetate (57 mg, 0.74 mmol) and sodium cyanoborohydride (9 mg, 0.15 mmol) in methanol (0.3 mL) and acetonitrile (0.3 mL) was heated at 65° C. overnight in a sealed tube. The mixture was cooled to room temperature, quenched with saturated sodium bicarbonate and extracted with dichloromethane. The combined extracts were dried over magnesium sulfate, filtered and concentrated to dryness. The resulting crude product was used directly in next step (20 mg, 80%). LCMS calculated for $C_{17}H_{16}ClFNO_2$ $(M-NH_2)^+$: m/z=320.1. found: 320.1.

Step 4. 3'-Chloro-3-fluoro-6'-methoxy-2'-methyl-5'-[1-(9H-purin-6-ylamino)ethyl]biphenyl-4-carboxamide

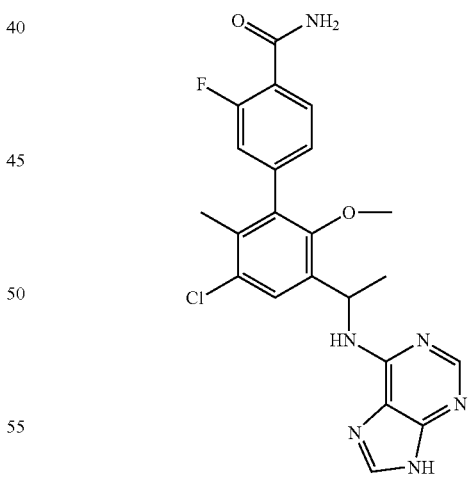

A mixture of 6-bromo-9H-purine (13 mg, 0.065 mmol), 3'-(1-aminoethyl)-5'-chloro-3-fluoro-2'-methoxy-6'-methylbiphenyl-4-carboxamide (20 mg, 0.06 mmol), and N,N-diisopropylethylamine (0.021 mL, 0.12 mmol) in isopropyl alcohol (0.2 mL) was heated at 90° C. under nitrogen overnight. The mixture was evaporated and the resulting mixture was purified on RP-HPLC (XBridge C18 Column, eluting with a gradient of acetonitrile in water with 0.2% ammonium hydroxide, at flow rate of 30 mL/min) to give the desired product. LCMS calculated for $C_{22}H_{21}ClFN_6O_2$ (M+H)$^+$: m/z=455.1. found: 455.0.

Example 63

1-({3'-Chloro-3-fluoro-6'-methoxy-2'-methyl-5'-[1-(9H-purin-6-ylamino)ethyl]biphenyl-4-yl}carbonyl)azetidine-3-carbonitrile

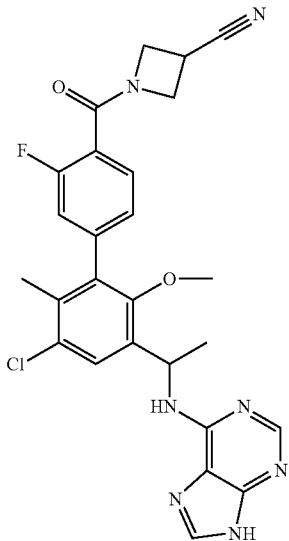 [SMILES: COc1c(C(C)Nc2ncnc3[nH]cnc23)cc(Cl)c(C)c1-c1ccc(C(=O)N2CC(C#N)C2)c(F)c1]

Step 1. 3'-Acetyl-5'-chloro-3-fluoro-2'-methoxy-6'-methylbiphenyl-4-carboxylic acid

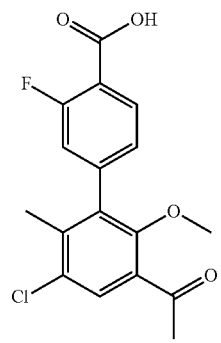 [SMILES: COc1c(C(C)=O)cc(Cl)c(C)c1-c1ccc(C(=O)O)c(F)c1]

A mixture of methyl 3'-acetyl-5'-chloro-3-fluoro-2'-methoxy-6'-methylbiphenyl-4-carboxylate (1.2 g, 3.4 mmol) and 3.75 M sodium hydroxide in water (10 mL, 38 mmol) in methanol (10 mL) was stirred at room temperature overnight. The mixture was neutralized with HCl and extracted with ethyl acetate. The combined organic layers were washed with brine, dried over magnesium sulfate, filtered and concentrated to dryness under reduced pressure. The residue was used directly in next step (704 mg, 61%). LCMS calculated for $C_{17}H_{15}ClFO_4$ (M+H)$^+$: m/z=337.1. found: 337.1.

Step 2. 1-[(3'-Acetyl-5'-chloro-3-fluoro-2'-methoxy-6'-methylbiphenyl-4-yl)carbonyl]azetidine-3-carbonitrile

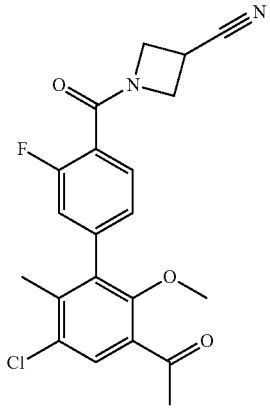 [SMILES: COc1c(C(C)=O)cc(Cl)c(C)c1-c1ccc(C(=O)N2CC(C#N)C2)c(F)c1]

To a solution of 3'-acetyl-5'-chloro-3-fluoro-2'-methoxy-6'-methylbiphenyl-4-carboxylic acid (70 mg, 0.2 mmol), azetidine-3-carbonitrile hydrochloride (30 mg, 0.25 mmol) and benzotriazol-1-yloxytris(dimethylamino)phosphonium hexafluorophosphate (0.11 g, 0.25 mmol) in N,N-dimethylformamide (0.42 mL) was added N,N-diisopropylethylamine (0.08 mL, 0.46 mmol). After being stirred at room temperature for 2 h, the mixture was diluted with ethyl acetate, washed with water, brine, dried and concentrated to dryness. The residue was purified on silica gel, eluting with 0 to 60% ethyl acetate in hexane, to give the desired product (25 mg, 30% in 3 steps). LCMS calculated for $C_{21}H_{19}ClFN_2O_3$ (M+H)$^+$: m/z=401.1. found: 401.1.

Step 3. 1-{[3'-(1-Aminoethyl)-5'-chloro-3-fluoro-2'-methoxy-6'-methylbiphenyl-4-yl]carbonyl}azetidine-3-carbonitrile

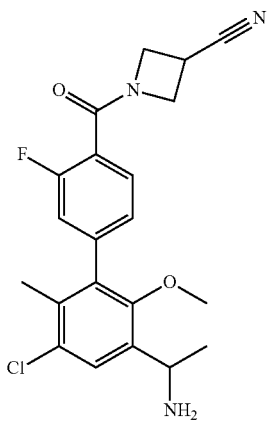 [SMILES: COc1c(C(C)N)cc(Cl)c(C)c1-c1ccc(C(=O)N2CC(C#N)C2)c(F)c1]

A mixture of 1-[(3'-acetyl-5'-chloro-3-fluoro-2'-methoxy-6'-methylbiphenyl-4-yl)carbonyl]azetidine-3-carbonitrile (25 mg, 0.062 mmol), ammonium acetate (48 mg, 0.62 mmol) and sodium cyanoborohydride (8 mg, 0.1 mmol) in methanol (0.2 mL) and acetonitrile (0.2 mL) was heated at 65° C. overnight in a sealed tube. The mixture was cooled to room temperature, quenched with saturated sodium bicarbonate and extracted with dichloromethane. The combined extracts were dried over magnesium sulfate, filtered and concentrated to dryness. The resulting crude product was used directly in next step (21 mg, 84%). LCMS calculated for $C_{21}H_{19}ClFN_2O_2$ (M-NH$_2$)$^+$: m/z=385.1. found: 385.1.

Step 4. 1-({3'-Chloro-3-fluoro-6'-methoxy-2'-methyl-5'-[1-(9H-purin-6-ylamino)ethyl]biphenyl-4-yl}carbonyl)azetidine-3-carbonitrile

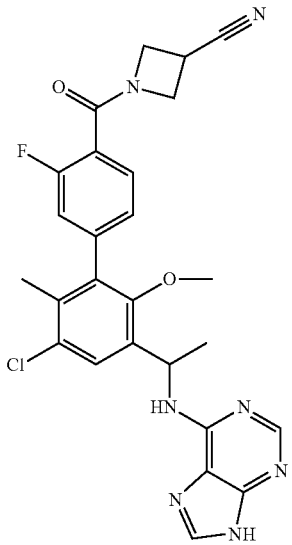 [SMILES: COc1c(C(C)Nc2ncnc3[nH]cnc23)cc(Cl)c(C)c1-c1ccc(C(=O)N2CC(C#N)C2)c(F)c1]

A mixture of 6-bromo-9H-purine (11 mg, 0.057 mmol), 1-{[3'-(1-aminoethyl)-5'-chloro-3-fluoro-2'-methoxy-6'-methylbiphenyl-4-yl]carbonyl}azetidine-3-carbonitrile (21 mg, 0.052 mmol), and N,N-diisopropylethylamine (0.018 mL, 0.10 mmol) in isopropyl alcohol (0.2 mL) was heated at 90° C. under nitrogen overnight. The mixture was evaporated and the resulting mixture was purified on RP-HPLC (XBridge C18 Column, eluting with a gradient of acetonitrile in water with 0.2% ammonium hydroxide, at flow rate of 30 mL/min) to give the desired product. LCMS calculated for $C_{26}H_{24}ClFN_7O_2$ (M+H)$^+$: m/z=520.2. found: 520.1.

Example 71

N-{1-[4-chloro-6-(3,5-dimethylisoxazol-4-yl)-3'-fluoro-5-methylbiphenyl-2-yl]ethyl}-9H-purin-6-amine trifluoroacetate

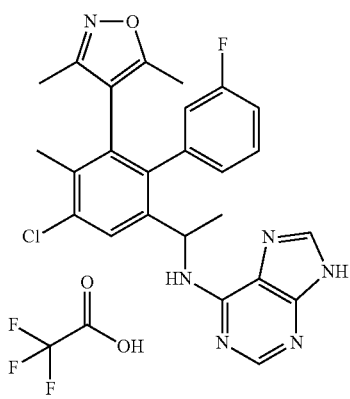

Step 1. 1-(6-Bromo-4-chloro-3'-fluoro-5-methylbiphenyl-2-yl) ethanone

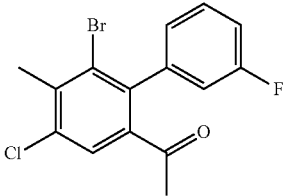 [SMILES: CC(=O)c1cc(Cl)c(C)c(Br)c1-c1cccc(F)c1]

To a solution of sodium hydrogenecarbonate (0.21 g, 2.5 mmol) in water (5 mL) was added a solution of 6-acetyl-2-bromo-4-chloro-3-methylphenyl trifluoromethanesulfonate (0.50 g, 1.3 mmol) in toluene (5 mL) followed by (3-fluorophenyl)boronic acid (0.21 g, 1.5 mmol) and tetrakis(triphenylphosphine)palladium(0) (75 mg, 0.065 mmol). The mixture was bubbled with N$_2$ for 5 min and then heated at 80° C. overnight. The reaction was diluted with water and extracted with ethyl acetate. The combined organic layers were dried over sodium sulfate, concentrated and purified on silica gel (eluting with 0-20% of ethyl acetate in hexanes) to give the desired product (0.40 g, 93%). LCMS calculated for $C_{15}H_{12}BrClFO$ (M+H)$^+$: m/z=341.0. found: 341.0.

Step 2. 1-[4-chloro-6-(3,5-dimethylisoxazol-4-yl)-3'-fluoro-5-methylbiphenyl-2-yl]ethanone

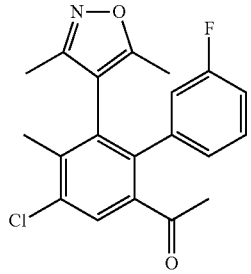 [SMILES: CC(=O)c1cc(Cl)c(C)c(-c2c(C)noc2C)c1-c1cccc(F)c1]

To a solution of sodium hydrogenecarbonate (49 mg, 0.58 mmol) in water (1 mL) was added a solution of 1-(6-bromo-4-chloro-3'-fluoro-5-methylbiphenyl-2-yl)ethanone (0.10 g, 0.29 mmol) in toluene (1 mL) followed by 3,5-dimethyl-4-(4,4,5,5-tetramethyl-1,3,2-dioxaborolan-2-yl)isoxazole (78 mg, 0.35 mmol) and tetrakis(triphenylphosphine)palladium (0) (17 mg, 0.015 mmol). The reaction mixture was bubbled with N$_2$ for 5 min and then heated at 80° C. overnight. The organic layer was concentrated and flashed on silica gel (eluting with 0-35% of ethyl acetate in hexanes) to afford the desired product (40 mg, 38%). LCMS calculated for $C_{20}H_{18}ClFNO_2$ (M+H)$^+$: m/z=358.1. found: 358.1.

Step 3. 1-[4-Chloro-6-(3,5-dimethylisoxazol-4-yl)-3'-fluoro-5-methylbiphenyl-2-yl]ethanamine

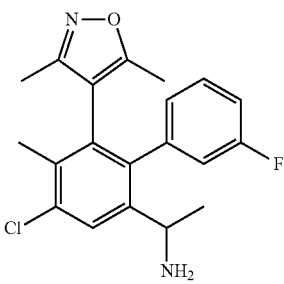 [SMILES: Cc1noc(C)c1-c1c(C)c(Cl)cc(C(C)N)c1-c1cccc(F)c1]

A mixture of 1-[4-chloro-6-(3,5-dimethylisoxazol-4-yl)-3'-fluoro-5-methylbiphenyl-2-yl]ethanone (40 mg, 0.11 mmol), ammonium acetate (86 mg, 1.1 mmol) and 1.0 M sodium cyanoborohydride in tetrahydrofuran (0.28 mL, 0.28 mmol) in methanol (0.6 mL) and acetonitrile (0.6 mL) was heated at 65° C. overnight. The mixture was cooled to room temperature, quenched with saturated sodium bicarbonate solution and extracted with dichloromethane. The combined organic layers were dried over MgSO$_4$, filtered and concentrated to give the desired product (35 mg, 87%). LCMS calculated for $C_{20}H_{21}ClFN_2O$ (M+H)$^+$: m/z=359.1. found: 359.1.

Step 4. N-{1-[4-chloro-6-(3,5-dimethylisoxazol-4-yl)-3'-fluoro-5-methylbiphenyl-2-yl]ethyl}-9H-purin-6-amine trifluoroacetate

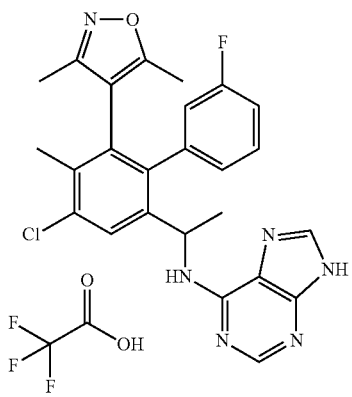

A mixture of 1-[4-chloro-6-(3,5-dimethylisoxazol-4-yl)-3'-fluoro-5-methylbiphenyl-2-yl]ethanamine (35 mg, 0.098 mmol), 6-bromo-9H-purine (29 mg, 0.15 mmol) and N,N-diisopropylethylamine (0.034 mL, 0.20 mmol) in ethanol (0.7 mL) was heated at 100° C. for 2 hours. The residue was concentrated and purified on prep LCMS (XBridge C18 Column, eluting with a gradient of acetonitrile in water with 0.05% trifluoroacetic acid, at flow rate of 30 mL/min) to afford the desired product as TFA salt. LCMS calculated for $C_{25}H_{23}ClFN_6O$ (M+H)$^+$: m/z=477.2. found: 477.1.

Example 72

N-{1-[4-Chloro-3'-fluoro-5-methyl-6-(1H-pyrazol-4-yl)biphenyl-2-yl]ethyl}-9H-purin-6-amine trifluoroacetate

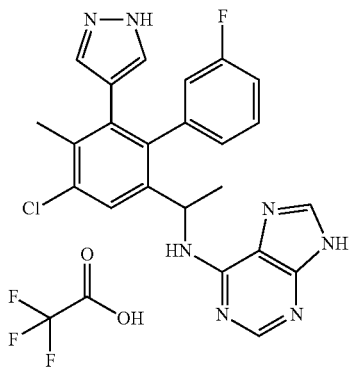

Step 1. 1-{4-Chloro-6-[1-(1-ethoxyethyl)-1H-pyrazol-4-yl]-3'-fluoro-5-methylbiphenyl-2-yl}ethanone

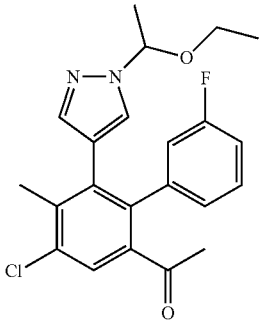 [SMILES: CCOC(C)n1cc(-c2c(C)c(Cl)cc(C(C)=O)c2-c2cccc(F)c2)cn1]

To a solution of sodium hydrogenecarbonate (0.049 g, 0.58 mmol) in water (1 mL) was added a solution of 1-(6-bromo-4-chloro-3'-fluoro-5-methylbiphenyl-2-yl)ethanone (0.10 g, 0.29 mmol) in toluene (1 mL) followed by 1-(1-ethoxyethyl)-4-(4,4,5,5-tetramethyl-1,3,2-dioxaborolan-2-yl)-1H-pyrazole (0.093 g, 0.35 mmol) and tetrakis(triphenylphosphine)palladium(0) (0.017 g, 0.015 mmol). The resulting mixture was bubbled with N$_2$ for 5 min and then heated at 80° C. over a weekend. The organic layer was concentrated and purified on silica gel (eluting with 0-30% of ethyl acetate in hexanes) to give the desired product (37 mg, 32%). LCMS calculated for $C_{22}H_{23}ClFN_2O_2$ (M+H)$^+$: m/z=401.1. found: 401.1.

Step 2. 1-{4-Chloro-6-[1-(1-ethoxyethyl)-1H-pyrazol-4-yl]-3'-fluoro-5-methylbiphenyl-2-yl}ethanamine

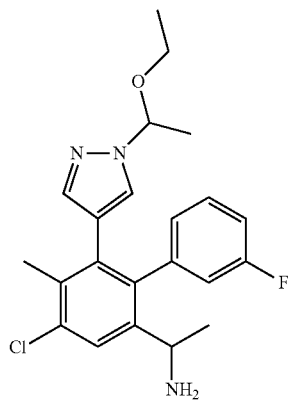 [SMILES: CCOC(C)n1cc(-c2c(C)c(Cl)cc(C(C)N)c2-c2cccc(F)c2)cn1]

A mixture of 1-{4-chloro-6-[1-(1-ethoxyethyl)-1H-pyrazol-4-yl]-3'-fluoro-5-methylbiphenyl-2-yl}ethanone (37 mg, 0.092 mmol), ammonium acetate (71 mg, 0.92 mmol) and 1.0 M sodium cyanoborohydride in tetrahydrofuran (0.23 mL, 0.23 mmol) in methanol (0.5 mL) and acetonitrile (0.5 mL) was heated at 65° C. overnight. The mixture was cooled to room temperature, quenched with saturated sodium bicarbonate solution, extracted with dichloromethane. The combined organic layers were dried over MgSO$_4$, filtered and concentrated to give the desired product (35 mg). LCMS calculated for $C_{22}H_{26}ClFN_3O$ (M+H)$^+$: m/z=402.2. found: 402.2.

Step 3. N-{1-[4-Chloro-3'-fluoro-5-methyl-6-(1H-pyrazol-4-yl)biphenyl-2-yl]ethyl}-9H-purin-6-amine trifluoroacetate

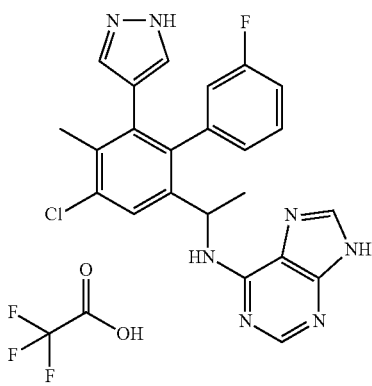 [SMILES: O=C(O)C(F)(F)F ; Cc1c(Cl)cc(C(C)Nc2ncnc3[nH]cnc23)c(-c2cccc(F)c2)c1-c1cn[nH]c1]

A mixture of 1-{4-chloro-6-[1-(1-ethoxyethyl)-1H-pyrazol-4-yl]-3'-fluoro-5-methylbiphenyl-2-yl}ethanamine (35 mg, 0.087 mmol), 6-bromo-9H-purine (26 mg, 0.13 mmol) and N,N-diisopropylethylamine (0.030 mL, 0.17 mmol) in ethanol (0.6 mL) was heated at 100° C. overnight. The residue was concentrated and treated with 1.0 M hydrogen chloride in water (0.50 mL, 0.50 mmol) in tetrahydrofuran (0.5 mL) overnight. The mixture was diluted with MeOH and purified on prep LCMS (XBridge C18 Column, eluting with a gradient of acetonitrile in water with 0.05% trifluoroacetic acid, at flow rate of 30 mL/min) to afford the desired product as TFA salt. LCMS calculated for $C_{23}H_{20}ClFN_7$ (M+H)+: m/z=448.1. found: 448.1.

Example 76

N-[1-(4-Chloro-3',5'-difluoro-5-methyl-6-pyridin-4-ylbiphenyl-2-yl)ethyl]-9H-purin-6-amine bis(trifluoroacetate)

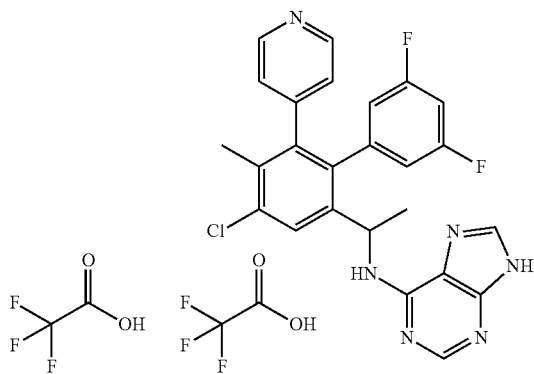

Step 1. 1-(6-Bromo-4-chloro-3',5'-difluoro-5-methylbiphenyl-2-yl) ethanone

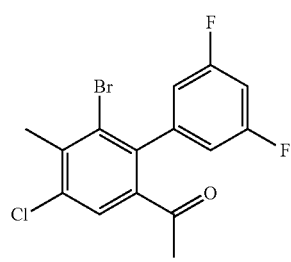 [SMILES: CC(=O)c1cc(Cl)c(C)c(Br)c1-c1cc(F)cc(F)c1]

To a solution of sodium hydrogenecarbonate (2.8 g, 34 mmol) in water (70 mL) was added a solution of 6-acetyl-2-bromo-4-chloro-3-methylphenyl trifluoromethanesulfonate (6.7 g, 17 mmol) in toluene (70 mL) followed by (3,5-difluorophenyl)boronic acid (2.9 g, 19 mmol) and tetrakis(triphenylphosphine)palladium(0) (0.98 g, 0.85 mmol). The mixture was bubbled with $N_2$ for 5 min and then heated at 80° C. overnight. The reaction was diluted with water and extracted with ethyl acetate. The combined organic layers were dried, filtered, concentrated and purified on silica gel (eluting with 0-15% of ethyl acetate in hexanes) to give the desired product (5.6 g). LCMS calculated for $C_{15}H_{11}BrClF_2O$ (M+H)+: m/z=359.0. found: 359.0.

Step 2. 1-(4-Chloro-3',5'-difluoro-5-methyl-6-pyridin-4-ylbiphenyl-2-yl)ethanone

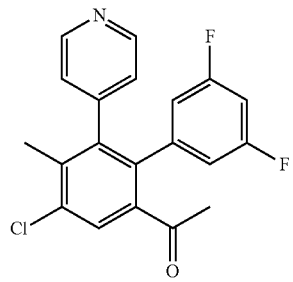 [SMILES: CC(=O)c1cc(Cl)c(C)c(-c2ccncc2)c1-c1cc(F)cc(F)c1]

To a solution of sodium hydrogenecarbonate (0.093 g, 1.1 mmol) in water (2 mL) was added a solution of 1-(6-bromo-4-chloro-3',5'-difluoro-5-methylbiphenyl-2-yl)ethanone (0.20 g, 0.56 mmol) in toluene (2 mL) followed by 4-pyridinylboronic Acid (0.082 g, 0.67 mmol) and tetrakis(triphenylphosphine)palladium(0) (0.033 g, 0.029 mmol). The mixture was bubbled with $N_2$ for 5 min and then heated at 80° C. overnight. The organic layer was concentrated and flashed on silica gel (eluting with 0-35% of ethyl acetate in hexanes) to afford the desired product (13 mg, 6.5%). LCMS calculated for $C_{20}H_{15}ClF_2NO$ (M+H)+: m/z=358.1. found: 358.1.

Step 3. 1-(4-Chloro-3',5'-difluoro-5-methyl-6-pyridin-4-ylbiphenyl-2-yl)ethanamine

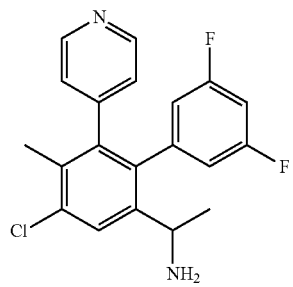 [SMILES: Cc1c(Cl)cc(C(C)N)c(-c2cc(F)cc(F)c2)c1-c1ccncc1]

A mixture of 1-(4-chloro-3',5'-difluoro-5-methyl-6-pyridin-4-ylbiphenyl-2-yl)ethanone (0.013 g, 0.036 mmol), ammonium acetate (0.028 g, 0.36 mmol) and 1.0 M sodium cyanoborohydride in tetrahydrofuran (0.091 mL, 0.091 mmol) in methanol (0.1 mL) and acetonitrile (0.1 mL) was heated at 65° C. overnight. The mixture was cooled to room Step 4. N-[1-(4-Chloro-3',5'-difluoro-5-methyl-6-pyridin-4-ylbiphenyl-2-yl)ethyl]-9H-purin-6-amine bis(trifluoroacetate)

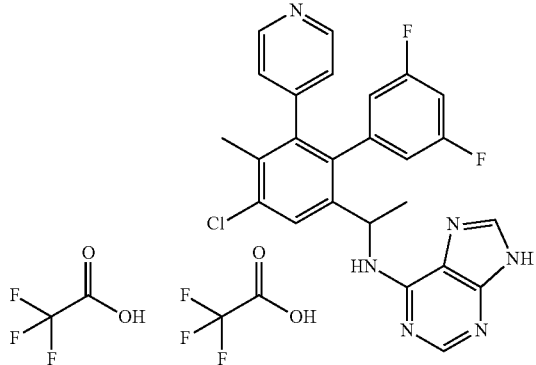

A mixture of 1-(4-chloro-3',5'-difluoro-5-methyl-6-pyridin-4-ylbiphenyl-2-yl)ethanamine (0.013 g, 0.036 mmol), 6-bromo-9H-purine (0.011 g, 0.054 mmol) and N,N-diisopropylethylamine (0.013 mL, 0.072 mmol) in ethanol (0.3 mL) was heated at 100° C. overnight. The mixture was purified on prep LCMS (XBridge C18 Column, eluting with a gradient of acetonitrile in water with 0.05% trifluoroacetic acid, at flow rate of 30 mL/min) to afford the desired product as TFA salt. LCMS calculated for $C_{25}H_{20}ClF_2N_6$ $(M+H)^+$: m/z=477.1. found: 477.1.

Example 106

N-{1-[4-Chloro-3',5'-difluoro-5-methyl-6-(1H-pyrazol-4-yl)biphenyl-2-yl]ethyl}-9H-purin-6-amine

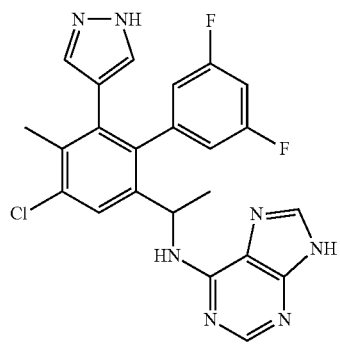 [SMILES: Cc1c(Cl)cc(C(C)Nc2ncnc3[nH]cnc23)c(-c2cc(F)cc(F)c2)c1-c1cn[nH]c1]

Step 1. 1-{4-Chloro-6-[1-(1-ethoxyethyl)-1H-pyrazol-4-yl]-3',5'-difluoro-5-methylbiphenyl-2-yl}ethanone

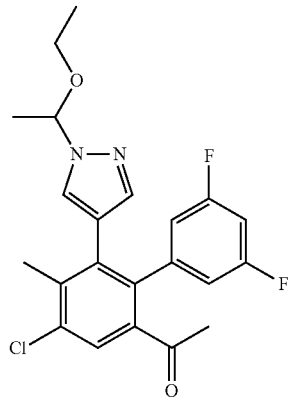 [SMILES: CCOC(C)n1cc(-c2c(C)c(Cl)cc(C(C)=O)c2-c2cc(F)cc(F)c2)cn1]

To a solution of sodium hydrogenecarbonate (0.093 g, 1.1 mmol) in water (2 mL) was added a solution of 1-(6-bromo-4-chloro-3',5'-difluoro-5-methylbiphenyl-2-yl)ethanone (0.20 g, 0.56 mmol) in toluene (2 mL) followed by 1-(1-ethoxyethyl)-4-(4,4,5,5-tetramethyl-1,3,2-dioxaborolan-2-yl)-1H-pyrazole (0.18 g, 0.67 mmol) and tetrakis(triphenylphosphine)palladium(0) (0.064 g, 0.056 mmol). The mixture was bubbled with $N_2$ for 5 min and then heated at 90° C. overnight. The organic layer was concentrated and flashed on silica gel (eluting with 0-20% of ethyl acetate in hexanes) to afford the desired product (94 mg, 40%). LCMS calculated for $C_{22}H_{22}ClF_2N_2O_2$ $(M+H)^+$: m/z=419.1. found: 419.1.

Step 2. 1-{4-Chloro-6-[1-(1-ethoxyethyl)-1H-pyrazol-4-yl]-3',5'-difluoro-5-methylbiphenyl-2-yl}ethanamine

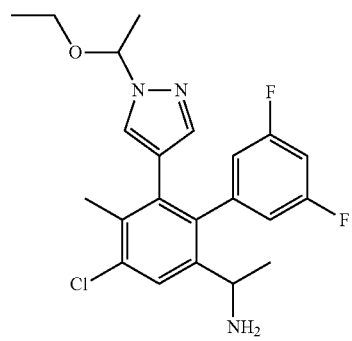 [SMILES: CCOC(C)n1cc(-c2c(C)c(Cl)cc(C(C)N)c2-c2cc(F)cc(F)c2)cn1]

A mixture of 1-{4-chloro-6-[1-(1-ethoxyethyl)-1H-pyrazol-4-yl]-3',5'-difluoro-5-methylbiphenyl-2-yl}ethanone (0.094 g, 0.22 mmol), ammonium acetate (0.17 g, 2.2 mmol) and 1.0 M sodium cyanoborohydride in tetrahydrofuran (0.56 mL, 0.56 mmol) in methanol (0.6 mL) and acetonitrile (0.6 mL) was heated at 65° C. overnight. The mixture was cooled to room temperature, quenched with saturated sodium bicarbonate solution and extracted with dichloromethane. The combined organic layers were dried over MgSO₄, filtered and concentrated to give the desired product. LCMS calculated for $C_{22}H_{25}ClF_2N_3O$ (M+H)⁺: m/z=420.2. found: 420.1.

Step 3. N-{1-[4-chloro-3',5'-difluoro-5-methyl-6-(1H-pyrazol-4-yl) biphenyl-2-yl]ethyl}-9H-purin-6-amine

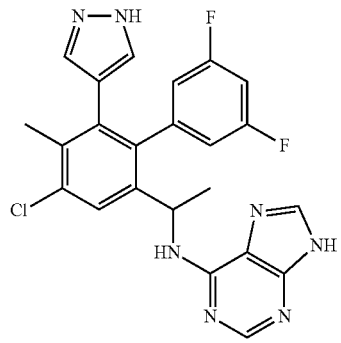 [SMILES: Cc1c(Cl)cc(C(C)Nc2ncnc3[nH]cnc23)c(-c2cc(F)cc(F)c2)c1-c1cn[nH]c1]

A mixture of 1-{4-chloro-6-[1-(1-ethoxyethyl)-1H-pyrazol-4-yl]-3',5'-difluoro-5-methylbiphenyl-2-yl}ethanamine (0.074 g, 0.18 mmol), 6-bromo-9H-purine (0.053 g, 0.26 mmol) and N,N-diisopropylethylamine (0.061 mL, 0.35 mmol) in ethanol (0.6 mL) was heated at 100° C. overnight. The residue was concentrated and treated with 1.0 M hydrogen chloride in water (1.0 mL, 1.0 mmol) in tetrahydrofuran (1 mL) overnight. The mixture was diluted with MeOH and purified on prep LCMS (XBridge C18 Column, eluting with a gradient of acetonitrile in water with 0.2% ammonium hydroxide, at flow rate of 30 mL/min) to afford the desired product. LCMS calculated for $C_{23}H_{19}ClF_2N_7$ (M+H)⁺: m/z=466.1. found: 466.1.

Example 108

N-{1-[5-Chloro-3-(5-fluoropyridin-3-yl)-2-methoxy-4-methylphenyl]ethyl}-9H-purin-6-amine

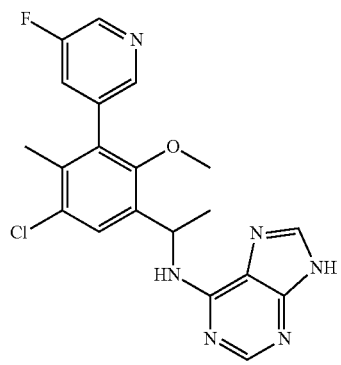 [SMILES: COc1c(C(C)Nc2ncnc3[nH]cnc23)cc(Cl)c(C)c1-c1cncc(F)c1]

Step 1. 6-Bromo-9-(tetrahydro-2H-pyran-2-yl)-9H-purine

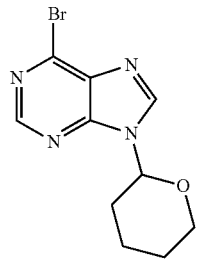 [SMILES: Brc1ncnc2c1ncn2C1CCCCO1]

A solution of 6-bromo-9H-purine (5.0 g, 25 mmol) and p-toluenesulfonic acid monohydrate (0.48 g, 2.5 mmol) in chloroform (100 mL) was cooled to 0° C., treated with dihydropyran (3.4 mL, 38 mmol) and stirred at room temperature for 1 hour. The reaction mixture was washed with saturated sodium bicarbonate, water and brine, dried with MgSO₄, filtered, concentrated and purified on silica gel (eluting with 0-50% of ethyl acetate in hexanes) to give the desired product (7.0 g, 98%).

Step 2. 1-(3-Bromo-5-chloro-2-methoxy-4-methylphenyl)ethanol

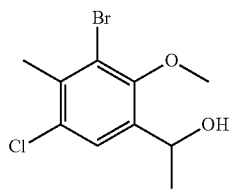

To a solution of 1-(3-bromo-5-chloro-2-methoxy-4-methylphenyl)ethanone (23 g, 83 mmol) in methanol (200 mL) was added sodium tetrahydroborate (5.0 g, 130 mmol) at 0° C. The mixture was stirred at 0° C. for 1 hour and quenched with water (10 mL). The resulting mixture was concentrated under reduced pressure to about 30 mL. The residue was diluted with ethyl acetate, washed with water and brine, dried over MgSO₄, filtered and evaporated to yield the desired product. LCMS calculated for $C_{10}H_{11}BrClO$ (M-OH)⁺: m/z=261.0, 263.0. found: 261.0, 263.0.

Step 3. 1-(1-Azidoethyl)-3-bromo-5-chloro-2-methoxy-4-methylbenzene

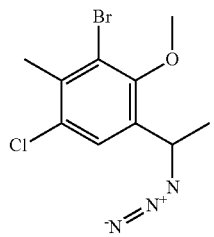

To a solution of 1-(3-bromo-5-chloro-2-methoxy-4-methylphenyl)ethanol (13.4 g, 47.9 mmol) in methylene chloride (150 mL), cooled at 0° C. was added N,N-diisopropylethylamine (14 mL, 80 mmol) followed by methanesulfonyl chloride (5.5 mL, 71 mmol). The mixture was stirred for 1 hour at 0° C. Water (100 mL) was added while cold. The organic layer was separated, washed with brine, dried over MgSO$_4$, filtered and concentrated to dryness under reduced pressure. The resulting crude mesylate was dissolved in N,N-dimethylformamide (140 mL) and sodium azide (6.2 g, 96 mmol) was added. The reaction was stirred at room temperature for 2 hours. The reaction mixture was diluted with ethyl acetate and washed with saturated sodium bicarbonate solution, water and brine, dried over MgSO$_4$, filtered and concentrated. The residue was purified on silica gel (eluting with 0-30% of ethyl acetate in hexanes) to afford the desired product (12.2 g, 82%). LCMS calculated for C$_{10}$H$_{11}$BrClO (M-N$_3$)$^+$: m/z=261.0, 263.0. found: 261.0, 263.0.

Step 4.
1-(3-Bromo-5-chloro-2-methoxy-4-methylphenyl)ethanamine

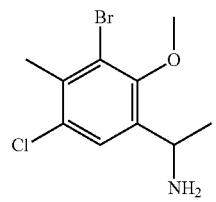

To a stirred solution of 1-(1-azidoethyl)-3-bromo-5-chloro-2-methoxy-4-methylbenzene6-(1-azidoethyl)-2-bromo-4-chloro-3-methylphenyl methyl ether (5.6 g, 18 mmol) in tetrahydrofuran (80 mL) and water (20 mL) was added 1.0 M trimethylphosphine in tetrahydrofuran (22 mL, 22 mmol) at room temperature and the mixture was stirred at room temperature for 1 hour. The mixture was diluted with ethyl acetate, washed with saturated sodium bicarbonate solution, water and brine, dried over MgSO$_4$, filtered and concentrated to give the desired product (5.0 g, 98%). LCMS calculated for C$_{10}$H$_{11}$BrClO (M-NH$_2$)$^+$: m/z=261.0, 263.0. found: 260.0, 262.9.

Step 5. N-[1-(3-bromo-5-chloro-2-methoxy-4-methylphenyl)ethyl]-9-(tetrahydro-2H-pyran-2-yl)-9H-purin-6-amine

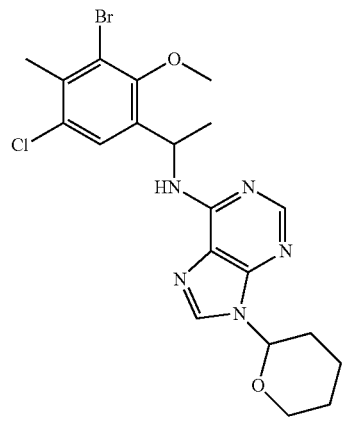 [SMILES: COc1c(C(C)Nc2ncnc3c2ncn3C2CCCCO2)cc(Cl)c(C)c1Br]

A mixture of 1-(3-bromo-5-chloro-2-methoxy-4-methylphenyl)ethanamine (5.0 g, 18 mmol), 6-bromo-9-(tetrahydro-2H-pyran-2-yl)-9H-purine (7.0 g, 25 mmol) and N,N-diisopropylethylamine (9.4 mL, 54 mmol) in ethanol (100 mL) was heated at 100° C. (flushed with nitrogen) overnight. The reaction mixture was cooled, poured into saturated sodium bicarbonate solution and extracted with ethyl acetate. The combined organic layers were washed with water and brine, dried over MgSO$_4$, filtered and concentrated. The residue was purified on silica gel (eluting with 0-65% ethyl acetate in hexane) to afford the desired product. LCMS calculated for C$_{20}$H$_{24}$BrClN$_5$O$_2$ (M+H)$^+$: m/z=480.1, 482.1. found: 480.0, 482.1.

Step 6. N-{1-[5-Chloro-3-(5-fluoropyridin-3-yl)-2-methoxy-4-methylphenyl]ethyl}-9H-purin-6-amine

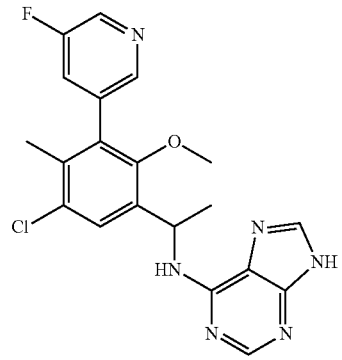 [SMILES: COc1c(C(C)Nc2ncnc3[nH]cnc23)cc(Cl)c(C)c1-c1cncc(F)c1]

Into a microwave vial was added N-[1-(3-bromo-5-chloro-2-methoxy-4-methylphenyl)ethyl]-9-(tetrahydro-2H-pyran-2-yl)-9H-purin-6-amine (0.046 g, 0.096 mmol), (5-fluoropyridin-3-yl)boronic acid (0.020 g, 0.14 mmol), 10% sodium carbonate solution (0.23 mL, 0.23 mmol), 1,4-dioxane (0.9 mL) and tetrakis(triphenylphosphine)palladium(0) (0.011 g, 0.0096 mmol). The mixture was bubbled with N$_2$ for 5 min and then heated at 100° C. for 2 hours. The cooled reaction was treated directly with 6.0 M hydrogen chloride in water (0.2 mL, 1 mmol) at room temperature for −30 min. The mixture was diluted with MeOH, filtered and purified on Prep LCMS (XBridge C18 Column, eluting with a gradient of acetonitrile in water with 0.2% ammonium hydroxide, at flow rate of 30 mL/min) to give the desired product. LCMS calculated for C$_{20}$H$_{19}$ClFN$_6$O (M+H)$^+$: m/z=413.1. found: 413.1.

Example 113

N-{1-[5-Chloro-2-methoxy-3-(5-methoxypyridin-3-yl)-4-methylphenyl]ethyl}-9H-purin-6-amine

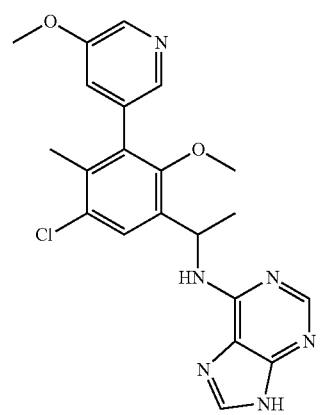 [SMILES: COc1cncc(-c2c(C)c(Cl)cc(C(C)Nc3ncnc4[nH]cnc34)c2OC)c1]

113

Step 1. tert-Butyl [1-(3-bromo-5-chloro-2-methoxy-4-methylphenyl)ethyl]carbamate

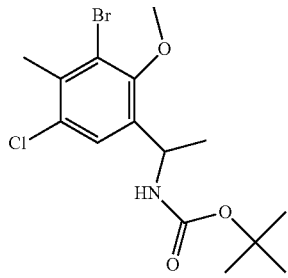 [SMILES: COc1c(C(C)NC(=O)OC(C)(C)C)cc(Cl)c(C)c1Br]

Di-tert-butyldicarbonate (10 g, 47 mmol) was added to a mixture of 1-(3-bromo-5-chloro-2-methoxy-4-methylphenyl)ethanamine (6.6 g, 24 mmol) and triethylamine (9.9 mL, 71 mmol) in tetrahydrofuran (120 mL). After 2 hours, the mixture was quenched with saturated sodium bicarbonate solution, extracted with ethyl acetate, washed with water and brine, dried over MgSO$_4$, filtered and concentrated under reduced pressure. The residue was purified on silica gel (eluting with 0-5% MeOH in dichloromethane) to give the desired product (6.0 g, 67%). LCMS calculated for C$_{10}$H$_{11}$BrClO (M-NHBoc)$^+$: m/z=261.0, 263.0. found: 261.0, 263.0. The material was separated on chiral HPLC (ChiralPak AD-H column, 20×250 mm, 5 micron particle size, eluting with 2% EtOH in hexanes at 15 ml/min, column loading ~60 mg/injection) to separate the two enantiomers.

Step 2. N-[1-(3-Bromo-5-chloro-2-methoxy-4-methylphenyl)ethyl]-9-(tetrahydro-2H-pyran-2-yl)-9H-purin-6-amine

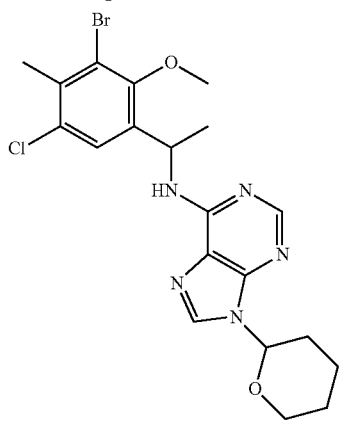

A mixture of tert-butyl [1-(3-bromo-5-chloro-2-methoxy-4-methylphenyl)ethyl]carbamate (0.84 g, 2.2 mmol) (second peak from chiral separation) was treated with 4.0 M hydrogen chloride in dioxane (3.0 mL, 12 mmol) at room temperature for 2 hours. The mixture was diluted with saturated sodium bicarbonate solution and extracted with dichloromethane. The combined organic layers were dried over MgSO$_4$, filtered and concentrated to give 1-(3-bromo-5-chloro-2-methoxy-4-methylphenyl)ethanamine, which was combined with 6-bromo-9-(tetrahydro-2H-pyran-2-yl)-9H-purine (0.82 g, 2.9 mmol, from Example 108, Step 1) and N,N-diisopropylethylamine (1.2 mL, 6.6 mmol) in ethanol (6 mL) and heated at 100° C. overnight. The reaction mixture was concentrated and purified on silica gel (eluting with 0-65% ethyl acetate in hexanes) to afford the desired product. LCMS calculated for C$_{20}$H$_{24}$BrClN$_5$O$_2$ (M+H)$^+$: m/z=480.1, 482.1. found: 480.0, 482.0.

Step 3. N-{1-[5-Chloro-2-methoxy-3-(5-methoxypyridin-3-yl)-4-methylphenyl]ethyl}-9H-purin-6-amine

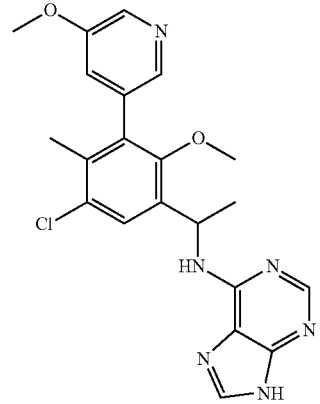 [SMILES: COc1cncc(-c2c(C)c(Cl)cc(C(C)Nc3ncnc4[nH]cnc34)c2OC)c1]

Into a microwave vial was added N-[1-(3-bromo-5-chloro-2-methoxy-4-methylphenyl)ethyl]-9-(tetrahydro-2H-pyran-2-yl)-9H-purin-6-amine (0.12 g, 0.25 mmol) isolated in step 2, (5-methoxypyridin-3-yl)boronic acid (0.046 g, 0.30 mmol), 10% sodium carbonate (0.60 mL, 0.62 mmol), 1,4-dioxane (1.5 mL) and tetrakis(triphenylphosphine)palladium(0) (0.017 g, 0.015 mmol), the mixture was bubbled with N$_2$ for 5 min and then heated at 100° C. for 2 hours. The resulting mixture was cooled to room temperature and then treated directly with 6.0 M hydrogen chloride in water (0.4 mL, 2 mmol) for ~30 minutes. The mixture was diluted with MeOH, filtered and purified on Prep LCMS (XBridge C18 Column, eluting with a gradient of acetonitrile in water with 0.2% ammonium hydroxide, at flow rate of 60 mL/min) to give the desired single enantiomer product. LCMS calculated for C$_{21}$H$_{22}$ClN$_6$O$_2$ (M+H)$^+$: m/z=425.1. found: 425.1. $^1$H NMR (DMSO-d$_6$, 300 MHz) δ 8.27-7.99 (6H, m), 7.63 (1H, s), 5.71 (1H, m), 3.79 (3H, s), 3.40 (3H, s), 1.94 (3H, s), 1.44 (3H, d, J=6.9 Hz) ppm.

Example 117

(4-{3-Chloro-6-methoxy-2-methyl-5-[1-(9H-purin-6-ylamino)ethyl]phenyl}-1H-pyrazol-1-yl)acetonitrile trifluoroacetate

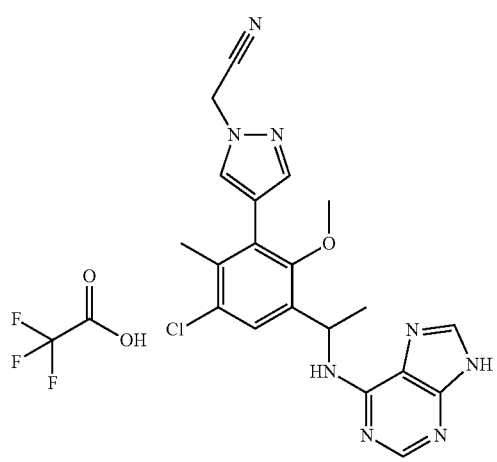

Step 1. 1-{5-Chloro-3-[1-(1-ethoxyethyl)-1H-pyrazol-4-yl]-2-methoxy-4-methylphenyl}ethanone

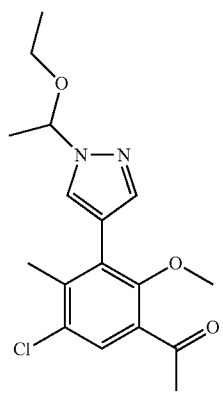 [SMILES: CCOC(C)n1cc(-c2c(C)c(Cl)cc(C(C)=O)c2OC)cn1]

A biphasic solution of 1-(3-bromo-5-chloro-2-methoxy-4-methylphenyl)ethanone (0.40 g, 1.4 mmol) and 1-(1-ethoxyethyl)-4-(4,4,5,5-tetramethyl-1,3,2-dioxaborolan-2-yl)-1H-pyrazole (0.46 g, 1.7 mmol) in toluene (4 mL) and 10% sodium carbonate in water (3.0 mL, 2.9 mmol) was degassed under $N_2$. Tetrakis(triphenylphosphine)palladium (0) (83 mg, 0.072 mmol) was added and the mixture was bubbled with $N_2$ for 5 min and heated at 100° C. overnight. The resulting solution was cooled to room temperature and the organic layer was purified on silica gel (eluting with 0-40% of ethyl acetate in hexanes) to give the desired product (0.22 g, 45%). LCMS calculated for $C_{17}H_{22}ClN_2O_3$ (M+H)$^+$: m/z=337.1. found: 337.1.

Step 2. 1-[5-Chloro-2-methoxy-4-methyl-3-(1H-pyrazol-4-yl)phenyl]ethanone

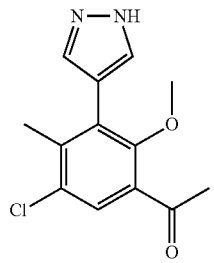 [SMILES: COc1c(C(C)=O)cc(Cl)c(C)c1-c1cn[nH]c1]

1-{5-Chloro-3-[1-(1-ethoxyethyl)-1H-pyrazol-4-yl]-2-methoxy-4-methylphenyl}ethanone (0.22 g, 0.65 mmol) was treated with 1.0 M hydrogen chloride in water (3.9 mL, 3.9 mmol) in tetrahydrofuran (4 mL) overnight. The mixture was quenched with saturated sodium bicarbonate and extracted with ethyl acetate. The organic layers were dried over MgSO$_4$, filtered, concentrated and purified on silica gel (eluting with 0-60% of ethyl acetate in hexane) to afford the desired product (0.13 g, 75%). LCMS calculated for $C_{13}H_{14}ClN_2O_2$ (M+H)$^+$: m/z=265.1. found: 265.0.

Step 3. [4-(3-Acetyl-5-chloro-2-methoxy-6-methylphenyl)-1H-pyrazol-1-yl]acetonitrile

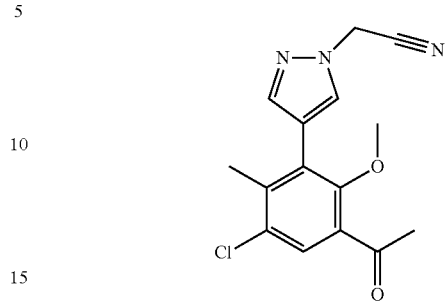

To a solution of 1-[5-chloro-2-methoxy-4-methyl-3-(1H-pyrazol-4-yl)phenyl]ethanone (0.13 g, 0.49 mmol) in N,N-dimethylformamide (2 mL) was added sodium hydride (60% in oil, 0.014 g, 0.59 mmol) at 0° C. The mixture was stirred for 1 hour at room temperature, followed by the addition of chloroacetonitrile (0.037 mL, 0.59 mmol) at 0° C. The reaction was stirred at room temperature for 1 hour, quenched with water and extracted with ethyl acetate. The organic layers were dried over MgSO$_4$, filtered and concentrated under reduced pressure. The resulting residue was purified on silica gel (eluting with 0-40% of ethyl acetate in hexanes) to afford the desired product (0.1 g, 67%). LCMS calculated for $C_{15}H_{15}ClN_3O_2$ (M+H)$^+$: m/z=304.1. found: 304.1.

Step 4. {4-[3-(1-Aminoethyl)-5-chloro-2-methoxy-6-methylphenyl]-1H-pyrazol-1-yl}acetonitrile

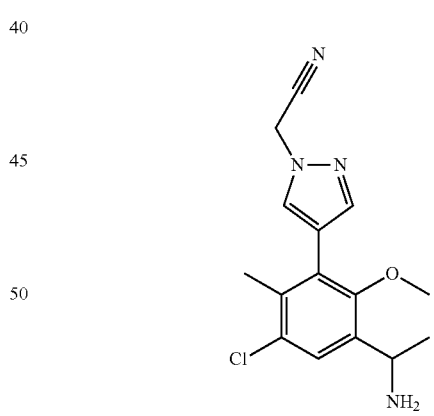

A mixture of [4-(3-acetyl-5-chloro-2-methoxy-6-methylphenyl)-1H-pyrazol-1-yl]acetonitrile (0.10 g, 0.33 mmol), ammonium acetate (0.254 g, 3.29 mmol) and 1.0 M sodium cyanoborohydride in tetrahydrofuran (0.82 mL, 0.82 mmol) in methanol (0.9 mL) and acetonitrile (0.9 mL) was heated at 65° C. overnight. The mixture was cooled to room temperature, quenched with saturated sodium bicarbonate solution and extracted with dichloromethane. The combined organic layers were dried over MgSO$_4$ and concentrated to give the desired product. LCMS calculated for $C_{15}H_{15}ClN_3O$ (M-NH$_2$)$^+$: m/z=288.1. found: 288.0.

Step 5. (4-{3-Chloro-6-methoxy-2-methyl-5-[1-(9H-purin-6-ylamino)ethyl]phenyl}-1H-pyrazol-1-yl) acetonitrile trifluoroacetate

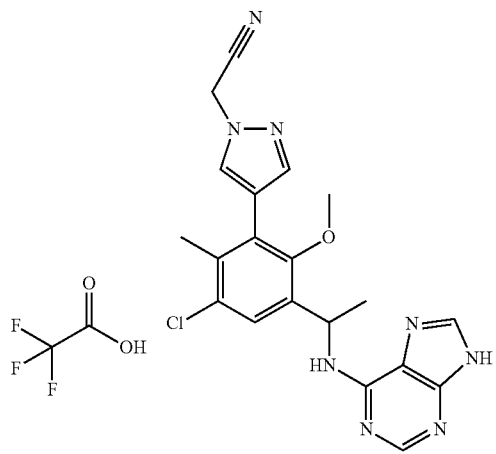 [SMILES: O=C(O)C(F)(F)F ; COc1c(C(C)Nc2ncnc3[nH]cnc23)cc(Cl)c(C)c1-c1cnn(CC#N)c1]

A mixture of {4-[3-(1-aminoethyl)-5-chloro-2-methoxy-6-methylphenyl]-1H-pyrazol-1-yl}acetonitrile (0.12 g, 0.39 mmol), 6-bromo-9H-purine (0.12 g, 0.59 mmol) and N,N-diisopropylethylamine (0.14 mL, 0.79 mmol) in ethanol (1 mL) was heated at 100° C. overnight. The mixture was purified on prep LCMS (XBridge C18 Column, eluting with a gradient of acetonitrile in water with 0.05% trifluoroacetic acid, at flow rate of 30 mL/min) to afford the desired product as TFA salt. LCMS calculated for $C_{20}H_{20}ClN_8O$ $(M+H)^+$: m/z=423.1. found: 423.1. $^1$H NMR (DMSO-$d_6$, 300 MHz) δ 9.06 (1H, br s), 8.44 (2H, m), 8.00 (1H, s), 7.70 (1H, s), 7.51 (1H, s), 5.73 (1H, m), 5.55 (2H, s), 3.42 (3H, s), 2.16 (3H, s), 1.53 (3H, d, J=6.9 Hz) ppm.

Compounds Synthesized

Experimental procedures for compounds below are summarized in Table 1 below.

TABLE 1

| Ex. No. | Name | R⁵ | R⁴ | R³ | Salt | Proc.[1] |
|---|---|---|---|---|---|---|
| 21 | N-{1-[5-chloro-2-methoxy-4-methyl-3-(1-methyl-1H-pyrazol-5-yl)phenyl]ethyl}-9H-purin-6-amine | Cl | Me | 1-methyl-1H-pyrazol-5-yl | | 20 |
| 22 | N-{1-[5-chloro-3-(3,5-dimethylisoxazol-4-yl)-2-methoxy-4-methylphenyl]ethyl}-9H-purin-6-amine | Cl | Me | 3,5-dimethylisoxazol-4-yl | | 20 |
| 23 | N-{1-[5-chloro-2-methoxy-3-(2-methoxypyrimidin-5-yl)-4-methylphenyl]ethyl}-9H-purin-6-amine | Cl | Me | 2-methoxypyrimidin-5-yl | | 20 |

TABLE 1-continued

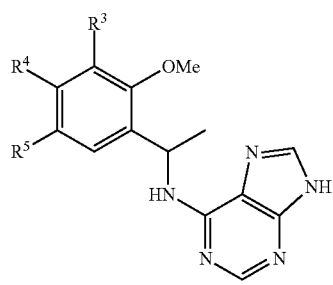

| Ex. No. | Name | R⁵ | R⁴ | R³ | Salt | Proc.[1] |
|---|---|---|---|---|---|---|
| 27 | N-{3'-chloro-6'-methoxy-2'-methyl-5'-[1-(9H-purin-6-ylamino)ethyl]biphenyl-4-yl}acetamide | Cl | Me | 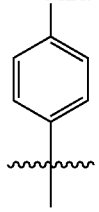 NHAc | | 20 |
| 28 | N-[1-(5-chloro-3'-fluoro-2-methoxy-6-methylbiphenyl-3-yl)ethyl]-9H-purin-6-amine | Cl | Me | 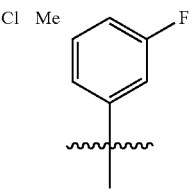 F | | 20 |
| 29 | N-[1-(5-chloro-3',5'-difluoro-2-methoxy-6-methylbiphenyl-3-yl)ethyl]-9H-purin-6-amine | Cl | Me | 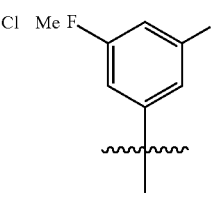 F, F | | 20 |
| 30 | 3'-chloro-6'-methoxy-2'-methyl-5'-[1-(9H-purin-6-ylamino)ethyl]biphenyl-4-carbonitrile | Cl | Me | 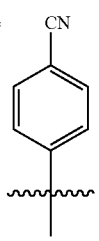 CN | | 20 |
| 31 | 3'-chloro-N-cyclopropyl-6'-methoxy-2'-methyl-5'-[1-(9H-purin-6-ylamino)ethyl]biphenyl-4-carboxamide | Cl | Me | 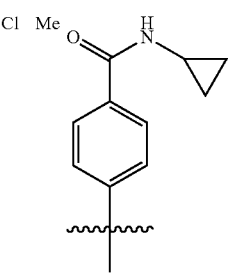 | | 20 |

TABLE 1-continued

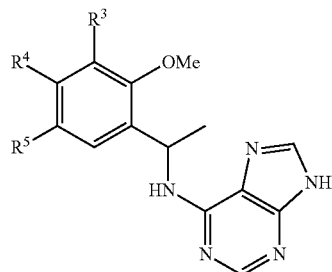

| Ex. No. | Name | R⁵ | R⁴ | R³ | Salt | Proc.¹ |
|---|---|---|---|---|---|---|
| 32 | N-{1-[5-chloro-2-methoxy-6-methyl-4'-(methylsulfonyl)biphenyl-3-yl]ethyl}-9H-purin-6-amine | Cl | Me | 4-(SO₂Me)phenyl | | 20 |
| 33 | N-{1-[3-(2-aminopyrimidin-5-yl)-5-chloro-2-methoxy-4-methylphenyl]ethyl}-9H-purin-6-amine | Cl | Me | 2-aminopyrimidin-5-yl | | 20 |
| 34 | N-{1-[5-chloro-2-methoxy-3-(5-methoxypyridin-3-yl)-4-methylphenyl]ethyl}-9H-purin-6-amine | Cl | Me | 5-methoxypyridin-3-yl | | 20 |
| 35 | N-[1-(3',5-dichloro-2-methoxy-6-methylbiphenyl-3-yl)ethyl]-9H-purin-6-amine | Cl | Me | 3-chlorophenyl | | 20 |
| 36 | N-{1-[5-chloro-3-(5-chloropyridin-3-yl)-2-methoxy-4-methylphenyl]ethyl}-9H-purin-6-amine | Cl | Me | 5-chloropyridin-3-yl | | 20 |

TABLE 1-continued

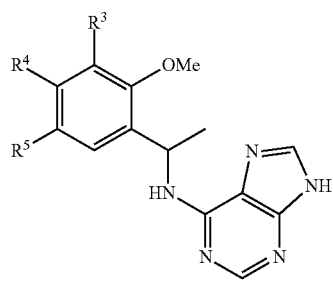

| Ex. No. | Name | R⁵ | R⁴ | R³ | Salt | Proc.¹ |
|---|---|---|---|---|---|---|
| 37 | 3,3'-dichloro-6'-methoxy-N,2'-dimethyl-5'-[1-(9H-purin-6-ylamino)ethyl]biphenyl-4-carboxamide | Cl | Me | 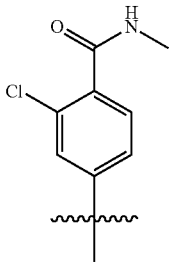 [SMILES: *c1ccc(C(=O)NC)c(Cl)c1] | | 20 |
| 38 | N-{1-[5-chloro-2-methoxy-6-methyl-4'-(trifluoromethyl)biphenyl-3-yl]ethyl}-9H-purin-6-amine | Cl | Me | 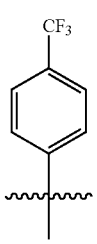 | | 20 |
| 39 | N-[1-(5-chloro-4'-ethoxy-3'-fluoro-2-methoxy-6-methylbiphenyl-3-yl)ethyl]-9H-purin-6-amine | Cl | Me | 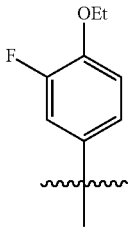 | | 20 |
| 40 | 3'-chloro-6'-methoxy-2'-methyl-5'-[1-(9H-purin-6-ylamino)ethyl]biphenyl-3-carbonitrile | Cl | Me | 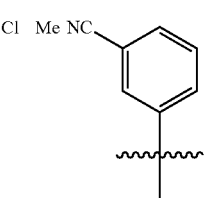 | | 20 |
| 41 | {3'-chloro-6'-methoxy-2'-methyl-5'-[1-(9H-purin-6-ylamino)ethyl]biphenyl-4-yl}acetonitril | Cl | Me | 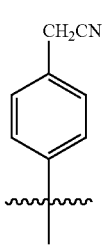 | | 20 |

TABLE 1-continued

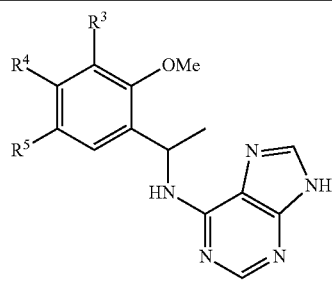

| Ex. No. | Name | R⁵ | R⁴ | R³ | Salt | Proc.¹ |
|---|---|---|---|---|---|---|
| 42 | N-{1-[5-chloro-2-methoxy-4'-(methoxymethyl)-6-methylbiphenyl-3-yl]ethyl}-9H-purin-6-amine | Cl | Me | CH₂OMe-(4-phenyl) | | 20 |
| 43 | N-{1-[5-chloro-2-methoxy-6-methyl-4'-(1H-pyrazol-1-yl)biphenyl-3-yl]ethyl}-9H-purin-6-amine | Cl | Me | 4-(1H-pyrazol-1-yl)phenyl | | 20 |
| 44 | N-{1-[5-chloro-2-methoxy-3'-(methoxymethyl)-6-methylbiphenyl-3-yl]ethyl}-9H-purin-6-amine | Cl | Me | 3-(CH₂OMe)phenyl | | 20 |
| 45 | N-(1-{5-chloro-2-methoxy-4-methyl-3-[6-(tetrahydro-2H-pyran-4-yloxy)pyridin-3-yl]phenyl}ethyl)-9H-purin-6-amine | Cl | Me | 6-(tetrahydro-2H-pyran-4-yloxy)pyridin-3-yl | | 20 |
| 46 | {3'-chloro-6'-methoxy-2'-methyl-5'-[1-(9H-purin-6-ylamino)ethyl]biphenyl-3-yl}acetonitrile | Cl | Me | 3-(NCCH₂)phenyl | | 20 |

TABLE 1-continued

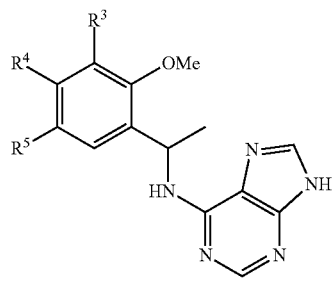

| Ex. No. | Name | R⁵ | R⁴ | R³ | Salt | Proc.[1] |
|---|---|---|---|---|---|---|
| 47 | N-[1-(3',5,5'-trichloro-2-methoxy-6-methylbiphenyl-3-yl)ethyl]-9H-purin-6-amine | Cl | Me | 3,5-dichlorophenyl | | 20 |
| 48 | N-{1-[5-chloro-2-methoxy-4-methyl-3-(6-morpholin-4-ylpyridin-3-yl)phenyl]ethyl}-9H-purin-6-amine | Cl | Me | 6-morpholin-4-ylpyridin-3-yl | | 20 |
| 49 | N-{1-[5-chloro-3-(3-fluoro-2-morpholin-4-ylpyridin-4-yl)-2-methoxy-4-methylphenyl]ethyl}-9H-purin-6-amine | Cl | Me | 3-fluoro-2-morpholin-4-ylpyridin-4-yl | | 20 |
| 50[2] | N-[1-(5-chloro-2',5'-difluoro-2-methoxy-6-methylbiphenyl-3-yl)ethyl]-9H-purin-6-amine | Cl | Me | 2,5-difluorophenyl | | 20 |
| 51 | N-{1-[5-chloro-3-(6-fluoropyridin-3-yl)-2-methoxy-4-methylphenyl]ethyl}-9H-purin-6-amine | Cl | Me | 6-fluoropyridin-3-yl | | 20 |

TABLE 1-continued

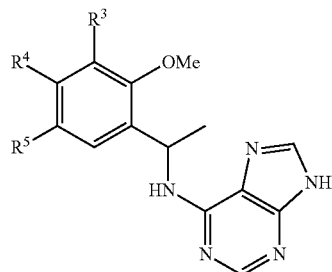

| Ex. No. | Name | R⁵ | R⁴ | R³ | Salt | Proc.¹ |
|---|---|---|---|---|---|---|
| 52 | N-{1-[5-chloro-2-methoxy-3-(6-methoxypyridin-3-yl)-4-methylphenyl]ethyl}-9H-purin-6-amine | Cl | Me | 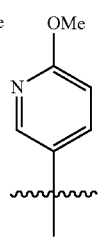 | | 20 |
| 53 | 5-{3-chloro-6-methoxy-2-methyl-5-[1-(9H-purin-6-ylamino)ethyl]phenyl}nicotinonitrile | Cl | Me | 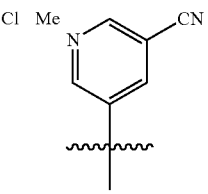 | | 20 |
| 54³ | 3-(4-{3-chloro-6-methoxy-2-methyl-5-[1-(9H-purin-6-ylamino)ethyl]phenyl}-1H-pyrazol-1-yl)-3-(cyanomethyl)cyclobutanecarbonitrile | Cl | Me | 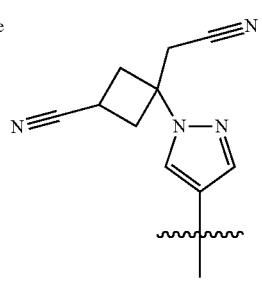 | | 20 |
| 55 | N-{1-[5-chloro-2-methoxy-4-methyl-3-(5-methylpyridin-3-yl)phenyl]ethyl}-9H-purin-6-amine | Cl | Me | 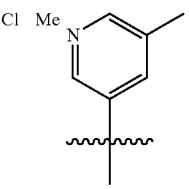 | | 20 |
| 56 | N-(1-{5-chloro-2-methoxy-4-methyl-3-[5-(methylsulfonyl)pyridin-3-yl]phenyl}ethyl)-9H-purin-6-amine | Cl | Me | 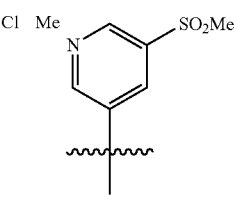 | | 20 |

TABLE 1-continued

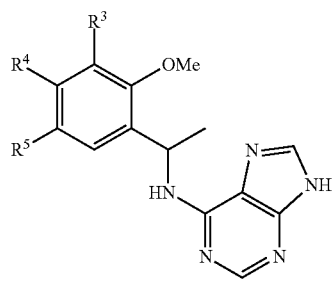

| Ex. No. | Name | R⁵ | R⁴ | R³ | Salt | Proc.¹ |
|---|---|---|---|---|---|---|
| 57 | N-{1-[3-(6-aminopyridin-3-yl)-5-chloro-2-methoxy-4-methylphenyl]ethyl}-9H-purin-6-amine | Cl | Me | 6-aminopyridin-3-yl | | 20 |
| 58 | 5-{3-chloro-6-methoxy-2-methyl-5-[1-(9H-purin-6-ylamino)ethyl]phenyl}pyridine-2-carbonitrile | Cl | Me | 6-cyanopyridin-3-yl | | 20 |
| 59 | N-{1-[5-chloro-3-(6-isopropoxypyridin-3-yl)-2-methoxy-4-methylphenyl]ethyl}-9H-purin-6-amine | Cl | Me | 6-isopropoxypyridin-3-yl | | 20 |
| 64 | 3'-chloro-N-ethyl-3-fluoro-6'-methoxy-2'-methyl-5'-[1-(9H-purin-6-ylamino)ethyl]biphenyl-4-carboxamid | Cl | Me | 3-fluoro-4-(N-ethylcarbamoyl)phenyl | | 63 |
| 65 | 3'-chloro-3-fluoro-6'-methoxy-N,N,2'-trimethyl-5'-[1-(9H-purin-6-ylamino)ethyl]biphenyl-4-carboxamide | Cl | Me | 3-fluoro-4-(N,N-dimethylcarbamoyl)phenyl | | 63 |

TABLE 1-continued

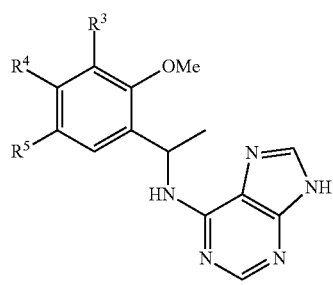

| Ex. No. | Name | R⁵ | R⁴ | R³ | Salt | Proc.¹ |
|---|---|---|---|---|---|---|
| 66 | N-{1-[5-chloro-3'-fluoro-2-methoxy-6-methyl-4'-(pyrrolidin-1-ylcarbonyl)biphenyl-3-yl]ethyl}-9H-purin-6-amine | Cl | Me | (2-fluoro-4-(pyrrolidin-1-ylcarbonyl)phenyl) | | 63 |
| 67 | N-{1-[5-chloro-3'-fluoro-2-methoxy-6-methyl-4'-(morpholin-4-ylcarbonyl)biphenyl-3-yl]ethyl}-9H-purin-6-amine | Cl | Me | (2-fluoro-4-(morpholin-4-ylcarbonyl)phenyl) | | 63 |
| 68 | 3'-chloro-3-fluoro-6'-methoxy-N,2'-dimethyl-5'-[1-(9H-purin-6-ylamino)ethyl]biphenyl-4-carboxamide | Cl | Me | (2-fluoro-4-(N-methylcarbamoyl)phenyl) | | 63 |
| 69 | 1-({3'-chloro-3-fluoro-6'-methoxy-2'-methyl-5'-[1-(9H-purin-6-ylamino)ethyl]biphenyl-4-yl}carbonyl)piperidin-4-ol | Cl | Me | (2-fluoro-4-(4-hydroxypiperidin-1-ylcarbonyl)phenyl) | | 63 |

TABLE 1-continued

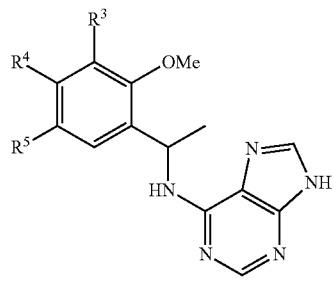

| Ex. No. | Name | R⁵ | R⁴ | R³ | Salt | Proc.¹ |
|---|---|---|---|---|---|---|
| 70 | 3'-chloro-N-cyclobutyl-3-fluoro-6'-methoxy-2'-methyl-5'-[1-(9H-purin-6-ylamino)ethyl]biphenyl-4-carboxamide | Cl | Me | 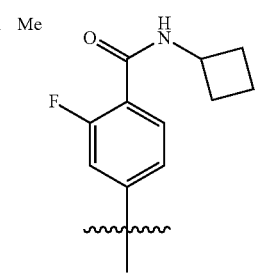 | | 63 |
| 84 | N-{1-[5-chloro-3-(2-fluoropyridin-4-yl)-2-methoxy-4-methylphenyl]ethyl}-9H-purin-6-amine | Cl | Me | 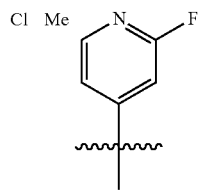 | 2 TFA | 20 |
| 85 | N-[1-(3',5-dichloro-5'-fluoro-2-methoxy-6-methylbiphenyl-3-yl)ethyl]-9H-purin-6-amine | Cl | Me | 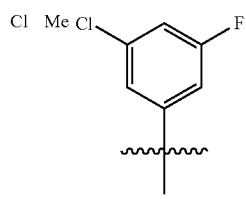 | TFA | 20 |
| 86² | N-{1-[5-chloro-2'-fluoro-2-methoxy-6-methyl-5'-(trifluoromethyl)biphenyl-3-yl]ethyl}-9H-purin-6-ami | Cl | Me | 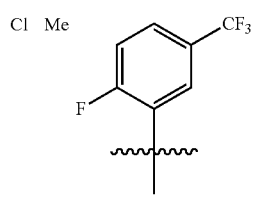 | TFA | 20 |
| 87 | N-{1-[5-chloro-3-(6-fluoro-5-methylpyridin-3-yl)-2-methoxy-4-methylphenyl]ethyl}-9H-purin-6-amine | Cl | Me | 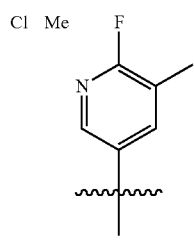 | 2 TFA | 20 |

TABLE 1-continued

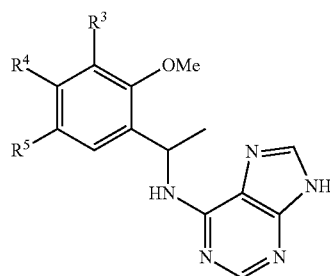

| Ex. No. | Name | R⁵ | R⁴ | R³ | Salt | Proc.¹ |
|---|---|---|---|---|---|---|
| 88 | N-[1-(5-chloro-2-methoxy-6-methyl-4'-morpholin-4-ylbiphenyl-3-yl)ethyl]-9H-purin-6-amine | Cl | Me | ![morpholinyl-phenyl] | 2 TFA | 20 |
| 89 | N-[1-(3',5-dichloro-4'-fluoro-2-methoxy-6-methylbiphenyl-3-yl)ethyl]-9H-purin-6-amine | Cl | Me | ![4-F-3-Cl-phenyl] | TFA | 20 |
| 90 | N-{1-[5-chloro-2-methoxy-6-methyl-4'-(trifluoromethoxy)biphenyl-3-yl]ethyl}-9H-purin-6-amine | Cl | Me | ![4-OCF3-phenyl] | TFA | 20 |
| 91 | N-[1-(5-chloro-3'-ethoxy-2-methoxy-6-methylbiphenyl-3-yl)ethyl]-9H-purin-6-amine | Cl | Me | ![3-OEt-phenyl] | TFA | 20 |
| 92 | N-[1-(4',5-dichloro-3'-fluoro-2-methoxy-6-methylbiphenyl-3-yl)ethyl]-9H-purin-6-amine | Cl | Me | ![4-Cl-3-F-phenyl] | TFA | 20 |

TABLE 1-continued

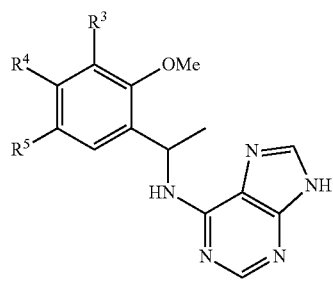

| Ex. No. | Name | R[5] | R[4] | R[3] | | Salt | Proc.[1] |
|---|---|---|---|---|---|---|---|
| 93 | N-{1-[5-chloro-4'-fluoro-2-methoxy-6-methyl-3'-(trifluoromethyl)biphenyl-3-yl]ethyl}-9H-purin-6-amine | Cl | Me | F | 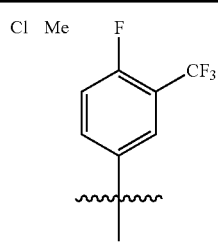 | TFA | 20 |
| 94 | 3'-chloro-4-fluoro-6'-methoxy-N,N,2'-trimethyl-5'-[1-(9H-purin-6-ylamino)ethyl]biphenyl-3-carboxamide | Cl | Me | F | 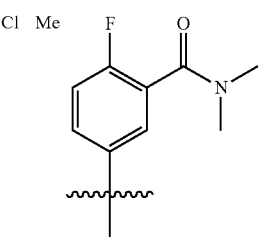 | TFA | 20 |
| 95 | N-[1-(5-chloro-4'-fluoro-2,3'-dimethoxy-6-methylbiphenyl-3-yl)ethyl]-9H-purin-6-amine | Cl | Me | F | 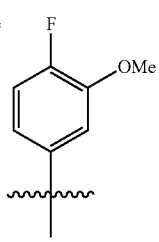 | TFA | 20 |
| 96 | N-[1-(5-chloro-2,3',4'-trimethoxy-6-methylbiphenyl-3-yl)ethyl]-9H-purin-6-amine | Cl | Me | OMe | 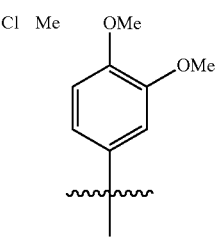 | TFA | 20 |
| 97 | N-[1-(3',5-dichloro-2,4'-dimethoxy-6-methylbiphenyl-3-yl)ethyl]-9H-purin-6-amine | Cl | Me | OMe | 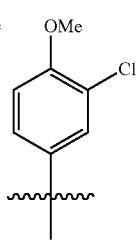 | TFA | 20 |

TABLE 1-continued

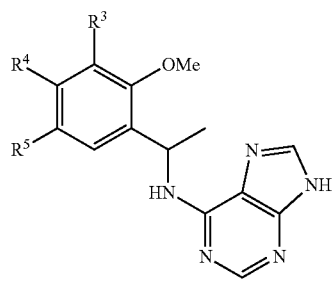

| Ex. No. | Name | R⁵ | R⁴ | R³ | Salt | Proc.¹ |
|---|---|---|---|---|---|---|
| 98 | N-{1-[5-chloro-3-(2-chloropyridin-4-yl)-2-methoxy-4-methylphenyl]ethyl}-9H-purin-6-amine | Cl | Me | 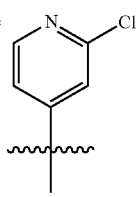 | 2 TFA | 20 |
| 99 | N-[1-(4',5-dichloro-2-methoxy-6-methylbiphenyl-3-yl)ethyl]-9H-purin-6-amine | Cl | Me | 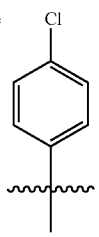 | TFA | 20 |
| 100 | N-{1-[5-chloro-3'-(dimethylamino)-2-methoxy-6-methylbiphenyl-3-yl]ethyl}-9H-purin-6-amine | Cl | Me | 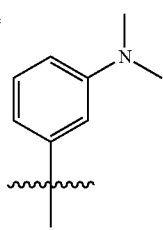 | 2 TFA | 20 |
| 101 | N-[1-(5-chloro-2,4'-dimethoxy-6-methylbiphenyl-3-yl)ethyl]-9H-purin-6-amine | Cl | Me | 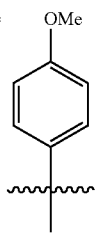 | TFA | 20 |
| 102 | N-[1-(5-chloro-2,4'-dimethoxy-3',6-dimethylbiphenyl-3-yl)ethyl]-9H-purin-6-amine | Cl | Me | 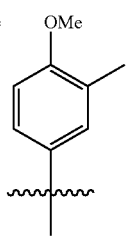 | TFA | 20 |

TABLE 1-continued

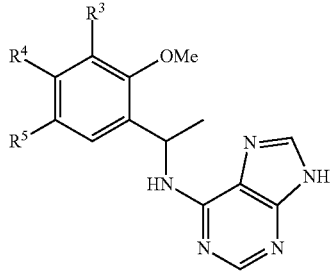

| Ex. No. | Name | R⁵ | R⁴ | R³ | Salt | Proc.¹ |
|---|---|---|---|---|---|---|
| 103 | N-[1-(5-chloro-2,3'-dimethoxy-6-methylbiphenyl-3-yl)ethyl]-9H-purin-6-amine | Cl | Me | 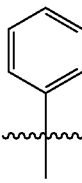 | TFA | 20 |
| 104 | N-{3'-chloro-6'-methoxy-2'-methyl-5'-[1-(9H-purin-6-ylamino)ethyl]biphenyl-3-yl}acetamide | Cl | Me | 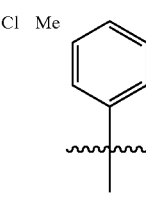 | TFA | 20 |
| 105 | N-[1-(5-chloro-3',4'-difluoro-2-methoxy-6-methylbiphenyl-3-yl)ethyl]-9H-purin-6-amine | Cl | Me | 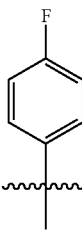 | TFA | 20 |
| 109 | N-{1-[5-chloro-3-(5-fluoro-6-methoxypyridin-3-yl)-2-methoxy-4-methylphenyl]ethyl}-9H-purin-6-amine | Cl | Me | 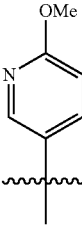 | | 108 |
| 110 | 3'-chloro-5-fluoro-6'-methoxy-2'-methyl-5'-[1-(9H-purin-6-ylamino)ethyl]biphenyl-3-carboxamide | Cl | Me |  | TFA | 108 |

TABLE 1-continued

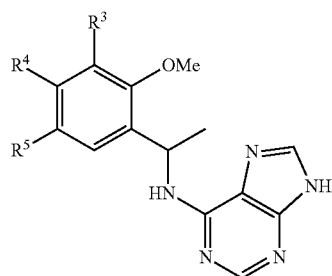

| Ex. No. | Name | R⁵ | R⁴ | R³ | Salt | Proc.¹ |
|---|---|---|---|---|---|---|
| 111 | N-(1-{5-chloro-2-methoxy-4-methyl-3-[5-(morpholin-4-ylcarbonyl)pyridin-3-yl]phenyl}ethyl)-9H-purin-6-amine | Cl | Me | (morpholin-4-ylcarbonyl)pyridin-3-yl | | 108 |
| 112 | N-(5-{3-chloro-6-methoxy-2-methyl-5-[1-(9H-purin-6-ylamino)ethyl]phenyl}pyridin-2-yl)acetamide | Cl | Me | 6-NHAc-pyridin-3-yl | | 108 |
| 114⁴ | 5-{3-chloro-6-methoxy-2-methyl-5-[1-(9H-purin-6-ylamino)ethyl]phenyl}nicotinonitrile | Cl | Me | 5-cyano-pyridin-3-yl | 2 TFA | 108 |
| 115⁴ | N-{1-[3-(2-aminopyrimidin-5-yl)-5-chloro-2-methoxy-4-methylphenyl]ethyl}-9H-purin-6-amine | Cl | Me | 2-NH₂-pyrimidin-5-yl | | 108 |
| 116⁴ | N-{1-[5-chloro-2-methoxy-6-methyl-4'-(methylsulfonyl)biphenyl-3-yl]ethyl}-9H-purin-6-amine | Cl | Me | 4-SO₂Me-phenyl | | 108 |

¹Synthesized according to the experimental procedure of compound listed;
²Two atropic isomers isolated;
³cis-and trans-isomers isolated;
⁴Single enantiomer.

Experimental procedures for compounds below are summarized in Table 2.

TABLE 2

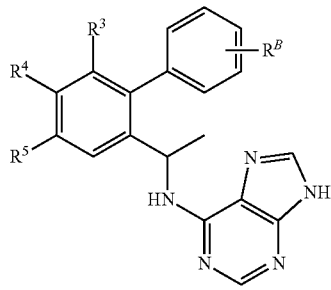

| Ex. No. | Name | R⁵ | R⁴ | R³ | R^B | Salt | Proc.[1] |
|---|---|---|---|---|---|---|---|
| 14 | N-{1-[5'-chloro-6'-methyl-4-(methylsulfonyl)-1,1':2',1''-terphenyl-3'-yl]ethyl}-9H-purin-6-amine | Cl | Me | 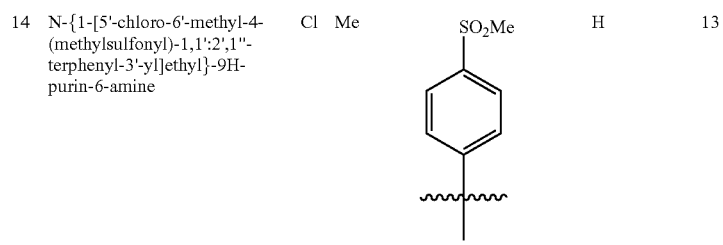 | H | | 13 |
| 15 | N-(1-{4-chloro-6-[2-(dimethylamino)pyrimidin-5-yl]-5-methylbiphenyl-2-yl}ethyl)-9H-purin-6-amine | Cl | Me | 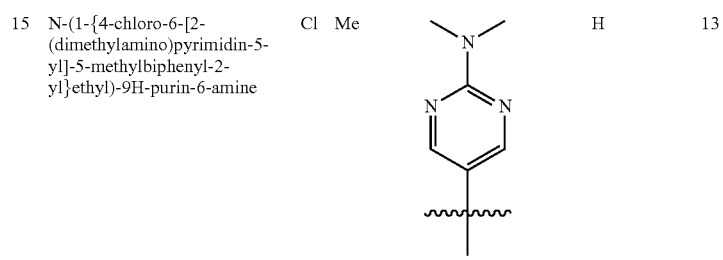 | H | | 13 |
| 16 | 5'-chloro-N-cyclopropyl-6'-methyl-3'-[1-(9H-purin-6-ylamino)ethyl]-1,1':2',1''-terphenyl-4-carboxamide | Cl | Me | 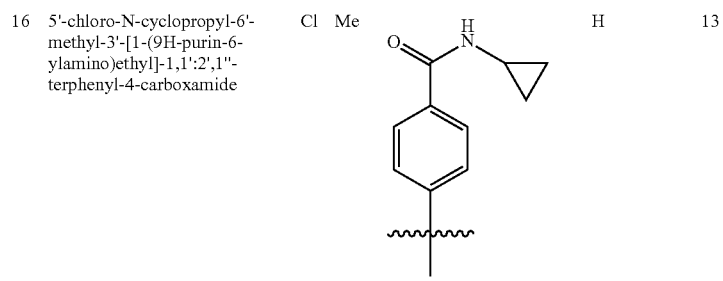 | H | | 13 |
| 17 | N-{1-[6-(2-aminopyrimidin-5-yl)-4-chloro-5-methylbiphenyl-2-yl]ethyl}-9H-purin-6-amine | Cl | Me | 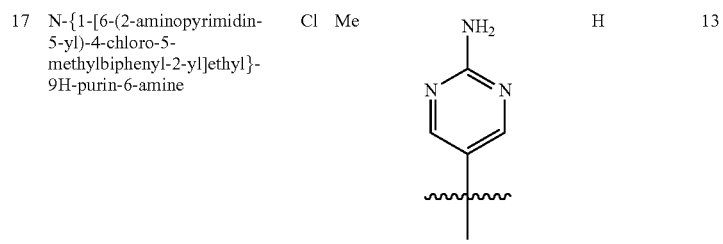 | H | | 13 |

TABLE 2-continued

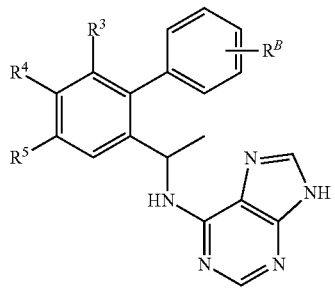

| Ex. No. | Name | $R^5$ | $R^4$ | $R^3$ | $R^B$ | Salt | Proc.[1] |
|---|---|---|---|---|---|---|---|
| 24 | 5'-chloro-6'-methyl-3'-[1-(9H-purin-6-ylamino)ethyl]-1,1':2',1''-terphenyl-4-carbonitrile | Cl | Me | 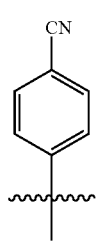 [SMILES: *c1ccc(C#N)cc1] | H | | 13 |
| 25 | N-{1-[4-chloro-6-(2-methoxypyrimidin-5-yl)-5-methylbiphenyl-2-yl]ethyl}-9H-purin-6-amine | Cl | Me | 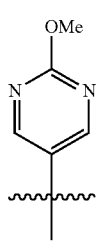 [SMILES: *c1cnc(OC)nc1] | H | | 13 |
| 26 | N-{5'-chloro-6'-methyl-3'-[1-(9H-purin-6-ylamino)ethyl]-1,1':2',1''-terphenyl-4-yl}acetamide | Cl | Me | 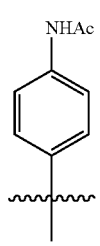 [SMILES: *c1ccc(NC(C)=O)cc1] | H | | 13 |
| 73 | N-{1-[4-chloro-3'-fluoro-5-methyl-6-(1-methyl-1H-pyrazol-4-yl)biphenyl-2-yl]ethyl}-9H-purin-6-amine | Cl | Me | 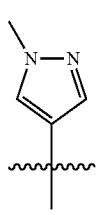 [SMILES: *c1cnn(C)c1] | 3-F | TFA | 71 |
| 74[2] | N-{1-[4-chloro-3'-fluoro-5-methyl-6-(1-methyl-1H-pyrazol-5-yl)biphenyl-2-yl]ethyl}-9H-purin-6-amine | Cl | Me | 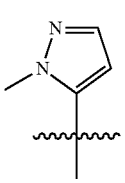 | 3-F | TFA | 71 |

TABLE 2-continued

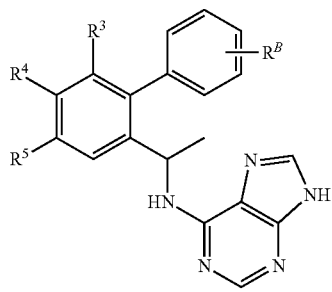

| Ex. No. | Name | R⁵ | R⁴ | R³ | Rᴮ | Salt | Proc.¹ |
|---|---|---|---|---|---|---|---|
| 75² | N-{1-[4-chloro-3'-fluoro-5-methyl-6-(1,3,5-trimethyl-1H-pyrazol-4-yl)biphenyl-2-yl]ethyl}-9H-purin-6-amine | Cl | Me | 1,3,5-trimethylpyrazol-4-yl | 3-F | TFA | 71 |
| 77 | N-{1-[4-chloro-6-(3,5-dimethylisoxazol-4-yl)-3',5'-difluoro-5-methylbiphenyl-2-yl]ethyl}-9H-purin-6-amine | Cl | Me | 3,5-dimethylisoxazol-4-yl | 3,5-diF | TFA | 76 |
| 78 | N-[1-(4-chloro-3',5'-difluoro-5-methyl-6-pyridin-3-ylbiphenyl-2-yl)ethyl]-9H-purin-6-amine | Cl | Me | pyridin-3-yl | 3,5-diF | 2 TFA | 76 |
| 79 | 5'-chloro-3'',5''-difluoro-6'-methyl-3'-[1-(9H-purin-6-ylamino)ethyl]-1,1':2',1''-terphenyl-4-carbonitrile | Cl | Me | 4-cyanophenyl | 3,5-diF | TFA | 76 |
| 80 | N-{1-[4-chloro-6-(2,6-difluoropyridin-4-yl)-3',5'-difluoro-5-methylbiphenyl-2-yl]ethyl}-9H-purin-6-amine | Cl | Me | 2,6-difluoropyridin-4-yl | 3,5-diF | 2 TFA | 76 |
| 81 | N-[1-(4-chloro-3',5'-difluoro-5-methyl-6-pyrimidin-5-ylbiphenyl-2-yl)ethyl]-9H-purin-6-amine | Cl | Me | pyrimidin-5-yl | 3,5-diF | 2 TFA | 76 |

TABLE 2-continued

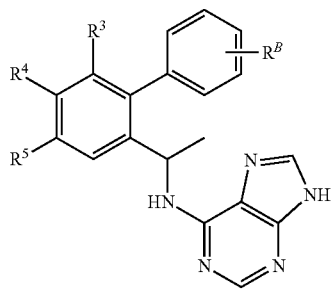

| Ex. No. | Name | R⁵ | R⁴ | R³ | Rᴮ | Salt | Proc.[1] |
|---|---|---|---|---|---|---|---|
| 82 | N-{1-[4-chloro-3',5'-difluoro-6-(2-methoxypyrimidin-5-yl)-5-methylbiphenyl-2-yl]ethyl}-9H-purin-6-amine | Cl | Me | (2-methoxypyrimidin-5-yl) | 3,5-diF | 2 TFA | 76 |
| 83 | N-{5'-chloro-3",5"-difluoro-6'-methyl-3'-[1-(9H-purin-6-ylamino)ethyl]-1,1':2',1"-terphenyl-4-yl}acetamide | Cl | Me | 4-NHAc-phenyl | 3,5-diF | TFA | 76 |
| 107 | N-{1-[4-chloro-6-(3,5-dimethyl-1H-pyrazol-4-yl)-3',5'-difluoro-5-methylbiphenyl-2-yl]ethyl}-9H-purin-6-amine | Cl | Me | 3,5-dimethyl-1H-pyrazol-4-yl | 3,5-diF | TFA | 106 |

[1]Synthesized according to the experimental procedure of compound listed;
[2]Two atropic isomers isolated.

Analytical Data

¹H NMR data (Varian Inova 500 spectrometer, a Mercury 400 spectrometer, or a Varian (or Mercury) 300 spectrometer) and LCMS mass spectral data (MS) for the compounds of the Examples above is provided below in Table 3.

TABLE 3

| Ex. No. | MS [M + H]⁺ | Solvent | MHz | ¹H NMR Spectra |
|---|---|---|---|---|
| 14 | 518.2 | — | — | — |
| 15 | 485.2 | — | — | — |
| 16 | 523.2 | — | — | — |
| 17 | 457.0 | — | — | — |
| 21 | 398.1 | — | — | — |
| 22 | 413.1 | DMSO-d₆ | 400 | 12.87 (1H, br s), 8.12~8.09 (3H, m), 7.67 (1H, m), 5.75 (1H, m), 3.48 (1.5H, s), 3.43 (1.5H, s), 2.21 (1.5H, s), 2.19 (1.5H, s), 2.01 (3H, s), 2.00 (1.5H, s), 1.98 (1.5H, s), 1.57 (3H, m) ppm. |
| 23 | 426.1 | — | — | — |
| 24 | 465.1 | — | — | — |

TABLE 3-continued

| Ex. No. | MS [M + H]+ | Solvent | MHz | ¹H NMR Spectra |
|---|---|---|---|---|
| 25 | 472.2 | DMSO-d₆ | 400 | 12.85 (1H, br s), 8.32 (1H, d, J = 3.2Hz), 8.17 (1H, m), 8.15 (1H, s), 8.11 (1H, s), 8.08 (1H, d, J = 2.8Hz), 7.83 (1H, s), 7.44 (1H, d, J = 6.0 Hz), 7.29 (1H, t, J = 6.8Hz), 7.19 (2H, m), 7.01 (1H, d, J = 7.2Hz), 5.05 (1H, m), 3.79 (3H, s), 2.03 (3H, s), 1.29 (3H, d, J = 6.8Hz) ppm. |
| 26 | 497.1 | — | — | — |
| 27 | 451.2 | — | — | — |
| 28 | 412.1 | — | — | — |
| 29 | 430.1 | — | — | — |
| 30 | 419.1 | — | — | — |
| 31 | 477.1 | — | — | — |
| 32 | 472.1 | — | — | — |
| 33 | 411.1 | — | — | — |
| 34 | 425.1 | — | — | — |
| 35 | 428.1 | — | — | — |
| 36 | 429.0 | DMSO-d₆ | 400 | 12.83 (1H, br s), 8.67 (1H, s), 8.52 (0.5H, s), 8.42 (1H, s), 8.10 (4H, m), 7.69 (1H, s), 5.75 (1H, m), 3.44 (3H, s), 2.00 (3H, s), 1.48 (1H, d, J = 7.2Hz) ppm. |
| 37 | 485.1 | — | — | — |
| 38 | 462.1 | — | — | — |
| 39 | 456.2 | — | — | — |
| 40 | 419.1 | DMSO-d₆ | 400 | 12.93 (1H, s), 8.23 (1H, m), 8.11 (1H, m), 7.87 (1H, m), 7.69~7.60 (4H, m), 5.74 (1H, m), 3.39 (3H, s), 1.97 (3H, s), 1.48 (3H, d, J = 4.4Hz) ppm. |
| 41 | 433.1 | — | — | — |
| 42 | 438.1 | — | — | — |
| 43 | 460.1 | — | — | — |
| 44 | 438.1 | — | — | — |
| 45 | 495.2 | — | — | — |
| 46 | 433.1 | — | — | — |
| 47 | 462.0 | — | — | — |
| 48 | 480.1 | — | — | — |
| 49 | 498.1 | DMSO-d₆ | 400 | 12.94 (1H, br s), 8.22~8.09 (4H, m), 7.71 (1H, m), 6.93 (0.5H, dd, J = 4.8 and 4.4Hz), 6.82 (0.5H, dd, J = 4.8 and 4.4Hz), 5.37 (1H, m), 3.72 (4H, m), 3.54 (1.5H, s), 3.51 (1.5H, s), 3.36 (4H, m), 1.99 (1.5H, s), 1.97 (1.5H, s), 1.47 (3H, m) ppm. |
| 50 | 430.1 | — | — | — |
| 51 | 413.1 | DMSO-d₆ | 400 | 12.91 (1H, br s), 8.22 (1H, s), 8.14~7.92 (3H, m), 8.03 (0.5H, m), 7.92 (0.5H, m), 7.68 (1H, s), 7.29 (1H, m), 5.73 (1H, m), 3.42 (3H, s), 2.00 (3H, s), 1.48 (3H, d, J = 6.8Hz) ppm. |
| 52 | 425.1 | DMSO-d₆ | 400 | 12.88 (1H, br s), 8.17~8.00 (4H, m), 7.64~7.60 (2H, m), 6.86 (1H, d, J = 8.4Hz), 5.69 (1H, m), 3.84 (3H, s), 3.36 (3H, s), 1.96 (3H, s), 1.43 (3H, d, J = 6.8Hz) ppm. |
| 53 | 420.1 | — | — | — |
| 54 | 502.1 | — | — | — |
| 55 | 409.0 | — | — | — |
| 56 | 473.0 | — | — | — |
| 57 | 410.1 | — | — | — |
| 58 | 420.1 | — | — | — |
| 59 | 453.1 | DMSO-d₆ | 300 | 8.19 (1H, m), 8.14 (1H, s), 8.12 (1H, s), 8.04 (1H, m), 7.62 (2H, m), 6.82 (1H, d, J = 8.4Hz), 5.73 (1H, m), 5.28 (1H, m), 3.41 (3H, s), 2.02 (3H, s), 1.48 (3H, d, J = 6.6Hz), 1.31 (6H, d, J = 6.0 Hz) ppm. |
| 64 | 483.1 | — | — | — |
| 65 | 483.1 | — | — | — |
| 67 | 509.2 | — | — | — |
| 68 | 525.2 | — | — | — |
| 69 | 469.1 | — | — | — |
| 70 | 539.2 | — | — | — |
| 71 | 509.1 | — | — | — |
| 73 | 462.0 | — | — | — |
| 74 | 462.2 | — | — | — |
| 75 | 490.0 | — | — | — |
| 77 | 495.1 | — | — | — |
| 78 | 477.1 | — | — | — |
| 79 | 501.1 | — | — | — |
| 80 | 513.1 | — | — | — |
| 81 | 478.0 | — | — | — |
| 82 | 508.1 | — | — | — |
| 83 | 533.2 | — | — | — |
| 84 | 413.1 | DMSO-d₆ | 300 | 9.19 (1H, br s), 8.47 (2H, m), 8.34 (1H, d, J = 5.1Hz), 7.65 (1H, s), 7.33 (1H, m), 7.22 (1H, m), 5.75 (1H, m), 3.42 (3H, s), 2.01 (3H, s), 1.55 (3H, d, J = 6.9Hz) ppm. |
| 85 | 446.1 | — | — | — |
| 86 | 480.1 | — | — | — |

TABLE 3-continued

| Ex. No. | MS [M + H]⁺ | Solvent | MHz | ¹H NMR Spectra |
|---|---|---|---|---|
| 87 | 427.1 | — | — | — |
| 88 | 479.2 | — | — | — |
| 89 | 446.1 | — | — | — |
| 90 | 478.1 | — | — | — |
| 91 | 438.1 | — | — | — |
| 92 | 446.0 | — | — | — |
| 93 | 480.1 | — | — | — |
| 94 | 483.2 | DMSO-d₆ | 300 | 9.24 (1H, br s), 8.49 (2H, m), 7.57 (1H, s), 7.39 (2H, m), 7.28 (1H, m), 5.75 (1H, m), 3.34 (3H, s), 2.99 (1.5H, s), 2.98 (1.5H, s), 2.87 (1.5H, s), 2.86 (1.5H, s), 2.02 (3H, s), 1.55 (3H, d, J = 6.9Hz) ppm. |
| 95 | 442.1 | — | — | — |
| 96 | 454.1 | — | — | — |
| 97 | 458.1 | — | — | — |
| 98 | 429.1 | DMSO-d₆ | 300 | 9.11 (1H, br s), 8.51 (1H, d, J = 4.8Hz), 8.45 (2H, m), 7.65 (1H, s), 7.54 (1H, m), 7.41 (1H, m), 5.74 (1H, m), 3.42 (3H, s), 2.01 (3H, s), 1.54 (3H, d, J = 7.2Hz) ppm. |
| 99 | 428.0 | — | — | — |
| 100 | 437.2 | — | — | — |
| 101 | 424.1 | — | — | — |
| 102 | 438.1 | — | — | — |
| 103 | 424.1 | — | — | — |
| 104 | 451.1 | — | — | — |
| 105 | 430.0 | — | — | — |
| 107 | 494.1 | — | — | — |
| 109 | 443.1 | DMSO-d₆ | 300 | 8.17 (1H, m), 8.10 (1H, m), 8.08 (1H, s), 7.86 (1H, m), 7.78 (1H, m), 7.61 (1H, s), 5.70 (1H, m), 3.94 (3H, s), 3.40 (3H, s), 1.98 (3H, s), 1.43 (3H, d, J = 6.6Hz) ppm. |
| 110 | 455.1 | DMSO-d₆ | 300 | 8.80 (1H, br s), 8.35 (2H, m), 8.08 (1H, m), 7.72 (1H, m), 7.65~7.59 (3H, m) 7.43 (0.5H, m), 7.35 (0.5H, m), 5.75 (1H, m), 3.40 (1.5H, s), 3.38 (1.5H, s), 2.00 (3H, s), 1.53 (3H, d, J = 6.6Hz) ppm. |
| 111 | 508.1 | DMSO-d₆ | 300 | 8.60 (1H, s), 8.57 (0.5H, m), 8.49 (0.5H, m), 8.16~8.07 (3H, m), 7.84 (0.5H, m), 7.73 (0.5H, m), 7.64 (1H, m), 5.67 (1H, m), 3.58 (4H, m), 3.35 (3H, s), 3.29 (4H, m), 1.99 (1.5H, s), 1.96 (1.5H, s), 1.44 (3H, d, J = 6.9Hz) ppm. |
| 112 | 452.1 | DMSO-d₆ | 300 | 10.55 (1H, s), 8.15 (2H, m), 8.12 (1H, s), 8.09 (1H, s), 8.06 (1H, s), 7.70 (1H, m), 7.59 (1H, m), 5.69 (1H, m), 3.37 (3H, s), 2.06 (3H, s), 1.97 (3H, s), 1.43 (3H, d, J = 6.6Hz) ppm. |
| 114 | 420.0 | DMSO-d₆ | 300 | 12.68 (1H, br s), 9.07 (1H, d, J = 0.9Hz), 8.21~7.99 (5H, m), 7.72 (1H, s), 5.73 (1H, m), 3.42 (3H, s), 2.00 (3H, s), 1.49 (3H, d, J = 7.2Hz) ppm. |
| 115 | 411.1 | DMSO-d₆ | 300 | 12.71 (1H, br s), 8.12~8.06 (4H, m), 7.55 (1H, s), 6.73 (2H, s), 5.68 (1H, m), 3.43 (3H, s), 2.03 (3H, s), 1.43 (3H, d, J = 7.2Hz) ppm. |
| 116 | 472.0 | DMSO-d₆ | 300 | 8.22 (1H, m), 8.15 (1H, s), 8.12 (1H, s), 8.01 (2H, d, J = 9.0 Hz), 7.67 (1H, s), 7.62 (1H, m), 7.55 ((1H, m), 5.73 (1H, m), 3.40 (3H, s), 3.29 (3H, s), 1.97 (3H, s), 1.49 (3H, d, J = 6.9Hz) ppm. |

Example 118

N-{1-[5-Fluoro-2-methoxy-6-methyl-4'-(methylsulfonyl)biphenyl-3-yl]ethyl}-9H-purin-6-amine

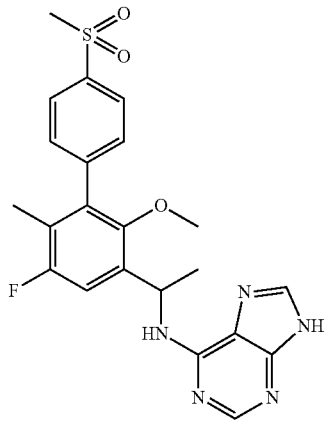 [SMILES: COc1c(C(C)Nc2ncnc3[nH]cnc23)cc(F)c(C)c1-c1ccc(S(C)(=O)=O)cc1]

Step 1. 4-Fluoro-3-methylphenyl acetate

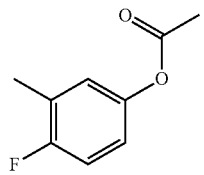

A solution of 4-fluoro-3-methylphenol (3.0 g, 23 mmol) and methylene chloride (96 mL) was cooled to 0° C. in an ice bath. Triethylamine (4.9 mL, 35 mmol) was introduced to the solution followed by dropwise addition of acetyl chloride (2.3 mL, 33 mmol). The ice bath was removed and the mixture was stirred for 1 hour. The mixture was then extracted with methylene chloride and washed with 0.5 N HCl, saturated sodium bicarbonate and brine. The extracts were dried over sodium sulfate, filtered and evaporated to give 4-fluoro-3-methylphenyl acetate (3.9 g, quantitative). 1H NMR (400 MHz, CDCl$_3$): δ 7.00 (m, 1H), 6.87 (m, 2H), 2.29 (m, 6H).

Step 2. 1-(5-Fluoro-2-hydroxy-4-methylphenyl)ethanone

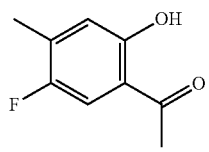

A suspension of 4-fluoro-3-methylphenyl acetate (3.9 g, 23 mmol) in boron trifluoride acetic acid complex (47 mL, 340 mmol) was heated at 155° C. for 14 hours. The mixture was then cooled to 0° C. in an ice bath and ice was added directly to the mixture. The ice bath was subsequently removed and the mixture stirred until the ice added to the mixture was dissolved. The mixture was then diluted with cold water and filtered. The isolated rust-colored solid was washed with cold water and allowed to dry in air to give 1-(5-Fluoro-2-hydroxy-4-methylphenyl)ethanone (3.2 g, 81%). 1H NMR (400 MHz, CDCl$_3$): δ 11.98 (s, 1H), 7.34 (m, 1H), 6.80 (m, 1H), 2.60 (s, 3H), 2.28 (s, 3H).

Step 3. 1-(3-Bromo-5-fluoro-2-hydroxy-4-methylphenyl)ethanone

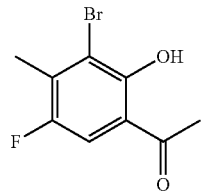

To a solution of 1-(5-fluoro-2-hydroxy-4-methylphenyl)ethanone (2.2 g, 13 mmol) and acetic acid (20 mL, 400 mmol) was added N-bromosuccinimide (2.8 g, 16 mmol). The resulting mixture was stirred at room temperature for 18 hours. The reaction mixture was then concentrated in vacuo, neutralized with saturated sodium bicarbonate and extracted with ethyl acetate. The combined organic layers were washed with brine, dried over sodium sulfate, filtered and concentrated to dryness under reduced pressure. Purification on silica gel with ethyl acetate/hexanes (0-50%) gave 1-(3-Bromo-5-fluoro-2-hydroxy-4-methylphenyl)ethanone (2.3 g, 71%). $^1$H NMR (400 MHz, CDCl$_3$): δ 12.80 (s, 1H), 7.40 (m, 1H), 2.60 (s, 3H), 2.40 (s, 3H).

Step 4. 1-(3-Bromo-5-fluoro-2-methoxy-4-methylphenyl)ethanone

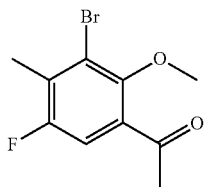

To a mixture of 1-(3-bromo-5-fluoro-2-hydroxy-4-methylphenyl)ethanone (0.3 g, 1 mmol) and potassium carbonate (0.43 g, 3.1 mmol) was added N,N-dimethylformamide (1 mL) and methyl iodide (0.17 mL, 2.7 mmol) with stirring. The resulting mixture was then heated at 60° C. for 1 hour. The mixture was diluted with water and extracted with ethyl acetate. The combined extracts were washed with brine, dried over sodium sulfate, and evaporated to dryness. The isolated residue was purified on silica gel, eluting with ethyl acetate/hexanes (0 to 20%) to yield 1-(3-Bromo-5-fluoro-2-methoxy-4-methylphenyl)ethanone (0.24 g, 80%). LCMS calculated for $C_{10}H_{11}BrFO_2$ (M+H)$^+$: m/z=261.0, 263.0. Found: 260.9, 262.9. $^1$H NMR (400 MHz, CDCl$_3$): δ 7.35 (m, 1H), 3.82 (s, 3H), 2.61 (s, 3H), 2.39 (s, 3H).

Step 5. 1-(3-Bromo-5-fluoro-2-methoxy-4-methylphenyl)ethanamine trifluoroacetate

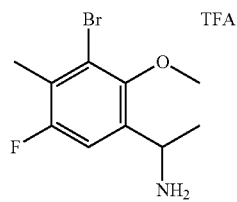

A mixture of 1-(3-bromo-5-fluoro-2-methoxy-4-methylphenyl)ethanone (140 mg, 0.55 mmol) and ammonium acetate (640 mg, 8.3 mmol) in acetonitrile (1.3 mL) and methanol (1.3 mL) was heated at 65° C. for 1 hour. Sodium cyanoborohydride (87 mg, 1.4 mmol) was added and the resulting mixture was heated at 65° C. for 3 hours. Purification by preparative LCMS (pH 2) RP-HPLC (XBridge C18 Column, eluting with a gradient of acetonitrile in water with 0.1% trifluoroacetic acid, at flow rate of 60 mL/min) gave 1-(3-Bromo-5-fluoro-2-methoxy-4-methylphenyl)ethanamine trifluoroacetate (150 mg, 70%). LCMS calculated for $C_{10}H_{11}BrFO$ (M-$NH_2$): m/z=245.0, 247.0. Found: 244.9, 246.9.

Step 6. N-[1-(3-Bromo-5-fluoro-2-methoxy-4-methylphenyl)ethyl]-9-(tetrahydro-2H-pyran-2-yl)-9H-purin-6-amine

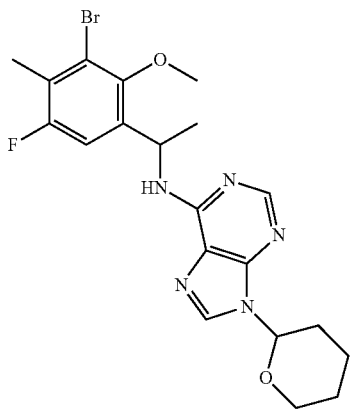 [SMILES: COc1c(C(C)Nc2ncnc3c2ncn3C2CCCCO2)cc(F)c(C)c1Br]

A mixture of 1-(3-bromo-5-fluoro-2-methoxy-4-methylphenyl)ethanamine trifluoroacetate (130 mg, 0.35 mmol), 6-bromo-9-(tetrahydro-2H-pyran-2-yl)-9H-purine (150 mg, 0.53 mmol, from Example 108, Step 1), N,N-diisopropylethylamine (0.31 mL, 1.8 mmol) and ethanol (2.0 mL) was heated at 95° C. for 1 hour. The resulting mixture was diluted with methanol and purified by preparative LCMS (pH 10) RP-HPLC (XBridge C18 Column, eluting with a gradient of acetonitrile in water with 0.2% ammonium hydroxide, at flow rate of 60 mL/min) to afford N-[1-(3-Bromo-5-fluoro-2-methoxy-4-methylphenyl)ethyl]-9-(tetrahydro-2H-pyran-2-yl)-9H-purin-6-amine (40 mg, 47%). LCMS calculated for $C_{20}H_{24}BrFN_5O_2$ (M+H)$^+$: m/z=464.0, 466.0. Found: 464.1, 466.1.

Step 7. N-{1-[5-Fluoro-2-methoxy-6-methyl-4'-(methylsulfonyl)biphenyl-3-yl]ethyl}-9H-purin-6-amine N-[1-(3-bromo-5-fluoro-2-methoxy-4-methylphenyl)ethyl]-9-(tetrahydro-2H-pyran-2-yl)-9H-purin-6-amine (21 mg, 0.044 mmol), [4-(methylsulfonyl)phenyl]boronic acid (13 mg, 0.066 mmol), potassium carbonate (15 mg, 0.11 mmol), water (0.2 mL), and 1,4-dioxane (0.40 mL) were added to a microwave vial. The mixture was degassed under nitrogen for 5 minutes. Tetrakis(triphenylphosphine)palladium(0) (5.1 mg, 4.4 μmol) was added to the mixture and the the vial was then sealed and bubbled under nitrogen for 5 minutes. The mixture was heated at 80° C. overnight. The cooled reaction mixture was then treated with 4.0 M hydrogen chloride in water (0.5 mL, 2 mmol) and was stirred at room temperature for 30 minutes. Purification by preparative LCMS (pH 10) RP-HPLC (XBridge C18 Column, eluting with a gradient of acetonitrile in water with 0.2% ammonium hydroxide, at flow rate of 60 mL/min) afforded N-{1-[5-Fluoro-2-methoxy-6-methyl-4'-(methylsulfonyl)biphenyl-3-yl]ethyl}-9H-purin-6-amine (13 mg, 66%). LCMS calculated for $C_{22}H_{23}FN_5O_3S$ (M+H)$^+$: m/z=456.1. Found: 456.0.

Experimental procedures for compounds of Examples 118-123 are summarized in Table 4 below.

TABLE 4

| Ex. No. | Name | R$^5$ | R$^4$ | R$^3$ | Salt | Proc.[1] |
|---|---|---|---|---|---|---|
| 118 | N-{1-[5-fluoro-2-methoxy-6-methyl-4'-(methylsulfonyl)biphenyl-3-yl]ethyl}-9H-purin-6-amine | F | Me | (4-methylsulfonylphenyl) | | Parent above |

TABLE 4-continued

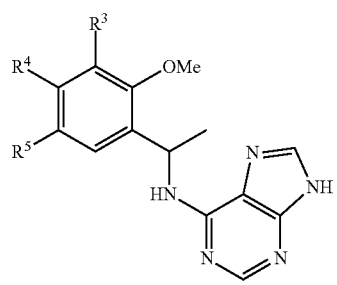

| Ex. No. Name | R⁵ | R⁴ | R³ | Salt | Proc.¹ |
|---|---|---|---|---|---|
| 119 N-[1-(3'-ethoxy-5-fluoro-2-methoxy-6-methylbiphenyl-3-yl)ethyl]-9H-purin-6-amine | F | Me | 3-ethoxyphenyl | Parent | 118 |
| 120 N-cyclopropyl-3'-fluoro-6'-methoxy-2'-methyl-5'-[1-(9H-purin-6-ylamino)ethyl]biphenyl-4-carboxamide | F | Me | 4-(cyclopropylcarbamoyl)phenyl | Parent | 118 |
| 121 N-{1-[5-fluoro-2-methoxy-4-methyl-3-(1-methyl-1H-pyrazol-4-yl)phenyl]ethyl}-9H-purin-6-amine | F | Me | 1-methyl-1H-pyrazol-4-yl | Parent | 118 |
| 122 N-{1-[5-fluoro-2-methoxy-4-methyl-3-(1-methyl-1H-pyrazol-5-yl)phenyl]ethyl}-9H-purin-6-amine | F | Me | 1-methyl-1H-pyrazol-5-yl | Parent | 118 |
| 123 N-{1-[3-(2-aminopyrimidin-5-yl)-5-fluoro-2-methoxy-4-methylphenyl]ethyl}-9H-purin-6-amine | F | Me | 2-aminopyrimidin-5-yl | Parent | 118 |

¹Synthesized according to the experimental procedure of compound listed.

Analytical Data $^1$H NMR data (Varian Inova 500 spectrometer, a Mercury 400 spectrometer, or a Varian (or Mercury) 300 spectrometer) and LCMS mass spectral data (MS) for the compounds of Examples 118-123 is provided below in Table 5.

TABLE 5

| Ex. No. | MS [M + H]$^+$ | Solvent | MHz | $^1$H NMR Spectra |
|---|---|---|---|---|
| 118 | 456.0 | DMSO-d$_6$ | 500 | δ 8.12 (m, 2H), 8.03 (m, 2H), 7.60 (br s, 1H), 7.40 (m, 1H), 5.80 (br s, 3H), 3.40 (s, 3H), 3.25 (s, 3H), 1.85 (s, 3H), 1.50 (m, 3H). |
| 119 | 422.2 | DMSO-d$_6$ | 500 | δ δ 8.12 (m, 2H), 8.00 (br s, 1H), 7.33 (m, 2H), 6.95 (m, 1H), 6.80 (m, 2H), 5.80 (br s, 1H), 4.03 (m, 2H), 3.40 (s, 3H), 1.85 (s, 3H), 1.50 (m, 3H), 1.31 (m, 3H). |
| 120 | 461.2 | DMSO-d$_6$ | 500 | δ 8.44 (m, 1H), 8.12 (m, 2H), 8.02 (br s, 1H), 7.90 (m 1H), 7.38 (m, 2H), 5.80 (br s, 1H), 3.40 (s, 3H), 2.89 (m, 1H), 1.85 (s, 3H), 1.50 (m, 3H), 0.70 (m, 2H), 0.59 (m, 2H). |
| 121 | 382.1 | DMSO-d$_6$ | 500 | δ 8.12 (m, 2H), 8.00 (br s, 1H), 7.83 (s, 1H), 7.51 (s, 1H), 7.20 (m, 1H), 5.80 (br s, 1H), 3.89 (s, 3H), 3.45 (s, 3H), 2.01 (s, 3H), 1.47 (m, 3H). |
| 122 | 382.2 | DMSO-d$_6$ | 500 | δ 8.12 (m, 2H), 8.00 (br s, 1H), 7.53 (m, 1H), 7.39 (m, 1H), 6.40 (m, 1H), 5.80 (br s, 1H), 3.56 (s, 3H), 3.50 (s, 3H), 1.85 (s, 3H), 1.48 (m, 3H). |
| 123 | 395.1 | DMSO-d$_6$ | 500 | δ 8.20 (s, 1H), 8.12 (m, 2H), 8.02 (br s, 1H), 7.32 (m, 1H), 6.73 (s, 1H), 5.80 (br s, 1H), 3.43 (s, 3H), 1.98 (s, 3H), 1.48 (m, 3H). |

The desired compound was prepared according to the procedure of Example 1, step 3, using 1-(3-bromo-5-chloro-2-hydroxyphenyl)ethanone as the starting material in 97% yield. LCMS for C$_9$H$_6$BrClF$_3$O$_4$S (M+H)$^+$: m/z=380.9, 382.9. Found: 380.8, 382.9.

Example 124

N-{1-[4-Chloro-3',5'-difluoro-6-(1H-pyrazol-4-yl)biphenyl-2-yl]ethyl}-9H-purin-6-amine

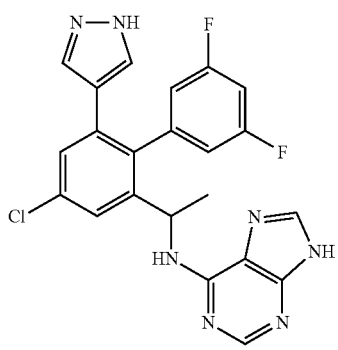 [SMILES: CC(Nc1ncnc2[nH]cnc12)c1cc(Cl)cc(-c2cn[nH]c2)c1-c1cc(F)cc(F)c1]

Step A: 2-Acetyl-6-bromo-4-chlorophenyl trifluoromethanesulfonate

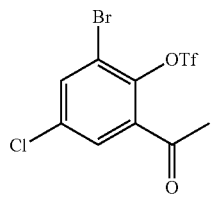 [SMILES: CC(=O)c1cc(Cl)cc(Br)c1OS(=O)(=O)C(F)(F)F]

Step B: 1-(6-Bromo-4-chloro-3',5'-difluorobiphenyl-2-yl)ethanone

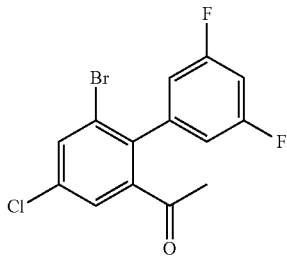 [SMILES: CC(=O)c1cc(Cl)cc(Br)c1-c1cc(F)cc(F)c1]

A solution of sodium hydrogenecarbonate (2.0 g, 23 mmol) in water (50 mL) was treated with a solution of 2-acetyl-6-bromo-4-chlorophenyl trifluoromethanesulfonate (4.5 g, 12 mmol) in toluene (50 mL) followed by (3,5-difluorophenyl)boronic acid (2.0 g, 13 mmol) and tetrakis(triphenylphosphine)palladium(0) (0.67 g, 0.58 mmol). The reaction mixture was degassed with nitrogen for 5 min and heated at 80° C. overnight. The reaction mixture was diluted wih water and extracted with ethyl acetate (2×100 mL). The combined organic layers were washed with sodium bicarbonate, water, and brine, dried with sodium sulfate, filtered, and concentrated to a crude residue. Purification by flash column chromatography using ethyl acetate in hexanes (0%-10%) gave the desired product (3.7 g, 82%). LCMS for C$_{14}$H$_9$BrClF$_2$O (M+H)$^+$: m/z=344.9, 346.9. Found: 344.9, 346.8.

Step C: 1-{4-Chloro-6-[1-(1-ethoxyethyl)-1H-pyrazol-4-yl]-3',5'-difluorobiphenyl-2-yl}ethanone

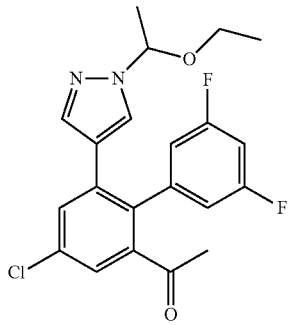 [SMILES: CCOC(C)n1cc(-c2cc(Cl)cc(C(C)=O)c2-c2cc(F)cc(F)c2)cn1]

A solution of 1-(6-bromo-4-chloro-3',5'-difluorobiphenyl-2-yl)ethanone (300 mg, 0.87 mmol), 1-(1-ethoxyethyl)-4-(4,4,5,5-tetramethyl-1,3,2-dioxaborolan-2-yl)-1H-pyrazole (250 mg, 0.96 mmol), and sodium carbonate (280 mg, 2.6 mmol) in 1,4-dioxane (3.0 mL, 38 mmol) was degassed with nitrogen 5 minutes, treated with tetrakis(triphenylphosphine)palladium(0) (100 mg, 0.087 mmol) degassed with additional nitrogen for 5 mins, and heated at 80° C. overnight. The reaction mixture was diluted with water and extracted with ethyl acetate (2×60 mL). The combined organic layers were washed with water and brine, dried with sodium sulfate, filtered, and concentrated to a crude residue. Purification via preparative LCMS (XBridge C18 column, eluting with a gradient of acetonitrile/water containing 0.1% ammonium hydroxide, at flow rate of 60 mL/min) gave the desired product (190 mg, 54%).

Step D: 1-{4-Chloro-6-[1-(1-ethoxyethyl)-1H-pyrazol-4-yl]-3',5'-difluorobiphenyl-2-yl}ethanamine

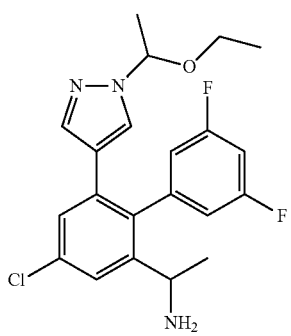 [SMILES: CCOC(C)n1cc(-c2cc(Cl)cc(C(C)N)c2-c2cc(F)cc(F)c2)cn1]

A solution of 1-{4-chloro-6-[1-(1-ethoxyethyl)-1H-pyrazol-4-yl]-3',5'-difluorobiphenyl-2-yl}ethanone (190 mg, 0.47 mmol), ammonium acetate (360 mg, 4.7 mmol) in methanol (2 mL) and acetonitrile (2 mL) was heated at 65° C. for 3 hours. The reaction mixture was quenched with acetic acid (~100 uL) and poured into sodium bicarbonate (50 mL). This mixture was extracted with dichloromethane (3×60 mL) and the combined organic layers were washed with brine, dried with sodium sulfate, filtered, and concentrated to a crude residue. Purification via preparative LCMS (XBridge C18 column, eluting with a gradient of acetonitrile/water containing 0.1% ammonium hydroxide, at flow rate of 60 mL/min) gave the desired product (60 mg, 32%). LCMS for $C_{21}H_{23}ClF_2N_3O$ $(M+H)^+$: m/z=406.1. Found: 406.1.

Step E: N-{1-[4-Chloro-3',5'-difluoro-6-(1H-pyrazol-4-yl)biphenyl-2-yl]ethyl}-9H-purin-6-amine A solution of 1-{4-chloro-6-[1-(1-ethoxyethyl)-1H-pyrazol-4-yl]-3',5'-difluorobiphenyl-2-yl}ethanamine (60 mg, 0.15 mmol), 6-bromo-9-(tetrahydro-2H-pyran-2-yl)-9H-purine (63 mg, 0.22 mmol, from Example 108, Step 1), and N,N-diisopropylethylamine (77 µL, 0.44 mmol) in ethanol (2.8 mL) was heated in the microwave at 130° C. for 30 minutes. Alternatively, this reaction can be heated at 90° C. overnight on the benchtop. The reaction mixture was cooled to room temperature, treated with 6 M Hydrogen chloride in water (0.49 mL, 3.0 mmol), and stirred for 30 minutes. The reaction mixture was diluted slightly with methanol, filtered, and directly purified via preparative LCMS (XBridge C18 column, eluting with a gradient of acetonitrile/water containing 0.1% ammonium hydroxide, at flow rate of 60 mL/min) to give the desired product (29 mg, 43%). LCMS for $C_{22}H_{17}ClF_2N_7$ $(M+H)^+$: m/z=452.1. Found: 452.0; $^1H$ NMR (300 MHz, DMSO-$d_6$): δ 12.8 (br s, 1H), 8.32-8.23 (m, 1H), 8.11 (s, 1H), 8.06 (s, 1H), 7.65 (s, 1H), 7.46 (s, 1H), 7.36-7.23 (m, 3H), 7.09-7.01 (m, 1H), 6.96 (d, J=8.5 Hz, 1H), 5.09-4.96 (m, 1H), 1.34 (d, J=6.7 Hz, 3H).

Example 125

N-{1-[5-Chloro-3-(5-chloropyridin-3-yl)-2-methoxyphenyl]ethyl}-9H-purin-6-amine

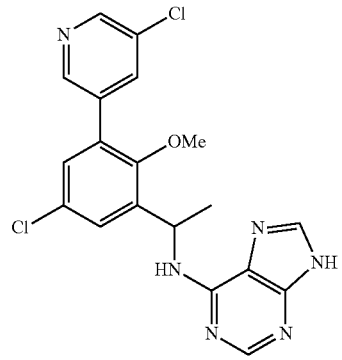 [SMILES: COc1c(-c2cncc(Cl)c2)cc(Cl)cc1C(C)Nc1ncnc2[nH]cnc12]

Step A:
1-(3-Bromo-5-chloro-2-methoxyphenyl)ethanone

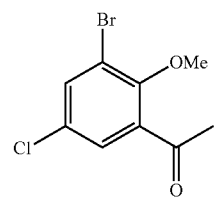

A solution of 1-(3-bromo-5-chloro-2-hydroxyphenyl)ethanone (5.0 g, 20 mmol) in N,N-dimethylformamide (40 mL) was treated with potassium carbonate (5.5 g, 40 mmol) followed by methyl iodide (1.9 mL, 30 mmol) and heated at 60° C. overnight. The reaction mixture was diluted with water (300 mL) and extracted with ethyl acetate (2×150 mL). The organic layers were washed with water (3×100 mL) and brine, dried with sodium sulfate, filtered, and concentrated to give the crude product. Purification by flash column chromatography using ethyl acetate in hexanes (0%-5%-25%) gave the desired product (5.1 g, 96%). LCMS for $C_9H_9BrClO_2$ $(M+H)^+$: m/z=262.9, 264.9. Found: 262.9, 264.9.

Step B:
1-(3-Bromo-5-chloro-2-methoxyphenyl)ethanamine

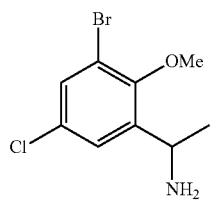

The desired compound was prepared according to the procedure of Example 124, step D, using 1-(3-bromo-5-chloro-2-methoxyphenyl)ethanone as the starting material in 56% yield. LCMS for $C_9H_{12}BrClNO$ $(M+H)^+$: m/z=264.0, 266.0. Found: 263.9, 265.9.

Step C: N-[1-(3-Bromo-5-chloro-2-methoxyphenyl)ethyl]-9-(tetrahydro-2H-pyran-2-yl)-9H-purin-6-amine

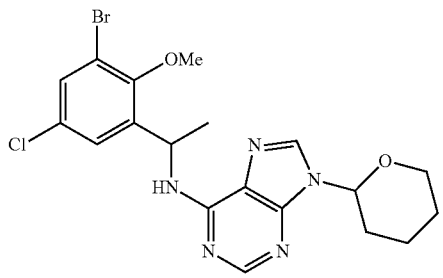 [SMILES: COc1c(Br)cc(Cl)cc1C(C)Nc1ncnc2c1ncn2C1CCCCO1]

A solution of 1-(3-bromo-5-chloro-2-methoxyphenyl)ethanamine (2.2 g, 8.5 mmol) in ethanol (69 mL), was treated with 6-bromo-9-(tetrahydro-2H-pyran-2-yl)-9H-purine (3.6 g, 13 mmol, from Example 108, Step 1) and N,N-diisopropylethylamine (4.4 mL, 25 mmol) and heated at reflux overnight. The reaction mixture was cooled, poured into sodium bicarbonate (150 mL) and extracted with ethyl acetate (2×150 mL). The combined organic layers were washed with water and brine, dried with sodium sulfate, filtered, and concentrated to a crude residue. Purification by flash column chromatography using acetonitrile in dichloromethane (5%-10%) and then ethyl acetate in hexanes (60%-100%) gave the desired product (3.9 g, 98%). LCMS for $C_{19}H_{22}BrClN_5O_2$ $(M+H)^+$: m/z=466.1, 468.1. Found: 466.0, 468.0.

Step D: N-{1-[5-Chloro-3-(5-chloropyridin-3-yl)-2-methoxyphenyl]ethyl}-9H-purin-6-amine A solution of N-[1-(3-bromo-5-chloro-2-methoxyphenyl)ethyl]-9-(tetrahydro-2H-pyran-2-yl)-9H-purin-6-amine (45 mg, 0.096 mmol) and (5-chloropyridin-3-yl)boronic acid (23 mg, 0.15 mmol) in water (0.5 mL) and 1,4-dioxane (1 mL) was treated with potassium carbonate (33 mg, 0.24 mmol) and tetrakis(triphenylphosphine)palladium(0) (11 mg, 9.6 µmol). The reaction mixture was degassed with nitrogen for 5 min and heated at 80° C. overnight. The reaction mixture was cooled treated directly with 6 M hydrogen chloride in water (170 µL, 1.0 mmol) and stirred at room temperature for ~30 minutes. The reaction mixture was diluted slightly with methanol, filtered, and directly purified via preparative LCMS (XBridge C18 column, eluting with a gradient of acetonitrile/water containing 0.1% ammonium hydroxide, at flow rate of 60 mL/min) to give the desired product (6 mg, 15%). LCMS for $C_{19}H_{17}Cl_2N_6O$ $(M+H)^+$: m/z=415.1. Found: 415.0; $^1H$ NMR (300 MHz, DMSO-$d_6$): δ 8.72 (d, J=1.8 Hz, 1H), 8.66 (d, J=2.3 Hz, 1H), 8.20-8.09 (m, 4H), 7.65 (d, J=2.1 Hz, 1H), 7.40 (d, J=2.6 Hz, 1H), 5.91-5.71 (m, 1H), 3.52 (s, 3H), 1.51 (d, J=7.0 Hz, 3H).

Example 126

N-{1-[5-Chloro-4-methyl-2-(2-morpholin-4-ylethoxy)-3-pyridin-4-ylphenyl]ethyl}-9H-purin-6-amine

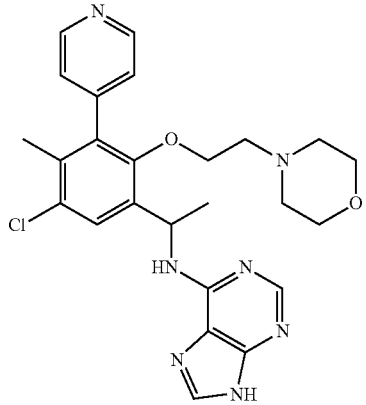 [SMILES: Cc1c(Cl)cc(C(C)Nc2ncnc3[nH]cnc23)c(OCCN2CCOCC2)c1-c1ccncc1]

Step A: 1-[3-Bromo-5-chloro-4-methyl-2-(2-morpholin-4-ylethoxy)phenyl]ethanone

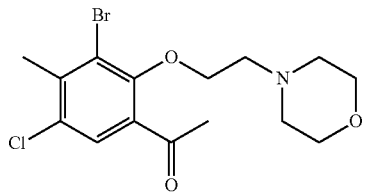 [SMILES: CC(=O)c1cc(Cl)c(C)c(Br)c1OCCN1CCOCC1]

A solution of 1-(3-bromo-5-chloro-2-hydroxy-4-methylphenyl)ethanone (34 mg, 0.13 mmol), triphenylphosphine (47 mg, 0.18 mmol), and 4-morpholineethanol (23 µL, 0.19 mmol) in tetrahydrofuran (0.38 mL, 4.6 mmol) at −10° C. was treated with diisopropyl azodicarboxylate (35 µL, 0.18 mmol) dropwise and stirred at −10° C. for 15 min and warmed to 20° C. for 30 minutes. The reaction mixture was concentrated, diluted with ethyl acetate (5 mL), and washed with water and brine, dried with magnesium sulfate, filtered, and concentrated to a crude oil. Purification by flash column chromatography using ethyl acetate in hexanes (0%-60%) gave the desired product (15 mg, 31%). LCMS for $C_{15}H_{20}BrClNO_3$ (M+H)$^+$: m/z=376.0, 378.0. Found: 375.9, 378.0.

Step B: 1-[5-Chloro-4-methyl-2-(2-morpholin-4-ylethoxy)-3-pyridin-4-ylphenyl]ethanone

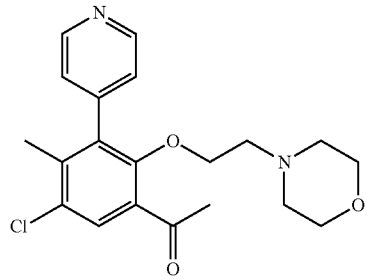 [SMILES: CC(=O)c1cc(Cl)c(C)c(-c2ccncc2)c1OCCN1CCOCC1]

The desired compound was prepared according to the procedure of Example 124, step C, using 1-[3-bromo-5-chloro-4-methyl-2-(2-morpholin-4-ylethoxy)phenyl]ethanone and cesium carbonate (instead of sodium carbonate) as the starting materials in 62% yield. LCMS for $C_{20}H_{24}ClN_2O_3$ (M+H)$^+$: m/z=375.1. Found: 375.1.

Step C: 1-[5-Chloro-4-methyl-2-(2-morpholin-4-ylethoxy)-3-pyridin-4-ylphenyl]ethanamine

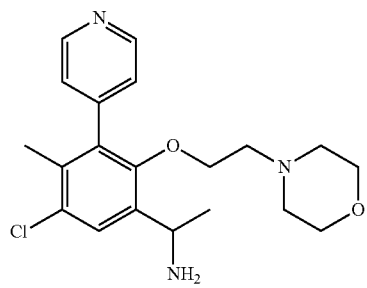 [SMILES: Cc1c(Cl)cc(C(C)N)c(OCCN2CCOCC2)c1-c1ccncc1]

The desired compound was prepared according to the procedure of Example 124, step D, using 1-[5-chloro-4-methyl-2-(2-morpholin-4-ylethoxy)-3-pyridin-4-ylphenyl]ethanone as the starting material in 98% yield. LCMS for $C_{20}H_{27}ClN_3O_2$ (M+H)$^+$: m/z=376.2. Found: 376.1.

Step D: N-{1-[5-Chloro-4-methyl-2-(2-morpholin-4-ylethoxy)-3-pyridin-4-ylphenyl]ethyl}-9H-purin-6-amine The desired compound was prepared according to the procedure of Example 124, step E, using 1-[5-chloro-4-methyl-2-(2-morpholin-4-ylethoxy)-3-pyridin-4-ylphenyl]ethanamine as the starting material in 12% yield. LCMS for $C_{25}H_{29}ClN_7O_2$ (M+H)$^+$: m/z=494.2. Found: 494.2; $^1$H NMR (300 MHz, DMSO-d$_6$): δ 12.9 (s, 1H), 8.65 (d, J=5.0 Hz, 2H), 8.26-8.15 (m, 1H), 8.12 (s, 1H), 8.06 (s, 1H), 7.68 (s, 1H), 7.47-7.29 (m, 2H), 5.86-5.72 (m, 1H), 4.08-4.00 (m, 1H), 3.41-3.37 (m, 4H), 2.31-2.28 (m, 2H), 2.21-2.14 (m, 2H) 2.10-2.04 (m, 2H), 1.96 (s, 3H), 1.48 (d, J=7.0 Hz, 3H).

Example 127

N-[1-(5-Chloro-2,4-dimethyl-3-pyridin-4-ylphenyl)ethyl]-9H-purin-6-amine

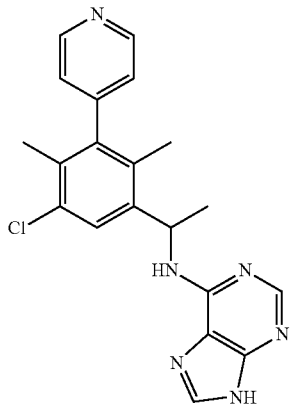 [SMILES: Cc1c(Cl)cc(C(C)Nc2ncnc3[nH]cnc23)c(C)c1-c1ccncc1]

Step A: 1-(5-Chloro-2-hydroxy-4-methyl-3-pyridin-4-ylphenyl)ethanone

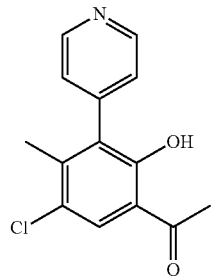 [SMILES: CC(=O)c1cc(Cl)c(C)c(-c2ccncc2)c1O]

A solution of 1-(3-bromo-5-chloro-2-hydroxy-4-methylphenyl)ethanone (2.6 g, 9.9 mmol), 4-pyridinylboronic acid (1.6 g, 13 mmol), and potassium carbonate (5.5 g, 40 mmol) in 1,2-dimethoxyethane (48 mL) and water (24 mL) was degassed with nitrogen and treated with triphenylphosphine (260 mg, 0.99 mmol) and palladium acetate (0.22 g, 0.99 mmol). The reaction mixture was degassed with nitrogen for 5 min and heated at 90° C. for 20 hours. The reaction mixture was cooled to room temperature, concentrated to remove most of the DME, diluted with ethyl acetate (200 ml) and water (100 ml), and filtered over celite. The aqueous layer was separated and extracted with ethyl acetate (100 mL). The combined organic layers were washed with brine (100 ml), dried over sodium sulfate, filtered, and concentrated to a crude brown foam. Purification by flash column chromatography using ethyl acetate in hexanes (0%-60%) gave the desired product (1.2 g, 45%). LCMS for $C_{14}H_{13}ClNO_2$ (M+H)$^+$: m/z=262.1. Found: 262.0.

Step B: 6-Acetyl-4-chloro-3-methyl-2-pyridin-4-ylphenyl trifluoromethanesulfonate

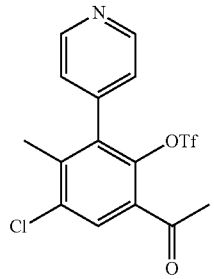 [SMILES: CC(=O)c1cc(Cl)c(C)c(-c2ccncc2)c1OS(=O)(=O)C(F)(F)F]

The desired compound was prepared according to the procedure of Example 1, step 3, using 1-(5-chloro-2-hydroxy-4-methyl-3-pyridin-4-ylphenyl)ethanone as the starting material in 81% yield. LCMS for $C_{15}H_{12}ClF_3NO_4S$ (M+H)$^+$: m/z=394.0. Found: 393.9.

Step C: 1-(5-Chloro-2,4-dimethyl-3-pyridin-4-ylphenyl)ethanone

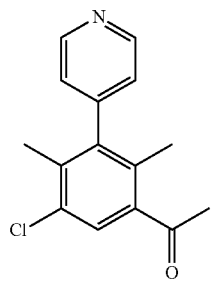 [SMILES: CC(=O)c1cc(Cl)c(C)c(-c2ccncc2)c1C]

A solution of 6-acetyl-4-chloro-3-methyl-2-pyridin-4-ylphenyl trifluoromethanesulfonate (0.40 g, 1.0 mmol) in 1,4-dioxane (10 mL, 130 mmol) was degassed with nitrogen and treated with [1,1'-bis(diphenylphosphino)ferrocene]dichloropalladium(II), complex with dichloromethane (1:1) (41 mg, 0.051 mmol). The reaction mixture was degassed with nitrogen for 5 minutes, treated with 2.0 M dimethylzinc in toluene (0.76 mL, 1.5 mmol), and heated at 70° C. for 1.5 hours. The reaction mixture was cooled to room temperature diluted with ethyl acetate and water and filtered over celite to remove solids. The ethyl acetate layer was separated, washed with brine, dried over sodium sulfate, filtered, and concentrated to a crude brown gum. Purification by flash column chromatography using ethyl acetate in hexanes (0%-20%) gave the desired product (0.18 g, 69%). LCMS for $C_{15}H_{15}ClNO$ (M+H)$^+$: m/z=260.1. Found: 260.1.

Step D: 1-(5-Chloro-2,4-dim ethyl-3-pyridin-4-ylphenyl)ethanamine

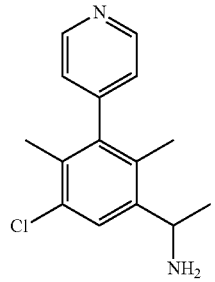 [SMILES: Cc1c(Cl)cc(C(C)N)c(C)c1-c1ccncc1]

The desired compound was prepared according to the procedure of Example 124, step D, using 1-(5-chloro-2,4-dimethyl-3-pyridin-4-ylphenyl)ethanone as the starting material in 40% yield. LCMS for $C_{15}H_{18}ClN_2$ (M+H)$^+$: m/z=261.1. Found: 261.0.

Step E: N-[1-(5-Chloro-2,4-dim ethyl-3-pyridin-4-ylphenyl)ethyl]-9H-purin-6-amine The desired compound was prepared according to the procedure of Example 124, step E, using 1-(5-chloro-2,4-dimethyl-3-pyridin-4-ylphenyl)ethanamine as the starting material in 32% yield. LCMS for $C_{20}H_{20}ClN_6$ (M+H)$^+$: m/z=379.1. Found: 379.1; 1H NMR (400 MHz, DMSO-$d_6$): δ 12.9 (br s, 1H), 8.67-8.64 (m, 2H), 8.32-8.24 (m, 1H), 8.12 (s, 2H), 7.68 (s, 1H), 7.22 (d, J=5.1 Hz, 1H), 7.21 (s, 1H), 5.69-5.60 (m, 1H), 2.04 (s, 3H), 1.89 (s, 3H), 1.47 (d, J=6.6 Hz, 3H).

Example 128

N-{1-[5-Chloro-6-methyl-4'-(methylsulfonyl)-2-(2-morpholin-4-ylethoxy)biphenyl-3-yl]ethyl}-9H-purin-6-amine

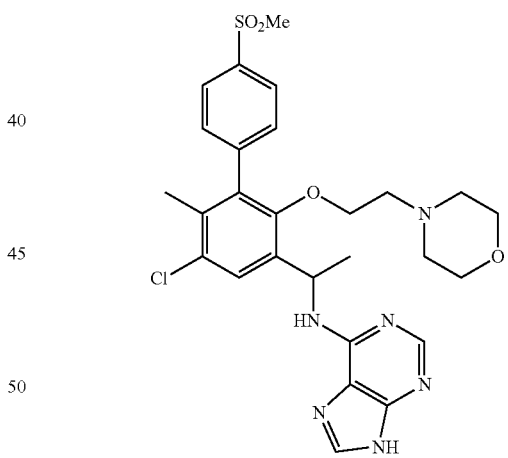

Step A: 1-[3-Bromo-5-chloro-4-methyl-2-(2-morpholin-4-ylethoxy)phenyl]ethanamine

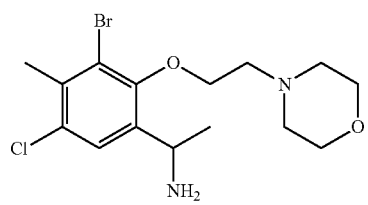 [SMILES: Cc1c(Cl)cc(C(C)N)c(OCCN2CCOCC2)c1Br]

The desired compound was prepared according to the procedure of Example 124, step D, using 1-[3-bromo-5-chloro-4-methyl-2-(2-morpholin-4-ylethoxy)phenyl]ethanone as the starting material in 95% yield. LCMS for $C_{15}H_{23}BrClN_2O_2$ (M+H)$^+$: m/z=377.1, 379.1. Found: 377.1, 379.1.

Step B: N-{1-[3-Bromo-5-chloro-4-methyl-2-(2-morpholin-4-ylethoxy)phenyl]ethyl}-9-(tetrahydro-2H-pyran-2-yl)-9H-purin-6-amine

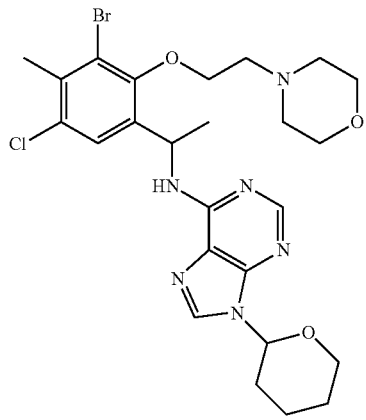 [SMILES: Cc1c(Cl)cc(C(C)Nc2ncnc3c2ncn3C2CCCCO2)c(OCCN2CCOCC2)c1Br]

The desired compound was prepared according to the procedure of Example 125, step C, using 1-[3-bromo-5-chloro-4-methyl-2-(2-morpholin-4-ylethoxy)phenyl]ethanamine as the starting material in 50% yield. LCMS for $C_{25}H_{33}BrClN_6O_3$ (M+H)$^+$: m/z=579.1, 581.1. Found: 579.2, 581.2.

Step C: N-{1-[5-Chloro-6-methyl-4'-(methylsulfonyl)-2-(2-morpholin-4-ylethoxy)biphenyl-3-yl]ethyl}-9H-purin-6-amine The desired compound was prepared according to the procedure of Example 125, step D, using N-{1-[3-bromo-5-chloro-4-methyl-2-(2-morpholin-4-ylethoxy)phenyl]ethyl}-9-(tetrahydro-2H-pyran-2-yl)-9H-purin-6-amine, [4-(methylsulfonyl)phenyl]boronic acid, and sodium carbonate (instead of potassium carbonate) as the starting materials in 27% yield. LCMS for $C_{27}H_{32}ClN_6O_4S$ (M+H)$^+$: m/z=571.2. Found: 571.3; $^1$H NMR (400 MHz, DMSO-d$_6$): δ 12.9 (s, 1H), 8.17-8.07 (m, 3H), 8.00 (d, J=7.9 Hz, 2H), 7.67 (s, 1H), 7.64 (d, J=7.2 Hz, 1H), 7.55 (d, J=7.4 Hz, 1H), 5.80 (s, 1H), 4.15-3.84 (m, 1H), 3.42-3.37 (m, 4H), 3.28 (s, 3H), 2.32-2.25 (m, 2H), 2.17-2.12 (m, 2H), 2.08-2.00 (m, 2H), 1.98 (s, 3H), 1.50 (d, J=6.9 Hz, 3H).

Experimental procedures for further compounds are summarized in Table 6 below.

TABLE 6

| Ex. No. | Name | R$_3$ | Salt | Proc.[1] |
|---|---|---|---|---|
| 129 | N-{1-[4-chloro-3',5'-difluoro-6-(2-methoxypyrimidin-5-yl)biphenyl-2-yl]ethyl}-9H-purin-6-amine | OMe (2-methoxypyrimidin-5-yl) | — | 124 |

TABLE 6-continued

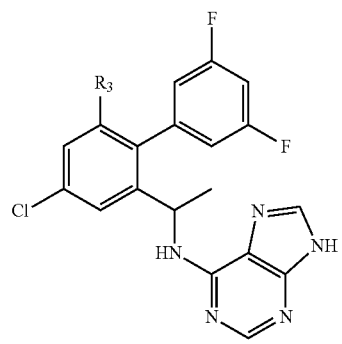

| Ex. No. Name | R₃ | Salt | Proc.[1] |
|---|---|---|---|
| 130 N-{5'-chloro-3″,5″-difluoro-3'-[1-(9H-purin-6-ylamino)ethyl]-1,1':2',1″-terphenyl-4-yl}acetamide | 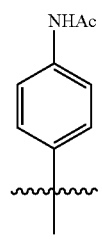 NHAc | — | 124 |
| 131 N-[1-(4-chloro-3',5'-difluoro-6-pyridin-4-ylbiphenyl-2-yl)ethyl]-9H-purin-6-amine | 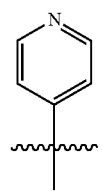 [SMILES: *c1ccncc1] | — | 124 |
| 132 N-[1-(4-chloro-3',5'-difluoro-6-pyrimidin-5-ylbiphenyl-2-yl)ethyl]-9H-purin-6-amine | 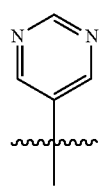 | — | 124 |
| 133 N-{1-[4-chloro-6-(2,6-difluoropyridin-4-yl)-3',5'-difluorobiphenyl-2-yl]ethyl}-9H-purin-6-amine | 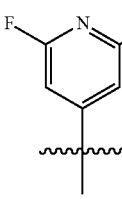 | — | 124 |
| 134 N-{1-[5'-chloro-3″,5″-difluoro-4-(methylsulfonyl)-1,1':2',1″-terphenyl-3'-yl]ethyl}-9H-purin-6-amine | 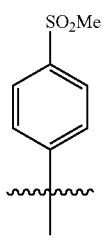 SO₂Me | — | 124 |

TABLE 6-continued
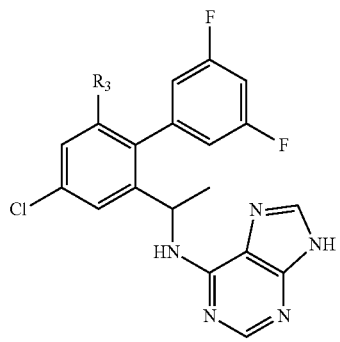
| Ex. No. | Name | R₃ | Salt | Proc.[1] |
|---|---|---|---|---|
| 135 | N-{1-[6-(2-aminopyrimidin-5-yl)-4-chloro-3',5'-difluorobiphenyl-2-yl]ethyl}-9H-purin-6-amine | 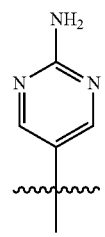 [SMILES: *c1cnc(N)nc1] | — | 124 |
Experimental procedures for further compounds are summarized in Table 7 below.
TABLE 7
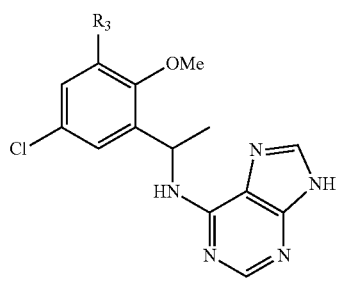
| Ex. No. | Name | R₃ | Salt | Proc.[1] |
|---|---|---|---|---|
| 136 | N-{1-[5-chloro-2-methoxy-3-(2-methoxypyrimidin-5-yl)phenyl]ethyl}-9H-purin-6-amine | 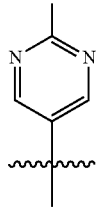 | — | 125 |
| 137 | N-{5'-chloro-2'-methoxy-3'-[1-(9H-purin-6-ylamino)ethyl]biphenyl-4-yl}acetamide | 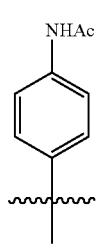 | — | 125 |

TABLE 7-continued
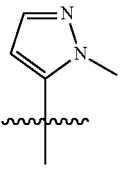 [SMILES: *c1ccnn1C]
| Ex. No. | Name | R₃ | Salt | Proc.[1] |
|---|---|---|---|---|
| 138 | N-{1-[5-chloro-2-methoxy-3-(1-methyl-1H-pyrazol-5-yl)phenyl]ethyl}-9H-purin-6-amine | 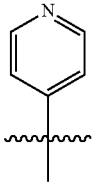 [SMILES: *c1ccncc1] | — | 125 |
| 139 | N-[1-(5-chloro-2-methoxy-3-pyridin-4-ylphenyl)ethyl]-9H-purin-6-amine | 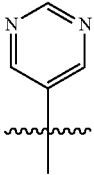 | — | 125 |
| 140 | N-[1-(5-chloro-2-methoxy-3-pyrimidin-5-ylphenyl)ethyl]-9H-purin-6-amine | 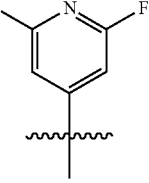 | — | 125 |
| 141 | N-{1-[5-chloro-3-(2,6-difluoropyridin-4-yl)-2-methoxyphenyl]ethyl}-9H-purin-6-amine | 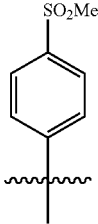 [SMILES: *c1ccc(S(C)(=O)=O)cc1] | — | 125 |
| 142 | N-{1-[5-chloro-2-methoxy-4'-(methylsulfonyl)biphenyl-3-yl]ethyl}-9H-purin-6-amine | SO₂Me | — | 125 |

TABLE 7-continued

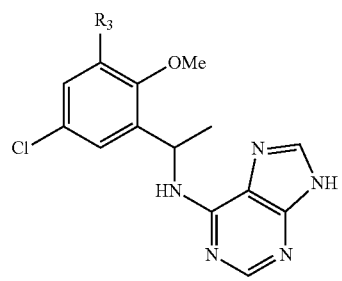

| Ex. No. Name | R₃ | Salt | Proc.[1] |
|---|---|---|---|
| 143 N-{1-[3-(2-aminopyrimidin-5-yl)-5-chloro-2-methoxyphenyl]ethyl}-9H-purin-6-amine | 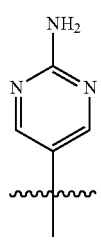 | — | 125 |
| 144 3,5'-dichloro-2'-methoxy-N-methyl-3'-[1-(9H-purin-6-ylamino)ethyl]biphenyl-4-carboxamide | 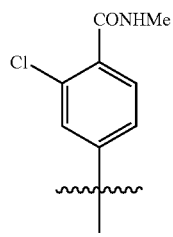 | — | 125 |
| 145 N-{1-[5-chloro-3-(2-fluoropyriidn-4-yl)-2-methoxyphenyl]ethyl}-9H-purin-6-amine | 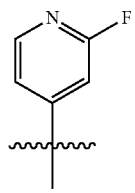 [SMILES: *c1ccnc(F)c1] | — | 125 |
| 146 N-{1-[5-chloro-2-methoxy-3-(5-methoxypyridin-3-yl)phenyl]ethyl}-9H-purin-6-amine | 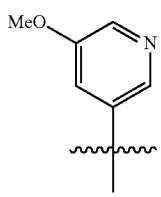 | — | 125 |
| 147 N-{1-[5-chloro-3-(6-fluoropyridin-3-yl)-2-methoxyphenyl]ethyl}-9H-purin-6-amine | 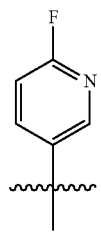 [SMILES: *c1ccc(F)nc1] | — | 125 |

TABLE 7-continued

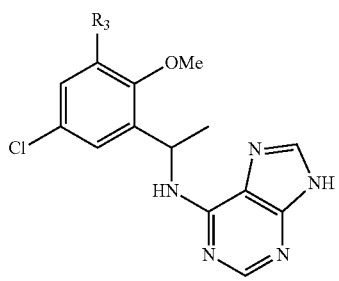

| Ex. No. | Name | R₃ | Salt | Proc.¹ |
|---|---|---|---|---|
| 148 | N-{1-[5-chloro-2-methoxy-3-(6-methoxypyridin-3-yl)phenyl]ethyl}-9H-purin-6-amine | 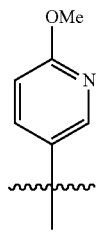 | — | 125 |

Experimental procedures for compounds below are summarized in Table 8.

TABLE 8

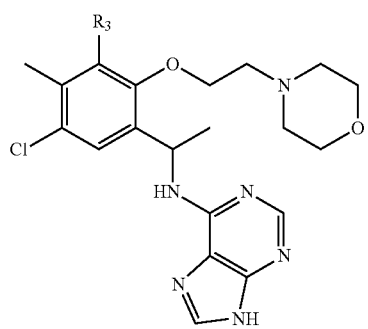

| Ex. No. | Name | R₃ | Salt | Proc.¹ |
|---|---|---|---|---|
| 149 | N-{1-[3-(2-aminopyrimidin-5-yl)-5-chloro-4-methyl-2-(2-morpholin-4-ylethoxy)phenyl]ethyl}-9H-purin-6-amine | 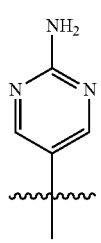 [SMILES: *c1cnc(N)nc1] | — | 128 |
| 150 | N-{1-[5-chloro-3'-methoxy-6-methyl-2-(2-morpholin-4-ylethoxy)biphenyl-3-yl]ethyl}-9H-purin-6-amine | 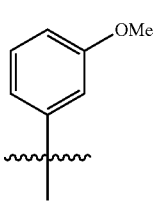 [SMILES: *c1cccc(OC)c1] | — | 128 |

TABLE 8-continued

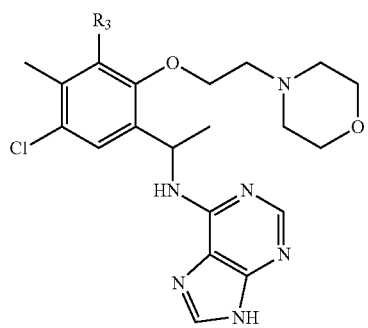

| Ex. No. | Name | R₃ | Salt | Proc.[1] |
|---|---|---|---|---|
| 151 | N-{1-[5-chloro-3-(5-chloropyridin-3-yl)-4-methyl-2-(2-morpholin-4-ylethoxy)phenyl]ethyl}-9H-purin-6-amine | 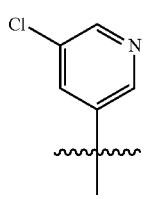 | — | 128 |
| 152 | N-{1-[5-chloro-4-methyl-3-(1-methyl-1H-pyrazol-5-yl)-2-(2-morpholin-4-ylethoxy)phenyl]ethyl}-9H-purin-6-amine | 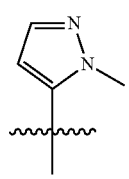 | — | 128 |
| 153 | N-{1-[5-chloro-3',4'-dimethoxy-6-methyl-2-(2-morpholin-4-ylethoxy)biphenyl-3-yl]ethyl}-9H-purin-6-amine | 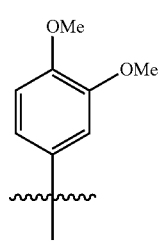 [SMILES: *c1ccc(OC)c(OC)c1] | — | 128 |
| 154 | 3,3'-dichloro-N,2'-dimethyl-6'-(2-morpholin-4-ylethoxy)-5'-[1-(9H-purin-6-ylamino)ethyl]biphenyl-4-carboxamide | 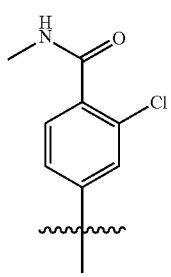 [SMILES: *c1ccc(C(=O)NC)c(Cl)c1] | — | 128 |
| 155 | N-{1-[5-chloro-4-methyl-3-[5-(morpholin-4-ylcarbonyl)pyridin-3-yl]-2-(2-morpholin-4-ylethoxy)phenyl]ethyl}-9H-purin-6-amine | 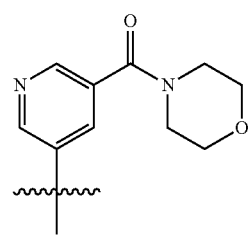 [SMILES: *c1cncc(C(=O)N2CCOCC2)c1] | — | 128 |

TABLE 8-continued

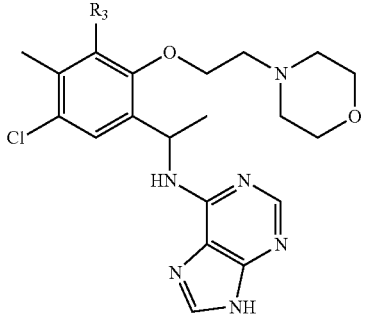

| Ex. No. Name | R₃ | Salt | Proc.¹ |
|---|---|---|---|
| 156 N-{1-[5-chloro-4-methyl-3-[5-(methylsulfonyl)pyridin-3-yl]-2-(2-morpholin-4-ylethoxy)phenyl]ethyl}-9H-purin-6-amine | pyridin-3-yl with SO₂Me | — | 128 |
| 157 N-{1-[5-chloro-3-(5-methoxypyridin-3-yl)-4-methyl-2-(2-morpholin-4-ylethoxy)phenyl]ethyl}-9H-purin-6-amine | pyridin-3-yl with OMe | — | 128 |
| 158 N-(5-{3-chloro-2-methyl-6-(2-morpholin-4-ylethoxy)-5-[1-(9H-purin-6-ylamino)ethyl]phenyl}pyridin-2-yl)acetamide | pyridin-5-yl with NHAc | — | 128 |
| 159 3'-chloro-5-fluoro-2'-methyl-6'-(2-morpholin-4-ylethoxy)-5'-[1-(9H-purin-6-ylamino)ethyl]biphenyl-3-carboxamide | 3-F, 5-C(O)NH₂ phenyl | — | 128 |
| 160 N-{1-[5-chloro-3-(5-fluoro-6-methoxypyridin-3-yl)-4-methyl-2-(2-morpholin-4-ylethoxy)phenyl]ethyl}-9H-purin-6-amine | 2-OMe, 3-F pyridin-5-yl | — | 128 |

TABLE 8-continued

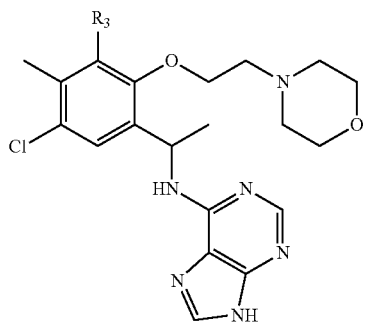

| Ex. No. | Name | R₃ | Salt | Proc.[1] |
|---|---|---|---|---|
| 161 | N-{1-[5-chloro-3-(2-methoxypyrimidin-5-yl)-4-methyl-2-(2-morpholin-4-ylethoxy)phenyl]ethyl}-9H-purin-6-amine | 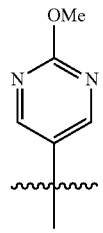 [SMILES: *c1cnc(OC)nc1] | — | 128 |
| 162 | N-{1-[5-chloro-3-(5-fluoropyridin-3-yl)-4-methyl-2-(2-morpholin-4-ylethoxy)phenyl]ethyl}-9H-purin-6-amine | 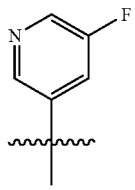 | — | 128 |

[1]Synthesized according to the experimental procedure of compound listed.

$^1$H NMR data (Varian Inova 500 spectrometer, a Mercury 400 spectrometer, or a Varian (or Mercury) 300 spectrometer) and LCMS mass spectral data (MS) for the compounds above is provided below in Table 9.

TABLE 9

| Ex. No. | MS [M + H]⁺ | Solvent | MHz | $^1$H NMR Spectra |
|---|---|---|---|---|
| 129 | 494.1 | DMSO-d₆ | 300 | δ 8.34 (s, 2H), 8.26-8.18 (m, 1H), 8.09 (s, 1H), 8.05 (s, 1H), 7.87 (d, J = 1.8Hz, 1H), 7.42 (d, J = 2.1Hz, 1H), 7.33 (d, J = 8.5Hz, 1H), 7.17 (dd, J = 9.4, 9.4Hz, 1H), 6.82 (d, J = 8.8Hz, 1H), 5.22-5.07 (m, 1H), 3.84 (s, 3H), 1.35 (d, J = 7.0 Hz, 3H) |
| 130 | 519.0 | DMSO-d₆ | 300 | δ 9.89 (s, 1H), 8.22-8.15 (m, 1H), 8.09 (s, 1H), 8.05 (s, 1H), 7.77 (d, J = 2.1Hz, 1H), 7.39 (d, J = 8.5Hz, 2H), 7.27 (d, J = 7.3Hz, 1H), 7.22 (d, J = 2.3Hz, 1H), 7.12-7.05 (m, 1H), 6.99 (d, J = 8.8Hz, 2H), 6.79 (d, J = 9.7Hz, 1H), 5.27-5.08 (m, 1H), 1.99 (s, 3H), 1.34 (d, J = 7.0 Hz, 3H) |
| 131 | 463.0 | DMSO-d₆ | 300 | δ 8.41 (dd, J = 4.7, 1.5Hz, 2H), 8.29-8.20 (m, 1H), 8.10 (s, 1H), 8.06 (s, 1H), 7.87 (d, J = 2.1Hz, 1H), 7.34-7.26 (m, 2H), 7.17-7.10 (m, 3H), 6.88 (d, J = 8.8Hz, 1H), 5.25-5.09 (m, 1H), 1.36 (d, J = 6.7Hz, 3H) |
| 132 | 464.0 | DMSO-d₆ | 300 | δ 8.99 (s, 1H), 8.56 (s, 2H), 8.26-8.18 (m, 1H), 8.09 (s, 1H), 8.05 (s, 1H), 7.91 (d, J = 1.8Hz, 1H), 7.48 (d, J = 2.1Hz, 1H), 7.35 (d, J = 9.1Hz, 1H), 7.15 (dd, J = 9.7, 9.4Hz, 1H), 6.95 (d, J = 8.8Hz, 1H), 5.26-5.06 (m, 1H), 1.36 (d, J = 6.7Hz, 3H) |
| 133 | 499.0 | DMSO-d₆ | 300 | δ 8.30-8.23 (m, 1H), 8.10 (s, 1H), 8.06 (s, 1H), 7.93 (d, J = 1.8Hz, 1H), 7.82 (s, 1H), 7.44 (d, J = 2.3Hz, 1H), 7.36 (d, J = 8.8Hz, 1H), 7.22-7.15 (m, 1H), 6.99 (s, 2H), 6.96 (d, J = 9.1Hz, 1H), 5.23-5.09 (m, 1H), 1.36 (d, J = 7.0 Hz, 3H) |
| 135 | 412.0 | DMSO-d₆ | 300 | δ 8.80 (s, 2H), 8.24-8.16 (m, 1H), 8.13 (s, 1H), 8.10 (s, 1H), 7.63 (br s, 1H), 7.39 (d, J = 2.6Hz, 1H), 5.88-5.72 (m, 1H), 3.96 (s, 3H), 3.55 (s, 3H), 1.51 (d, J = 7.0 Hz, 3H) |

TABLE 9-continued

| Ex. No. | MS [M + H]+ | Solvent | MHz | 1H NMR Spectra |
|---|---|---|---|---|
| 136 | 437.0 | DMSO-d6 | 300 | δ 10.1 (s, 1H), 8.17-8.09 (m, 3H), 7.65 (d, J = 8.5Hz, 2H), 7.51-7.48 (m, 3H), 7.18 (d, J = 2.6Hz, 1H), 5.89-5.73 (m, 1H), 3.45 (s, 3H), 2.05 (s, 3H), 1.50 (d, J = 6.8Hz, 3H) |
| 137 | 384.0 | DMSO-d6 | 300 | δ 8.20-8.09 (m, 3H), 7.65 (br s, 1H), 7.50 (d, J = 1.8Hz, 1H), 7.22 (d, J = 2.9Hz, 1H), 6.40 (d, J = 1.8Hz, 1H), 5.91-5.72 (m, 1H), 3.67 (s, 3H), 3.46 (s, 3H), 1.49 (d, J = 7.0 Hz, 3H) |
| 138 | 381.0 | DMSO-d6 | 300 | δ 8.64 (dd, J = 4.4, 1.5Hz, 2H), 8.25-8.17 (m, 1H), 8.13 (s, 1H), 8.10 (s, 1H), 7.65 (br s, 1H), 7.59 (dd, J = 4.4, 1.5Hz, 2H), 7.33 (d, J = 2.6Hz, 1H), 5.90-5.72 (m, 1H), 3.50 (s, 3H), 1.51 (d, J = 7.0 Hz, 3H) |
| 139 | 382.0 | DMSO-d6 | 300 | δ 13.0-12.8 (br s, 1H), 9.21 (s, 1H), 9.01 (s, 2H), 8.28-8.19 (m, 1H), 8.14 (s, 1H), 8.10 (s, 1H), 7.68 (br s, 1H), 7.46 (d, J = 2.6Hz, 1H), 5.88-5.74 (m, 1H), 3.53 (s, 3H), 1.52 (d, J = 7.0 Hz, 3H) |
| 140 | 417.0 | DMSO-d6 | 300 | δ 8.22-8.16 (m, 1H), 8.11 (s, 1H), 8.08 (s, 1H), 7.71 (d, J = 2.1Hz, 1H), 7.45 (d, J = 2.6Hz, 1H), 7.43 (s, 2H), 5.88-5.75 (m, 1H), 3.59 (s, 3H), 1.51 (d, J = 7.0 Hz, 3H) |
| 134 | 540.0 | DMSO-d6 | 300 | δ 12.9 (br s, 1H), 8.30 (br s, 1H), 8.13 (s, 1H), 8.07 (s, 1H), 7.87 (s, 1H), 7.75 (d, J = 8.2Hz, 2H), 7.38 (d, J = 8.5Hz, 2H), 7.33 (d, J = 2.1Hz, 1H), 7.28 (d, J = 9.1Hz, 1H), 7.12 (dd, J = 9.4Hz, 1H), 6.88 (d, J = 8.5Hz, 1H), 5.23-5.09 (m, 1H), 3.18 (s, 3H), 1.36 (d, J = 6.7Hz, 3H) |
| 135 | 479.0 | DMSO-d6 | 300 | δ 12.9 (br s, 1H), 8.29 (br s, 1H), 8.12 (s, 1H), 8.06 (s, 1H), 7.92 (s, 1H), 7.79 (s, 1H), 7.34-7.27 (m, 2H), 7.16 (dd, J = 9.4, 9.1Hz, 1H), 6.93 (d, J = 8.8Hz, 1H), 6.64 (s, 2H), 5.19-5.07 (m, 1H), 1.34 (d, J = 7.0 Hz, 3H) |
| 142 | 458.0 | DMSO-d6 | 300 | δ 8.28-8.23 (m, 1H), 8.15 (s, 1H), 8.12 (s, 1H), 8.00 (d, J = 8.5Hz, 2H), 7.85 (s, J = 8.5Hz, 2H), 7.64 (s, 1H), 7.32 (d, J = 2.6Hz, 1H), 5.88-5.75 (m, 1H), 3.47 (s, 3H), 3.27 (s, 3H), 1.52 (d, J = 7.0 Hz, 3H) |
| 143 | 397.0 | DMSO-d6 | 300 | δ 12.9 (br s, 1H), 8.44 (s, 2H), 8.25-8.09 (m, 3H), 7.52 (br s, 1H), 7.28 (d, J = 2.6Hz, 1H), 6.85 (s, 2H), 5.85-5.71 (m, 1H), 3.57 (s, 3H), 1.50 (d, J = 6.7Hz, 3H) |
| 144 | 471.0 | DMSO-d6 | 300 | δ 12.9 (s, 1H), 8.46-8.42 (m, 1H), 8.28-8.22 (m, 1H), 8.14-8.09 (m, 2H), 7.69 (s, 1H), 7.64-7.57 (m, 2H), 7.49 (d, J = 7.9Hz, 1H), 7.28 (d, J = 2.3Hz, 1H), 5.87-5.73 (m, 1H), 3.51 (s, 3H), 2.76 (d, J = 4.7Hz, 3H), 1.51 (d, J = 7.0 Hz, 3H) |
| 145 | 399.1 | DMSO-d6 | 300 | δ 13.0 (s, 1H), 8.39-8.20 (m, 2H), 8.20-8.06 (m, 2H), 7.70 (s, 1H), 7.59 (d, J = 5.1Hz, 1H), 7.41 (s, 2H), 5.82 (s, 1H), 3.55 (s, 3H), 1.52 (d, J = 6.9Hz, 3H) |
| 146 | 411.1 | DMSO-d6 | 300 | δ 8.35 (d, J = 1.8Hz, 1H), 8.31 (d, J = 2.6Hz, 1H), 8.25-8.20 (m, 1H), 8.14 (s, 1H), 8.11 (s, 1H), 7.62 (s, 1H), 7.55 (d, J = 2.9, 2.1Hz, 1H), 7.35 (d, J = 2.9Hz, 1H), 5.88-5.74 (m, 1H), 3.87 (s, 3H), 3.50 (s, 3H), 1.52 (d, J = 7.0 Hz, 3H) |
| 147 | 399.1 | DMSO-d6 | 300 | δ 8.42 (d, J = 2.3Hz, 1H), 8.27-8.11 (m, 4H), 7.63 (s, 1H), 7.35 (d, J = 2.6Hz, 1H), 7.29 (dd, J = 8.5, 2.6Hz, 1H), 5.88-5.74 (m, 1H), 3.50 (s, 3H), 1.52 (d, J = 6.7Hz, 3H) |
| 148 | 411.0 | DMSO-d6 | 300 | δ 8.34 (d, J = 2.3Hz, 1H), 8.25-8.06 (m, 3H), 7.93 (dd, J = 8.6, 2.4Hz, 1H), 7.57 (s, 1H), 7.28 (d, J = 2.6Hz, 1H), 6.91 (d, J = 8.6Hz, 1H), 5.82 (s, 1H), 3.90 (s, 3H), 3.50 (s, 3H), 1.51 (d, J = 6.9Hz, 3H) |
| 149 | 510.2 | DMSO-d6 | 400 | δ 12.7 (s, 1H), 8.22-8.10 (m, 3H), 8.07 (s, 1H), 7.60 (s, 1H), 6.78 (s, 2H), 5.86-5.70 (m, 1H), 4.11-3.94 (m, 1H), 3.55-3.37 (m, 5H), 2.46-2.35 (m, 2H), 2.32-2.21 (m, 2H), 2.21-2.11 (m, 2H), 2.08 (s, 3H), 1.48 (d, J = 6.9Hz, 3H) |
| 150 | 523.3 | DMSO-d6 | 400 | δ 12.9 (s, 1H), 8.21-8.00 (m, 2H), 7.61 (d, J = 3.3Hz, 1H), 7.41-7.30 (m, 1H), 6.95 (dd, J = 8.0, 2.3Hz, 1H), 6.89-6.74 (m, 2H), 5.90-5.73 (m, 1H), 4.05-3.92 (m, 1H), 3.76 (d, J = 4.9Hz, 4H), 3.53-3.39 (m, 5H), 2.41-2.22 (m, 2H), 2.20-2.12 (m, 2H), 2.11-2.01 (m, 2H), 1.98 (s, 3H), 1.49-1.48 (m, 3H) |
| 151 | 528.2 | DMSO-d6 | 400 | δ 8.68 (s, 1H), 8.54 (s, 0.5H), 8.42 (s, 0.5H), 8.18-7.99 (m, 3.5H), 7.92 (s, 0.5H), 7.70 (s, 1H), 5.80 (s, 1H), 4.16-4.07 (m, 1H), 3.43 (s, 5H), 2.35-2.25 (m, 2H), 2.24-2.14 (m, 2H), 2.15-2.05 (m, 2H), 2.01 (s, 3H), 1.49 (d, J = 6.8Hz, 3H) |
| 152 | 497.3 | DMSO-d6 | 400 | δ 8.25-7.89 (m, 3H), 7.74 (s, 0.33H), 7.66 (s, 0.66H), 7.57-7.48 (m, 1H), 6.38 (d, J = 1.7Hz, 0.66H), 6.31 (d, J = 1.7Hz, 0.33H), 5.98-5.67 (m, 1H), 4.28-4.00 (m, 1H), 3.87-3.70 (m, 1H), 3.65-3.33 (m, 7H), 2.47-2.12 (m, 6H), 2.02 (s, 2H), 1.97 (s, 1H), 1.59-1.39 (m, 3H) |

TABLE 9-continued

| Ex. No. | MS [M + H]+ | Solvent | MHz | 1H NMR Spectra |
|---|---|---|---|---|
| 153 | 553.3 | DMSO-d6 | 400 | δ 12.9 (s, 1H), 8.11-8.07 (m, 3H), 7.59 (d, J = 7.3Hz, 1H), 7.01 (d, J = 8.1Hz, 1H), 6.89 (s, 0.66H), 6.84-6.71 (m, 1.33H), 6.05-5.60 (m, 1H), 3.99-3.95 (m, 1H), 3.79 (s, 3H), 3.73 (d, J = 6.7Hz, 3H), 3.53-3.36 (m, 5H), 2.41-2.23 (m, 2H), 2.23-2.02 (m, 4H), 2.00 (s, 3H), 1.49 (d, J = 4.9Hz, 3H) |
| 154 | 584.2 | DMSO-d6 | 400 | δ 12.87 (s, 1H), 8.39 (dd, J = 4.5, 4.5Hz, 1H), 8.12 (s, 2H), 8.07 (d, J = 5.0 Hz, 1H), 7.65 (s, 1H), 7.55-7.47 (m, 1.5H), 7.41-7.32 (m, 1H), 7.26 (d, J = 7.7Hz, 0.5H), 5.79 (s, 1H), 4.02 (s, 1H), 3.44 (s, 5H), 2.77 (d, J = 4.6Hz, 3H), 2.38-2.25 (m, 2H), 2.27-2.15 (m, 2H), 2.15-2.05 (m, 2H), 1.99 (s, 3H), 1.50 (d, J = 6.5Hz, 3H) |
| 155 | 607.3 | DMSO-d6 | 400 | δ 12.9 (s, 1H), 8.66-8.61 (m, 1.5H), 8.51 (s, 0.5H), 8.27-8.20 (m, 1H), 8.12 (s, 1H), 8.06 (s, 1H), 7.90 (s, 0.5H), 7.76 (s, 0.5H), 7.70 (s, 1H), 5.79 (br s, 1H), 4.10-4.01 (m, 1H), 3.68-3.55 (m, 6H), 3.42-3.33 (m, 7H), 2.32-2.24 (m, 2H), 2.23-2.15 (m, 2H), 2.11-2.05 (m, 2H), 2.02 (s, 1.5H), 1.99 (s, 1.5H), 1.49 (d, J = 6.1Hz, 3H) |
| 156 | 572.3 | DMSO-d6 | 400 | δ 9.01 (s, 1H), 8.93 (s, 0.5H), 8.81 (s, 0.5H), 8.38 (s, 0.5H), 8.26-8.18 (m, 1.5H), 8.14 (s, 1H), 8.07 (s, 1H), 7.72 (s, 1H), 5.78 (br s, 1H), 4.14-4.03 (m, 1H), 3.40-3.36 (m, 5H), 3.32 (s, 3H), 2.30-2.24 (m, 2H), 2.20-2.14 (m, 2H), 2.12-2.05 (m, 2H), 2.02 (s, 3H), 1.50 (d, J = 6.8Hz, 3H) |
| 157 | 524.3 | DMSO-d6 | 400 | δ 12.9 (br s, 1H), 8.31 (s, 1H), 8.15-8.06 (m, 2.5H), 8.02 (m, 0.5H), 7.69-7.63 (m, 1H), 7.44 (s, 0.5H), 7.29 (s, 0.5H), 5.78 (br s, 1H), 4.07-3.99 (m, 1H), 3.84 (s, 1.5H), 3.83 (s, 1.5H), 3.42-3.38 (m, 5H), 2.32-2.25 (m, 2H), 2.21-2.13 (m, 2H), 2.12-2.04 (m, 2H), 1.99 (s, 3H), 1.49 (d, J = 6.8Hz, 3H) |
| 158 | 551.3 | DMSO-d6 | 400 | δ 12.9 (br s, 1H), 10.6-10.6 (m, 1H), 8.22-8.10 (m, 3H), 8.07 (s, 1H), 5.77 (br s, 1H), 4.05-3.96 (m, 1H), 3.41-3.36 (m, 5H), 2.38-2.27 (m, 2H), 2.20-2.13 (m, 2H), 2.11 (s, 3H), 2.09-2.04 (m, 2H), 2.01 (s, 3H), 1.49 (d, J = 6.6Hz, 3H) |
| 159 | 554.3 | DMSO-d6 | 400 | δ 12.9 (br s, 1H), 8.19-8.05 (m, 4H), 7.72-7.64 (m, 2.5H), 7.61 (s, 0.5H), 7.58 (s, 1H), 7.47 (d, J = 8.4Hz, 0.5H), 7.32 (d, J = 9.4Hz, 0.5H), 5.77 (br s, 1H), 4.08-4.01 (m, 1H), 3.40-3.35 (m, 5H), 2.33-2.27 (m, 2H), 2.19-2.12 (m, 2H), 2.08-2.02 (m, 2H), 1.98 (s, 3H), 1.49 (d, J = 5.1Hz, 3H) |
| 160 | 542.3 | DMSO-d6 | 400 | δ 12.9 (br s, 1H), 8.17-8.10 (m, 2H), 8.07 (s, 1H), 7.97-7.94 (m, 0.5H), 7.87-7.80 (m, 1H), 7.67-7.64 (m, 1.5H), 5.78 (br s, 1H), 4.08-4.01 (m, 1H), 3.98 (s, 3H), 3.42-3.39 (m, 5H), 2.41-2.30 (m, 2H), 2.24-2.17 (m, 2H), 2.14-2.07 (m, 2H), 2.02 (s, 3H), 1.48 (d, J = 6.8Hz, 3H) |
| 161 | 525.3 | DMSO-d6 | 400 | δ 12.9 (br s, 1H), 8.64-8.54 (m, 2H), 8.20-8.10 (m, 2H), 8.07 (s, 1H), 7.67 (s, 1H), 5.77 (br s, 1H), 4.09-4.04 (m, 1H), 3.96 (s, 3H), 3.43-3.34 (m, 5H), 2.41-2.29 (m, 2H), 2.25-2.19 (m, 2H), 2.13-2.09 (m, 2H), 2.04 (s, 3H), 1.49 (d, J = 7.0 Hz, 3H) |
| 162 | 512.3 | DMSO-d6 | 400 | δ 12.9 (br s, 1H), 8.63 (s, 1H), 8.44 (s, 0.5H), 8.33 (s, 0.5H), 8.19-8.11 (m, 2H), 8.07 (s, 1H), 7.91 (d, J = 8.8Hz, 0.5H), 7.74 (d, J = 10.0 Hz, 0.5H), 7.69 (s, 1H), 5.77 (br s, 1H), 4.10-4.01 (m, 1H), 3.42-3.38 (m, 5H), 2.32-2.27 (m, 2H), 2.23-2.16 (m, 2H), 2.13-2.05 (m, 2H), 2.00 (s, 3H), 1.49 (d, J = 6.8Hz, 3H) |

Example 163

N-[1-(5-Chloro-2-methoxy-4-methyl-3-pyridazin-4-ylphenyl)ethyl]-9H-purin-6-amine bis(trifluoroacetate)

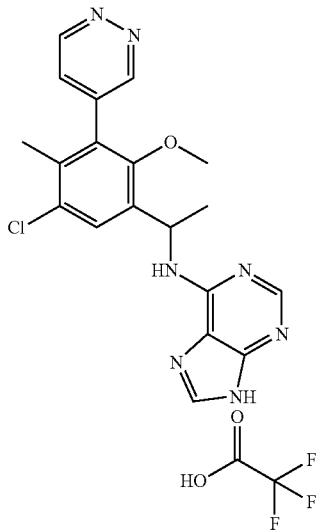
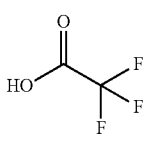

A mixture of N-[1-(3-bromo-5-chloro-2-methoxy-4-methylphenyl)ethyl]-9-(tetrahydro-2H-pyran-2-yl)-9H-purin-6-amine (0.030 g, 0.062 mmol, from Example 113, step 2 chiral intermediate), 4-(4,4,5,5-tetramethyl-1,3,2-dioxaborolan-2-yl)pyridazine (0.015 g, 0.075 mmol, from Milestone Pharmtech), 1 M sodium carbonate solution (0.15 mL, 0.16 mmol) and tetrakis(triphenylphosphine)palladium(0) (4.3 mg, 0.0037 mmol) in 1,4-dioxane (0.5 mL) was bubbled with $N_2$ for 5 minutes, then heated at 90° C. overnight. The cooled reaction was treated directly with 6.0 M hydrogen chloride in water (0.1 mL, 0.6 mmol) at room temperature (rt) for ~30 minutes. The mixture was diluted with MeOH, filtered and purified on prep-LCMS (XBridge C18 Column, eluting with a gradient of acetonitrile in water with 0.05% trifluoroacetic acid, at flow rate of 30 mL/min) to afford the desired product as TFA salt. LCMS calculated for $C_{19}H_{19}ClN_7O$ $(M+H)^+$: m/z=396.1. found: 396.1.

Example 164

N-{1-[5-Chloro-2-methoxy-4-methyl-3-(1,3-thiazol-4-yl)phenyl]ethyl}-9H-purin-6-amine trifluoroacetate

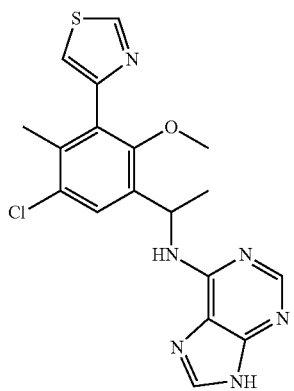
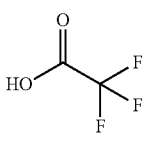

Step 1. 1-[5-Chloro-2-methoxy-4-methyl-3-(4,4,5,5-tetramethyl-1,3,2-dioxaborolan-2-yl)phenyl]ethanone 4,4,5,5-Tetramethyl-1,3,2-dioxaborolane (2.2 mL, 15 mmol) was added to a mixture of 1-(5-chloro-3-iodo-2-methoxy-4-methylphenyl)ethanone (2.0 g, 6.2 mmol, from Example 60, Step 2), bis(acetonitrile)palladium(II) chloride (32 mg, 0.12 mmol), 2-(dicyclohexylphosphino)-2',6'-dimethoxy-1,1'-biphenyl (0.20 g, 0.49 mmol) and triethylamine (2.6 mL, 18 mmol) in 1,4-dioxane (3.7 mL) under $N_2$ and then the mixture was degassed with $N_2$. The reaction was then heated at 100° C. for 3 hours. The mixture was cooled to room temperature, filtered and purified on silica gel column (eluting with 0 to 20% EtOAc in hexanes) to give the desired product (1.3 g, 65%). LCMS calculated for $C_{16}H_{23}BClO_4$ $(M+H)^+$: m/z=325.1. found: 325.1.

Step 2. 1-[5-Chloro-2-methoxy-4-methyl-3-(1,3-thiazol-4-yl)phenyl]ethanone

Into a microwave vial was added 1-[5-chloro-2-methoxy-4-methyl-3-(4,4,5,5-tetramethyl-1,3,2-dioxaborolan-2-yl)phenyl]ethanone (0.040 g, 0.12 mmol), 4-bromo-1,3-thiazole (0.024 g, 0.15 mmol), 1 M sodium carbonate solution (0.30 mL, 0.31 mmol), 1,4-dioxane (1 mL) and tetrakis(triphenylphosphine)palladium(0) (8.5 mg, 0.0074 mmol). The mixture was bubbled with $N_2$ for 5 minutes, and then heated at 95° C. overnight. The cooled reaction was purified on silica gel column (eluting with 0 to 30% EtOAc in hexanes) to give the desired product. LCMS calculated for $C_{13}H_{13}ClNO_2S$ $(M+H)^+$: m/z=282.0. found: 282.0.

Step 3. 1-[5-Chloro-2-methoxy-4-methyl-3-(1,3-thiazol-4-yl)phenyl]ethanamine

A mixture of 1-[5-chloro-2-methoxy-4-methyl-3-(1,3-thiazol-4-yl)phenyl]ethanone (6.0 mg, 0.021 mmol), ammonium acetate (20 mg, 0.2 mmol) and 1.0 M sodium cyanoborohydride in THF (0.053 mL, 0.053 mmol) in methanol (0.05 mL)/acetonitrile (0.05 mL) was heated at 65° C. overnight. The mixture was cooled to room temperature, quenched with sat. $NaHCO_3$ solution, extracted with dichloromethane. The combined organic layers were dried over $MgSO_4$ and concentrated to give the crude product, which was used in the next step directly. LCMS calculated for $C_{13}H_{13}ClNO_2S$ $(M-NH_2)^+$: m/z=266.1. found: 266.0.

Step 4. N-{1-[5-Chloro-2-methoxy-4-methyl-3-(1,3-thiazol-4-yl)phenyl]ethyl}-9H-purin-6-amine trifluoroacetate A mixture of 1-[5-chloro-2-methoxy-4-methyl-3-(1,3-thiazol-4-yl)phenyl]ethanamine (5.5 mg, 0.019 mmol), 6-bromo-9H-purine (5.8 mg, 0.029 mmol) and N,N-diisopropylethylamine (DIPEA) (0.010 mL, 0.058 mmol) in ethanol (0.1 mL) was heated at 100° C. overnight. The mixture was diluted with MeOH and purified on prep-LCMS (XBridge C18 Column, eluting with a gradient of acetonitrile in water with 0.05% trifluoroacetic acid, at flow rate of 30 mL/min) to afford the desired product as TFA salt. LCMS calculated for $C_{18}H_{18}ClN_6OS$ $(M+H)^+$: m/z=401.1. found: 401.0.

Example 165

N-[1-(3-azetidin-3-yl-5-chloro-2-methoxy-4-methyl-phenyl)ethyl]-9H-purin-6-amine bis(trifluoroacetate)

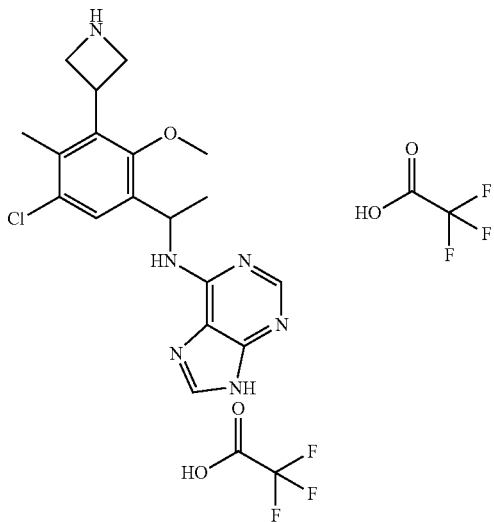

Step 1. tert-Butyl 3-(3-acetyl-5-chloro-2-methoxy-6-methylphenyl)azetidine-1-carboxylate Zinc (0.227 g, 3.48 mmol) was suspended with 1,2-dibromoethane (0.0434 g, 0.231 mmol) in N,N-dimethylformamide (DMF) (4.1 mL). The mixture was heated at 70° C. for 10 min and then cooled to room temperature. Chlorotrimethylsilane (0.029 mL, 0.23 mmol) was added dropwise and stirring was continued for 1 hour. A solution of tert-butyl 3-iodoazetidine-1-carboxylate (0.82 g, 2.9 mmol, from Oakwood) in DMF (3 mL) was then added and the mixture was heated at 40° C. for 1 h before a mixture of 1-(5-chloro-3-iodo-2-methoxy-4-methylphenyl)ethanone (0.987 g, 3.04 mmol, from Example 60, Step 2), tris(dibenzylideneacetone)dipalladium(0) (0.052 g, 0.057 mmol) and tri-(2-furyl)phosphine (0.027 g, 0.12 mmol) in DMF (8 mL) was added. The reaction mixture was warmed to 70° C. and stirred overnight. The mixture was then cooled to room temperature and partitioned between EtOAc and sat. NH$_4$Cl solution. The organic layer was washed with water, dried over MgSO$_4$, concentrated and purified on silica gel (eluting with 0 to 30% EtOAc in hexanes) to give the desired product (0.57 g, 56%). LCMS calculated for $C_{18}H_{24}ClNO_4Na$ (M+Na)$^+$: m/z=376.1. found: 376.1.

Step 2. tert-Butyl 3-[3-(1-aminoethyl)-5-chloro-2-methoxy-6-methylphenyl]azetidine-1-carboxylate A mixture of tert-butyl 3-(3-acetyl-5-chloro-2-methoxy-6-methylphenyl)azetidine-1-carboxylate (0.56 g, 1.6 mmol), ammonium acetate (1.0 g, 20 mmol) and 1.0 M sodium cyanoborohydride in THF (4.0 mL, 4.0 mmol) in methanol (4 mL)/acetonitrile (4 mL) was heated at 65° C. overnight. The mixture was cooled to room temperature, quenched with sat. NaHCO$_3$ solution, extracted with dichloromethane. The organic extracts were dried over MgSO$_4$ and concentrated to give the crude product, which was used in the next step without further purifications. LCMS calculated for $C_{18}H_{27}ClN_2O_3Na$ (M+Na)$^+$: m/z=377.2. found: 377.1.

Step 3. N-[1-(3-Azetidin-3-yl-5-chloro-2-methoxy-4-methylphenyl)ethyl]-9H-purin-6-amine bis(trifluoroacetate)

A mixture of tert-butyl 3-[3-(1-aminoethyl)-5-chloro-2-methoxy-6-methylphenyl]azetidine-1-carboxylate (0.36 g, 1.0 mmol), 6-bromo-9-(tetrahydro-2H-pyran-2-yl)-9H-purine (0.43 g, 1.5 mmol, from Example 108, Step 1) and DIPEA (0.53 mL, 3.0 mmol) in ethanol (6 mL) was heated at 100° C. overnight. The mixture was concentrated and purified on silica gel column (eluting with 0 to 100% EtOAc in hexanes) to give tert-butyl 3-[3-chloro-6-methoxy-2-methyl-5-(1-{[9-(tetrahydro-2H-pyran-2-yl)-9H-purin-6-yl]amino}ethyl)phenyl]azetidine-1-carboxylate. LCMS calculated for $C_{28}H38ClN_6O_4$ (M+H)$^+$: m/z=557.3. found: 557.3. The Boc intermediate isolated was treated with trifluoroacetic acid (0.8 mL, 10 mmol) in methylene chloride (5 mL) at room temperature for 1 hour. The mixture was stripped to dryness to give the desired product as TFA salt. 4 mg of the salt was purified on prep-LCMS (XBridge C18 Column, eluting with a gradient of acetonitrile in water with 0.05% trifluoroacetic acid, at flow rate of 30 mL/min) to afford the desired product as TFA salt. LCMS calculated for $C_{18}H_{22}ClN_6O$ (M+H)$^+$: m/z=373.2. found: 373.1.

Example 166

N-{1-[3-(1-Acetylazetidin-3-yl)-5-chloro-2-methoxy-4-methylphenyl]ethyl}-9H-purin-6-amine trifluoroacetate

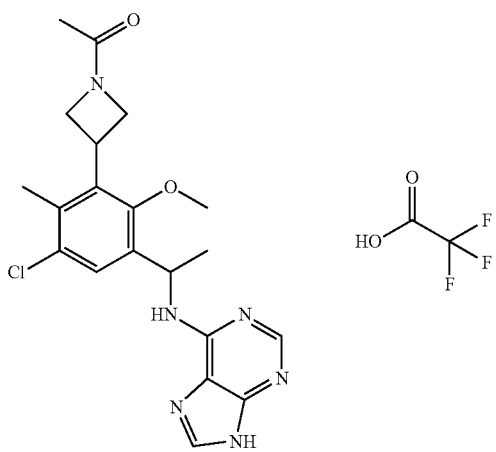 [SMILES: COc1c(C(C)Nc2ncnc3[nH]cnc23)cc(Cl)c(C)c1C1CN(C(C)=O)C1 ; O=C(O)C(F)(F)F]

Acetic anhydride (2.0 µL, 0.021 mmol) was added to a solution of N-[1-(3-azetidin-3-yl-5-chloro-2-methoxy-4-methylphenyl)ethyl]-9H-purin-6-amine bis(trifluoroacetate) (8.5 mg, 0.014 mmol, from Example 165) and DIPEA (0.015 mL, 0.085 mmol) in methylene chloride (0.5 mL) at 0° C. and then the reaction was stirred at room temperature for 30 minutes. The crude mixture was purified on prep-LCMS (XBridge C18 Column, eluting with a gradient of acetonitrile in water with 0.05% trifluoroacetic acid, at flow rate of 30 mL/min) to afford the desired product as TFA salt. LCMS calculated for $C_{20}H_{24}ClN_6O_2$ (M+H)$^+$: m/z=415.2. found: 415.1.

Example 167

Methyl 3-{3-chloro-6-methoxy-2-methyl-5-[1-(9H-purin-6-ylamino)ethyl]phenyl}azetidine-1-carboxylate trifluoroacetate

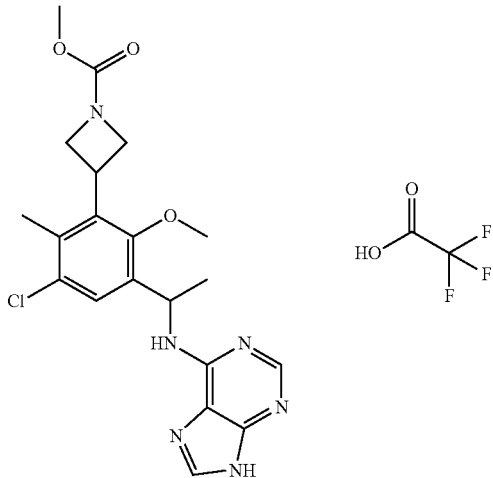 [SMILES: COC(=O)N1CC(c2c(C)c(Cl)cc(C(C)Nc3ncnc4[nH]cnc34)c2OC)C1 ; O=C(O)C(F)(F)F]

Methyl chloroformate (1.6 µL, 0.021 mmol) was added to a solution of N-[1-(3-azetidin-3-yl-5-chloro-2-methoxy-4-methylphenyl)ethyl]-9H-purin-6-amine bis(trifluoro acetate) (8.5 mg, 0.014 mmol, from Example 165) and DIPEA (0.015 mL, 0.085 mmol) in methylene chloride (0.5 mL) at 0° C. and then the reaction was stirred at room temperature for 30 minutes. The crude mixture was purified on prep-LCMS (XBridge C18 Column, eluting with a gradient of acetonitrile in water with 0.05% trifluoroacetic acid, at flow rate of 30 mL/min) to afford the desired product as TFA salt. LCMS calculated for $C_{20}H_{24}ClN_6O_3$ (M+H)$^+$: m/z=431.2. found: 431.1. $^1$H NMR (300 MHz, DMSO-d$_6$) δ 8.30 (1H, br s), 8.18 (2H, m), 7.46 (1H, s), 5.68 (1H, m), 4.31 (3H, m), 4.14 (1H, m), 4.02 (1H, m), 3.75 (3H, s), 3.55 (3H, s), 2.16 (3H, s), 1.44 (3H, d, J=6.9 Hz) ppm.

Example 168

3-{3-Chloro-6-methoxy-2-methyl-5-[1-(9H-purin-6-ylamino)ethyl]phenyl}-N-methylazetidine-1-carboxamide trifluoroacetate

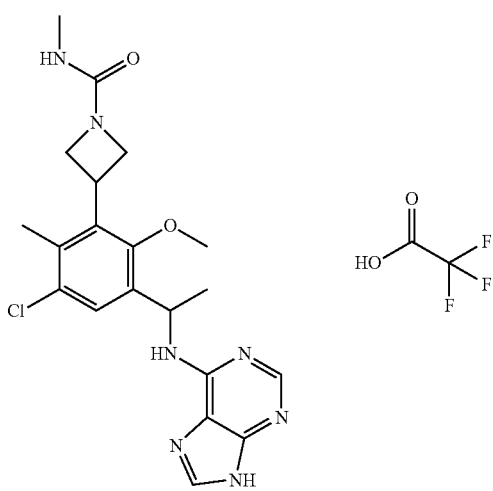 [SMILES: CNC(=O)N1CC(c2c(C)c(Cl)cc(C(C)Nc3ncnc4[nH]cnc34)c2OC)C1 ; O=C(O)C(F)(F)F]

Methyl isocyanate (1.3 µL, 0.021 mmol) was added to a solution of N-[1-(3-azetidin-3-yl-5-chloro-2-methoxy-4-methylphenyl)ethyl]-9H-purin-6-amine bis(trifluoroacetate) (8.5 mg, 0.014 mmol, from Example 165) and DIPEA (0.015 mL, 0.085 mmol) in methylene chloride (0.5 mL) at 0° C. and then the reaction was stirred at room temperature for 30 minutes. The crude mixture was purified on prep-LCMS (XBridge C18 Column, eluting with a gradient of acetonitrile in water with 0.05% trifluoroacetic acid, at flow rate of 30 mL/min) to afford the desired product as TFA salt. LCMS calculated for $C_{20}H_{25}ClN_7O_2$ (M+H)$^+$: m/z=430.2. found: 430.2. $^1$H NMR (300 MHz, DMSO-d$_6$) δ 8.32 (1H, br s), 8.18 (2H, m), 7.44 (1H, s), 6.31 (1H, m), 5.68 (1H, m), 4.20 (3H, m), 3.96 (1H, m), 3.82 (1H, m), 3.75 (3H, s), 2.52 (3H, s), 2.15 (3H, s), 1.44 (3H, d, J=6.9 Hz) ppm.

Example 169

N-(1-{5-Chloro-2-methoxy-4-methyl-3-[1-(methylsulfonyl)azetidin-3-yl]phenyl}ethyl)-9H-purin-6-amine trifluoroacetate

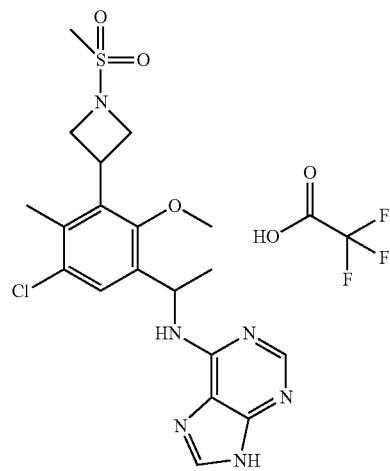 [SMILES: COc1c(C(C)Nc2ncnc3[nH]cnc23)cc(Cl)c(C)c1C1CN(S(C)(=O)=O)C1 ; O=C(O)C(F)(F)F]

Methanesulfonyl chloride (1.6 µL, 0.021 mmol) was added to a solution of N-[1-(3-azetidin-3-yl-5-chloro-2-methoxy-4-methylphenyl)ethyl]-9H-purin-6-amine bis(trifluoro acetate) (8.5 mg, 0.014 mmol, from Example 165) and DIPEA (0.015 mL, 0.085 mmol) in methylene chloride (0.5 mL) at 0° C. and then the reaction was stirred at room temperature for 30 minutes. The crude mixture was purified on prep-LCMS (XBridge C18 Column, eluting with a gradient of acetonitrile in water with 0.05% trifluoroacetic acid, at flow rate of 30 mL/min) to afford the desired product as TFA salt. LCMS calculated for $C_{19}H_{24}ClN_6O_3S$ (M+H)$^+$: m/z=451.1. found: 451.0. $^1$H NMR (300 MHz, DMSO-d$_6$) δ 8.22 (1H, brs), 8.15 (2H, m), 7.48 (1H, s), 5.67 (1H, m), 4.21 (3H, m), 4.05 (1H, m), 3.96 (1H, m), 3.76 (3H, s), 2.96 (3H, s), 2.10 (3H, s), 1.45 (3H, d, J=6.9 Hz) ppm.

Example 170

N-{1-[5-Chloro-3-(1-isopropylazetidin-3-yl)-2-methoxy-4-methylphenyl]ethyl}-9H-purin-6-amine bis(trifluoroacetate)

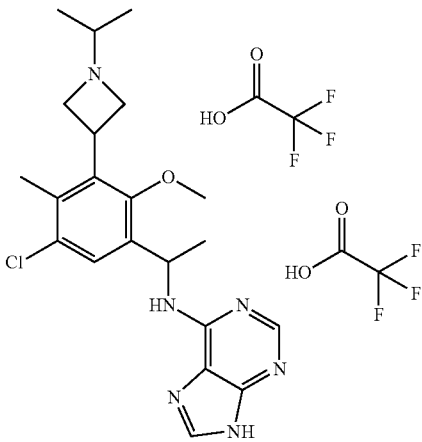 [SMILES: COc1c(C(C)Nc2ncnc3[nH]cnc23)cc(Cl)c(C)c1C1CN(C(C)C)C1 ; O=C(O)C(F)(F)F ; O=C(O)C(F)(F)F]

Step 1. Benzyl 3-(3-acetyl-5-chloro-2-methoxy-6-methylphenyl)azetidine-1-carboxylate Zinc (1.15 g, 17.6 mmol) was suspended with 1,2-dibromoethane (0.101 mL, 1.17 mmol) in DMF (21 mL). The mixture was heated at 70° C. for 10 min and then cooled to room temperature. Chlorotrimethylsilane (0.149 mL, 1.17 mmol) was added dropwise and stirring was continued for 1 hour. A solution of benzyl 3-iodoazetidine-1-carboxylate (4.6 g, 15 mmol, from Pharmablock) in DMF (20 mL) was then added and the mixture was heated at 40° C. for 1 h before a mixture of 1-(5-chloro-3-iodo-2-methoxy-4-methylphenyl)ethanone (5.0 g, 15 mmol, from Example 60, Step 2), tris(dibenzylideneacetone)dipalladium(0) (0.27 g, 0.29 mmol) and tri-(2-furyl)phosphine (0.14 g, 0.59 mmol) in DMF (40 mL) was added. The reaction mixture was warmed to 70° C. and stirred overnight. The mixture was then cooled to room temperature and partitioned between ether and sat. NH$_4$Cl solution. The organic layer was washed with water, dried over MgSO$_4$, concentrated and purified on silica gel (eluting with 0 to 20% EtOAc in hexane) to give the desired product (2.5 g, 44%). LCMS calculated for C$_{21}$H$_{23}$ClNO$_4$ (M+H)$^+$: m/z=338.1. found: 388.1.

Step 2. Benzyl 3-[3-(1-aminoethyl)-5-chloro-2-methoxy-6-methylphenyl]azetidine-1-carboxylate Titanium tetraethanolate (2.70 mL, 12.9 mmol) was added to a mixture of benzyl 3-(3-acetyl-5-chloro-2-methoxy-6-methylphenyl)azetidine-1-carboxylate (2.5 g, 6.4 mmol) in 2.0 M ammonia in ethanol (16.1 mL, 32.2 mmol) at 0° C. The solution was stirred at 60° C. under N$_2$ overnight. Sodium tetrahydroborate (0.366 g, 9.67 mmol) was added to the above mixture at 0° C. and the solution was stirred at room temperature for another 1 hour. The reaction mixture was quenched with 2 M ammonia in water and filtered. The solid was washed with acetonitrile. The solvent was removed and the residue was diluted with dichloromethane, washed with water and brine, dried over MgSO$_4$ and concentrated to give the desired product (2.47 g, 98%). LCMS calculated for C$_{21}$H$_{26}$ClN$_2$O$_3$ (M+H)$^+$: m/z=389.2. found: 389.1.

Step 3. Benzyl 3-(3-{1-[(tert-butoxycarbonyl)amino]ethyl}-5-chloro-2-methoxy-6-methylphenyl)azetidine-1-carboxylate Di-tert-butyldicarbonate (2.8 g, 13 mmol) was added to a mixture of benzyl 3-[3-(1-aminoethyl)-5-chloro-2-methoxy-6-methylphenyl]azetidine-1-carboxylate (2.47 g, 6.35 mmol) and DIPEA (3.3 mL, 19 mmol) in THF (32 mL). After stirring for 2 h at room temperature, the mixture was quenched with sat. NaHCO$_3$ solution, extracted with EtOAc. The combined organic layers were washed with water and brine, dried over MgSO$_4$, concentrated and purified on silica gel (eluting with 0 to 30% EtOAc in hexanes) to give the desired product (1.8 g, 58%). LCMS calculated for C$_{26}$H$_{33}$ClN$_2$O$_5$Na (M+Na)$^+$: m/z=511.2. found: 511.0. The material was applied on chiral HPLC (ChiralPak AD-H column, 20×250 mm, 5 micron particle size, eluting with 20% EtOH in hexanes at 15 mL/min, column loading ~20 mg/injection) to separate the two enantiomers (Retention times: 7.08 min and 8.46 min).

Step 4. tert-Butyl [1-(3-azetidin-3-yl-5-chloro-2-methoxy-4-methylphenyl)ethyl]carbamate Benzyl 3-(3-{1-[(tert-butoxycarbonyl)amino]ethyl}-5-chloro-2-methoxy-6-methylphenyl)azetidine-1-carboxylate (720 mg, 1.5 mmol) (second peak from chiral separation of previous step) and 5% palladium on carbon (100 mg) were combined in methanol (40 mL), to which was added 0.25 M HCl in water (11 mL, 2.8 mmol). The suspension was hydrogenated under balloon pressure of H$_2$ at room temperature for 1 hour. The suspension was then filtered, neutralized with sat. NaHCO$_3$ solution, concentrated, and extracted with dichloromethane. The combined organic layers were dried over MgSO$_4$ and concentrated to give the desired product (0.4 g). LCMS calculated for C$_{18}$H$_{28}$ClN$_2$O$_3$ (M+H)$^+$: m/z=355.2. found: 355.1.

Step 5. tert-Butyl {1-[5-chloro-3-(1-isopropylazetidin-3-yl)-2-methoxy-4-methylphenyl]ethyl}carbamate To a mixture of tert-butyl [1-(3-azetidin-3-yl-5-chloro-2-methoxy-4-methylphenyl)ethyl]carbamate (20 mg, 0.06 mmol) in acetonitrile (0.2 mL)/methanol (0.2 mL)/THF (0.2 mL) was added acetone (48 µL, 0.65 mmol). The mixture was stirred at room temperature for 30 min before the addition of sodium triacetoxyborohydride (36 mg, 0.17 mmol). The mixture was stirred at room temperature for 4 hours. The mixture was then diluted with water and extracted with dichloromethane. The organic layers were dried over MgSO$_4$ and concentrated to give the crude product. LCMS calculated for C$_{21}$H$_{34}$ClN$_2$O$_3$ (M+H)$^+$: m/z=397.2. found: 397.2.

Step 6. N-{1-[5-Chloro-3-(1-isopropylazetidin-3-yl)-2-methoxy-4-methylphenyl]ethyl}-9H-purin-6-amine bis(trifluoroacetate)

tert-Butyl {1-[5-chloro-3-(1-isopropylazetidin-3-yl)-2-methoxy-4-methylphenyl]ethyl}carbamate (19 mg, 0.048 mmol) was treated with 4.0 M HCl in dioxane (60 µL, 0.24 mmol) in methylene chloride (50 µL) at room temperature for 2 hours. The resultant mixture was concentrated to dryness to give 1-[5-chloro-3-(1-isopropylazetidin-3-yl)-2-methoxy-4-methylphenyl]ethanamine dihydrochloride. A mixture of the HCl salt, 6-bromo-9-(tetrahydro-2H-pyran-2-yl)-9H-purine (20 mg, 0.072 mmol, from Example 108, Step 1) and DIPEA (42 µL, 0.24 mmol) in ethanol (0.3 mL) was heated at 100° C. overnight. The mixture was treated with 6.0 M HCl in water (80 µL, 0.5 mmol) at room temperature for 10 min and then purified on prep-LCMS (XBridge C18 Column, eluting with a gradient of acetonitrile in water with 0.05% trifluoroacetic acid, at flow rate of 30 mL/min) to afford the desired product as TFA salt. LCMS calculated for $C_{21}H_{28}ClN_6O$ (M+H)$^+$: m/z=415.2. found: 415.1.

Example 171

N-{1-[5-Chloro-2-methoxy-4-methyl-3-(1-methylazetidin-3-yl)phenyl]ethyl}-9H-purin-6-amine bis(trifluoroacetate)

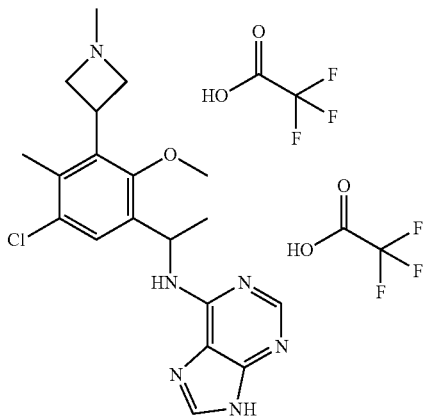 [SMILES: COc1c(C(C)Nc2ncnc3[nH]cnc23)cc(Cl)c(C)c1C1CN(C)C1 ; O=C(O)C(F)(F)F ; O=C(O)C(F)(F)F]

Step 1. Benzyl 3-{3-chloro-6-methoxy-2-methyl-5-[1-(9H-purin-6-ylamino)ethyl]phenyl}azetidine-1-carboxylate Benzyl 3-(3-{1-[(tert-butoxycarbonyl)amino]ethyl}-5-chloro-2-methoxy-6-methylphenyl)azetidine-1-carboxylate (0.45 g, 0.92 mmol, from Example 170, Step 3, chiral intermediate) and was treated with 4.0 M HCl in dioxane (2 mL, 8 mmol) in methylene chloride (6 mL) at room temperature for 2 hours. The reaction mixture was then stripped to dryness to give benzyl 3-{3-[1-amino ethyl]-5-chloro-2-methoxy-6-methylphenyl}azetidine-1-carboxylate as a HCl salt. LCMS calculated for $C_{21}H_{26}ClN_2O_3$ (M+H)$^+$: m/z=389.2. found: 389.1. A mixture of the above HCl salt, 6-bromo-9H-purine (0.20 g, 1.0 mmol) and DIPEA (0.80 mL, 4.6 mmol) in ethanol (9 mL) was heated at 100° C. overnight. The mixture was concentrated and purified on silica gel (eluting with 0 to 5% MeOH in dichloromethane) to give the desired product (0.25 g, 55% in 2 steps). LCMS calculated for $C_{26}H_{28}ClN_6O_3$ (M+H)$^+$: m/z=507.2. found: 507.1.

Step 2. N-{1-[5-Chloro-2-methoxy-4-methyl-3-(1-methylazetidin-3-yl)phenyl]ethyl}-9H-purin-6-amine bis(trifluoroacetate)

Benzyl 3-{3-chloro-6-methoxy-2-methyl-5-[1-(9H-purin-6-ylamino)ethyl]phenyl}azetidine-1-carboxylate (255 mg, 0.503 mmol) and 5% palladium (125 mg) was combined in methanol (15 mL), to which was added 0.25 M HCl in water (5.0 mL, 1.2 mmol). The suspension was hydrogenated under balloon pressure of $H_2$ at room temperature overnight. The suspension was filtered and concentrated to give N-[1-(3-azetidin-3-yl-5-chloro-2-methoxy-4-methylphenyl)ethyl]-9H-purin-6-amine. LCMS calculated for $C_{18}H_{22}ClN_6O$ (M+H)$^+$: m/z=373.2. found: 373.1. The azetidine intermediate made above was combined with DIPEA (0.26 mL, 1.5 mmol) in methanol (0.5 mL)/acetonitrile (0.5 mL)/THF (0.5 mL), followed by the addition of 37% formaldehyde (0.19 mL, 2.5 mmol). The mixture was stirred at room temperature for 10 min before the addition of sodium triacetoxyborohydride (0.32 g, 1.5 mmol). The mixture was stirred at room temperature overnight, then diluted with MeOH and purified on prep-LCMS (XBridge C18 Column, eluting with a gradient of acetonitrile in water with 0.05% trifluoroacetic acid, at flow rate of 30 mL/min) to afford the desired product as TFA salt. LCMS calculated for $C_{19}H_{24}ClN_6O$ (M+H)$^+$: m/z=387.2. found: 387.1.

Example 172

N-{1-[5-Chloro-4-fluoro-3-(1-isopropylazetidin-3-yl)-2-methoxyphenyl]ethyl}-9H-purin-6-amine bis(trifluoroacetate)

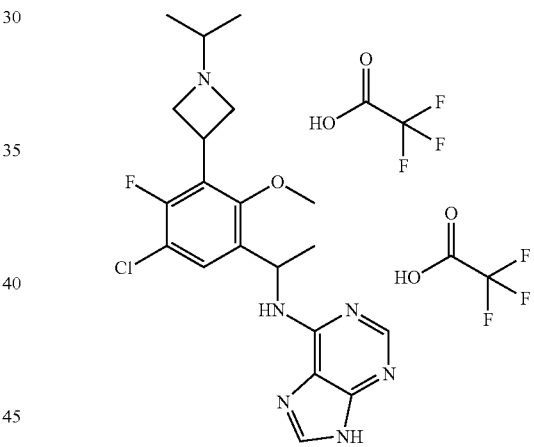

Step 1. 1-(5-Chloro-4-fluoro-2-hydroxyphenyl)ethanone

To 4-chloro-3-fluorophenol (20 g, 100 mmol, from Aldrich) was added acetyl chloride (14.1 mL, 199 mmol) under $N_2$ with stirring. The resulting mixture turned into a clear solution at room temperature and was heated at 60° C. for 2 hours. To the resultant mixture was added aluminum trichloride (25.0 g, 187 mmol) in portions and the mixture was heated at 180° C. for 30 minutes. The solids slowly dissolved at high temp. The reaction mixture was then cooled to room temperature while the flask was swirled carefully in order for the solid to form a thin layer inside the flask and then slowly quenched with 1.0 N HCl (300 mL) while cooling in an ice-bath and stirred overnight. The yellow precipitate was washed well with water and dried under vacuum to give the desired product as a yellow solid (23.8 g), which was directly used in the next step without further purification.

Step 2. 1-(5-Chloro-4-fluoro-2-hydroxy-3-iodophenyl)ethanone

A solution of 1-(5-chloro-4-fluoro-2-hydroxyphenyl)ethanone (23.8 g, 126 mmol) in acetic acid (100 mL) was treated with N-iodosuccinimide (34.1 g, 151 mmol) and stirred at 70° C. for 2 hours. The reaction mixture was concentrated, diluted with EtOAc and quenched with sat. NaHCO$_3$ solution. The organic layer was separated, washed with water, dried over MgSO$_4$ and concentrated under reduced pressure to give the desired product to be used in the next step without further purification.

Step 3. 1-(5-Chloro-4-fluoro-3-iodo-2-methoxyphenyl)ethanone 1-(5-Chloro-4-fluoro-2-hydroxy-3-iodophenyl)ethanone (13 g, 41 mmol) was dissolved in DMF (41.3 mL). Methyl iodide (3.9 mL, 62 mmol) was added followed by potassium carbonate (11 g, 83 mmol). The reaction was heated at 60° C. for 1 hour. The mixture was cooled to room temperature, diluted with ether, washed with water, dried over MgSO$_4$, concentrated. The residue was purified on silica gel (eluting with 0 to 10% EtOAc in hexanes) to give the desired product (10 g, 70%). LCMS calculated for C$_9$H$_8$ClFIO$_2$ (M+H)$^+$: m/z=328.9. found: 328.9.

Step 4. tert-Butyl 3-(3-acetyl-5-chloro-6-fluoro-2-methoxyphenyl)azetidine-1-carboxylate Zinc (0.682 g, 10.4 mmol) was suspended with 1,2-dibromoethane (0.060 mL, 0.69 mmol) in DMF (12 mL). The mixture was heated at 70° C. for 10 min and then cooled to room temperature. Chlorotrimethylsilane (0.088 mL, 0.69 mmol) was added dropwise and stirring was continued for 1 hour. A solution of tert-butyl 3-iodoazetidine-1-carboxylate (2.5 g, 8.7 mmol, from Oakwood) in DMF (10 mL) was then added and the mixture was heated at 40° C. for 1 h before a mixture of 1-(5-chloro-4-fluoro-3-iodo-2-methoxyphenyl)ethanone (3.0 g, 9.1 mmol), tris(dibenzylideneacetone)dipalladium(0) (0.16 g, 0.17 mmol) and tri-(2-furyl)phosphine (0.081 g, 0.35 mmol) in DMF (20 mL) was added. The reaction mixture was warmed to 70° C. and stirred overnight. The mixture was then cooled to room temperature and partitioned between ether and sat. NH$_4$Cl solution. The organic layer was washed with water, dried over MgSO$_4$, concentrated and purified on silica gel (eluting with 0 to 25% EtOAc in hexanes) to give the desired product (0.8 g). LCMS calculated for C$_{17}$H$_{21}$ClFNO$_4$Na (M+Na)$^+$: m/z=380.1. found: 380.1.

Step 5. tert-Butyl 3-[3-chloro-2-fluoro-5-(1-hydroxyethyl)-6-methoxyphenyl]azetidine-1-carboxylate To a solution of tert-butyl 3-(3-acetyl-5-chloro-6-fluoro-2-methoxyphenyl)azetidine-1-carboxylate (0.17 g, 0.48 mmol) in methanol (3 mL) cooled at 0° C. was added sodium tetrahydroborate (0.022 g, 0.57 mmol). The mixture was stirred at room temperature for 1 hour, then diluted with water and extracted with EtOAc. The combined organic layers were dried over MgSO$_4$ and concentrated to give the desired product (0.19 g). LCMS calculated for C$_{17}$H$_{23}$ClFNO$_4$Na (M+Na)$^+$: m/z=382.1. found: 382.0.

Step 6. tert-Butyl 3-[3-chloro-5-(1-chloroethyl)-2-fluoro-6-methoxyphenyl]azetidine-1-carboxylate Cyanuric chloride (140 mg, 0.78 mmol) was added to DMF (0.059 mL, 0.77 mmol). After the formation of a white solid (10 min), methylene chloride (4 mL) was added, followed by tert-butyl 3-[3-chloro-2-fluoro-5-(1-hydroxyethyl)-6-methoxyphenyl]azetidine-1-carboxylate (197 mg, 0.547 mmol). After the addition, the mixture was stirred at room temperature overnight. Water was added, and the resulting mixture was then diluted with dichloromethane. The organic phase was separated, washed with sat. NaHCO$_3$ solution, water and brine, dried over MgSO$_4$, concentrated and purified on silica gel (eluting with 0 to 30% EtOAc in hexanes) to give the desired product (110 mg, 53%).

Step 7. tert-Butyl 3-[3-(1-azidoethyl)-5-chloro-6-fluoro-2-methoxyphenyl]azetidine-1-carboxylate A mixture of tert-butyl 3-[3-chloro-5-(1-chloroethyl)-2-fluoro-6-methoxyphenyl]azetidine-1-carboxylate (0.070 g, 0.18 mmol) and sodium azide (0.036 g, 0.56 mmol) in DMF (0.66 mL) was stirred at room temperature overnight. After diluting with ether, the mixture was washed with water, dried over MgSO$_4$ and concentrated to give the crude azide which was used in the next step without further purification. LCMS calculated for C$_{17}$H$_{22}$ClFN$_4$O$_3$Na (M+Na)$^+$: m/z=407.1. found: 407.0.

Step 8. tert-Butyl 3-[3-(1-aminoethyl)-5-chloro-6-fluoro-2-methoxyphenyl]azetidine-1-carboxylate To a stirred solution of tert-butyl 3-[3-(1-azidoethyl)-5-chloro-6-fluoro-2-methoxyphenyl]azetidine-1-carboxylate (0.084 g, 0.22 mmol) in THF (1 mL)/water (0.2 mL) was added 1.0 M trimethylphosphine in THF (0.33 mL, 0.33 mmol) at room temperature and the mixture was stirred at room temperature for 2 hours. The reaction mixture was diluted with water and extracted with EtOAc. The combined organic layers were dried over MgSO$_4$ and concentrated to give the desired product to be used in the next step without further purification.

Step 9. N-{1-[5-Chloro-4-fluoro-3-(1-isopropylazetidin-3-yl)-2-methoxyphenyl]ethyl}-9H-purin-6-amine bis(trifluoroacetate)

A mixture of tert-butyl 3-[3-(1-aminoethyl)-5-chloro-6-fluoro-2-methoxyphenyl]azetidine-1-carboxylate (22.5 mg, 0.0627 mmol), 6-bromo-9-(tetrahydro-2H-pyran-2-yl)-9H-purine (24 mg, 0.085 mmol, from Example 108, Step 1) and DIPEA (33 µL, 0.19 mmol) in ethanol (1.0 mL) was heated at 100° C. overnight. The mixture was diluted with sat. NaHCO$_3$ solution, extracted with dichloromethane. The combined organic layers were dried over MgSO$_4$ and concentrated to give tert-butyl 3-[3-chloro-2-fluoro-6-methoxy-5-(1-{[9-(tetrahydro-2H-pyran-2-yl)-9H-purin-6-yl]amino}ethyl)phenyl]azetidine-1-carboxylate (34 mg). LCMS calculated for C$_{27}$H$_{35}$ClFN$_6$O$_4$ (M+H)$^+$: m/z=561.2. found: 561.2. The coupling product made above was treated with 4.0 M HCl in dioxane (0.5 mL, 2 mmol) in methylene chloride (0.2 mL) at room temperature for 1 hour. The reaction mixture was then evaporated to dryness to give N-[1-(3-azetidin-3-yl-5-chloro-4-fluoro-2-methoxyphenyl)ethyl]-9H-purin-6-amine dihydrochloride. The resultant HCl salt was dissolved in methanol (0.2 mL)/acetonitrile (0.2 mL)/THF (0.2 mL) and treated with DIPEA (0.1 mL, 0.6 mmol) until the solid dissolved. Acetone (0.05 mL, 0.6 mmol) was added and the resulting mixture was stirred at room temperature for 30 min before the addition of sodium triacetoxyborohydride (0.066 g, 0.31 mmol). The reaction mixture was stirred at room temperature for 4 h and then purified on prep-LCMS (XBridge C18 Column, eluting with a gradient of acetonitrile in water with 0.05% trifluoroacetic acid, at flow rate of 30 mL/min) to afford the desired product as TFA salt. LCMS calculated for $C_{20}H_{25}ClFN_6O$ (M+H)$^+$: m/z=419.2. found: 419.1. $^1$H NMR (300 MHz, DMSO-d$_6$) δ 9.96 (1H, m), 8.41 (1H, m), 8.23 (1H, s), 8.20 (1H, s), 7.53 (1H, s), 5.69 (1H, m), 4.52 (2H, m), 4.26 (1H, m), 4.12 (2H, m), 3.77 (3H, s), 2.08 (3H, m), 1.46 (3H, d, J=6.9 Hz), 1.11 (6H, m) ppm.

Example 173

N-{1-[5-chloro-2-ethoxy-4-methyl-3-(1-methylazetidin-3-yl)phenyl]ethyl}-9H-purin-6-amine

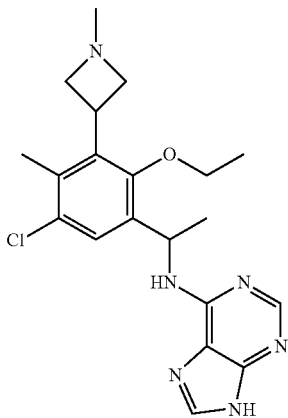 [SMILES: CCOc1c(C(C)Nc2ncnc3[nH]cnc23)cc(Cl)c(C)c1C1CN(C)C1]

Step 1.
1-(5-Chloro-2-ethoxy-3-iodo-4-methylphenyl) ethanone 1-(5-Chloro-2-hydroxy-3-iodo-4-methylphenyl)ethanone (18.9 g, 60.9 mmol, from Example 60, Step 1) was dissolved in DMF (61 mL). Iodoethane (7.3 mL, 91 mmol) was added followed by potassium carbonate (17.0 g, 120 mmol). The reaction was heated at 60° C. for 1 hour. The mixture was cooled to room temperature, diluted with ether, washed with water, dried over MgSO$_4$, concentrated. The resulting residue was purified on silica gel (eluting with 0 to 10% EtOAc in hexanes) to give the desired product (18.9 g, 91.7%). LCMS calculated for $C_{11}H_{13}ClIO_2$ (M+H)$^+$: m/z=339.0. found: 339.0.

Step 2. Benzyl 3-(3-acetyl-5-chloro-2-ethoxy-6-methylphenyl) azetidine-1-carboxylate Zinc (0.967 g, 14.8 mmol) was suspended with 1,2-dibromoethane (0.085 mL, 0.98 mmol) in DMF (17 mL). The mixture was heated at 70° C. for 10 min and then cooled to room temperature. Chlorotrimethylsilane (0.13 mL, 0.98 mmol) was added dropwise and stirring was continued for 1 hour. A solution of benzyl 3-iodoazetidine-1-carboxylate (3.9 g, 12 mmol, from Pharmablock) in DMF (10 mL) was then added and the mixture was heated at 40° C. for 1 h before a mixture of 1-(5-chloro-2-ethoxy-3-iodo-4-methylphenyl)ethanone (4.4 g, 13 mmol), tris(dibenzylideneacetone)dipalladium(0) (0.22 g, 0.24 mmol) and tri-(2-furyl) phosphine (0.12 g, 0.50 mmol) in DMF (30 mL) was added. The reaction mixture was warmed to 70° C. and stirred overnight. The mixture was then cooled to room temperature and partitioned between ether and sat. NH$_4$Cl solution. The organic layer was washed with water, dried over MgSO$_4$, concentrated and purified on silica gel (eluting with 0 to 20% EtOAc in hexanes) to give the desired product (3.87 g, 78%). LCMS calculated for $C_{22}H_{25}ClNO_4$ (M+H)$^+$: m/z=402.1. found: 402.1.

Step 3. Benzyl 3-[3-(1-aminoethyl)-5-chloro-2-ethoxy-6-methylphenyl]azetidine-1-carboxylate Titanium tetraethanolate (3.3 mL, 16 mmol) was added to a mixture of benzyl 3-(3-acetyl-5-chloro-2-ethoxy-6-methylphenyl)azetidine-1-carboxylate (3.2 g, 8.0 mmol) in 2.0 M ammonia in ethanol (19.9 mL, 39.8 mmol) at 0° C. The solution was stirred at 60° C. under N$_2$ overnight. Sodium tetrahydroborate (0.452 g, 11.9 mmol) was added to the resultant mixture at 0° C. and the reaction mixture was stirred at room temperature for another 1 hour. The mixture was then quenched with 2 M ammonia in water and filtered. The solid was washed with acetonitrile. The solvent was removed and the residue was diluted with dichloromethane, washed with water and brine, dried over MgSO$_4$ and concentrated to give the desired product (2.99 g, 93%). LCMS calculated for $C_{22}H_{28}ClN_2O_3$ (M+H)$^+$: m/z=403.2. found: 403.2.

Step 4. Benzyl 3-(3-{1-[(tert-butoxycarbonyl) amino]ethyl}-5-chloro-2-ethoxy-6-methylphenyl) azetidine-1-carboxylate Di-tert-butyldicarbonate (3.2 g, 15 mmol) was added to a mixture of benzyl 3-[3-(1-aminoethyl)-5-chloro-2-ethoxy-6-methylphenyl]azetidine-1-carboxylate (2.99 g, 7.42 mmol) and DIPEA (3.9 mL, 22 mmol) in THF (37 mL). After stirring overnight at room temperature, the mixture was quenched with sat. NaHCO$_3$ solution, extracted with EtOAc. The combined organic layers were washed with water and brine, dried over MgSO$_4$, concentrated and purified on silica gel (eluting with 0 to 25% EtOAc in hexane) to give the desired product (2.1 g, 56%). LCMS calculated for $C_{27}H_{35}ClN_2O_5Na$ (M+Na)$^+$: m/z=525.2. found: 525.2. The material was applied on chiral HPLC (ChiralPak AD-H column, 20×250 mm, 5 micron particle size, eluting with 20% EtOH in hexanes at 15 ml/min, column loading ~20 mg/injection) to separate the two enantiomers (Retention times: 7.08 min and 8.46 min).

Step 5. Benzyl 3-{3-chloro-6-ethoxy-2-methyl-5-[1-(9H-purin-6-ylamino)ethyl]phenyl}azetidine-1-carboxylate Benzyl 3-(3-{1-[(tert-butoxycarbonyl)amino]ethyl}-5-chloro-2-ethoxy-6-methylphenyl)azetidine-1-carboxylate (65 mg, 0.13 mmol, second peak from chiral separation in previous step) was treated with 4.0 M HCl in dioxane (0.4 mL, 2 mmol) in methylene chloride (0.4 mL, 6 mmol) at room temperature for 2 hours. The reaction mixture was evaporated to dryness to give benzyl 3-{3-[1-aminoethyl]-5-chloro-2-ethoxy-6-methylphenyl}azetidine-1-carboxylate hydrochloride. LCMS calculated for $C_{22}H_{28}ClN_2O_3$ (M+H)$^+$: m/z=403.2. found: 403.1. A mixture of the above HCl salt, 6-bromo-9H-purine (31 mg, 0.16 mmol) and DIPEA (0.11 mL, 0.65 mmol) in ethanol (1 mL) was heated at 100° C. overnight. The mixture was diluted with sat. NaHCO$_3$ solution, extracted with dichloromethane. The combined organic layers were dried over MgSO₄ and concentrated to give the desired product (83 mg). LCMS calculated for $C_{27}H_{30}ClN_6O_3$ (M+H)⁺: m/z=521.2. found: 521.1.

Step 6. N-{1-[5-chloro-2-ethoxy-4-methyl-3-(1-methylazetidin-3-yl)phenyl]ethyl}-9H-purin-6-amine Benzyl 3-{3-chloro-6-ethoxy-2-methyl-5-[1-(9H-purin-6-ylamino)ethyl]phenyl}azetidine-1-carboxylate (83 mg, 0.16 mmol) and 5% palladium (74 mg) was combined in methanol (5 mL), to which was added 0.25 M HCl in water (1.6 mL, 0.40 mmol). The suspension was hydrogenated under balloon pressure of H₂ at room temperature overnight. The suspension was filtered and concentrated to give N-[1-(3-azetidin-3-yl-5-chloro-2-ethoxy-4-methylphenyl)ethyl]-9H-purin-6-amine. LCMS calculated for $C_{19}H_{24}ClN_6O$ (M+H)⁺: m/z=387.2. found: 387.1. The azetidine made above was combined with DIPEA (0.1 mL, 0.6 mmol) in methanol (0.5 mL)/acetonitrile (0.5 mL)/THF (0.5 mL), followed by the addition of 37% formaldehyde (0.1 mL, 2 mmol). The mixture was stirred at room temperature for 10 min before the addition of sodium triacetoxyborohydride (0.17 g, 0.80 mmol 1). The reaction mixture was stirred at room temperature overnight, then diluted with MeOH and purified on RP-HPLC (XBridge C18 Column, eluting with a gradient of acetonitrile in water with 0.2% ammonium hydroxide, at flow rate of 30 mL/min) to give the desired product. LCMS calculated for $C_{20}H_{26}ClN_6O$ (M+H)⁺: m/z=401.2. found: 401.1.

Example 174

N-{1-[5-chloro-2-methoxy-4-methyl-3-(1-piperidin-4-yl-1H-pyrazol-4-yl)phenyl]ethyl}-9H-purin-6-amine tris(trifluoroacetate)

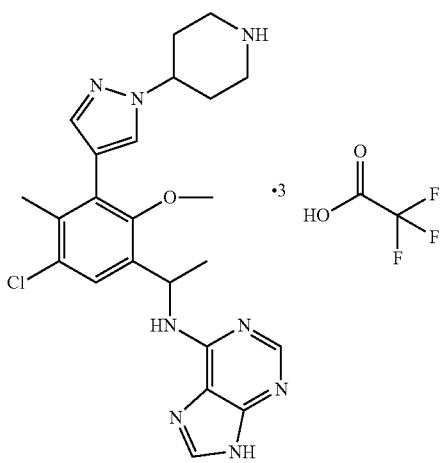 [SMILES: COc1c(C(C)Nc2ncnc3[nH]cnc23)cc(Cl)c(C)c1-c1cnn(C2CCNCC2)c1 ; O=C(O)C(F)(F)F]

Step 1. tert-Butyl 4-{4-[3-chloro-6-methoxy-2-methyl-5-(1-{[9-(tetrahydro-2H-pyran-2-yl)-9H-purin-6-yl]amino}ethyl)phenyl]-H-pyrazol-1-yl}piperidine-1-carboxylate

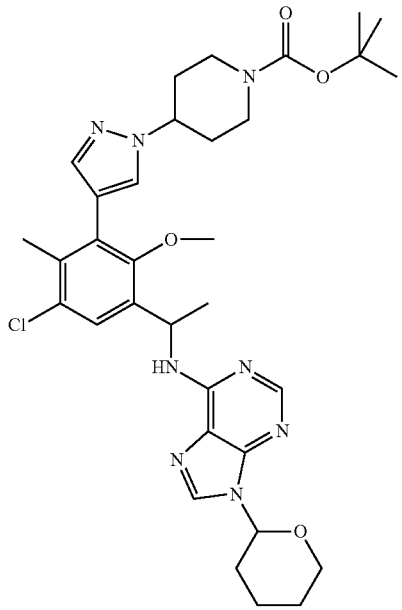 [SMILES: COc1c(C(C)Nc2ncnc3c2ncn3C2CCCCO2)cc(Cl)c(C)c1-c1cnn(C2CCN(C(=O)OC(C)(C)C)CC2)c1]

Into a microwave vial was added N-[1-(3-bromo-5-chloro-2-methoxy-4-methylphenyl)ethyl]-9-(tetrahydro-2H-pyran-2-yl)-9H-purin-6-amine (0.032 g, 0.066 mmol, from Example 113, Step 2, chiral intermediate), tert-butyl 4-[4-(4,4,5,5-tetramethyl-1,3,2-dioxaborolan-2-yl)-1H-pyrazol-1-yl]piperidine-1-carboxylate (0.030 g, 0.080 mmol, from Combi-Blocks), sodium carbonate (0.014 g, 0.13 mmol), 1,4-dioxane (0.6 mL)/water (0.2 mL) and tetrakis(triphenylphosphine)palladium(0) (4.6 mg, 0.0040 mmol). The mixture was degassed with N₂ for 5 minutes, and then heated at 120° C. overnight. The mixture was diluted with EtOAc, washed with sat. NaHCO₃, water, brine, dried over Na₂SO₄, filtered and concentrated to give the crude product (0.040 g) which was used in the next step directly. LCMS calculated for $C_{33}H_{44}ClN_8O_4$ (M+H)⁺: m/z=651.3. found: 651.2.

Step 2. N-{1-[5-chloro-2-methoxy-4-methyl-3-(1-piperidin-4-yl-1H-pyrazol-4-yl)phenyl]ethyl}-9H-purin-6-amine tris(trifluoroacetate)

tert-Butyl 4-{4-[3-chloro-6-methoxy-2-methyl-5-(1-{[9-(tetrahydro-2H-pyran-2-yl)-9H-purin-6-yl]amino}ethyl)phenyl]-1H-pyrazol-1-yl}piperidine-1-carboxylate (0.040 g) was dissolved in CH₂Cl₂ (0.4 mL) and then TFA (0.4 mL) was added. The mixture was stirred at room temperature for 1 hour. After evaporated to dryness, the residue was purified on RP-HPLC (XBridge C18 Column, eluting with a gradient of acetonitrile in water with 0.05% trifluoroacetic acid, at flow rate of 30 mL/min) to give the desired product. LCMS calculated for $C_{23}H_{28}ClN_8O$ (M+H)⁺: m/z=467.2. found: 467.2.

Example 175

4-{3-Chloro-6-methoxy-2-methyl-5-[1-(9H-purin-6-ylamino)ethyl]phenyl}-N,1-dimethyl-1H-pyrrole-2-carboxamide

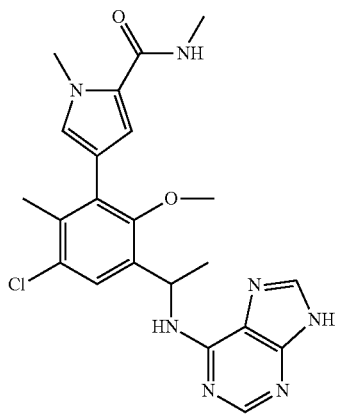 [SMILES: CNC(=O)c1cc(-c2c(C)c(Cl)cc(C(C)Nc3ncnc4[nH]cnc34)c2OC)cn1C]

Step 1. 2-Benzyl 1-tert-butyl 4-iodo-1H-pyrrole-1,2-dicarboxylate

A mixture of 2,2,2-trichloro-1-(4-iodo-1H-pyrrol-2-yl)ethanone (15.0 g, 44.3 mmol, from Ryan Scientific), benzyl alcohol (9.2 mL, 89 mmol), and triethylamine (8.0 mL, 58 mmol) was heated at 60° C. with stirring overnight. After cooling to room temperature, di-tert-butyldicarbonate (10.6 g, 48.8 mmol), 4-dimethylaminopyridine (542 mg, 4.43 mmol) and methylene chloride (75.0 mL) was added. The mixture was stirred at room temperature for 3 hours. The reaction was then diluted with EtOAc and washed with water, aqueous citric acid, brine, dried and concentrated. The product was isolated by chromatography eluting with 0 to 10% EtOAc in hexanes. LCMS calculated for $C_{17}H_{18}INO_4Na$ (M+Na)$^+$: m/z=450.0. found: 450.0.

Step 2. 2-Benzyl 1-tert-butyl 4-(4,4,5,5-tetramethyl-1,3,2-dioxaborolan-2-yl)-1H-pyrrole-1,2-dicarboxylate At −78° C. to a solution of 2-benzyl 1-tert-butyl 4-iodo-1H-pyrrole-1,2-dicarboxylate (10.0 g, 23.4 mmol), and 2-isopropoxy-4,4,5,5-tetramethyl-1,3,2-dioxaborolane (9.6 mL, 47 mmol) in THF (120 mL) was added dropwise a solution of 2.5 M n-butyllithium in hexane (11.2 mL, 28.1 mmol) with stirring. After completion of addition the mixture was stirred at this temperature for 35 min and then 2.5 M n-butyllithium in hexane (1.87 mL, 4.68 mmol) was added and stirred for another 30 minutes. The reaction was quenched with sat. NH$_4$Cl solution and then diluted with EtOAc. The organic layer was separated, washed with water twice, washed with brine, dried over Na$_2$SO$_4$, and concentrated under reduced pressure. The product was isolated by chromatography eluting with 0 to 10% EtOAc in hexanes. LCMS calculated for $C_{19}H_{23}BNO_6$ (M−[$^t$Bu+1]+1)$^+$: m/z=372.2. found: 372.2.

Step 3. Benzyl 1-methyl-4-(4,4,5,5-tetramethyl-1,3,2-dioxaborolan-2-yl)-1H-pyrrole-2-carboxylate 2-Benzyl 1-tert-butyl 4-(4,4,5,5-tetramethyl-1,3,2-dioxaborolan-2-yl)-1H-pyrrole-1,2-dicarboxylate (0.5 g) was dissolved in CH$_2$Cl$_2$ (1 mL) and then 4 N HCl in dioxane (1 mL) was added. The reaction was stirred at room temperature for 1 hour. The solvent was removed under vacuum. The residue was redissolved in DMF (4 mL). To the resulting solution was added NaH (60% dispersion in mineral oil, 0.08 g, 2.0 mmol) at 0° C. The reaction mixture was stirred at 0° C. for 10 minutes. Methyl iodide (0.11 mL, 2.0 mmol) was added and the reaction was stirred at room temperature for 3 hours. The reaction was quenched with sat. NH$_4$Cl solution and then diluted with EtOAc. After separation of layers, the organic phase was washed with water (twice) and brine; dried over Na$_2$SO$_4$. The solvent was removed to provide the desired crude product which was used in the next step without further purification. LCMS calculated for $C_{19}H_{25}BNO_4$ (M+H)$^+$: m/z=342.2. found: 342.2.

Step 4. Benzyl 4-[3-chloro-6-methoxy-2-methyl-5-(1-{[9-(tetrahydro-2H-pyran-2-yl)-9H-purin-6-yl]amino}ethyl)phenyl]-1-methyl-1H-pyrrole-2-carboxylate A mixture of N-[1-(3-bromo-5-chloro-2-methoxy-4-methylphenyl)ethyl]-9-(tetrahydro-2H-pyran-2-yl)-9H-purin-6-amine (0.032 g, 0.066 mmol, from Example 113, Step2, Chiral intermediate), benzyl 1-methyl-4-(4,4,5,5-tetramethyl-1,3,2-dioxaborolan-2-yl)-1H-pyrrole-2-carboxylate (0.027 g, 0.080 mmol), sodium carbonate (0.16 mL, 0.17 mmol), 1,4-dioxane (0.6 mL)/water (0.2 mL) and tetrakis(triphenylphosphine)palladium(0) (4.6 mg, 0.0040 mmol) was degassed with N$_2$ for 5 minutes, then heated at 95° C. overnight. The mixture was diluted with EtOAc, washed with sat. NaHCO$_3$, water, brine, and dried over Na$_2$SO$_4$ and concentrated. The crude product (20 mg, 50%) was purified by chromatography eluting with 0 to 40% EtOAc in CH$_2$Cl$_2$. LCMS calculated for $C_{33}H_{36}ClN_6O_4$ (M+H)$^+$: m/z=615.2. found: 615.2.

Step 5. 4-{3-Chloro-6-methoxy-2-methyl-5-[1-(9H-purin-6-ylamino)ethyl]phenyl}-1-methyl-1H-pyrrole-2-carboxylic acid Pd/C (5%, 20 mg) was added to a solution of benzyl 4-[3-chloro-6-methoxy-2-methyl-5-(1-{[9-(tetrahydro-2H-pyran-2-yl)-9H-purin-6-yl]amino}ethyl)phenyl]-1-methyl-1H-pyrrole-2-carboxylate (20 mg) in methanol (2.0 mL) and the reaction was stirred at room temperature under balloon pressure of H$_2$ for 4 hours. The reaction mixture was filtered and to the filtrate was added conc. HCl (30 µL). The mixture was stirred for 0.5 h to remove the THP group. The solvent was removed to yield the crude product which was used in the next step without further purification. LCMS calculated for $C_{21}H_{22}ClN_6O_3$ (M+H)$^+$: m/z=441.1. found: 441.2.

Step 6. 4-{3-Chloro-6-methoxy-2-methyl-5-[1-(9H-purin-6-ylamino)ethyl]phenyl}-N,1-dimethyl-1H-pyrrole-2-carboxamide 2.0 M Methylamine in THF (0.2 mL, 0.4 mmol) was added to a solution of 4-{3-chloro-6-methoxy-2-methyl-5-[1-(9H-purin-6-ylamino)ethyl]phenyl}-1-methyl-1H-pyrrole-2-carboxylic acid (10.0 mg, 0.02 mmol) and benzotriazol-1-yloxytris(dimethylamino)phosphonium hexafluorophosphate (24 mg, 0.054 mmol) in DMF (0.8 mL) at room temperature followed by addition of triethylamine (33 µL, 0.24 mmol). The reaction was stirred for 2 hours. The mixture was purified on RP-HPLC (XBridge C18 Column, eluting with a gradient of acetonitrile in water with

Example 176

N-{1-[5-Chloro-2-methoxy-4-methyl-3-(1-methylpiperidin-4-yl)phenyl]ethyl}-9H-purin-6-amine

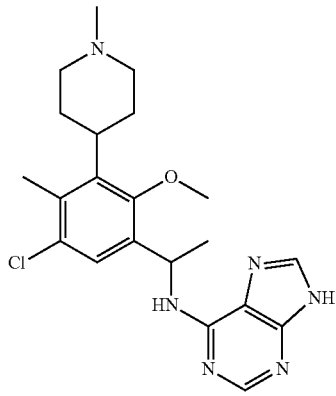 [SMILES: COc1c(C(C)Nc2ncnc3[nH]cnc23)cc(Cl)c(C)c1C1CCN(C)CC1]

Step 1. Benzyl [1-(3-bromo-5-chloro-2-methoxy-4-methylphenyl)ethyl]-carbamate Benzyl chloroformate (0.41 mL, 2.8 mmol) was added to a mixture of 1-(3-bromo-5-chloro-2-methoxy-4-methylphenyl)ethanamine hydrochloride (0.50 g, 1.6 mmol, made from Example 113, step 1, chiral intermediate), and sodium carbonate (670 mg, 6.3 mmol) in methylene chloride (5 mL)/water (1 mL) at 0° C. The reaction was stirred at room temperature for 4 hours. The mixture was diluted with EtOAc, washed with water, brine, dried over $Na_2SO_4$, filtered and concentrated. The resultant residue was purified by chromatography eluting with 0 to 20% EtOAc in hexanes to provide the desired product (0.5 g, 76%). LCMS calculated for $C_{18}H_{19}BrClNO_3Na$ (M+Na)$^+$: m/z=434.0. found: 434.1.

Step 2. tert-Butyl 4-[3-(1-{[(benzyloxy)carbonyl]amino}ethyl)-5-chloro-2-methoxy-6-methylphenyl]-3,6-dihydropyridine-1(2H)-carboxylate A mixture of benzyl [1-(3-bromo-5-chloro-2-methoxy-4-methylphenyl)ethyl]carbamate (0.48 g, 1.2 mmol), tert-butyl 4-(4,4,5,5-tetramethyl-1,3,2-dioxaborolan-2-yl)-3,6-dihydropyridine-1(2H)-carboxylate (0.40 g, 1.3 mmol, from Aldrich), sodium carbonate (250 mg, 2.3 mmol) and [1,1'-bis(diphenylphosphino)ferrocene]dichloropalladium(II), complex with dichloromethane (1:1) (110 mg, 0.14 mmol) in acetonitrile (4.0 mL)/water (1 mL) was placed under vacuum and then refilled with $N_2$. The reaction was stirred at 95° C. for 3 hours. The mixture was diluted with EtOAc, washed with sat. $NaHCO_3$, water, brine, dried over $Na_2SO_4$, filtered and concentrated. The resultant residue was purified by chromatography eluting with 0 to 20% EtOAc in hexanes to provide the desired product (0.55 g, 90%). LCMS calculated for $C_{28}H_{35}ClN_2O_5Na$ (M+Na)$^+$: m/z=537.2. found: 537.3.

Step 3. tert-Butyl 4-{3-[1-aminoethyl]-5-chloro-2-methoxy-6-methylphenyl}-piperidine-1-carboxylate Platinum on carbon (10 wt. % loading (dry basis), matrix activated carbon, 200 mg) was added to a solution of tert-butyl 4-[3-(1-{[(benzyloxy)carbonyl]amino}ethyl)-5-chloro-2-methoxy-6-methylphenyl]-3,6-dihydropyridine-1(2H)-carboxylate (200 mg, 0.388 mmol) in ethanol (30 mL)/0.25 M HCl in water (3.9 mL, 0.97 mmol) and then the reaction was stirred at room temperature under 30 psi of hydrogen atmosphere for 3 d. The mixture was adjusted to basic pH with ammonia and then the solvent was removed. The residue was diluted with methylene chloride, washed with sat. $NaHCO_3$, water, brine, dried over $Na_2SO_4$, filtered and concentrated to give the crude desired product (0.15 g) which was used in the next step without further purification. LCMS calculated for $C_{20}H_{32}ClN_2O_3$ (M+H)$^+$: m/z=383.2. found: 383.3.

Step 4. 6-Chloro-9-(tetrahydro-2H-pyran-2-yl)-9H-purine

To a solution of 6-chloropurine (2.70 g, 17.5 mmol) and p-toluenesulfonic acid monohydrate (0.14 g, 0.71 mmol) in methylene chloride (30 mL) was added dihydropyran (2.39 mL, 26.2 mmol). The suspension was stirred for 3 h. The reaction mixture was washed with 2.5% $Na_2CO_3$ solution (100 mL×2), and brine (50 mL). The organic layer was dried over sodium sulfate and concentrated. The oil was treated with hexanes (100 mL) and stirred. The hexanes layer was decanted. The oil solidified upon standing to give the desired product (4.17 g, 98%).

Step 5. tert-Butyl 4-[3-chloro-6-methoxy-2-methyl-5-(1-{[9-(tetrahydro-2H-pyran-2-yl)-9H-purin-6-yl]amino}ethyl)phenyl]piperidine-1-carboxylate A mixture of tert-butyl 4-{3-[1-aminoethyl]-5-chloro-2-methoxy-6-methylphenyl}piperidine-1-carboxylate (150 mg, 0.392 mmol), 6-chloro-9-(tetrahydro-2H-pyran-2-yl)-9H-purine (122 mg, 0.509 mmol), and sodium bicarbonate (35 mg, 0.41 mmol) in 1-butanol (4.7 mL) was degassed with $N_2$ for 5 minutes. The mixture was heated at 110° C. for 3 h under nitrogen. The solvent was removed under reduced pressure and the resulting residue was diluted with EtOAc, washed with sat. $NaHCO_3$, water, brine, dried over $Na_2SO_4$, filtered and concentrated. The residue was purified by chromatography eluting with 0 to 80% EtOAc in $CH_2Cl_2$ to provide the desired product (0.25 g). LCMS calculated for $C_{30}H_{42}ClN_6O_4$ (M+H)$^+$: m/z=585.3. found: =585.3.

Step 6. N-[1-(5-Chloro-2-methoxy-4-methyl-3-piperidin-4-ylphenyl)ethyl]-9H-purin-6-amine 4.0 M HCl in dioxane (2.0 mL, 8 mmol) was added to a solution of tert-butyl 4-[3-chloro-6-methoxy-2-methyl-5-(1-{[9-(tetrahydro-2H-pyran-2-yl)-9H-purin-6-yl]amino}ethyl)phenyl]piperidine-1-carboxylate (250 mg, 0.43 mmol) in methylene chloride (1.0 mL, 16 mmol) and the reaction was stirred at room temperature for 1 hour. The solvent was removed to provide the desired product as HCl salt which was used in the next step without further purification. LCMS calculated for $C_{20}H_{26}ClN_6O$ (M+H)$^+$: m/z=401.2. found: =401.2.

Step 7. N-{-[5-chloro-2-methoxy-4-methyl-3-(1-methylpiperidin-4-yl)phenyl]ethyl}-9H-purin-6-amine 12.0 M Formaldehyde in water (0.4 mL, 5 mmol) was added to a mixture of N-[1-(5-chloro-2-methoxy-4-methyl- 3-piperidin-4-ylphenyl)ethyl]-9H-purin-6-amine (200 mg, 0.5 mmol) and DIPEA (0.35 mL, 2.0 mmol) in methylene chloride (5 mL) at 0° C. The reaction was stirred for 10 minutes, and after this time sodium triacetoxyborohydride (160 mg, 0.75 mmol) was added. The reaction was stirred at 0° C. for 1 hour. The mixture was purified on RP-HPLC (XBridge C18 Column, eluting with a gradient of acetonitrile in water with 0.2% ammonium hydroxide, at flow rate of 30 mL/min) to give the desired product. LCMS calculated for $C_{21}H_{28}ClN_6O$ (M+H)$^+$: m/z=415.2. found: 415.3. $^1$H NMR (DMSO-d$_6$, 500 MHz) δ 9.67 (1H, br s), 8.72 (1H, br s), 8.35 (2H, s), 7.51 (1H, s), 5.75 (1H, m), 3.88 (3H, s), 3.49 (2H, m), 3.34 (1H, m), 3.12 (2H, m), 2.81 (1.5H, s), 2.80 (1.5H, s), 2.44-2.31 (2H, m), 2.36 (3H, s), 1.79 (2H, m), 1.49 (3H, d, J=6.5 Hz) ppm.

Example 177

6-{3-chloro-6-methoxy-2-methyl-5-[1-(9H-purin-6-ylamino)ethyl]phenyl}-N,N-dimethylpyridine-2-carboxamide bis(2,2,2-trifluoroacetate)

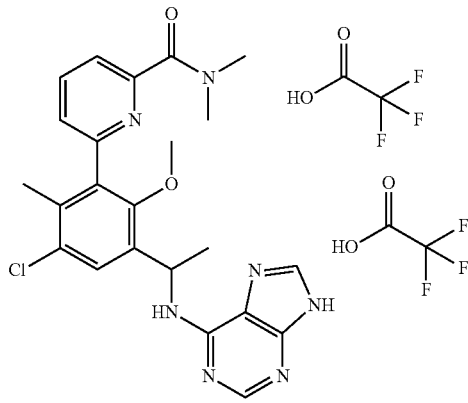

Step 1. tert-butyl {1-[5-chloro-2-methoxy-4-methyl-3-(4,4,5,5-tetramethyl-1,3,2-dioxaborolan-2-yl)phenyl]ethyl}carbamate The tert-butyl [1-(3-bromo-5-chloro-2-methoxy-4-methylphenyl)ethyl]carbamate (1.5 g, 4.0 mmol, from Example 113, Step 1 Peak 2), was combined with potassium acetate (1.2 g, 12 mmol) and 4,4,5,5,4',4',5',5'-octamethyl-[2,2']bi [[1,3,2]dioxaborolanyl](2.0 g, 7.9 mmol) in dimethyl sulfoxide (15 mL, 210 mmol) at room temperature. The reaction was degassed with nitrogen and the [1,1'-bis(diphenylphosphino)ferrocene]dichloropalladium(II), complex with dichloromethane (1:1) (0.3 g, 0.4 mmol) was added. The reaction vessel was sealed and heated in an oil bath to 95° C. After heating for 20 h the starting material was consumed. The reaction was allowed to cool and then diluted with EtOAc and washed with water, brine, dried over magnesium sulfate and concentrated to give the crude product as a dark colored oil. The oil was purified by chromatography on silica gel eluting with a hexane:EtOAc gradient to give tert-butyl {1-[5-chloro-2-methoxy-4-methyl-3-(4,4,5,5-tetramethyl-1,3,2-dioxaborolan-2-yl)phenyl] ethyl}carbamate as a semisolid (1.1 g, 65%). LCMS calculated for $C_{16}H_{24}BClO_3$ (M+H)$^+$: m/z=310.6. found: 310.0.

Step 2. methyl 6-(3-{1-[(tert-butoxycarbonyl) amino]ethyl}-5-chloro-2-methoxy-6-methylphenyl) pyridine-2-carboxylate The tert-butyl {1-[5-chloro-2-methoxy-4-methyl-3-(4,4,5,5-tetramethyl-1,3,2-dioxaborolan-2-yl)phenyl] ethyl}carbamate (0.3 g, 0.7 mmol), methyl 6-bromopyridine-2-carboxylate (0.38 g, 1.8 mmol), [1,1'-bis(diphenylphosphino)ferrocene]dichloropalladium(II) complex with dichloromethane (1:1) (0.0575 g, 0.0705 mmol), palladium acetate (0.008 g, 0.04 mmol), cuprous monochloride (0.070 g, 0.70 mmol), and cesium carbonate (0.46 g, 1.4 mmol) were combined in DMF (18 mL). The mixture was degassed with nitrogen gas for 5 min and heated to 100° C. overnight in a sealed tube. The reaction was allowed to cool, diluted with EtOAc and washed with water, brine, dried over magnesium sulfate and concentrated to give crude product as a dark oil. The product was purified by chromatography on silica gel eluting with hexane:EtOAc gradient to give methyl 6-(3-{1-[(tert-butoxycarbonyl) amino]ethyl}-5-chloro-2-methoxy-6-methylphenyl)pyridine-2-carboxylate as a viscous oil (0.15 g, 50%). LCMS calculated for $C_{22}H_{28}ClN2O_5$ (M+H)$^+$: m/z=435.1. found: 435.1.

Step 3. 6-(3-{1-[(tert-butoxycarbonyl)amino]ethyl}-5-chloro-2-methoxy-6-methylphenyl)pyridine-2-carboxylic acid The methyl 6-(3-{1-[(tert-butoxycarbonyl)amino]ethyl}-5-chloro-2-methoxy-6-methylphenyl)pyridine-2-carboxylate (0.075 g, 0.17 mmol) was dissolved in methanol (5.0 mL) and the lithium hydroxide-monohydrate (0.022 g, 0.52 mmol) dissolved in water (0.5 mL) was added. The reaction was stirred at room temperature and monitored by LC/MS. After stirring for 18 h the reaction was complete. Acetic acid was added to adjust the pH 5 and the reaction was concentrated to give a semisolid residue. The crude was diluted with acetonitrile and concentrated 3× to remove residual water and finally give 6-(3-{1-[(tert-butoxycarbonyl)amino] ethyl}-5-chloro-2-methoxy-6-methylphenyl)pyridine-2-carboxylic acid as a crude solid residue. LCMS calculated for $C_{17}H_{18}ClN_2O_5$ (M+H)$^+$: m/z=365.1. found: 365.0.

Step 4. tert-butyl [1-(5-chloro-3-{6-[(dimethylamino)carbonyl]pyridin-2-yl}-2-methoxy-4-methylphenyl)ethyl]carbamate The 6-(3-{1-[(tert-butoxycarbonyl)amino]ethyl}-5-chloro-2-methoxy-6-methylphenyl)pyridine-2-carboxylic acid (0.07 g, 0.2 mmol) was combined with DMF (3.0 mL) and DIPEA (0.14 mL, 0.83 mmol) at room temperature and the N,N,N',N'-tetramethyl-O-(7-azabenzotriazol-1-yl)uronium hexafluorophosphate (0.13 g, 0.33 mmol) was added. The reaction stirred for 10 min and dimethylamine hydrochloride (0.041 g, 0.50 mmol) was added. The reaction was stirred at room temperature for 3 h and was complete by LC/MS. The reaction mixture was diluted with EtOAc and washed with water, saturated ammonium chloride, brine, dried over magnesium sulfate and concentrated to give the desired product as an oil (0.06 g, 83%). LCMS calculated for $C_{23}H_{31}ClN_3O_4$ (M+H)$^+$: m/z=448.2. found: 448.1.

Step 5. 6-{3-[1-aminoethyl]-5-chloro-2-methoxy-6-methylphenyl}-N,N-dimethylpyridine-2-carboxamide dihydrochloride The tert-butyl [1-(5-chloro-3-{6-[(dimethylamino)carbonyl]pyridin-2-yl}-2-methoxy-4-methylphenyl)ethyl]carbamate (0.06 gm, 0.13 mmol) was dissolved in 4 M HCl in dioxane (3 mL) and was stirred for 1 hour. The reaction was complete and the mixture was concentrated in vacuo to give the crude product as an oil. LCMS calculated for $C_{18}H_{23}ClN_3O_2$ (M+H)$^+$: m/z=348.1. found: 348.1.

Step 6. 6-[3-chloro-6-methoxy-2-methyl-5-(1-{[9-(tetrahydro-2H-pyran-2-yl)-9H-purin-6-yl]amino}ethyl)phenyl]-N,N-dimethylpyridine-2-carboxamide The 6-{3-[1-aminoethyl]-5-chloro-2-methoxy-6-methylphenyl}-N,N-dimethylpyridine-2-carboxamide (0.025 g, 0.072 mmol) was combined with 6-chloro-9-(tetrahydro-2H-pyran-2-yl)-9H-purine (0.022 g, 0.14 mmol, from Example 176, Step 4) in 2-methoxyethanol (1.0 mL, 13 mmol) and DIPEA (0.037 g, 0.29 mmol) in a sealed tube. The reaction was heated to 105° C. in an oil bath for 18 hours. Without workup, the reaction was carried into the next step.

Step 7. 6-{3-chloro-6-methoxy-2-methyl-5-[1-(9H-purin-6-ylamino)ethyl]phenyl}-N,N-dimethylpyridine-2-carboxamide bis(2,2,2-trifluoroacetate)

6-[3-Chloro-6-methoxy-2-methyl-5-(1-{[9-(tetrahydro-2H-pyran-2-yl)-9H-purin-6-yl]amino}ethyl)phenyl]-N,N-dimethylpyridine-2-carboxamide (0.04 gm, 0.072 mmol, from Example 177, Step 6) was dissolved in a solution of 4 M HCl in dioxane (2 mL) and was stirred for 1 hour. The reaction mixture was purified without workup by prep HPLC on a C-18 column eluting a water:acetonitrile gradient buffered with TFA (pH 2) to give the desired compound as a white amorphous solid (0.015 g, 45%). LCMS calculated for $C_{23}H_{25}ClN_7O_2$ $(M+H)^+$: m/z=466.1. found: 466.0. $^1$H NMR (300 MHz, DMSO-$d_6$) δ 8.59 (s, 1H), 8.29 (m, 2H), 8.03 (t, J=7.8 Hz, 1H), 7.64 (s, 1H), 7.57 (d, J=7.7 Hz, 1H), 7.49 (d, J=7.7 Hz, 1H), 5.72 (m, 1H), 3.41 (s, 3H), 2.99 (s, 3H), 2.91 (s, 3H), 1.96 (s, 3H), 1.52 (d, J=6.9 Hz, 3H).

Example 178

6-{3-chloro-6-methoxy-2-methyl-5-[1-(9H-purin-6-ylamino)ethyl]phenyl}-N,N-dimethylpyridazine-4-carboxamide bis(2,2,2-trifluoroacetate)

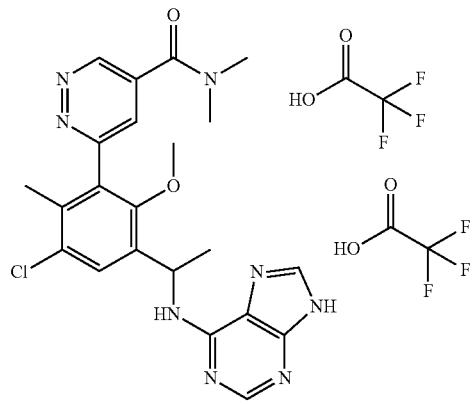

Step 1. 6-chloropyridazine-4-carbonyl chloride 6-oxo-1,6-dihydropyridazine-4-carboxylic acid (0.20 g, 1.4 mmol, Ark Pharm, Inc, catalog# AK-26372) was dissolved in phosphoryl chloride (8.0 mL, 86 mmol) and DMF (0.080 mL) under nitrogen. The reaction was heated to 80° C. in an oil bath and monitored by LC/MS. After heating for 3 h the starting material was consumed (monitored for the methyl ester by adding aliquot to methanol). This reaction mixture was allowed to cool to room temperature and was concentrated in vacuo to remove the residual phosphoryl chloride. The crude product was used in the next step without purification.

Step 2. 6-chloro-N,N-dimethylpyridazine-4-carboxamide

The 6-chloropyridazine-4-carbonyl chloride (0.18 g, 1.04 mmol was dissolved in methylene chloride (12.0 mL) and a 2.0 M dimethylamine in THF (1.4 mL) was added at room temperature. The reaction was stirred for 1 h and was complete. The reaction was partitioned between EtOAc and water. The organic layer was washed with 1 N HCl, brine, dried over magnesium sulfate and concentrated to give the crude product as an amber oil. The product was purified by chromatography on silica gel eluting with hexane:EtOAc gradient to give 6-chloro-N,N-dimethylpyridazine-4-carboxamide as a colorless viscous oil, (0.16 gm, 60%). LCMS calculated for $C_7H_9ClN_3O$ $(M+H)^+$: m/z=186.0. found: 185.9.

Step 3. 6-{3-chloro-6-methoxy-2-methyl-5-[1-(9H-purin-6-ylamino)ethyl]phenyl}-N,N-dimethylpyridazine-4-carboxamide bis(2,2,2-trifluoroacetate)

Using procedures analogous to Example 177, but using 6-chloro-N,N-dimethylpyridazine-4-carboxamide from Example 178, Step 2, the title compound was prepared and purified by prep HPLC on a C-18 column eluting with water:acetontrile gradient buffered to pH 2 with TFA to give 6-{3-chloro-6-methoxy-2-methyl-5-[1-(9H-purin-6-ylamino)ethyl]phenyl}-N,N-dimethylpyridazine-4-carboxamide as a white amorphous solid (0.015 g, 20%). LCMS calculated for $C_{22}H_{24}ClN_8O_2$ $(M+H)^+$: m/z=467.2. found: 467.2. $^1$H NMR (300 MHz, DMSO-$d_6$) δ 9.34 (d, J=2.0 Hz, 1H), 8.70 (s, 1H), 8.32 (m, 2H), 7.86 (d, J=2.0 Hz, 1H), 7.73 (s, 1H), 5.74 (m, 1H), 3.43 (s, 3H), 3.02 (s, 3H), 2.93 (s, 3H), 2.01 (s, 3H), 1.54 (d, J=6.9 Hz, 3H).

Example 179

5-{3-chloro-2-cyano-6-ethoxy-5-[1-(9H-purin-6-ylamino)ethyl]phenyl}-N,N-dimethylpyridine-2-carboxamide bis(2,2,2-trifluoroacetate)

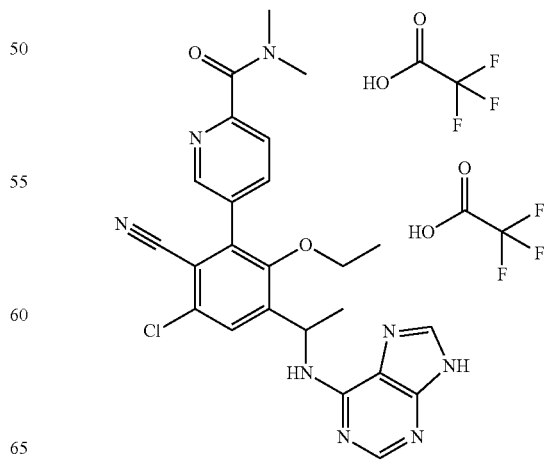

Step 1.
4-acetyl-2-bromo-6-chloro-3-ethoxybenzonitrile

The 1-(3-bromo-5-chloro-4-fluoro-2-hydroxyphenyl)ethanone (3.0 g, 11 mmol, from Example 187, Step 2) was dissolved in DMF (24 mL) and potassium cyanide (0.88 g, 13 mmol) was added. The reaction was heated to 85° C. and monitored by LC/MS. After heating for 18 h the reaction was complete. The reaction was allowed to cool to room temperature and then potassium carbonate (3.1 g, 22 mmol) and iodoethane (1.3 mL, 17 mmol) were added. The reaction was heated to 60° C. overnight. After stirring for 18 h the reaction was complete. The crude was diluted with EtOAc and washed with water, brine, dried over magnesium sulfate and concentrated to give the crude product as a dark oil. The product was purified by chromatography on silica gel eluting with hexane:EtOAc gradient to give 4-acetyl-2-bromo-6-chloro-3-ethoxybenzonitrile as an oil which solidified (2.1 g, 62%). LCMS calculated for $C_{11}H_{10}BrClNO_2$ $(M+H)^+$: m/z=301.9, 303.9. found: 301.6, 303.6.

Step 2. 4-(1-aminoethyl)-2-bromo-6-chloro-3-ethoxybenzonitrile

Titanium tetraisopropoxide (0.82 mL, 2.8 mmol) was added to a mixture of 4-acetyl-2-bromo-6-chloro-3-ethoxybenzonitrile (0.70 g, 2.3 mmol) and 2.0 M ammonia in ethanol (5.78 mL) at 0° C. The reaction was heated and stirred at 60° C. under nitrogen for 3 hours. The reaction was allowed to cool to room temperature, cooled in an ice bath and sodium tetrahydroborate (0.131 g, 3.47 mmol) was added, the solution was stirred at room temperature for another 2 hours. The reaction mixture was quenched with 2 M ammonia in water, and was stirred to allow a precipitate to form. The slurry was filtered and the solid was washed with EtOAc. The organic solvent was removed under vacuum and the residue was dissolved in methylene chloride. The organic layer was then washed with sat'd $NaHCO_3$, water, brine, dried over $MgSO_4$, filtered and concentrated to give 4-(1-aminoethyl)-2-bromo-6-chloro-3-ethoxybenzonitrile as an oil (0.7 g, 100%). The crude was used in the next step without purification. LCMS calculated for $C_{11}H_{13}BrClN_2O$ $(M+H)^+$: m/z=302.9, 304.9. found: 302.9, 304.9.

Step 3. tert-butyl [1-(3-bromo-5-chloro-4-cyano-2-ethoxyphenyl)ethyl]carbamate The 4-(1-aminoethyl)-2-bromo-6-chloro-3-ethoxybenzonitrile (0.7 g, 2.3 mmol) was dissolved in 1,4-dioxane (13 mL) and DIPEA (1.3 mL, 7.7 mmol) and the di-tert-butyldicarbonate (0.757 g, 3.47 mmol) was added. The reaction was allowed to stir at room temperature overnight. The reaction was complete by LC/MS, and the reaction mixture was diluted with EtOAc and washed with 1 N HCl, brine, dried over magnesium sulfate and concentrated to give the crude product as an oil. The product was purified by chromatography on silica gel eluting with hexane:EtOAc gradient to give tert-butyl [1-(3-bromo-5-chloro-4-cyano-2-ethoxyphenyl)ethyl]carbamate as a semi-solid (0.85 g, 90%). LCMS calculated for $C_{11}H_{10}BrClNO$ $(M+H)^+$: m/z=285.9, 287.9. found: 285.9, 287.9. This racemic material was separated by chiral column HPLC: ChiralPak OJ-H 20×250 mm, 15% ethanol:hexane, 15 mL/min, loading 25 mg/mL to give the separated enantiomers (Peak 1 retention time: 5.25 min, Peak 2 retention time: 6.45 min). The peak 2 enantiomer was used further in synthesis.

Step 4.
5-Bromo-N,N-dimethylpyridine-2-carboxamide

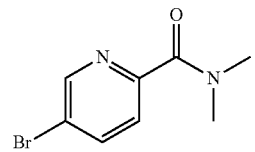

5-Bromopyridine-2-carboxylic acid (20 g, 100 mmol, Frontier Scientific catalog#B1704) was stirred in methylene chloride (30 mL) and cooled to 0° C. 2.0 M Oxalyl chloride in methylene chloride (100 mL) was added slowly followed by DMF (0.8 mL). Vigorous degassing occurred. The mixture was stirred at 0° C. for 30 min and at rt overnight. The mixture was evaporated and redissolved in methylene chloride (130 mL). Dimethylamine hydrochloride (9.8 g, 120 mmol) was added and the mixture was cooled to 0° C. Triethylamine (56.1 mL, 400 mmol) was added slowly (over 5 minutes) which caused significant exotherm and precipitation of a brown/orange solid. The mixture was stirred at rt for 2 h. The mixture was diluted with methylene chloride and washed with saturated sodium bicarbonate, brine, dried over sodium sulfate, filtered and evaporated. Purification on silica gel using ethyl acetate in hexanes (0-60%) gave the desired compound, (22.0 g, 100%). LCMS calculated for $C_8H_{10}BrN_2O$ $(M+H)^+$: m/z=229.0, 231.0. found: 228.9, 230.9.

Step 5. {6-[(Dimethylamino)carbonyl]pyridin-3-yl}boronic acid

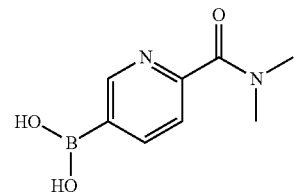

A mixture of 5-bromo-N,N-dimethylpyridine-2-carboxamide (23 g, 98 mmol), 4,4,5,5,4',4',5',5'-octamethyl-[2,2']bi[[1,3,2]dioxaborolanyl](27 g, 110 mmol), [1,1'-bis(diphenylphosphino)ferrocene]dichloropalladium(II), complex with dichloromethane (1:1) (4.8 g, 5.9 mmol), 1,1'-bis(diphenylphosphino)ferrocene (3.3 g, 5.9 mmol), and potassium acetate (30 g, 300 mmol) in 1,4-dioxane (600 mL) was heated at 120° C. for 16 h. The mixture was cooled to rt and diluted with EtOAc. The organic solution was washed with saturated ammonium chloride solution which was discarded and then with water (1 L). The water wash was evaporated to give the desired compound (10 g, 50%). LCMS calculated for $C_8H_{12}BN_2O_3$ $(M+H)^+$: m/z=195.1. found: 195.1.

Step 6. tert-butyl [1-(5-chloro-4-cyano-3-{6-[(dimethylamino)carbonyl]pyridin-3-yl}-2-ethoxyphenyl)ethyl]carbamate The tert-butyl [1-(3-bromo-5-chloro-4-cyano-2-ethoxyphenyl)ethyl]carbamate (0.05 g, 0.1 mmol, Example 179,

223 peak 2) was combined with {6-[(dimethylamino)carbonyl]pyridin-3-yl}boronic acid (0.034 g, 0.17 mmol, Example 179, Step 5) in 1,4-dioxane (3.0 mL) and potassium carbonate (0.034 g, 0.25 mmol) dissolved in water (1.0 mL) in a tube. The reaction was degassed with nitrogen and the tetrakis(triphenylphosphine)palladium(0) (0.03 g, 0.02 mmol) was added and degassed again. The tube was sealed and heated in an oil bath to 90° C. After heating for 18 h the reaction was complete. This was allowed to cool to room temperature and partitioned between EtOAc and water. The organic layer was washed with brine, dried over magnesium sulfate and concentrated to give the crude as a dark oil. The product was purified by chromatography on silica gel eluting with hexane:EtOAc gradient to give tert-butyl [1-(5-chloro-4-cyano-3-{6-[(dimethylamino)carbonyl]pyridin-3-yl}-2-ethoxyphenyl)ethyl]carbamate as a viscous oil (0.04 g, 66%). LCMS calculated for $C_{24}H_{30}ClN_4O_4$ (M+H)$^+$: m/z=473.2. found: 473.1.

Step 7. 5-{3-[1-aminoethyl]-5-chloro-6-cyano-2-ethoxyphenyl}-N,N-dimethylpyridine-2-carboxamide dihydrochloride The tert-butyl [1-(5-chloro-4-cyano-3-{6-[(dimethylamino)carbonyl]pyridin-3-yl}-2-ethoxyphenyl)ethyl]carbamate from the above step (0.04 g, 0.085 mmol) was treated with 4 M HCl in dioxane (4 mL) and stirred at room temperature for 1 hour. The reaction was concentrated in vacuo to give 5-{3-[1-aminoethyl]-5-chloro-6-cyano-2-ethoxyphenyl}-N,N-dimethylpyridine-2-carboxamide as a semi-solid residue (0.05 g, 100%). LCMS calculated for $C_{19}H_{22}ClN_4O_2$ (M+H)$^+$: m/z=373.1. found: 373.1.

Step 8. 5-{3-chloro-2-cyano-6-ethoxy-5-[1-(9H-purin-6-ylamino)ethyl]phenyl}-N,N-dimethylpyridine-2-carboxamide bis(2,2,2-trifluoroacetate)

The 5-{3-[1-aminoethyl]-5-chloro-6-cyano-2-ethoxyphenyl}-N,N-dimethylpyridine-2-carboxamide (0.05 g, 0.1 mmol) was combined with 6-chloro-9-(tetrahydro-2H-pyran-2-yl)-9H-purine (0.047 g, 0.20 mmol, from Example 176, Step 4) in 2-methoxyethanol (3.0 mL) and DIPEA (0.069 mL, 0.39 mmol) in a sealed tube and heated to 105° C. After heating for 18 h the reaction was complete. This was allowed to cool to room temperature and 4 M HCl in dioxane (3 mL) was added. The reaction was stirred for 2 h and was complete. This was concentrated in vacuo and purified by prep HPLC on a C-18 column eluting with water:acetonitrile gradient (buffered to pH 2 with TFA) to give 5-{3-chloro-2-cyano-6-ethoxy-5-[1-(9H-purin-6-ylamino)ethyl]phenyl}-N,N-dimethylpyridine-2-carboxamide as a white amorphous solid (0.020 g, 33%). LCMS calculated for $C_{24}H_{24}ClN_8O_2$ (M+H)$^+$: m/z=491.1. found: 491.1. $^1$H NMR (300 MHz, DMSO-d$_6$) δ 8.75 (s, 1H), 8.53 (m, 1H), 8.33-8.05 (m, 3H), 7.92 (s, 1H), 7.73 (d, J=8.1 Hz, 1H), 5.81 (m, 1H), 4.07-3.89 (m, 1H), 3.42 (m, 1H), 3.04 (s, 3H), 2.96 (s, 3H), 1.56 (d, J=6.9 Hz, 3H), 1.00 (t, J=7.0 Hz, 3H).

224

Example 180

6-chloro-3-ethoxy-2-[6-(1-hydroxyethyl)pyridin-3-yl]-4-[1-(9H-purin-6-ylamino)ethyl]benzonitrile bis (2,2,2-trifluoroacetate)

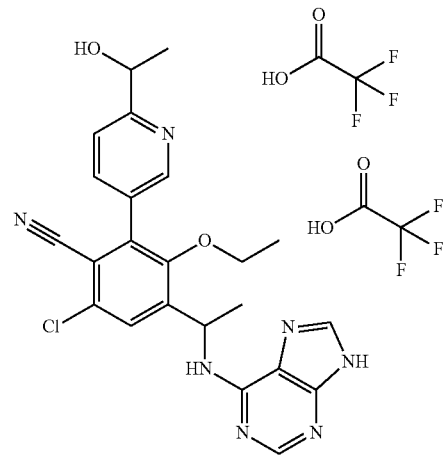

Step 1. [6-(1-hydroxyethyl)pyridin-3-yl]boronic acid 1.0 M Methylmagnesium chloride in THF (0.4 mL, 0.4 mmol) was added dropwise to a mixture of 5-(4,4,5,5-tetramethyl-1,3,2-dioxaborolan-2-yl)pyridine-2-carbaldehyde (50 mg, 0.2 mmol, Frontier Scientific, catalog#F2110) in THF (2 mL) at 0° C. After stirring for 1 h at room temperature, the reaction was quenched with 1 N NH$_4$Cl and was extracted with EtOAc. The organic layer was washed with brine, dried over MgSO$_4$, and concentrated to give the crude [6-(1-hydroxyethyl)pyridin-3-yl]boronic acid. This was used in the next step without purification.

Step 2. 6-chloro-3-ethoxy-2-[6-(1-hydroxyethyl)pyridin-3-yl]-4-[-1-(9H-purin-6-ylamino)ethyl]benzonitrile bis(2,2,2-trifluoroacetate)

Using procedures analogous to Example 179, but using [6-(1-hydroxyethyl)pyridin-3-yl]boronic acid from Step 1 above, in Example 179 Step 4, the title compound was prepared and purified by prep HPLC on a C-18 column eluting with a water:acetonitrile gradient buffered to pH 2 with TFA, to give 6-chloro-3-ethoxy-2-[6-(1-hydroxyethyl)pyridin-3-yl]-4-[1-(9H-purin-6-ylamino)ethyl]benzonitrile as a white amorphous solid (0.011 g, 35%). LCMS calculated for $C_{23}H_{23}ClN_7O_2$ (M+H)$^+$: m/z=464.1. found: 464.0. $^1$H NMR (300 MHz, CD$_3$OD) δ 8.74 (d, J=1.8 Hz, 1H), 8.38 (m 2H), 8.29-8.18 (m, 2H), 7.89 (d, J=8.2 Hz, 1H), 7.76 (s, 1H), 5.86 (m, 1H), 5.05 (m, J=6.5 Hz, 1H), 4.08-3.87 (m, 1H), 3.58-3.43 (m, 1H), 1.70 (d, J=6.9 Hz, 3H), 1.57 (d, J=6.6 Hz, 3H), 1.08 (t, J=7.0 Hz, 3H).

Example 181

N-{1-[5-chloro-3-(5-fluoropyridin-3-yl)-2-methoxy-4-methylphenyl]propyl}-9H-purin-6-amine bis(2,2,2-trifluoroacetate)

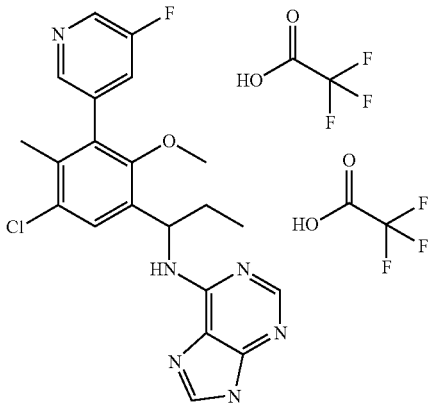

Step 1.
1-(5-chloro-2-hydroxy-4-methylphenyl)propan-1-one

The 4-chloro-3-methyl-phenol (2 g, 10 mmol) and the propionyl chloride (1.8 mL, 20. mmol) were combined and the mixture was heated at 60° C. for 2 hours. The reaction was concentrated in vacuo to remove excess propionyl chloride to give an oil. To this was added aluminum trichloride (2.7 g, 20. mmol) and the mixture was heated at 180° C. for 30 minutes. The reaction mixture was then cooled to room temperature and slowly quenched with 1 N HCl while cooling in an ice bath. The reaction was partitioned between EtOAc and water. The organic layer was washed with 1 N HCl, water, brine, dried over magnesium sulfate and concentrated to give the crude product as a dark oil. The product was purified by chromatography on silica gel eluting with hexane:EtOAc gradient to give 1-(5-chloro-2-hydroxy-4-methylphenyl)propan-1-one as a solid (1.5 g, 60%). LCMS calculated for $C_{10}H_{12}ClO_2$ (M+H)$^+$: m/z=199.0. found: 198.9.

Step 2. 1-(3-bromo-5-chloro-2-methoxy-4-methylphenyl)propan-1-one

The 1-(5-chloro-2-hydroxy-4-methylphenyl)propan-1-one (1.6 g, 8.0 mmol) was dissolved in acetic acid (20.0 mL) and N-bromosuccinimide (1.7 g, 9.7 mmol) was added. The reaction was warmed in an oil bath to 65° C. and monitored by LC/MS. After heating for 3 h the reaction was complete. This was allowed to cool to room temperature and was concentrated in vacuo. The residue was diluted with EtOAc and washed with water (twice), brine, dried over magnesium sulfate and concentrated to give 1-(3-bromo-5-chloro-2-hydroxy-4-methylphenyl)propan-1-one as an amber oil. This oil was dissolved in DMF (10.0 mL) and potassium carbonate (3.3 g, 24 mmol) and methyl iodide (0.75 mL, 12 mmol) were added. The reaction was stirred at 65° C. for 18 hours. The reaction was complete, and the reaction mixture was diluted with EtOAc, washed with water, brine, dried over magnesium sulfate and concentrated to give the crude product as a dark oil. The product was purified by chromatography on silica gel eluting with a hexane:EtOAc gradient to give 1-(3-bromo-5-chloro-2-methoxy-4-methylphenyl)propan-1-one as an oil (1.8 g, 81%). LCMS calculated for $C_{11}H_{13}BrClO_2$ (M+H)$^+$: m/z=290.9, 292.9. found: 290.8, 292.9.

Step 3. tert-butyl [1-(3-bromo-5-chloro-2-methoxy-4-methylphenyl)propyl]carbamate Titanium tetraisopropoxide (3.0 mL, 10 mmol) was added to a mixture of 1-(3-bromo-5-chloro-2-methoxy-4-methylphenyl)propan-1-one (2.5 g, 8.6 mmol) and 2.0 M ammonia in ethanol (21.4 mL) at 0° C. The reaction was heated and stirred at 60° C. under nitrogen for 3 hours. The reaction was allowed to cool to room temperature, cooled in an ice bath and the sodium tetrahydroborate (0.486 g, 12.9 mmol) was added, the solution was stirred at room temperature for another 2 hours. The reaction mixture was quenched with 2 M ammonia in water, and was stirred to form the precipitate. The slurry was filtered, the solids were washed with EtOAc and the organic layer was concentrated in vacuo. The residue was diluted with methylene chloride, washed with sat'd NaHCO$_3$, water, brine, dried over MgSO$_4$, filtered and concentrated to give 1-(3-bromo-5-chloro-2-methoxy-4-methylphenyl)propan-1-amine as an oil. This was diluted with 1,4-dioxane (48 mL) and DIPEA (5.0 mL) and the di-tert-butyldicarbonate (2.81 g, 12.9 mmol) was added. The reaction was allowed to stir at room temperature overnight. The reaction was complete by LC/MS, and the reaction mixture was diluted with EtOAc and washed with 1 N HCl, brine, dried over magnesium sulfate and concentrated to give the crude product as an oil. The product was purified by chromatography on silica gel eluting with a hexane:EtOAc gradient to give tert-butyl [1-(3-bromo-5-chloro-2-methoxy-4-methylphenyl)propyl]carbamate as a semisolid (2.0 g, 80%). LCMS calculated for $C_{11}H_{13}BrClO$ (M+H)$^+$: m/z=274.9, 276.9. found: 274.9, 276.8. This racemic material was separated by chiral column HPLC: ChiralPak AD-H 20×250 mm, 3% ethanol:hexane, 18 mL/min, loading 10 mg/mL, to give the separated enantiomers. Peak 2 tert-butyl [1-(3-bromo-5-chloro-2-methoxy-4-methylphenyl)propyl]carbamate was used further in synthesis.

Step 4. tert-butyl {1-[5-chloro-3-(5-fluoropyridin-3-yl)-2-methoxy-4-methylphenyl]propy}lcarbamate The tert-butyl [1-(3-bromo-5-chloro-2-methoxy-4-methylphenyl)propyl]carbamate peak 2 (0.075 g, 0.19 mmol) was combined with 3-fluoro-5-(4,4,5,5-tetramethyl-1,3,2-dioxaborolan-2-yl)pyridine (0.081 g, 0.29 mmol, Frontier Scientific, catalog #F2018) in 1,4-dioxane (4.6 mL) and potassium carbonate (0.053 g, 0.38 mmol) in water (1.5 mL) in a tube. This was degassed with nitrogen and the tetrakis(triphenylphosphine)palladium(0) (0.02 g, 0.02 mmol) was added. The reaction was degassed with nitrogen, sealed and heated to 90° C. in an oil bath. The reaction was complete after 18 h, and the reaction mixture was allowed to cool and partitioned between EtOAc and water. The organic layer was washed with brine, dried over magnesium sulfate and concentrated to give the crude product as an oil. The product was purified by chromatography on silica gel eluting with a hexane:EtOAc gradient to give tert-butyl {1-[5-chloro-3-(5-fluoropyridin-3-yl)-2-methoxy-4-methylphenyl]propyl}carbamate as a viscous oil (0.05 g, 77%). LCMS calculated for $C_{21}H_{27}ClFN_2O_3$ (M+H)$^+$: m/z=409.1. found: 409.1.

Step 5. 1-[5-chloro-3-(5-fluoropyridin-3-yl)-2-methoxy-4-methylphenyl]propan-1-amine dihydrochloride The tert-butyl {1-[5-chloro-3-(5-fluoropyridin-3-yl)-2-methoxy-4-methylphenyl]propyl}carbamate (0.05 g, 0.12 mmol) was diluted with 4 M HCl in dioxane (4 mL) and was stirred at room temperature for 1 hour. The reaction was complete and the reaction mixture was concentrated to give 1-[5-chloro-3-(5-fluoropyridin-3-yl)-2-methoxy-4-methylphenyl]propan-1-amine as a semi-solid (100%). LCMS calculated for $C_{16}H_{16}ClFNO$ $(M+H)^+$: m/z=292.0. found: 292.0.

Step 6. N-{1-[5-chloro-3-(5-fluoropyridin-3-yl)-2-methoxy-4-methylphenyl]propyl}-9H-purin-6-amine bis(2,2,2-trifluoroacetate)

The 1-[5-chloro-3-(5-fluoropyridin-3-yl)-2-methoxy-4-methylphenyl]propan-1-amine (0.030 g, 0.097 mmol) was combined with 6-chloro-9-(tetrahydro-2H-pyran-2-yl)-9H-purine (0.035 g, 0.14 mmol, from Example 176, Step 4) in 2-methoxyethanol (2.0 mL) and DIPEA (0.051 mL, 0.29 mmol) in a sealed tube. The reaction was heated to 105° C. After heating overnight, the reaction was allowed to cool to room temperature and was treated with 4 M HCl in dioxane (3.0 mL) at room temperature. After stirring for 2 h the reaction was concentrated in vacuo to give a residue that was purified by prep HPLC on C-18 column eluting with a water:acetonitrile gradient buffered to pH 2 with TFA to give N-{1-[5-chloro-3-(5-fluoropyridin-3-yl)-2-methoxy-4-methylphenyl]propyl}-9H-purin-6-amine as a white amorphous solid (0.012 g, 50%). LCMS calculated for $C_{21}H_{21}ClFN_6O$ $(M+H)^+$: m/z=427.1. found: 427.1. $^1H$ NMR (300 MHz, DMSO-$d_6$) δ 8.90 (m, 1H), 8.65 (d, J=2.1 Hz, 1H), 8.38 (m, 3H), 7.82 (d, J=26.1 Hz, 1H), 7.67 (s, 1H), 5.57 (m, 1H), 3.39 (s, 3H), 2.03 (s, 3H), 1.99-1.76 (m, 2H), 0.95 (t, J=7.3 Hz, 3H).

Example 182

N-(1-{5-chloro-2-methoxy-4-methyl-3-[5-(methylsulfonyl)pyridin-3-yl]phenyl}propyl)-9H-purin-6-amine bis(2,2,2-trifluoroacetate)

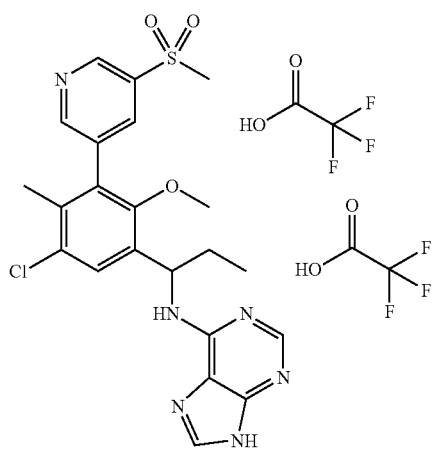

The title compound was prepared by methods analogous to Example 181, but using 3-(methylsulfonyl)-5-(4,4,5,5-tetramethyl-1,3,2-dioxaborolan-2-yl)pyridine (Peptech, catalog#BE358) in Step 4. The product was purified by prep HPLC on a C-18 column eluting with water: acetonitrile gradient buffered to pH 2 with TFA to give N-(1-{5-chloro-2-methoxy-4-methyl-3-[5-(methylsulfonyl)pyridin-3-yl]phenyl}propyl)-9H-purin-6-amine as white amorphous solid (0.012 g, 30%). LCMS calculated for $C_{22}H_{24}ClN_6O_3S$ $(M+H)^+$: m/z=487.1. found: 487.0. $^1H$ NMR (300 MHz, DMSO-$d_6$) δ 9.12 (s, 1H), 8.87 (m, 2H), 8.32 (m, 3H), 7.71 (s, 1H), 5.57 (m, 1H), 3.39 (s, 6H), 2.05 (s, 3H), 1.91 (m, 2H), 0.96 (t, J=7.3 Hz, 3H).

Example 183

(5-{3-chloro-6-methoxy-2-methyl-5-[1-(9H-purin-6-ylamino)ethyl]phenyl}pyridin-2-yl)methanol bis(2,2,2-trifluoroacetate)

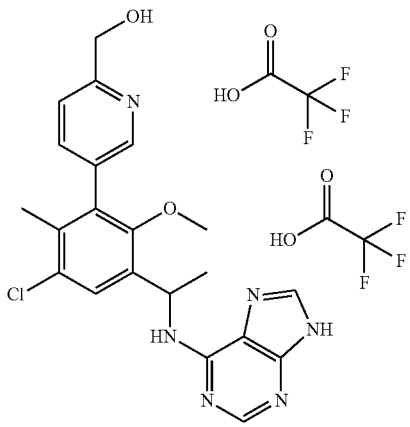

Step 1. tert-butyl {1-[5-chloro-3-(6-formylpyridin-3-yl)-2-methoxy-4-methylphenyl]ethyl}carbamate To a mixture of tert-butyl [1-(3-bromo-5-chloro-2-methoxy-4-methylphenyl)ethyl]carbamate (200 mg, 0.5 mmol, from Example 113, Step 1 peak 2) and 5-(4,4,5,5-tetramethyl-1,3,2-dioxaborolan-2-yl)pyridine-2-carbaldehyde (150 mg, 0.63 mmol, Frontier Scientific, catalog#F2110) in 1,4-dioxane (4 mL) was added potassium carbonate (200 mg, 2 mmol) in water (2 mL). The reaction was degassed with $N_2$ and tetrakis(triphenylphosphine)palladium(0) (40 mg, 0.04 mmol) was added and degassed again with $N_2$. The reaction was heated at 100° C. overnight. The reaction was allowed to cool to room temperature and was partitioned between water and EtOAc. The organic layer was washed with brine, dried over $MgSO_4$, filtered and concentrated to give the crude product. The product was purified by chromatography on silica gel eluting with a hexane:EtOAc gradient to give tert-butyl {1-[5-chloro-3-(6-formylpyridin-3-yl)-2-methoxy-4-methylphenyl]ethyl}carbamate as a yellow oil (0.15 g, 70%). LCMS calculated for $C_{21}H_{26}ClN_2O_4$ $(M+H)^+$: m/z=405.2. found: 405.1.

Step 2. tert-butyl (1-{5-chloro-3-[6-(hydroxymethyl)pyridin-3-yl]-2-methoxy-4-methylphenyl}ethyl) carbamate Sodium tetrahydroborate (2.8 mg, 0.074 mmol) was added to a mixture of tert-butyl {1-[5-chloro-3-(6-formylpyridin-3-yl)-2-methoxy-4-methylphenyl]ethyl}carbamate (20 mg, 0.05 mmol) in methanol (2 mL) at 0° C. The reaction was stirred for 1 h at 0° C. The reaction mixture was partitioned between water and EtOAc. The combined organic layers was washed with brine, dried over MgSO$_4$, filtered and concentrated to give crude product. This crude was used for next step.

Step 3. (5-{3-chloro-6-methoxy-2-methyl-5-[1-(9H-purin-6-ylamino)ethyl]phenyl}pyridin-2-yl)methanol bis(2,2,2-trifluoroacetate)

The title compound was prepared by methods analogous to Example 177 starting with Step 5, but using tert-butyl (1-{5-chloro-3-[6-(hydroxymethyl)pyridin-3-yl]-2-methoxy-4-methylphenyl}ethyl)carbamate from Step 2 above to give the crude product. The reaction product was purified on prep HPLC on a C-18 column eluting with a water:acetonitrile gradient buffered with TFA to give (5-{3-chloro-6-methoxy-2-methyl-5-[1-(9H-purin-6-ylamino)ethyl]phenyl}pyridin-2-yl)methanol as a white amorphous solid (0.005 g, 20%). LCMS calculated for C$_{21}$H$_{22}$ClN$_6$O$_2$ (M+H)$^+$: m/z=425.2. found: 425.1. $^1$H NMR (500 MHz, CD$_3$OD) δ 8.54 (s, 1H), 8.37 (s, 1H), 8.27 (s, 1H), 8.09 (bs, 1H), 7.85 (d, J=8.1 Hz, 1H), 7.62 (s, 1H), 5.86 (m, 1H), 4.91 (s, 2H), 3.48 (s, 3H), 2.18 (s, 3H), 1.70 (d, J=6.9 Hz, 3H).

Example 184

2-(5-{3-chloro-6-methoxy-2-methyl-5-[1-(9H-purin-6-ylamino)ethyl]phenyl}pyridin-2-yl)propan-2-ol bis(2,2,2-trifluoroacetate)

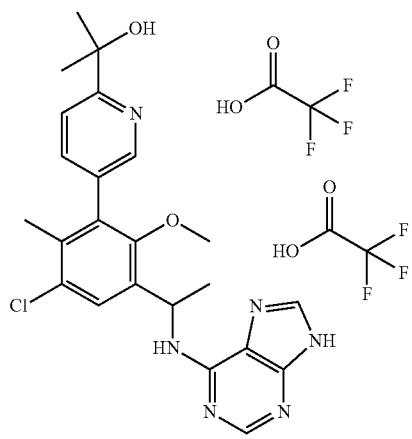

Step 1.
5-bromo-N-methoxy-N-methylpyridine-2-carboxamide

N,O-dimethylhydroxylamine hydrochloride (500 mg, 5 mmol) was added to a mixture of N,N,N',N'-tetramethyl-O-(7-azabenzotriazol-1-yl)uronium hexafluorophosphate (1400 mg, 3.7 mmol), DIPEA (1000 μL, 7 mmol) and 5-bromopyridine-2-carboxylic acid (500 mg, 2 mmol, Frontier Scientific catalog#B1704) in DMF (10 mL) at room temperature. The reaction was stirred overnight and was partitioned between water and EtOAc. The combined organic layer was washed with brine, dried over MgSO$_4$, filtered and concentrated to give the crude product. The product was purified by chromatography on silica gel eluting with a hexane:EtOAc gradient to give 5-bromo-N-methoxy-N-methylpyridine-2-carboxamide as a clear oil (0.5 g, 60%). LCMS calculated for C$_8$H$_{10}$BrN$_2$O$_2$ (M+H)$^+$: m/z=244.9, 246.9. found: 244.9, 246.9.

Step 2. 1-(5-bromopyridin-2-yl)ethanone 3.0 M Methylmagnesium chloride in THF (0.5 mL) was added dropwise to a mixture of 5-bromo-N-methoxy-N-methylpyridine-2-carboxamide (200 mg, 0.8 mmol) in THF (10 mL) at 0° C. After stirring for 1 h at room temperature, the reaction was quenched with 1 N NH$_4$Cl and was extracted with EtOAc. The combined organic layer was washed with brine and dried over MgSO$_4$, concentrated to give the crude product (0.15 g, 90%). This was used in the next step without purification. LCMS calculated for C$_7$H$_7$BrNO (M+H)$^+$: m/z=199.9, 201.9. found: 199.9, 201.9.

Step 3. 2-(5-bromopyridin-2-yl)propan-2-ol 3.0 M Methylmagnesium chloride in THF (0.3 mL) was added dropwise to a mixture of 1-(5-bromopyridin-2-yl)ethanone (100 mg, 0.5 mmol) in THF (10 mL) at 0° C. After stirring for 1 h at room temperature, the reaction was quenched with 1 N NH$_4$Cl and was extracted with EtOAc. The combined organic layer was washed with brine and dried over MgSO$_4$ to give crude product (0.1 g, 100%). Crude was used in next step without purification. LCMS calculated for C$_8$H$_{11}$BrNO (M+H)$^+$: m/z=215.9, 217.9. found: 215.8, 217.8.

Step 4. 2-(5-{3-chloro-6-methoxy-2-methyl-5-[1-(9H-purin-6-ylamino)ethyl]phenyl}pyridin-2-yl)propan-2-ol bis(2,2,2-trifluoroacetate)

The title compound was prepared by methods analogous to Example 177, but using 2-(5-bromopyridin-2-yl)propan-2-ol from Step 3 above to give the crude product. The reaction product was purified by prep HPLC on a C-18 column eluting with a water:acetonitrile gradient buffered with TFA to give 2-(5-{3-chloro-6-methoxy-2-methyl-5-[1-(9H-purin-6-ylamino)ethyl]phenyl}pyridin-2-yl)propan-2-ol as a white amorphous solid (0.005 g, 20%). LCMS calculated for C$_{23}$H$_{26}$ClN$_6$O$_2$ (M+H)$^+$: m/z=453.1. found: 453.0. $^1$H NMR (300 MHz, DMSO-d$_6$) δ 8.85 (m, 1H), 8.42 (m, 3H), 7.86 (m, 2H), 7.64 (s, 1H), 5.75 (m, 1H), 3.36 (s, 3H), 2.03 (s, 3H), 1.55 (d, J=6.9 Hz, 3H), 1.51 (s, 6H).

Example 185

N-(1-{5-chloro-2-methoxy-3-[6-(1-methoxy-1-methylethyl)pyridin-3-yl]-4-methylphenyl}ethyl)-9H-purin-6-amine bis(2,2,2-trifluoroacetate)

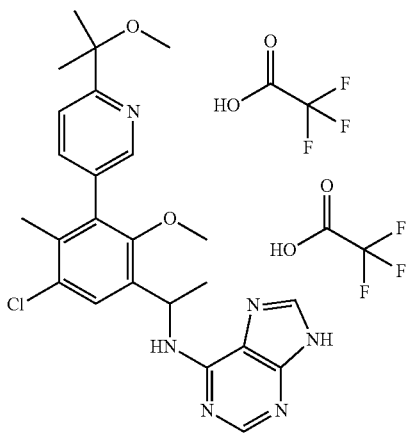

Step 1.
5-bromo-2-(1-methoxy-1-methylethyl)pyridine 2-(5-bromopyridin-2-yl)propan-2-ol (50 mg, 0.2 mmol, from Example 184, Step 3) was added to a mixture of NaH in mineral oil (10 mg, 0.5 mmol) in DMF (5 mL). The reaction was stirred for 30 min and the methyl iodide (30 μL, 0.5 mmol) was added and stirred for 2 hours. The reaction was partitioned between EtOAc and water. The combined organic layer was washed with brine, dried over MgSO$_4$, filtered and concentrated to give crude product 5-bromo-2-(1-methoxy-1-methylethyl)pyridine as an oil (0.05 g, 90%). LCMS calculated for C$_9$H$_{13}$BrNO (M+H)$^+$: m/z=230.0, 232.0. found: 230.0, 231.8.

Step 2. N-(1-{5-chloro-2-methoxy-3-[6-(1-methoxy-1-methylethyl)pyridin-3-yl]-4-methylphenyl}ethyl)-9H-purin-6-amine bis(2,2,2-trifluoroacetate)

The title compound was prepared by methods analogous to Example 177, but using 5-bromo-2-(1-methoxy-1-methylethyl)pyridine from Step 1 above to give the crude product. The reaction product was purified by prep HPLC on a C-18 column eluting with a water:acetonitrile gradient buffered with TFA to give N-(1-{5-chloro-2-methoxy-3-[6-(1-methoxy-1-methylethyl)pyridin-3-yl]-4-methylphenyl}ethyl)-9H-purin-6-amine as a white amorphous solid (0.005 g, 30%). LCMS calculated for C$_{24}$H$_{28}$ClN$_6$O$_2$ (M+H)$^+$: m/z=467.2. found: 467.1. $^1$H NMR (300 MHz, DMSO-d$_6$) δ 9.30 (m, 1H), 8.50 (m, 3H), 7.84 (m, 1H), 7.68 (d, J=8.1 Hz, 1H), 7.62 (s, 1H), 5.76 (m, 1H), 3.31 (s, 3H), 3.10 (s, 3H), 2.04 (s, 3H), 1.57 (d, J=6.8 Hz, 3H), 1.52 (s, 6H).

Example 186

3-ethoxy-6-methyl-2-[5-(methylsulfonyl)pyridin-3-yl]-4-[1-(9H-purin-6-ylamino)ethyl]benzonitrile bis(2,2,2-trifluoroacetate)

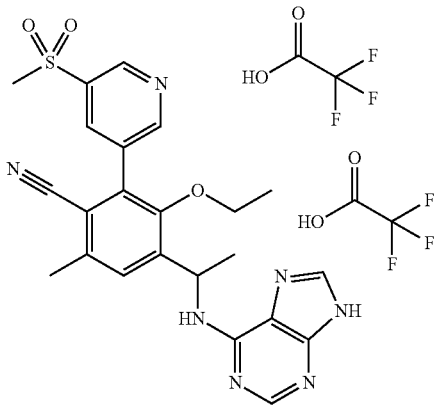

Step 1. tert-butyl (1-{5-chloro-4-cyano-2-ethoxy-3-[5-(methylsulfonyl)pyridin-3-yl]phenyl}ethyl) carbamate To tert-butyl [-1-(3-bromo-5-chloro-4-cyano-2-ethoxyphenyl)ethyl]carbamate (50 mg, 0.1 mmol, from Example 179, Step 3) and 3-(methylsulfonyl)-5-(4,4,5,5-tetramethyl-1,3,2-dioxaborolan-2-yl)pyridine (30. mg, 0.11 mmol, Peptech, catalog #BE358) in 1,4-dioxane (4 mL) was added potassium carbonate (30 mg, 0.2 mmol) in water (2 mL). The reaction was degassed with N$_2$. Tetrakis(triphenylphosphine)palladium(0) (40 mg, 0.04 mmol) was added and degassed again with N$_2$. The reaction was heated at 100° C. overnight. The reaction was allowed to cool to room temperature and was partitioned between EtOAc and water. The combined organic layer was washed with brine, dried over MgSO$_4$, filtered and concentrated to give crude product. The product was purified by chromatography on silica gel eluting with a hexane:EtOAc gradient to give tert-butyl (1-{5-chloro-4-cyano-2-ethoxy-3-[5-(methylsulfonyl)pyridin-3-yl]phenyl}ethyl)carbamate as a yellow oil (0.030 g, 60%). LCMS calculated for C$_{22}$H$_{27}$ClN$_3$O$_5$S (M+H)$^+$: m/z=480.1. found: 480.1.

Step 2. tert-butyl (1-{4-cyano-2-ethoxy-5-methyl-3-[5-(methylsulfonyl)pyridin-3-yl]phenyl}ethyl) carbamate To tert-butyl (1-{5-chloro-4-cyano-2-ethoxy-3-[5-(methylsulfonyl)pyridin-3-yl]phenyl}ethyl)carbamate (60 mg, 0.1 mmol) and methylboronic acid (6.4 mg, 0.11 mmol) in 1,4-dioxane (4 mL) was added sodium carbonate (20 mg, 0.2 mmol) in water (2 mL). The reaction was degassed with N$_2$. Dichloro(bis{di-tert-butyl [4-(dimethylamino)phenyl]phosphoranyl})palladium (4 mg, 0.005 mmol) was added and degassed again with N$_2$. The reaction was heated at 90° C. overnight. The reaction was allowed to cool to room temperature and was partitioned between EtOAc and water. The combined organic layer was washed with brine, dried over MgSO$_4$, filtered and concentrated to give crude product. The product was purified by chromatography on silica gel eluting with a hexane:EtOAc gradient to give tert-butyl (1-{4-cyano-2-ethoxy-5-methyl-3-[5-(methylsulfonyl)pyridin-3-yl]phenyl}ethyl)carbamate as a yellow oil (0.030 g, 50%). LCMS calculated for C$_{23}$H$_{30}$N$_3$O$_5$S (M+H)$^+$: m/z=460.1. found: 460.2.

Step 3. 4-(−1-aminoethyl)-3-ethoxy-6-methyl-2-[5-(methylsulfonyl)pyridin-3-yl]benzonitrile dihydrochloride The tert-butyl (1-{4-cyano-2-ethoxy-5-methyl-3-[5-(methylsulfonyl)pyridin-3-yl]phenyl}ethyl)carbamate (0.030 gm, 0.065 mmol) was dissolved in 4.0 M HCl in dioxane (2 mL) and was stirred for 1 hour. The reaction was concentrated in vacuo to give 4-(1-aminoethyl)-3-ethoxy-6-methyl-2-[5-(methylsulfonyl)pyridin-3-yl]benzonitrile as a semi-solid (0.035 g, 100%). LCMS calculated for C$_{18}$H$_{22}$N$_3$O$_3$S (M+H)$^+$: m/z=360.1. found: 360.2.

Step 4. 3-ethoxy-6-methyl-2-[5-(methylsulfonyl)pyridin-3-yl]-4-[(1S)-1-(9H-purin-6-ylamino)ethyl]benzonitrile bis(2,2,2-trifluoroacetate)

6-Chloro-9-(tetrahydro-2H-pyran-2-yl)-9H-purine (35 mg, 0.15 mmol, from Example 176, Step 4) and DIPEA (0.04 mL, 0.2 mmol) were added to 4-(1-aminoethyl)-3-ethoxy-6-methyl-2-[5-(methylsulfonyl)pyridin-3-yl]benzonitrile in ethanol (2 mL). The reaction was heated to 120° C. overnight. The reaction was allowed to cool to room temperature and was concentrated in vacuo to give 3-ethoxy-6-methyl-2-[5-(methylsulfonyl)pyridin-3-yl]-4-(1-{[9-(tetrahydro-2H-pyran-2-yl)-9H-purin-6-yl]amino}ethyl)benzonitrile as a solid residue. This intermediate was dissolved in 4.0 M HCl in dioxane (1 mL) and was stirred for 10 minutes. The reaction was concentrated and was purified on prep HPLC on a C-18 column eluting with water:acetonitrile gradient buffered with TFA to give 3-ethoxy-6-methyl-2-[5-(methylsulfonyl)pyridin-3-yl]-4-[1-(9H-purin-6-ylamino)ethyl]benzonitrile as a white solid (0.010 g, 16%). LCMS calculated for $C_{23}H_{24}N_7O_3S$ (M+H)$^+$: m/z=478.1. found: 478.1. $^1$H NMR (300 MHz, DMSO-d$_6$) δ 9.18 (d, J=2.2 Hz, 1H), 9.09 (d, J=2.0 Hz, 1H), 8.75 (m, 1H), 8.54 (t, J=2.1 Hz, 1H), 8.33 (m, 2H), 7.68 (s, 1H), 5.80 (m, 1H), 3.99-3.79 (m, 1H), 3.40 (s, 3H), 3.34 (m, 1H), 2.47 (s, 3H), 1.58 (d, J=6.9 Hz, 3H), 0.98 (t, J=6.9 Hz, 3H).

Example 187

N-{1-[5-Chloro-4-fluoro-2-methoxy-3-(1,2,3,6-tetra-hydropyridin-4-yl)phenyl]ethyl}-9H-purin-6-amine hydrochloride

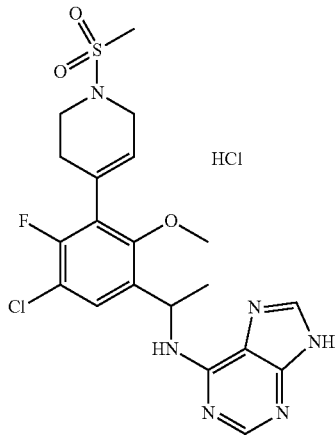 [SMILES: COc1c(C(C)Nc2ncnc3[nH]cnc23)cc(Cl)c(F)c1C1=CCN(S(C)(=O)=O)CC1 ; Cl]

Step 1.
1-(5-Chloro-4-fluoro-2-hydroxyphenyl)ethanone

Acetyl chloride (3.6 mL, 51 mmol) was added to 4-chloro-3-fluorophenol (5.1 g, 35 mmol) and the resulting mixture was heated at 60° C. for 2 hours. Aluminum trichloride (7.0 g, 52 mmol) was added and the mixture was heated at 180° C. for 30 minutes. The mixture was cooled to room temperature. The mixture was cooled to 0° C. and 1 N HCl solution (100 mL) was added dropwise over 30 minutes. The precipitate was washed well with water and dried under vacuum to give the desired compound (6.6 g, 100%).

Step 2. 1-(3-Bromo-5-chloro-4-fluoro-2-hydroxyphenyl)ethanone

To a stirred solution of 1-(5-chloro-4-fluoro-2-hydroxyphenyl)ethanone (8.0 g, 42 mmol) in acetic acid (80 mL) was added N-bromosuccinimide (9.0 g, 50 mmol) and the resulting mixture was stirred at room temperature for 18 hours. The reaction mixture was concentrated, neutralized with saturated sodium bicarbonate solution and extracted with EtOAc. The combined organic layers were washed with brine, dried over sodium sulfate, and then concentrated to dryness under reduced pressure. The residue was purified on silica gel, eluting with 0 to 20% EtOAc in hexane, to yield the desired product (10.5 g, 93%). LCMS calculated for $C_8H_6BrClFO_2$ (M+H)$^+$: m/z=266.9, 268.9. found: 267.1, 269.1.

Step 3.
1-(3-Bromo-5-chloro-4-fluoro-2-methoxyphenyl)ethanone

A mixture of 1-(3-bromo-5-chloro-4-fluoro-2-hydroxyphenyl)ethanone (4.8 g, 18 mmol), potassium carbonate (6.5 g, 47 mmol) and methyl iodide (2.5 mL, 40 mmol) in DMF (10 mL) was heated at 60° C. for 1 hour. The mixture was diluted with water and extracted with EtOAc. The combined organic layers were washed with brine, dried over sodium sulfate, and evaporated. The residue was purified on silica gel, eluting with 0 to 20% EtOAc in hexane, to yield the desired compound (2.2 g, 44%). LCMS calculated for $C_9H_8BrClFO_2$ (M+H)$^+$: m/z=280.9, 282.9. found: 281.0, 283.0.

Step 4.
1-(3-Bromo-5-chloro-4-fluoro-2-methoxyphenyl)ethanol

To a solution of 1-(3-bromo-5-chloro-4-fluoro-2-methoxyphenyl)ethanone (3.8 g, 14 mmol) in methanol (30 mL, 800 mmol) was added sodium tetrahydroborate (0.83 g, 22 mmol) at 0° C. The mix was stirred at 0° C. for 1 hour. Water (10 mL) was added to the mixture. The mixture was concentrated to about 30 mL. The residue was diluted with EtOAc, washed with water and brine, dried over magnesium sulfate and evaporated to yield the desired compound (3.9 g, 100%). LCMS calculated for $C_9H_8BrClFO$ (M-OH)$^+$: m/z=264.9, 266.9. found: 265.0, 267.0.

Step 5. 1-(1-azidoethyl)-3-bromo-5-chloro-4-fluoro-2-methoxybenzene

To a solution of 1-(3-bromo-5-chloro-4-fluoro-2-methoxyphenyl)ethanol (3.9 g, 14 mmol) in methylene chloride (42 mL), cooled at 0° C. was added DIPEA (4.0 mL, 23 mmol) followed by methanesulfonyl chloride (1.6 mL, 20 mmol). The mixture was stirred for 1 h at 0° C. Water (100 mL) was added while cold. The organic layer was separated, washed with brine, dried over magnesium sulfate and concentrated to give 1-(3-bromo-5-chloro-4-fluoro-2-methoxyphenyl)ethyl methanesulfonate. The mesylate was dissolved in DMF (41 mL) and sodium azide (1.8 g, 27 mmol) was added. The reaction was stirred for 2 hours. The reaction mixture was diluted with EtOAc and washed with saturated sodium bicarbonate solution, water and brine, dried over magnesium sulfate and concentrated. Purification on silica gel using 0-30% EtOAc in hexane gave the desired compound (3.3 g, 78%). LCMS calculated for $C_9H_8BrClFO$ (M-N$_3$)$^+$: m/z=264.9, 266.9. found: 265.0, 267.0.

Step 6.
1-(3-Bromo-5-chloro-4-fluoro-2-methoxyphenyl)ethanamine

To the stirred solution of 1-(1-azidoethyl)-3-bromo-5-chloro-4-fluoro-2-methoxybenzene (3.3 g, 11 mmol) in THF (50 mL) and water (10 mL) was added 1.0 M trimethylphosphine in THF (13 mL) at room temperature and the mixture was stirred for 1 hour. The mixture was diluted with EtOAc, washed with saturated sodium bicarbonate solution, water, brine, dried over magnesium sulfate and concentrated to give the desired compound (2.9 g, 95%). LCMS calculated for $C_9H_8BrClFO$ $(M-NH_2)^+$: m/z=264.9, 266.9. found: 265.0, 267.0.

Step 7. N-[1-(3-Bromo-5-chloro-4-fluoro-2-methoxyphenyl)ethyl]-9-(tetrahydro-2H-pyran-2-yl)-9H-purin-6-amine A mix of 1-(3-bromo-5-chloro-4-fluoro-2-methoxyphenyl)ethanamine (1.6 g, 5.7 mmol) 6-chloro-9-(tetrahydro-2H-pyran-2-yl)-9H-purine (2.0 g, 8.5 mmol, from Example 176, Step 4) and DIPEA (3.0 mL, 17 mmol) in ethanol (30 mL) was heated at 100° C. overnight. The reaction mixture was cooled and poured into saturated sodium bicarbonate solution, extracted into EtOAc, washed with water, brine, dried over magnesium sulfate and concentrated. Purification on silica gel using 0-65% EtOAc gave the desired compound (2.8 g, 100%). LCMS calculated for $C_{19}H_{21}BrClFN_5O_2$ $(M+H)^+$: m/z=484.1, 486.1. found: 484.0, 486.0.

Step 8. tert-butyl 4-{3-chloro-2-fluoro-6-methoxy-5-[1-(9H-purin-6-ylamino)ethyl]phenyl}-3,6-dihydropyridine-1(2H)-carboxylate Into a microwave vial was added N-[1-(3-bromo-5-chloro-4-fluoro-2-methoxyphenyl)ethyl]-9-(tetrahydro-2H-pyran-2-yl)-9H-purin-6-amine (85 mg, 0.17 mmol), tert-butyl 4-(4,4,5,5-tetramethyl-1,3,2-dioxaborolan-2-yl)-3,6-dihydropyridine-1(2H)-carboxylate (65 mg, 0.21 mmol, Aldrich #706531), sodium carbonate (420 μL, 0.44 mmol), 1,4-dioxane (1 mL) and tetrakis(triphenylphosphine)palladium(0) (12 mg, 0.010 mmol). The mixture was bubbled with nitrogen for 5 min and heated at 90° C. overnight. The mixture was diluted with water, extracted with EtOAc, dried over magnesium sulfate and concentrated.

Purification on silica gel using 0-100% EtOAc in hexane gave the desired compound (47 mg, 46%). LCMS calculated for $C_{29}H_{37}ClFN_6O_4$ $(M+H)^+$: m/z=586.3. found: 587.2.

Step 9. N-{1-[5-Chloro-4-fluoro-2-methoxy-3-(1,2,3,6-tetrahydropyridin-4-yl)phenyl]ethyl}-9H-purin-6-amine hydrochloride Into a microwave vial was added tert-butyl 4-{3-chloro-2-fluoro-6-methoxy-5-[1-(9H-purin-6-ylamino)ethyl]phenyl}-3,6-dihydropyridine-1(2H)-carboxylate (10.5 mg, 0.021 mmol) and 4.0 M HCl in 1,4-dioxane (1.0 mL). The mixture was stirred for 30 min and evaporated. Methylene chloride (1.0 mL) and DIPEA (15.6 μL, 0.090 mmol) were added followed by methanesulfonyl chloride (4.8 μL, 0.063 mmol). The mixture was stirred for 15 minutes. The solvents were evaporated. 1 N sodium hydroxide solution (1.0 mL) and methanol (1.0 mL) were added and the mixture was stirred for 1 hour. The solvents were evaporated and purification by preparative LC/MS (pH 10) gave the desired compound (4.0 mg, 40%). LCMS calculated for $C_{20}H_{23}ClFN_6O_3S$ $(M+H)^+$: m/z=481.1. found: 481.0. $^1H$ NMR (DMSO-$d_6$, 500 MHz) δ 12.88 (1H, br s), 8.18 (2H, m), 7.63 (1H, m), 5.91 (1H, m), 5.78 (1H, br s), 3.94 (5H, m), 3.40 (2H, m), 2.98 (3H, s), 2.55 (2H, m), 2.39 (2H, m), 1.42 (3H, m).

Example 188

N-{1-[5-Chloro-4-fluoro-2-methoxy-3-(morpholin-4-ylmethyl)phenyl]ethyl}-9H-purin-6-amine

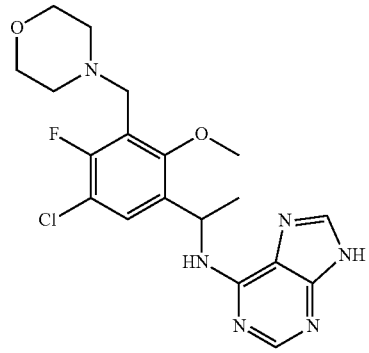 [SMILES: COc1c(C(C)Nc2ncnc3[nH]cnc23)cc(Cl)c(F)c1CN1CCOCC1]

Step 1. N-[1-(5-Chloro-4-fluoro-2-methoxy-3-vinylphenyl)ethyl]-9-(tetrahydro-2H-pyran-2-yl)-9H-purin-6-amine To a solution of N-[1-(3-bromo-5-chloro-4-fluoro-2-methoxyphenyl)ethyl]-9-(tetrahydro-2H-pyran-2-yl)-9H-purin-6-amine (50 mg, 0.10 mmol, from Example 187, Step 7) in water (0.21 mL) was added 1,2-dimethoxyethane (0.7 mL), potassium carbonate (14 mg, 0.10 mmol), pyridine: trivinylboroxin (1:1) (26 mg, 0.10 mmol) and tetrakis(triphenylphosphine)Pd(0) (5.2 mg, 0.0045 mmol). The mixture was bubbled with nitrogen for five min and heated at 80° C. overnight. The reaction was diluted with water and EtOAc. The combined organic layers were washed with brine, dried over sodium sulfate and concentrated. Purification on silica gel using 0-100% EtOAc in hexane gave the desired compound (29 mg, 60%). LCMS calculated for $C_{21}H_{24}ClFN_5O_2$ $(M+H)^+$: m/z=432.2. found: 432.1.

Step 2. 3-Chloro-2-fluoro-6-methoxy-5-(1-{[9-(tetrahydro-2H-pyran-2-yl)-9H-purin-6-yl]amino}ethyl)benzaldehyde N-[1-(5-Chloro-4-fluoro-2-methoxy-3-vinylphenyl)ethyl]-9-(tetrahydro-2H-pyran-2-yl)-9H-purin-6-amine (240 mg, 0.56 mmol) was dissolved in THF (10 mL) and 0.16 M osmium tetraoxide in water (700 μL) was added. Sodium metaperiodate (360 mg, 1.7 mmol) and water (1 mL, 60 mmol) were added. The reaction was stirred at 60° C. for 2 hours. Reagents were doubled. 0.16 M osmium tetraoxide in water (700 μL) was added. Sodium metaperiodate (360 mg, 1.7 mmol) and water (1 mL) were added and the mixture was warmed to 60° C. for another 2 hours. The mixture was evaporated and the solids were extracted with dichloromethane. The extracts were purified on silica gel using 0-60% EtOAc in hexanes to give the desired compound (50 mg, 20%). LCMS calculated for $C_{20}H_{22}ClFN_5O_3$ $(M+H)^+$: m/z=434.1. found: 434.1.

Step 3. N-{1-[5-Chloro-4-fluoro-2-methoxy-3-(morpholin-4-ylmethyl)phenyl]ethyl}-9H-purin-6-amine A mixture of 3-chloro-2-fluoro-6-methoxy-5-(1-{[9-(tetrahydro-2H-pyran-2-yl)-9H-purin-6-yl]amino}ethyl)benzaldehyde (10 mg, 0.023 mmol), in THF (0.95 mL) was stirred at 40° C. for 1 hour. Sodium triacetoxyborohydride (15 mg, 0.069 mmol) and acetic acid (50 μL, 0.88 mmol) were added and the mixture was stirred at 40° C. overnight.

Morpholine (20 μL, 0.23 mmol) and sodium cyanoborohydride (14 mg, 0.23 mmol) were added and the mixture was heated at 40° C. for 1 hour. The solvents were stripped down and few drops of trifluoroacetic acid/THF solution (1:1) were added and the mixture stirred for 30 minutes. The mixture was treated with 6.0 M HCl in water (0.5 mL, 3 mmol) for 30 minutes. Purification by preparative LCMS (pH 10) gave the desired compound (3.4 mg, 35%). LCMS calculated for $C_{19}H_{23}ClFN_6O_2$ (M+H)$^+$: m/z=421.2. found: 421.1. $^1$H NMR (DMSO-d$_6$, 500 MHz) δ 12.91 (1H, br s), 8.17 (2H, m), 7.72 (1H, m), 5.89 (1H, br s), 4.05 (3H, s), 3.50 (7H, m), 2.41 (4H, m), 1.42 (3H, m).

Example 189

5-{3-Chloro-6-methoxy-2-methyl-5-[1-(9H-purin-6-ylamino)ethyl]phenyl}-3-isopropyl-1,3-oxazolidin-2-one trifluoroacetate

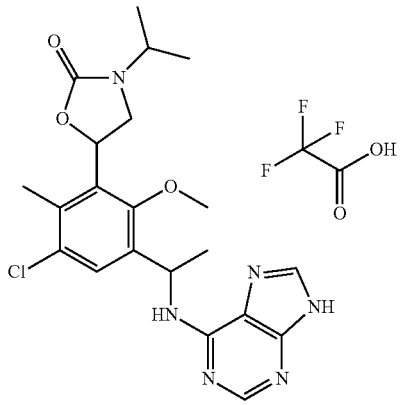 [SMILES: COc1c(C(C)Nc2ncnc3[nH]cnc23)cc(Cl)c(C)c1C1CN(C(C)C)C(=O)O1 ; O=C(O)C(F)(F)F]

Step 1. tert-Butyl [1-(5-chloro-2-methoxy-4-methyl-3-vinylphenyl)ethyl]carbamate To a solution of tert-butyl [1-(3-bromo-5-chloro-2-methoxy-4-methylphenyl)ethyl]carbamate (80 mg, 0.20 mmol) (Example 113, Step 1; peak 2 from chiral separation) in water (0.44 mL) was added 1,2-dimethoxyethane (1.0 mL), potassium carbonate (29 mg, 0.21 mmol), pyridine:trivinylboroxin (1:1) (80 mg, 0.32 mmol) and tetrakis(triphenylphosphine)palladium(0) (11 mg, 0.0092 mmol). The resulting suspension was heated at 80° C. overnight. The reaction was diluted with water and EtOAc. The aqueous phase was extracted with EtOAc once. The combined organic solutions were washed with brine, dried over sodium sulfate and concentrated. The residue was purified on silica gel using 0-100% EtOAc in hexane to give the desired compound (68 mg, 100%). LCMS calculated for $C_{12}H_{14}ClO$ (M-NHBoc): m/z=209.1. found: 209.0.

Step 2. N-[1-(5-Chloro-2-methoxy-4-methyl-3-vinylphenyl)ethyl]-9-(tetrahydro-2H-pyran-2-yl)-9H-purin-6-amine tert-Butyl [1-(5-chloro-2-methoxy-4-methyl-3-vinylphenyl)ethyl]carbamate was stirred in 4 N HCl (1.0 mL) for 30 min and evaporated to give 1-(5-chloro-2-methoxy-4-methyl-3-vinylphenyl)ethanamine hydrochloride (480 mg, 1.8 mmol) which was stirred in 1-butanol (86 mL), with DIPEA (1.6 mL, 9.1 mmol) and 6-chloro-9-(tetrahydro-2H-pyran-2-yl)-9H-purine (650 mg, 2.7 mmol, from Example 176, Step 4). The reaction mixture was heated at 120° C. for 2 hours. The reaction mixture was cooled to room temperature and extracted with EtOAc. The extracts were washed with brine and evaporated. Purification on silica gel using 0-50% EtOAc in hexane gave the desired compound (780 mg, 100%). LCMS calculated for $C_{22}H_{27}ClN_5O_2$ (M+H)$^+$: m/z=428.2. found: 428.1.

Step 3. N-[1-(5-Chloro-2-methoxy-4-methyl-3-oxiran-2-ylphenyl)ethyl]-9-(tetrahydro-2H-pyran-2-yl)-9H-purin-6-amine N-[1-(5-chloro-2-methoxy-4-methyl-3-vinylphenyl) ethyl]-9-(tetrahydro-2H-pyran-2-yl)-9H-purin-6-amine (740 mg, 1.7 mmol) was stirred in methylene chloride (5.7 mL) and m-chloroperbenzoic acid (2.1 g, 8.7 mmol) was added. The mixture was stirred overnight. The suspension was filtered and the solids were washed with dichloromethane. Evaporation of the filtrates gave the desired compound.

Step 4. 1-[3-Chloro-6-methoxy-2-methyl-5-(1-{[9-(tetrahydro-2H-pyran-2-yl)-9H-purin-6-yl] amino}ethyl)phenyl]-2-(isopropylamino)ethanol N-[1-(5-chloro-2-methoxy-4-methyl-3-oxiran-2-ylphenyl)ethyl]-9-(tetrahydro-2H-pyran-2-yl)-9H-purin-6-amine (140.0 mg, 0.32 mmol) was stirred in methylene chloride (1.1 mL). Isopropylamine (124 μL, 1.6 mmol) and DIPEA (282 μL, 1.62 mmol) were added. The mixture was stirred at 80° C. overnight. Methanol was added and purification by preparative LC/MS (pH 10) gave the desired compound (12.9 mg, 8%). LCMS calculated for $C_{25}H_{36}ClN_6O_3$ (M+H)$^+$: m/z=503.3. found: 503.1.

Step 5. 5-{3-Chloro-6-methoxy-2-methyl-5-[1-(9H-purin-6-ylamino)ethyl]phenyl}-3-isopropyl-1,3-oxazolidin-2-one trifluoroacetate To a solution of 1-[3-chloro-6-methoxy-2-methyl-5-((1S)-1-{[9-(tetrahydro-2H-pyran-2-yl)-9H-purin-6-yl] amino}ethyl)phenyl]-2-(ispropylamino)ethanol (7.0 mg, 0.014 mmol) in THF (0.2 mL, 2 mmol), N,N-carbonyldiimidazole (3.1 mg, 0.019 mmol) was added and the mixture was heated at 70° C. for 1 hour. The solvents were evaporated. 4.0 M HCl in 1,4-dioxane (1.0 mL) was added and the mixture was stirred for 30 minutes. Evaporation and purification by preparative LC/MS (pH 2) gave the desired compound (2.0 mg, 37%). LCMS calculated for $C_{21}H_{26}ClN_6O_3$ (M+H)$^+$: m/z=445.2. found: 445.1.

Example 190

1-{3-Chloro-6-methoxy-2-methyl-5-[1-(9H-purin-6-ylamino)ethyl]phenyl}-2-morpholin-4-ylethanol bis(trifluoroacetate)

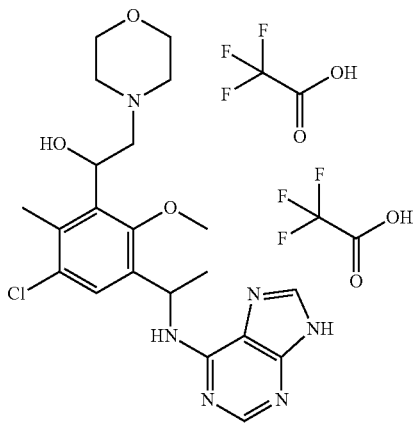

Step 1. tert-Butyl [1-(5-chloro-2-methoxy-4-methyl-3-oxiran-2-ylphenyl)ethyl]carbamate tert-Butyl [1-(5-chloro-2-methoxy-4-methyl-3-vinylphenyl)ethyl]carbamate (460 mg, 1.4 mmol, from Example 189, Step 1) was stirred in methylene chloride (4.6 mL) and m-chloroperbenzoic acid (2.1 g, 8.5 mmol) was added. The mixture was stirred overnight at room temperature. The suspension was filtered and the collected solids were washed with methylene chloride. The filtrates were evaporated to give the desired compound.

Step 2. 1-[3-(1-aminoethyl)-5-chloro-2-methoxy-6-methylphenyl]-2-morpholin-4-ylethanol hydrochloride tert-Butyl [1-(5-chloro-2-methoxy-4-methyl-3-oxiran-2-ylphenyl)ethyl]carbamate (100.0 mg, 0.29 mmol) was stirred in ethanol (2.00 mL, 34 mmol), with morpholine (130 mg, 1.5 mmol) and DIPEA (260 µL, 1.5 mmol). The mixture was stirred at 80° C. over the weekend. Purification by preparative LC/MS (pH 10) gave the Boc intermediate. LCMS calculated for $C_{21}H_{34}ClN_2O_5$ (M-NH$_2$)$^+$: m/z=429.2. found: 429.2. 4 N HCl (3.0 mL) was added and the mixture stirred for 30 minutes. Evaporation gave the desired compound as the hydrochloride salt (8.8 mg, 8%).

Step 3. 1-{3-chloro-6-methoxy-2-methyl-5-[1-(9H-purin-6-ylamino)ethyl]phenyl}-2-morpholin-4-ylethanol bis(trifluoroacetate)

To a solution of 1-{3-[1-aminoethyl]-5-chloro-2-methoxy-6-methylphenyl}-2-morpholin-4ylethanol hydrochloride (4.6 mg, 0.014 mmol) in 1-butanol (0.67 mL), DIPEA (12 µL, 0.071 mmol) was added followed by 6-chloro-9-(tetrahydro-2H-pyran-2-yl)-9H-purine (5.1 mg, 0.021 mmol, from Example 176, Step 4) and the reaction mixture was heated at 120° C. for 1 hour. The reaction mixture was cooled to room temperature and 4.0 M HCl in 1,4-dioxane (0.34 mL) was added. The mixture was stirred for 30 minutes. Purification by preparative LC/MS (pH 2) gave the desired compound (3.6 mg, 45%). LCMS calculated for $C_{21}H_{28}ClN_6O_3$ (M+H)$^+$: m/z=447.2. found: 447.1.

Example 191

6-{3-Chloro-6-methoxy-2-methyl-5-[1-(9H-purin-6-ylamino)ethyl]phenyl}-4-isopropylmorpholin-3-one trifluoroacetate

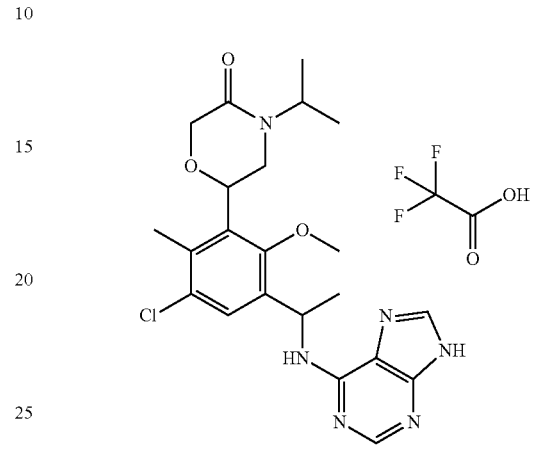

Step 1. tert-Butyl (1-{5-chloro-3-[1-hydroxy-2-(isopropylamino)ethyl]-2-methoxy-4-methylphenyl}ethyl) carbamate tert-Butyl [1-(5-chloro-2-methoxy-4-methyl-3-oxiran-2-ylphenyl)ethyl]carbamate (100 mg, 0.29 mmol, from Example 190, Step 1) was stirred in ethanol (2.0 mL, 34 mmol), 2-propanamine (120 µL, 1.5 mmol) and DIPEA (260 µL, 1.5 mmol) was added. The mixture was stirred at 80° C. over the weekend. Purification by preparative LC/MS (pH 10) gave the desired compound (5.7 mg, 5%). LCMS calculated for $C_{20}H_{34}ClN_2O_4$ (M+H)$^+$: m/z=401.2. found: 401.1.

Step 2. tert-Butyl [1-(5-chloro-3-{2-[(chloroacetyl)(isopropyl)amino]-1-hydroxyethyl}-2-methoxy-4-methylphenyl)ethyl]carbamate To a solution of tert-butyl 1-{5-chloro-3-[1-hydroxy-2-(isopropylamino)ethyl]-2-methoxy-4-methylphenyl}ethyl) carbamate (17 mg, 0.041 mmol) in methylene chloride (0.5 mL), triethylamine (17 µL, 0.12 mmol) was added followed by the addition of chloroacetyl chloride (3.9 µL, 0.049 mmol). The reaction mixture was stirred at room temperature for 30 minutes. Purification by preparative LC/MS (pH 10) gave the desired compound (17 mg, 100%). LCMS calculated for $C_{22}H_{34}C_{12}N_2O_5Na$ (M+Na)$^+$: m/z=499.2. found: 499.2.

Step 3. tert-Butyl {1-[5-chloro-3-(4-isopropyl-5-oxomorpholin-2-yl)-2-methoxy-4-methylphenyl]ethyl}carbamate To a solution of tert-butyl [1-(5-chloro-3-{2-[(chloroacetyl)(isopropyl)amino]-1-hydroxyethyl}-2-methoxy-4-methylphenyl)ethyl]carbamate (22 mg, 0.047 mmol) in THF (1.0 mL) cooled at 0° C., sodium hydride (3.6 mg, 0.094 mmol; 60% dispersion in mineral oil) was added and the mixture was stirred for 1 hour. The mixture was quenched with water and extracted with EtOAc. The combined extracts were washed with brine, dried over sodium sulfate, and concentrated to give the desired compound (20 mg, 97%). LCMS calculated for $C_{22}H_{33}ClN_2O_5Na$ (M+Na)$^+$: m/z=463.2. found: 463.1.

Step 4. 6-{3-Chloro-6-methoxy-2-methyl-5-[1-(9H-purin-6-ylamino)ethyl]phenyl}-4-isopropylmorpholin-3-one trifluoroacetate To tert-butyl {1-[5-chloro-3-(4-isopropyl-5-oxomorpholin-2-yl)-2-methoxy-4-methylphenyl]ethyl}carbamate (20 mg, 0.045 mmol), 4.0 M HCl in 1,4-dioxane (0.80 mL) was added and the mixture was stirred for 15 minutes. The solvents were evaporated to give the intermediate. To the residue was added 1-butanol (1.2 mL, 13 mmol), DIPEA (40 μL, 0.23 mmol) and 6-chloro-9-(tetrahydro-2H-pyran-2-yl)-9H-purine (16 mg, 0.068 mmol, from Example 176, Step 4) and the reaction mixture was heated at 120° C. for 1 hour. The reaction mixture was cooled to room temperature and 4.0 M HCl in 1,4-dioxane (0.80 mL) was added. The mixture was stirred for 30 minutes. Purification by preparative LC/MS (pH 2) gave the desired compound (8.2 mg, 32%). LCMS calculated for $C_{22}H_{28}ClN_6O_3$ (M+H)$^+$: m/z=459.2. found: 459.2. $^1$H NMR (DMSO-$d_6$, 500 MHz) δ 8.92 (1H, br s), 8.17 (2H, m), 7.60 (1H, s), 5.89 (1H, br s), 5.23 (1H, m), 4.63 (1H, m), 4.12 (2H, m), 3.95 (3H, m), 3.62 (1H, m), 3.20 (1H, m), 2.45 (3H, s), 1.43 (3H, m), 1.04 (6H, m).

Example 192

Diastereoisomers of 4-{3-chloro-6-methoxy-2-methyl-5-[1-(9H-purin-6-ylamino)ethyl]phenyl}pyrrolidin-2-one

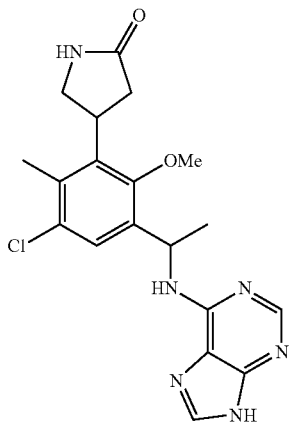 [SMILES: COc1c(C(C)Nc2ncnc3[nH]cnc23)cc(Cl)c(C)c1C1CNC(=O)C1]

Step 1. Methyl (2E)-3-(3-{1-[(tert-butoxycarbonyl)amino]ethyl}-5-chloro-2-methoxy-6-methylphenyl)acrylate Into a sealed tube was placed a suspension of tert-butyl [1-(3-bromo-5-chloro-2-methoxy-4-methylphenyl)ethyl]carbamate [from Example 113, step 1, peak 2](1.0 g, 2.6 mmol) in DMF (15 mL) that was degassed with nitrogen and treated with methyl acrylate (0.83 mL, 9.2 mmol), triphenylphosphine (97 mg, 0.37 mmol), and palladium acetate (59 mg, 0.26 mmol). Lastly, triethylamine (1.1 mL, 7.9 mmol) was added and the reaction mixture was heated at 130° C. for 16 hours. After cooling to room temperature, the mixture was filtered over Celite and the Celite was washed with EtOAc (100 mL). The EtOAc was washed with water, brine, dried over anhydrous sodium sulfate, filtered, and concentrated to a crude foam. The crude material was dissolved in 2:1 hexane/dichloromethane and purified by flash column chromatography using EtOAc in hexanes (0%-30% over 30 min) to give the desired product (0.68 g, 68%) as a white foam. LCMS for $C_{14}H_{16}ClO_3$ (M-NHBoc)$^+$: m/z=267.1. Found: 266.9.

Step 2. Methyl 3-(3-{1-[(tert-butoxycarbonyl)amino]ethyl}-5-chloro-2-methoxy-6-methylphenyl)-4-nitrobutanoate A solution of methyl (2E)-3-(3-{1-[(tert-butoxycarbonyl)amino]ethyl}-5-chloro-2-methoxy-6-methylphenyl)acrylate (1.5 g, 3.9 mmol) in nitromethane (11 mL) at 0° C. was treated with 1,8-diazabicyclo[5.4.0]undec-7-ene (0.59 mL, 3.9 mmol) and allowed to warm to room temperature. The reaction mixture was heated at 60° C. for 21 h, cooled to room temperature, poured into water (100 ml) and extracted with EtOAc (2×75 mL). The organic layer was separated, washed with brine solution, dried over anhydrous sodium sulfate, filtered, and concentrated to give a orange foam. The crude material was dissolved in dichloromethane and purified by flash column chromatography using EtOAc in hexanes (0%-30% over 30 min) to give the desired product (0.93 g, 53%) as a white foam. LCMS for $C_{20}H_{29}ClN_2O_7Na$ (M+Na)$^+$: m/z=467.2. Found: 467.1.

Step 3. Diastereoisomers of tert-butyl {1-[5-chloro-2-methoxy-4-methyl-3-(5-oxopyrrolidin-3-yl)phenyl]ethyl}carbamate A solution of methyl 3-(3-{1-[(tert-butoxycarbonyl)amino]ethyl}-5-chloro-2-methoxy-6-methylphenyl)-4-nitrobutanoate (0.92 g, 2.1 mmol) in methanol (15 mL) was treated with nickel chloride hexahydrate (0.99 g, 4.1 mmol) and stirred for 5 minutes. The reaction mixture was cooled to 0° C. and treated with sodium tetrahydroborate (0.84 g, 22 mmol) in four portions. The ice bath was removed and the reaction mixture was stirred for 30 min and heated at 60° C. for 4.5 hours. The reaction mixture was diluted with saturated sodium bicarbonate (20 mL) and EtOAc (50 mL) and filtered over Celite. The Celite was washed with EtOAc and the filtrate was concentrated to give the desired product as a mixture of diastereoisomers at the lactam carbon. The mixture of diastereoisomers was separated by chiral HPLC (ChiralPak AD-H column, 20×250 mm, 5 micron particle size, eluting with 60% ethanol in hexanes at 9 mL/min, column loading ~3 mg/injection) to give peak 1 (0.39 g, 49%, retention time: 6.25 min) and peak 2 (0.32 g, 40%, retention time: 9.34 min) as white solids.

Step 4. Diastereoisomers of 4-[3-(1-aminoethyl)-5-chloro-2-methoxy-6-methylphenyl]pyrrolidin-2-one Solutions of the individual diastereoisomers of tert-butyl {1-[5-chloro-2-methoxy-4-methyl-3-(5-oxopyrrolidin-3-yl)phenyl]ethyl}carbamate (75 mg, 0.20 mmol [peak 1 from step 3]; 75 mg, 0.20 mmol [peak 2 from step 3]) in separate reaction flasks in methylene chloride (1 mL) were each treated individually with trifluoroacetic acid (1 mL) dropwise and stirred for 30 minutes. The reaction mixtures were individually concentrated to residues, diluted with saturated sodium bicarbonate, and extracted several times with dichloromethane to give diastereoisomer from peak 1 (60 mg, quantitative) and diastereoisomer from peak 2 (55 mg, quantitative) as colorless residues that were used without further purification. Peak 1: LCMS for $C_{14}H_{17}ClNO_2$ (M-NH$_2$)$^+$: m/z=266.1. Found: 266.1. Peak 2: LCMS for $C_{14}H_{20}ClN_2O_2$ (M+H)$^+$: m/z=283.1. Found: 283.1.

Step 5. Diastereoisomers of 4-{3-chloro-6-methoxy-2-methyl-5-[1-(9H-purin-6-ylamino)ethyl]phenyl}pyrrolidin-2-one Solutions of 4-[3-(1-amino ethyl)-5-chloro-2-methoxy-6-methylphenyl]pyrrolidin-2-one (43 mg, 0.15 mmol [peak 1 from step 4]; 43 mg, 0.15 mmol [peak 2 from step 4]) in separate reaction flasks in 1-butanol (2.4 mL) were each treated individually with 6-chloro-9-(tetrahydro-2H-pyran-2-yl)-9H-purine (54 mg, 0.23 mmol, from Example 176, Step 4), and DIPEA (80 mL, 0.46 mmol) and heated at 105° C. for 20 hours. The reaction mixtures were individually concentrated on the rotary evaporator at 40° C. to remove 1-butanol to give the THP-containing intermediates. These intermediates were diluted with methanol (2 mL) and 6.0 M HCl in water (0.25 mL, 1.5 mmol) and stirred for 30 min to remove the THP protecting groups. The reaction mixtures were individually diluted with methanol and purified by preparative LCMS (XBridge C18 Column, eluting with a gradient of acetonitrile in water with 0.1% trifluoroacetic acid, at flow rate of 60 mL/min). The LCMS fractions were concentrated to remove acetonitrile, treated with solid sodium bicarbonate, and extracted into EtOAc. The EtOAc was concentrated and the residues were reconcentrated from EtOAc/heptane to give diastereoisomer from peak 1 (43 mg, 70%) and diastereoisomer from peak 2 (42 mg, 69%) as white solids. Peak 1: $^1$H NMR (400 MHz, DMSO-$d_6$) δ 12.94 (br s, 1H), 8.25-8.16 (m, 1H), 8.15-8.08 (m, 1H), 7.88 (s, 1H), 7.52 (br s, 1H), 5.86-5.50 (m, 1H), 4.37-4.22 (m, 1H), 3.88 (s, 3H), 3.61 (dd, J=10.1, 10.1 Hz, 1H), 3.26-3.17 (m, 1H), 2.59 (dd, J=17.3, 11.5 Hz, 1H), 2.36 (dd, J=17.2, 8.5 Hz, 1H), 2.22 (s, 3H), 1.43 (d, J=6.9 Hz, 3H). LCMS for $C_{19}H_{22}ClN_6O_2$ (M+H)$^+$: m/z=401.1. Found: 401.2. Peak 2: $^1$H NMR (400 MHz, DMSO-$d_6$) δ 12.94 (br s, 1H), 8.26-8.16 (m, 1H), 8.13-8.04 (m, 1H), 7.88 (s, 1H), 7.53 (br s, 1H), 5.81-5.59 (m, 1H), 4.38-4.23 (m, 1H), 3.88 (s, 3H), 3.66 (dd, J=10.1, 10.1 Hz, 1H), 3.31-3.24 (m, 1H), 2.59-2.52 (m, 1H), 2.29 (dd, J=17.4, 8.4 Hz, 1H), 2.21 (s, 3H), 1.44 (d, J=6.9 Hz, 3H). LCMS for $C_{19}H_{22}ClN_6O_2$ (M+H)$^+$: m/z=401.1. Found: 401.1.

Example 193

Diastereoisomers of 4-{3-chloro-6-methoxy-2-methyl-5-[1-(9H-purin-6-ylamino)ethyl]phenyl}-1-methylpyrrolidin-2-one

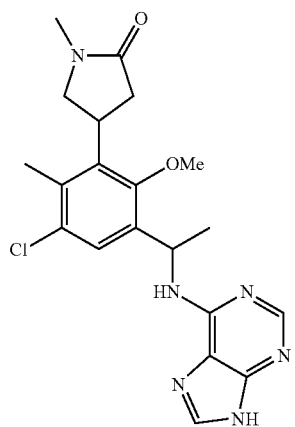 [SMILES: COc1c(C(C)Nc2ncnc3[nH]cnc23)cc(Cl)c(C)c1C1CC(=O)N(C)C1]

Step 1. Diastereoisomers of tert-butyl {1-[5-chloro-2-methoxy-4-methyl-3-(1-methyl-5-oxopyrrolidin-3-yl)phenyl]ethyl}carbamate Solutions of the individual diastereoisomers of tert-butyl {1-[5-chloro-2-methoxy-4-methyl-3-(5-oxopyrrolidin-3-yl)phenyl]ethyl}carbamate (0.31 g, 0.80 mmol [peak 1 from Examples 192, step 3]; 0.31 g, 0.80 mmol [peak 2 from Examples 192, step 3]) in DMF (4 mL) at 0° C. were each treated individually with sodium hydride dispersed in mineral oil (80 mg, 2.0 mmol). The ice bath was removed and the reaction mixtures were stirred for 30 min and heated at 60° C. for 30 minutes. The reaction mixtures were cooled down to 0° C., treated with methyl iodide (0.060 mL, 0.96 mmol) in DMF (2 mL, 26 mmol), and stirred at room temperature for 16 hours. The reaction mixtures were cooled to 0° C., quenched with saturated ammonium chloride, and extracted with EtOAc. The organic extract was concentrated to give a crude oil which was purified by preparative LCMS (XBridge C18 column, eluting with a gradient of acetonitrile/water containing 0.1% ammonium hydroxide, at flow rate of 60 mL/min) to give diastereoisomer from peak 1 (28 mg, 9%, retention time: 2.52 min) and diastereoisomer from peak 2 (56 mg, 18%, retention time: 2.51 min). Peak 1: LCMS for $C_{20}H_{29}ClN_2O_4Na$ (M+Na)$^+$: m/z=419.2. Found: 419.1. Peak 2: LCMS for $C_{20}H_{29}ClN_2O_4Na$ (M+Na)$^+$: m/z=419.2. Found: 419.1.

Step 2. Diastereoisomers of 4-[3-(1-aminoethyl)-5-chloro-2-methoxy-6-methylphenyl]-1-methylpyrrolidin-2-one trifluoroacetate Solutions of the individual diastereoisomers of tert-butyl {1-[5-chloro-2-methoxy-4-methyl-3-(1-methyl-5-oxopyrrolidin-3-yl)phenyl]ethyl}carbamate (28 mg, 0.070 mmol [peak 1 from step 1]; 56 mg, 0.14 mmol [peak 2 from step 1]) in separate reaction flasks in methylene chloride (1 mL) were each treated individually with trifluoroacetic acid (1 mL) dropwise and stirred for 30 minutes. The reaction mixtures were individually concentrated to give diastereoisomer from peak 1 (38 mg, quantitative) and diastereoisomer from peak 2 (65 mg, quantitative) as residues that were used without further purification. Peak 1: LCMS for $C_{15}H_{19}ClNO_2$ (M-NH$_2$)$^+$: m/z=280.1. Found: 280.1. Peak 2: LCMS for $C_{15}H_{22}ClN_2O_2$ (M+H)$^+$: m/z=297.1. Found: 297.1.

Step 3. Diastereoisomers of 4-{3-chloro-6-methoxy-2-methyl-5-[1-(9H-purin-6-ylamino)ethyl]phenyl}-1-methylpyrrolidin-2-one The desired diastereoisomers were prepared according to the procedure of Examples 192, step 5, using the diastereoisomers of 4-[3-(1-aminoethyl)-5-chloro-2-methoxy-6-methylphenyl]-1-methylpyrrolidin-2-one trifluoroacetate as the starting materials in 48% yield (peak 1) and 67% yield (peak 2). Peak 1: $^1$H NMR (400 MHz, DMSO-$d_6$) δ 12.94 (br s, 1H), 8.31-7.96 (m, 3H), 7.51 (br s, 1H), 5.89-5.52 (m, 1H), 4.31-4.10 (m, 1H), 3.86 (s, 3H), 3.71 (dd, J=10.1, 10.1 Hz, 1H), 2.79 (s, 3H), 2.75-2.65 (m, 1H), 2.46-2.38 (m, 1H), 2.16 (s, 3H), 1.43 (d, J=6.4 Hz, 3H). LCMS for $C_{20}H_{24}ClN_6O_2$ (M+H)$^+$: m/z=415.2. Found: 415.2. Peak 2: $^1$H NMR (400 MHz, DMSO-$d_6$) δ 12.94 (br s, 1H), 8.29-8.17 (m, 1H), 8.16-8.07 (m, 2H), 7.54 (br s, 1H), 5.91-5.47 (m, 1H), 4.32-4.10 (m, 1H), 3.87 (s, 3H), 3.76 (dd, J=10.1, 10.1 Hz, 1H), 3.44-3.36 (m, 1H), 2.79 (s, 3H), 2.68 (dd, J=17.4, 11.7 Hz, 1H), 2.36 (dd, J=17.4, 7.6 Hz, 1H), 2.16 (s, 3H), 1.44 (d, J=6.9 Hz, 3H). LCMS for $C_{20}H_{24}ClN_6O_2$ (M+H)$^+$: m/z=415.2. Found: 415.2.

Example 194

N-{1-[4,5-Dichloro-3-(1-isopropylazetidin-3-yl)-2-methoxyphenyl]ethyl}-9H-purin-6-amine bis(trifluoroacetate)

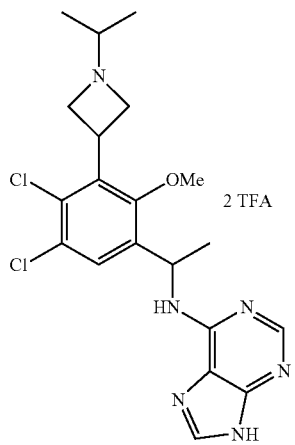 [SMILES: COc1c(C(C)Nc2ncnc3[nH]cnc23)cc(Cl)c(Cl)c1C1CN(C(C)C)C1]

Step 1. 1-(4,5-Dichloro-2-hydroxyphenyl)ethanone

A solution of 3,4-dichlorophenol [AK Scientific] (30 g, 18 mmol) in acetyl chloride (19 mL, 270 mmol) was stirred at 60° C. for 2 hours. The reaction mixture was cooled to 20° C., treated with aluminum trichloride (37 g, 280 mmol) portionwise, and heated at 180° C. for 30 minutes. The reaction mixture was cooled to 20° C. and the solution hardened into a solid block that was not easy to break apart. This material was cooled to 0° C. and quenched slowly with 1 M HCl in portions. The solid block of material slowly broke apart with enough HCl and this heterogenous mixture was stirred at 20° C. overnight to ensure uniformity. The solid was filtered, washed with copious amounts of water, and dried under vacuum to give the desired product (38 g, quantitative) as a tan solid.

Step 2. 1-(4,5-Dichloro-2-hydroxy-3-iodophenyl)ethanone

A solution of 1-(4,5-dichloro-2-hydroxyphenyl)ethanone (12 g, 59 mmol) in acetic acid (70 mL) was treated with N-iodosuccinimide (16 g, 71 mmol) and stirred at 90° C. for 18 hours. The reaction mixture was treated with additional N-iodosuccinimide (8 g, 36 mmol) and stirred at 90° C. for 4 hours. The reaction mixture was concentrated, diluted with EtOAc, and quenched with saturated sodium bicarbonate until the bubbling stopped. The organic layer was separated and the aqueous phase was re-extracted with EtOAc. The combined organic layers were dried and concentrated to give a brown solid. This material was recrystallized from methanol to give desired product (9.0 g, 46%) as a tan solid. LCMS for $C_8H_6Cl_2IO_2$ (M+H)$^+$: m/z=330.9, 332.9. Found: 330.8, 332.9.

Step 3. 1-(4,5-Dichloro-3-iodo-2-methoxyphenyl)ethanone

A solution of 1-(4,5-dichloro-2-hydroxy-3-iodophenyl)ethanone (16 g, 47 mmol) and potassium carbonate (17 g, 120 mmol) in DMF (40 mL) was treated with methyl iodide (6.4 mL, 100 mmol) and stirred at 60° C. for 1 hour. The reaction mixture was diluted with water and extracted with EtOAc (twice). The combined organic layers were dried with magnesium sulfate, filtered, and concentrated to give a crude solid. The crude material was purified by flash column chromatography using EtOAc in hexanes (5%-30%) to give the desired product (14 g, 84%) as an orange solid. LCMS for $C_9H_8Cl_2IO_2$ (M+H)$^+$: m/z=344.9, 346.9. Found: 344.8, 346.9.

Step 4. tert-Butyl 3-(3-acetyl-5,6-dichloro-2-methoxyphenyl)azetidine-1-carboxylate Zinc (4.5 g, 69 mmol) was suspended with 1,2-dibromoethane (420 µL, 4.9 mmol) in DMF (54 mL). The mixture was heated at 70° C. for 10 min and then cooled to room temperature. Chlorotrimethylsilane (620 µL, 4.9 mmol) was added dropwise and stirring was continued for 1 hour. A solution of tert-butyl 3-iodoazetidine-1-carboxylate (17 g, 61 mmol) in DMF (30 mL) was then added and the mixture was heated at 40° C. for 1 h before a mixture of 1-(4,5-dichloro-3-iodo-2-methoxyphenyl)ethanone (14 g, 41 mmol), tris(dibenzylideneacetone)dipalladium(0) (710 mg, 0.77 mmol) and tri-(2-furyl)phosphine (360 mg, 1.6 mmol) in DMF (120 mL) was added quickly. The reaction mixture was stirred overnight at room temperature. The reaction mixture was then partitioned between EtOAc and saturated ammonium chloride solution. The organic layer was washed with water, dried with magnesium sulfate, filtered, and concentrated to a crude residue that was purified by flash column chromatography using EtOAc in hexanes (0%-25%) to give the desired product (12 g, 77%). LCMS for $C_{17}H_{21}Cl_2NO_4Na$ (M+Na)$^+$: m/z=396.1. Found: 396.0.

Step 5. tert-Butyl 3-[3-(1-aminoethyl)-5,6-dichloro-2-methoxyphenyl]azetidine-1-carboxylate A solution of tert-butyl 3-(3-acetyl-5,6-dichloro-2-methoxyphenyl)azetidine-1-carboxylate (1.0 g, 2.7 mmol) in 2.0 M ammonia in ethanol (13 mL, 27 mmol) at 0° C. was treated with titanium tetraisopropoxide (1.6 mL, 5.3 mmol) and stirred at 60° C. overnight. The reaction mixture was treated with sodium tetrahydroborate (0.15 g, 4.0 mmol) at 0° C. and the solution was stirred at room temperature for another 1 hour. The reaction mixture was quenched with 2 M ammonia in water and filtered. The solid was washed with acetonitrile. The filtrate was concentrated and the residue was diluted with dichloromethane, washed with water, dried with magnesium sulfate, filtered, and concentrated to give the desired product (1.0 g, 97%) that was used without further purification. LCMS for $C_{13}H_{14}Cl_2NO_3$ (M-[NH$_2$]-[t-Bu]+H)$^+$: m/z=302.0, 304.0. Found: 301.9, 304.0.

Step 6. tert-Butyl 3-[3-(1-{[(benzyloxy)carbonyl]amino}ethyl)-5,6-dichloro-2-methoxyphenyl]azetidine-1-carboxylate A solution of tert-butyl 3-[3-(1-aminoethyl)-5,6-dichloro-2-methoxyphenyl]azetidine-1-carboxylate (4.1 g, 9.7 mmol) and DIPEA (3.4 mL, 20 mmol) in methylene chloride (49 mL) at 0° C. was treated with benzyl chloroformate (1.8 mL, 13 mmol) and stirred at 20° C. for 1 hour. The reaction mixture was diluted with dichloromethane (300 mL), washed with saturated sodium bicarbonate solution, water, and brine, dried with sodium sulfate, filtered and concentrated to a crude residue that was purified by flash column chromatography using EtOAc in hexanes (5%-40%) to give the desired racemic product (4 g, 81%). This racemic material was separated by chiral HPLC (ChiralPak AD-H column, 20×250 mm, 5 micron particle size, eluting with 30% ethanol in hexanes at 12 mL/min, column loading ~135 mg/injection) to give the desired peak 2 isomer (1.9 g, 38%). Peak 2 isomer: LCMS for $C_{25}H_{30}Cl_2N_2O_5Na$ (M+Na)$^+$: m/z=531.2. Found: 531.2.

Step 7. Single enantiomer of tert-butyl 3-[3-(1-aminoethyl)-5,6-dichloro-2-methoxyphenyl]azetidine-1-carboxylate A solution of tert-butyl 3-[3-(1-{[(benzyloxy)carbonyl]amino}ethyl)-5,6-dichloro-2-methoxyphenyl]azetidine-1-carboxylate [peak 2 isomer from step 6](0.29 g, 0.57 mmol) in methanol (17 mL) and 0.25 M HCl in water (5.7 mL, 1.4 mmol) was degassed with nitrogen, treated with 5% Pt/C (Degussa type) (73 mg, 25 wt %), and stirred under a balloon of hydrogen for 1 hour. The reaction mixture was treated with additional 5% Pt/C (Degussa type) (100 mg) and stirred under a balloon of hydrogen for an additional 1 hour. The reaction mixture was filtered over Celite and neutralized with saturated sodium bicarbonate solution. The reaction mixture was concentrated to remove the methanol, extracted with dichloromethane, and concentrated to give the desired product (0.21 g, 99%) as a colorless foam that was used without further purification. LCMS for $C_{13}H_{14}Cl_2NO_3$ (M-[NH$_2$]-[t-Bu]+H)$^+$: m/z=302.0, 304.0. Found: 301.9, 304.0.

Step 8. N-[1-(3-Azetidin-3-yl-4,5-dichloro-2-methoxyphenyl)ethyl]-9H-purin-6-amine A solution of tert-butyl 3-[3-(1-amino ethyl)-5,6-dichloro-2-methoxyphenyl]azetidine-1-carboxylate (0.11 g, 0.28 mmol), 6-chloro-9-(tetrahydro-2H-pyran-2-yl)-9H-purine (0.10 g, 0.42 mmol, from Example 176, Step 4), and DIPEA (0.15 mL, 0.85 mmol) in 1-butanol (2.8 mL) was heated at 105° C. for 20 hours. The reaction mixture was concentrated under high vacuum at 40° C. to remove the butanol to give the THP-containing intermediate. This intermediate was diluted with methanol (1.5 mL) and 6.0 M HCl in water (0.94 mL, 5.7 mmol) and stirred at room temperature for 30 minutes. The reaction mixture was concentrated to give the Boc-containing intermediate which was dissolved in methylene chloride (1 mL) and trifluoroacetic acid (1 mL) and stirred at room temperature for 30 minutes. The reaction mixture was concentrated to a residue, diluted with methanol, and purified by preparative LCMS (XBridge C18 Column, eluting with a gradient of acetonitrile in water with 0.1% trifluoroacetic acid, at flow rate of 60 mL/min). The LCMS fractions were concentrated to remove acetonitrile, treated with solid sodium bicarbonate, and extracted into EtOAc. The organic phase was concentrated and the residues were reconcentrated from EtOAc/heptane to give the desired product (38 mg, 34%) as a white solid. LCMS for $C_{17}H_{19}Cl_2N_6O$ (M+H)$^+$: m/z=393.1. Found: 393.0.

Step 9. N-{1-[4,5-Dichloro-3-(1-isopropylazetidin-3-yl)-2-methoxyphenyl]ethyl}-9H-purin-6-amine bis(trifluoroacetate)

A solution of N-[1-(3-azetidin-3-yl-4,5-dichloro-2-methoxyphenyl)ethyl]-9H-purin-6-amine (18 mg, 0.045 mmol) in methanol (1 mL) was treated with acetone (0.026 mL, 0.36 mmol), stirred for 30 mins, treated with sodium triacetoxyborohydride (0.028 g, 0.13 mmol), and stirred at room temperature for 16 hours. The reaction mixture was purified by preparative LCMS (XBridge C18 Column, eluting with a gradient of acetonitrile in water with 0.1% trifluoroacetic acid, at flow rate of 60 mL/min) to give the desired product (16 mg, 54%). $^1$H NMR (400 MHz, DMSO-d$_6$) δ 10.16 (br s, 1H), 8.65 (br s, 1H), 8.36-8.15 (m, 2H), 7.76 (s, 1H), 5.87-5.54 (m, 1H), 4.58-4.41 (m, 2H), 4.40-4.30 (m, 1H), 4.28-4.15 (m, 2H), 3.84 (d, J=6.7 Hz, 3H), 3.49-3.28 (m, 1H), 1.49 (d, J=6.9 Hz, 3H), 1.25 (d, J=6.5 Hz, 0.5H), 1.12 (dd, J=6.4, 3.2 Hz, 5.5H). LCMS for $C_{20}H_{25}Cl_2N_6O$ (M+H)$^+$: m/z=435.1. Found: 435.1.

Example 195

N-{1-[3-(1-Acetylazetidin-3-yl)-4,5-dichloro-2-methoxyphenyl]ethyl}-9H-purin-6-amine

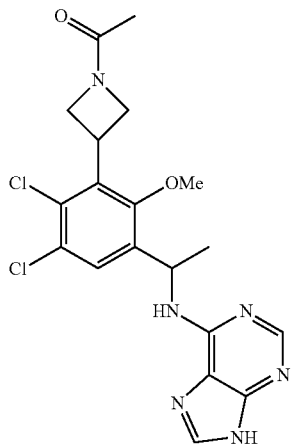 [SMILES: COc1c(C(C)Nc2ncnc3[nH]cnc23)cc(Cl)c(Cl)c1C1CN(C(C)=O)C1]

A solution of N-[1-(3-azetidin-3-yl-4,5-dichloro-2-methoxyphenyl)ethyl]-9H-purin-6-amine (25 mg, 0.064 mmol, from Example 194, Step 8) in acetonitrile (0.3 mL) was treated with DIPEA (28 μL, 0.16 mmol) followed by acetyl chloride (5.4 μL, 0.076 mmol) and stirred at room temperature for 1 hour. The reaction mixture was treated with 1N sodium hydroxide (200 μL) and heated briefly with a heat gun. The reaction mixture was diluted with methanol and purified by preparative LCMS (XBridge C18 column, eluting with a gradient of acetonitrile/water containing 0.1% ammonium hydroxide, at flow rate of 60 mL/min) to give the desired product (6.3 mg, 23%). $^1$H NMR (300 MHz, DMSO-d$_6$) δ 8.15-8.06 (m, 2H), 7.72 (s, 1H), 5.82-5.61 (m, 1H), 4.56-4.45 (m, 1H), 4.43-4.30 (m, 1H), 4.29-4.17 (m, 1H), 4.14-4.03 (m, 0.5H), 3.86 (s, 3H), 1.84-1.71 (m, 5H), 1.45 (d, J=6.8 Hz, 3H). LCMS for $C_{19}H_{21}Cl_2N_6O_2$ (M+H)$^+$: m/z=435.1. Found: 435.0.

Example 196

2-(3-{2,3-Dichloro-6-methoxy-5-[1-(9H-purin-6-ylamino)ethyl]phenyl}azetidin-1-yl)ethanol bis(trifluoroacetate)

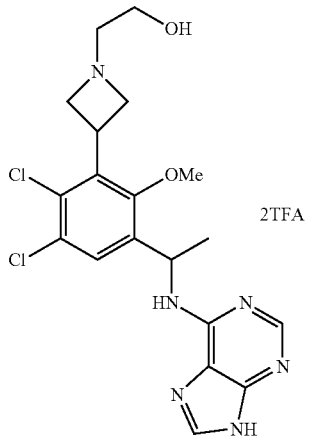 [SMILES: COc1c(C(C)Nc2ncnc3[nH]cnc23)cc(Cl)c(Cl)c1C1CN(CCO)C1]

A solution of N-[1-(3-azetidin-3-yl-4,5-dichloro-2-methoxyphenyl)ethyl]-9H-purin-6-amine (25 mg, 0.064 mmol, from Example 194, Step 8) in methanol (1 mL) was treated with sodium cyanoborohydride (10 mg, 0.16 mmol) followed by {[tert-butyl(dimethyl)silyl]oxy}acetaldehyde (36 µL, 0.19 mmol) and stirred at room temperature for 2 hours. The reaction mixture was diluted with EtOAc and washed with saturated sodium bicarbonate, water, and brine, dried with sodium sulfate, filtered and concentrated to give the intermediate silyl ether. This intermediate was dissolved in THF (1 mL), cooled at 0° C., treated with 1.0 M tetra-N-butylammonium fluoride in THF (0.64 mL, 0.64 mmol), and stirred at room temperature for 3 hours. The reaction mixture was diluted with methanol and purified by preparative LCMS (XBridge C18 column, eluting with a gradient of acetonitrile in water with 0.1% trifluoroacetic acid, at flow rate of 60 mL/min) to give the desired product (19 mg, 54%). $^1$H NMR (300 MHz, DMSO-$d_6$) δ 9.96 (br s, 1H), 8.50 (br s, 1H), 8.31-8.15 (m, 2H), 7.76 (s, 1H), 5.85-5.59 (m, 1H), 4.64-4.17 (m, 7H), 3.88-3.77 (m, 3H), 3.76-3.65 (m, 0.5H), 3.63-3.54 (m, 1H), 3.52-3.43 (m, 0.5H), 3.32-3.09 (m, 1H), 1.48 (d, J=6.9 Hz, 3H). LCMS for $C_{19}H_{23}Cl_2N_6O_2$ (M+H)$^+$: m/z=437.1, 439.1. Found: 437.1, 439.1.

Example 206

(3-{2,3-Dichloro-6-methoxy-5-[1-(9H-purin-6-ylamino)ethyl]phenyl}azetidin-1-yl)acetonitrile bis(trifluoroacetate)

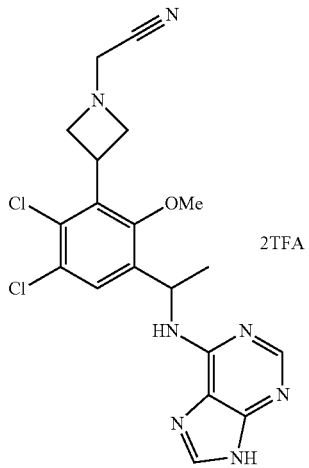 [SMILES: COc1c(C(C)Nc2ncnc3[nH]cnc23)cc(Cl)c(Cl)c1C1CN(CC#N)C1]

A solution of N-[1-(3-azetidin-3-yl-4,5-dichloro-2-methoxyphenyl)ethyl]-9H-purin-6-amine (20 mg, 0.051 mmol, from Example 194, Step 8) in acetonitrile (1 mL) was treated with DIPEA (22 µL, 0.13 mmol), cooled to 0° C., treated with bromoacetonitrile (4.3 µL, 0.061 mmol), and stirred at 0° C. for 30 minutes. The reaction mixture was purified by preparative LCMS (XBridge C18 Column, eluting with a gradient of acetonitrile in water with 0.1% trifluoroacetic acid, at flow rate of 60 mL/min) to give the desired product (13 mg, 47%). $^1$H NMR (300 MHz, DMSO-$d_6$) δ 8.95 (br s, 1H), 8.48-8.22 (m, 2H), 7.71 (s, 1H), 5.88-5.55 (m, 1H), 4.30 (br s, 2H), 4.13 (s, 1H), 4.01-3.84 (m, 2H), 3.80 (s, 3H), 1.50 (d, J=6.9 Hz, 3H). LCMS for $C_{19}H_{20}Cl_2N_7O$ (M+H)$^+$: m/z=432.1, 434.1. Found: 432.1, 434.1.

Example 207

N-(1-{4,5-Dichloro-2-methoxy-3-[1-(2,2,2-trifluoroethyl)azetidin-3-yl]phenyl}ethyl)-9H-purin-6-amine bis(trifluoroacetate)

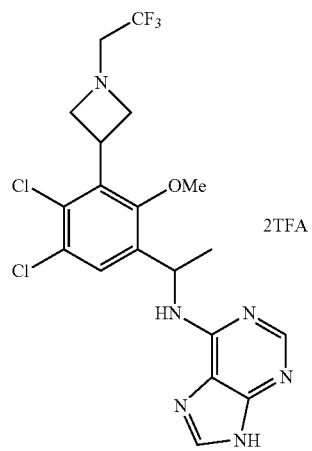 [SMILES: COc1c(C(C)Nc2ncnc3[nH]cnc23)cc(Cl)c(Cl)c1C1CN(CC(F)(F)F)C1]

Step 1. Benzyl [1-(3-azetidin-3-yl-4,5-dichloro-2-methoxyphenyl)ethyl]carbamate A solution of tert-butyl 3-[3-(1-{[(benzyloxy)carbonyl]amino}ethyl)-5,6-dichloro-2-methoxyphenyl]azetidine-1-carboxylate (200 mg, 0.39 mmol, from Example 194, Step 6) in methylene chloride (10 mL) was treated with trifluoroacetic acid (5 mL) and stirred at room temperature for 30 minutes. The reaction mixture was concentrated to give a residue that was dissolved in methanol (~20 mL) and treated with saturated sodium bicarbonate solution (pH-8). The methanol was then removed in vacuo to give an aqueous suspension that was diluted with EtOAc. The organic layer was separated and washed with water and brine, dried over anhydrous sodium sulfate, filtered, and concentrated to give the desired product (180 mg, 98%) that was used without further purification. LCMS for $C_{20}H_{23}Cl_2N_2O_3$ (M+H)$^+$: m/z=409.1, 411.1. Found: 409.1, 411.1.

Step 2. Benzyl (1-{4,5-dichloro-2-methoxy-3-[1-(2,2,2-trifluoroethyl)azetidin-3-yl]phenyl}ethyl) carbamate A solution of benzyl [1-(3-azetidin-3-yl-4,5-dichloro-2-methoxyphenyl)ethyl]carbamate (170 mg, 0.43 mmol) in THF (5.8 mL) was treated with triethylamine (110 μL, 0.82 mmol), cooled to 0° C., treated with 2,2,2-trifluoroethyl trifluoromethanesulfonate (150 mg, 0.64 mmol) and stirred at room temperature for 30 minutes. The reaction mixture was diluted with EtOAc and washed with saturated sodium bicarbonate, water, and brine, dried with sodium sulfate, filtered and concentrated to give the desired product (190 mg, 92%) that was used without further purification. LCMS for $C_{22}H_{24}Cl_2F_3N_2O_3$ (M+H)$^+$: m/z=491.1, 493.1. Found: 491.1, 493.1.

Step 3. 1-{4,5-Dichloro-2-methoxy-3-[1-(2,2,2-trifluoroethyl)azetidin-3-yl]phenyl}ethanamine dihydrochloride A solution of benzyl (1-{4,5-dichloro-2-methoxy-3-[1-(2,2,2-trifluoroethyl)azetidin-3-yl]phenyl}ethyl)carbamate (190 mg, 0.39 mmol) in methanol (11 mL) was treated with 0.25 M HCl in water (3.9 mL, 0.98 mmol), degassed with nitrogen for 5 minutes, treated with 5% Pt/C (Degussa type) (96 mg, 50 wt %), and stirred under a balloon of hydrogen for 1 hour. The reaction mixture was filtered over a PTFE disposable filter. The filtrate was concentrated to give the desired product (180 mg, 99%) that was used without further purification. LCMS for $C_{14}H_{18}Cl_2F_3N_2O$ (M+H)$^+$: m/z=357.1, 359.1. Found: 357.0, 359.0.

Step 4. N-(1-{4,5-Dichloro-2-methoxy-3-[1-(2,2,2-trifluoroethyl)azetidin-3-yl]phenyl}ethyl)-9H-purin-6-amine bis(trifluoroacetate)

The desired compound was prepared according to the procedure of Example 194, step 8, using 1-{4,5-dichloro-2-methoxy-3-[1-(2,2,2-trifluoroethyl)azetidin-3-yl]phenyl}ethanamine dihydrochloride as the starting material in 42% yield. $^1$H NMR (300 MHz, DMSO-d$_6$) δ 8.91-8.72 (m, 1H), 8.55-8.16 (m, 2H), 7.69 (s, 1H), 6.00-5.50 (m, 1H), 4.51-4.18 (m, 3H), 4.13-3.50 (m, 7H), 1.50 (d, J=6.9 Hz, 3H). LCMS for $C_{19}H_{20}Cl_2F_3N_6O$ (M+H)$^+$: m/z=475.1, 477.1. Found: 475.0, 477.0.

Example 210

N-(1-{4,5-Dichloro-3-[1-(2,2-difluoroethyl)azetidin-3-yl]-2-methoxyphenyl}ethyl)-9H-purin-6-amine bis(trifluoroacetate)

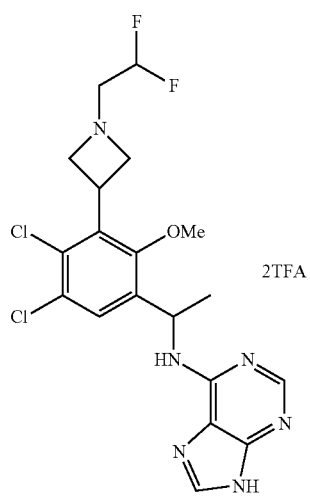 [SMILES: COc1c(C(C)Nc2ncnc3[nH]cnc23)cc(Cl)c(Cl)c1C1CN(CC(F)F)C1]

A solution of N-[1-(3-azetidin-3-yl-4,5-dichloro-2-methoxyphenyl)ethyl]-9H-purin-6-amine (15 mg, 0.038 mmol, from Example 194, Step 8) in DMF (1 mL) was treated with triethylamine (13 μL, 0.095 mmol), cooled to 0° C., treated with 2,2-difluoroethyl trifluoromethanesulfonate (12 mg, 0.058 mmol) and stirred at 0° C. for 20 minutes. The reaction mixture was purified by preparative LCMS (XBridge C18 Column, eluting with a gradient of acetonitrile in water with 0.1% trifluoroacetic acid, at flow rate of 60 mL/min) to give the desired product (12 mg, 46%). $^1$H NMR (300 MHz, DMSO-d$_6$) δ 8.61 (br s, 1H), 8.40-8.11 (m, 2H), 7.76 (s, 1H), 5.89-5.55 (m, 1H), 4.66-4.33 (m, 7H), 3.90-3.65 (m, 4H), 1.49 (d, J=6.1 Hz, 3H). LCMS for $Cl_9H_{21}Cl_2F_2N_6O$ (M+H)$^+$: m/z=457.1, 459.1. Found: 457.1, 459.1.

Example 211

5-{3-Cyano-6-ethoxy-2-fluoro-5-[1-(9H-purin-6-ylamino)ethyl]phenyl}-N,N-dimethylpyridine-2-carboxamide bis(trifluoroacetate)

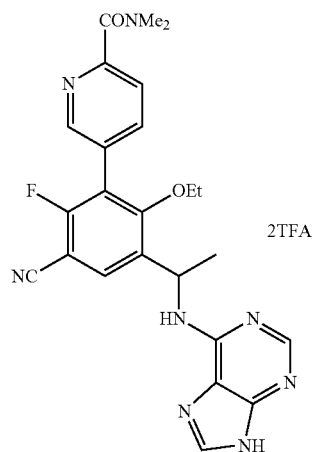

Step 1.
1-(5-Chloro-2-ethoxy-4-fluoro-3-iodophenyl)ethanone

The desired compound was prepared according to the procedure of Example 172, Step 3, using ethyl iodide as the starting material in 90% yield. LCMS for $C_{10}H_{10}ClFIO_2$ (M+H)$^+$: m/z=342.9, 344.9. Found: 342.9, 344.8.

Step 2.
1-(5-Chloro-2-ethoxy-4-fluoro-3-iodophenyl)ethanamine

The desired compound was prepared according to the procedure of Example 179, step 2, using 1-(5-chloro-2-ethoxy-4-fluoro-3-iodophenyl)ethanone as the starting material in 22% yield. LCMS for $C_{10}H_{10}ClFIO$ (M-[NH$_2$])$^+$: m/z=326.9. Found: 327.0.

Step 3. Enantiomer of tert-butyl [1-(5-chloro-2-ethoxy-4-fluoro-3-iodophenyl)ethyl]carbamate The desired racemic compound was prepared according to the procedure of Example 179, step 3, using 1-(5-chloro-2- ethoxy-4-fluoro-3-iodophenyl)ethanamine as the starting material in 80% yield. This racemic material was separated by chiral HPLC (Chiralcel AD-H column, 20×250 mm, 5 micron particle size, eluting with 30% ethanol in hexanes at 12 mL/min, column loading ~30 mg/injection) to give the desired peak 2 isomer. LCMS for $C_{10}H_{10}ClFIO$ (M-[NH-Boc])$^+$: m/z=326.9. Found: 326.9.

Step 4. N-[1-(5-Chloro-2-ethoxy-4-fluoro-3-iodophenyl)ethyl]-9-(tetrahydro-2H-pyran-2-yl)-9H-purin-6-amine A solution of tert-butyl [1-(5-chloro-2-ethoxy-4-fluoro-3-iodophenyl)ethyl]carbamate (1.0 g, 2.3 mmol) in methylene chloride (48 mL) was treated with trifluoroacetic acid (24 mL) and stirred at room temperature for 0.5 hour. The reaction mixture was concentrated and the residue was re-evaporated from methanol/toluene (2×50 mL) in order to remove all residual TFA to give the desired amine intermediate. A solution of the amine intermediate in ethanol (20 mL) was treated with DIPEA (1.2 mL, 6.8 mmol) followed by 6-chloro-9-(tetrahydro-2H-pyran-2-yl)-9H-purine (0.81 g, 3.4 mmol, from Example 176, Step 4) and heated at 80° C. overnight. The reaction mixture was diluted with saturated sodium bicarbonate and diluted with EtOAc. The organic layer was separated and washed with water and brine, dried with sodium sulfate, filtered and concentrated to a crude residue which was purified by flash column chromatography using EtOAc in hexanes (0%-65%) to give the desired product (1.2 g, 94%). LCMS for $C_{20}H_{23}ClFIN_5O_2$ (M+H)$^+$: m/z=546.1. Found: 546.0.

Step 5. 5-[3-Chloro-6-ethoxy-2-fluoro-5-(1-{[9-(tetrahydro-2H-pyran-2-yl)-9H-purin-6-yl]amino}ethyl)phenyl]pyridine-2-carbonitrile A solution of N-[1-(5-chloro-2-ethoxy-4-fluoro-3-iodophenyl)ethyl]-9-(tetrahydro-2H-pyran-2-yl)-9H-purin-6-amine (170 mg, 0.31 mmol), 5-(4,4,5,5-tetramethyl-1,3,2-dioxaborolan-2-yl)pyridine-2-carbonitrile (86 mg, 0.37 mmol, Frontier Scientific, Cat. No. C1628), sodium carbonate (66 mg, 0.62 mmol) and [1,1'-bis(diphenylphosphino)ferrocene]dichloropalladium-(II), complex with dichloromethane (1:1) (31 mg, 0.037 mmol) in acetonitrile (1.5 mL) and water (0.4 mL) was degassed with nitrogen for 10 min and stirred at 95° C. for 2 hours. The reaction mixture was diluted with EtOAc, washed with saturated sodium bicarbonate, water, and brine, dried over sodium sulfate, filtered and concentrated to a crude residue which was purified by flash column chromatography using EtOAc in hexanes (25%-100%) to give the desired product (81 mg, 50%). LCMS for $C_{26}H_{26}ClFN_7O_2$ (M+H)$^+$: m/z=522.2. Found: 522.2.

Step 6. 5-{3-Chloro-6-ethoxy-2-fluoro-5-[1-(9H-purin-6-ylamino)ethyl]phenyl}pyridine-2-carboxylic acid A solution of 5-[3-chloro-6-ethoxy-2-fluoro-5-(1-{[9-(tetrahydro-2H-pyran-2-yl)-9H-purin-6-yl]amino}ethyl)phenyl]pyridine-2-carbonitrile (0.070 g, 0.13 mmol) in ethanol (1.2 mL) was treated with 3 M sodium hydroxide in water (0.6 mL, 2 mmol) and stirred at 90° C. for 4 h in a sealed tube. The reaction mixture was cooled to 0° C., quenched with 12 M HCl in water (0.1 mL, 2 mmol), and stirred at 20° C. for 30 minutes. The reaction mixture was treated with additional 12 M HCl in water (0.2 mL, 2 mmol) and stirred at 20° C. for 15 minutes. The reaction mixture was concentrated to give the desired product (61 mg, quantitative) which was used without further purification. LCMS for $C_{21}H_{19}ClFN_6O_3$ (M+H)$^+$: m/z=457.1. Found: 457.1.

Step 7. 5-{3-Chloro-6-ethoxy-2-fluoro-5-[1-(9H-purin-6-ylamino)ethyl]phenyl}-N,N-dimethylpyridine-2-carboxamide A solution of 5-{3-chloro-6-ethoxy-2-fluoro-5-[1-(9H-purin-6-ylamino)ethyl]phenyl}pyridine-2-carboxylic acid (61 mg, 0.13 mmol) and benzotriazol-1-yloxytris(dimethylamino)phosphonium hexafluorophosphate (0.11 g, 0.26 mmol) in DMF (1.4 mL) was treated with 2.0 M dimethylamine in THF (0.26 mL, 0.52 mmol) followed by triethylamine (0.072 mL, 0.52 mmol) and stirred at 20° C. for 3 hours. The reaction mixture was diluted with EtOAc and washed with water and brine. The organic layer was separated, dried with magnesium sulfate, filtered, and concentrated to give a crude oil. The crude material was purified by flash column chromatography using EtOAc in hexanes (0%-70%) to give the desired product (4.7 mg, 7%). LCMS for $C_{23}H_{24}ClFN_7O_2$ (M+H)$^+$: m/z=484.2. Found: 484.1.

Step 8. 5-{3-Cyano-6-ethoxy-2-fluoro-5-[1-(9H-purin-6-ylamino)ethyl]phenyl}-N,N-dimethylpyridine-2-carboxamide bis(trifluoroacetate)

N,N-Dimethylacetamide (10 mL) was degassed with nitrogen for 10 minutes, then 27 uL of concentrated sulfuric acid was added (to generate a 50 mM solution), and then bubbled again with nitrogen for 10 minutes. Transferred 2.0 mL of this 50 mM sulfuric acid/DMA solution to a microwave vial and degassed again with nitrogen. Palladium acetate (23 mg, 0.10 mmol) was added, followed by dicyclohexyl (2',4',6'-triisopropylbiphenyl-2-yl)phosphine (96 mg, 0.20 mmol). The vial was crimp-capped and the mixture was again degassed with nitrogen bubbling for 10 minutes, and then heated at 80° C. for 30 min to give a homogeneous brown solution. This catalyst solution was used immediately.

A solution of 5-{3-Chloro-6-ethoxy-2-fluoro-5-[1-(9H-purin-6-ylamino)ethyl]phenyl}-N,N-dimethylpyridine-2-carboxamide (20 mg, 0.041 mmol), zinc (1.2 mg, 0.0179 mmol), and zinc cyanide (5.3 mg, 0.045 mmol) in N,N-dimethylacetamide (0.5 mL, 5.4 mmol) in a microwave tube was degassed by bubbling nitrogen through the solution for 10 min. The above palladium catalyst solution (150 uL) was added and the resulting mixture degassed again briefly with nitrogen and heated at 110° C. for 1 hour. The reaction mixture was purified by preparative LCMS (XBridge C18 Column, eluting with a gradient of acetonitrile in water with 0.1% trifluoroacetic acid, at flow rate of 60 mL/min) to give the desired product (20 mg, 83%). $^1$H NMR (300 MHz, DMSO-d$_6$) δ 8.85-8.79 (m, 1H), 8.77 (dd, J=2.2, 0.8 Hz, 1H), 8.37 (s, 2H), 8.10 (d, J=7.4 Hz, 1H), 8.02 (dd, J=8.0, 2.2 Hz, 1H), 7.70 (d, J=8.0 Hz, 1H), 5.94-5.59 (m, 1H), 3.91-3.73 (m, 1H), 3.66-3.44 (m, 1H), 3.03 (s, 3H), 2.96 (s, 3H), 1.56 (d, J=6.9 Hz, 3H), 1.23 (s, 1H), 1.02 (t, J=6.9 Hz, 3H). LCMS for $C_{24}H_{24}FN_8O_2$ (M+H)$^+$: m/z=475.2. Found: 475.2.

Example 212

4-Ethoxy-2-fluoro-3-[5-(methylsulfonyl)pyridin-3-yl]-5-[1-(9H-purin-6-ylamino)ethyl]benzonitrile bis(trifluoroacetate)

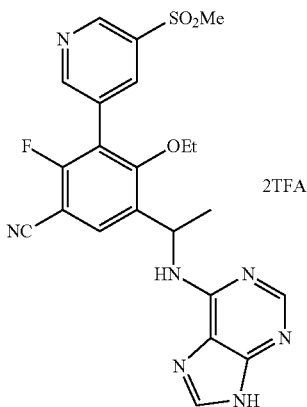 [SMILES: CCOc1c(C(C)Nc2ncnc3[nH]cnc23)cc(C#N)c(F)c1-c1cncc(S(C)(=O)=O)c1]

Step 1. 1-{5-Chloro-4-fluoro-2-hydroxy-3-[5-(methylsulfonyl)pyridin-3-yl]phenyl}ethanone The desired compound was prepared according to the procedure of Example 127, step A, using 1-(5-chloro-4-fluoro-2-hydroxy-3-iodophenyl)ethanone (See, Example 172, Step 2) and 3-(methylsulfonyl)-5-(4,4,5,5-tetramethyl-1,3,2-dioxaborolan-2-yl)pyridine (PepTech Corp., Cat. No. BE358) as the starting materials in 87% yield. LCMS for $C_{14}H_{12}ClFNO_4S$ (M+H)$^+$: m/z=344.0. Found: 343.9.

Step 2. 1-{5-Chloro-2-ethoxy-4-fluoro-3-[5-(methylsulfonyl)pyridin-3-yl]phenyl}ethanone A solution of 1-{5-chloro-4-fluoro-2-hydroxy-3-[5-(methylsulfonyl)pyridin-3-yl]phenyl}ethanone (1.3 g, 3.6 mmol) in THF (32 mL) was treated with ethanol (0.28 mL, 4.73 mmol) and triphenylphosphine (1.3 g, 5.1 mmol). The reaction mixture was cooled to 0° C., treated with diisopropyl azodicarboxylate (1.1 mL, 5.5 mmol) dropwise, and stirred at 20° C. for 1 hour. The reaction mixture was concentrated to remove most of the THF, diluted with EtOAc, washed with saturated sodium bicarbonate, water, brine, dried over sodium sulfate, filtered and concentrated to a crude residue which was purified by flash column chromatography using EtOAc in hexanes (15%-65%) to give the desired product (1.2 g, 87%). LCMS for $C_{16}H_{16}ClFNO_4S$ (M+H)$^+$: m/z=372.0. Found: 372.1.

Step 3. 1-{5-Chloro-2-ethoxy-4-fluoro-3-[5-(methylsulfonyl)pyridin-3-yl]phenyl}ethanamine The desired compound was prepared according to the procedure of Example 194, step 5, using 1-{5-chloro-2-ethoxy-4-fluoro-3-[5-(methylsulfonyl)pyridin-3-yl]phenyl}ethanone as the starting material in 92% yield. LCMS for $C_{16}H_{16}ClFNO_3S$ (M-[NH$_2$])$^+$: m/z=356.1. Found: 356.0.

Step 4. Enantiomer of tert-butyl (1-{5-chloro-2-ethoxy-4-fluoro-3-[5-(methylsulfonyl)pyridin-3-yl]phenyl}ethyl)carbamate The desired racemic compound was prepared according to the procedure of Example 179, step 3, using 1-{5-chloro-2-ethoxy-4-fluoro-3-[5-(methylsulfonyl)pyridin-3-yl]phenyl}ethanamine as the starting material. This racemic material was separated by chiral HPLC (ChiralPak AD-H column, 20×250 mm, 5 micron particle size, eluting with 10% ethanol in hexanes at 12 mL/min) to give the desired peak 1 isomer. LCMS for $C_{21}H_{27}ClFN_2O_5S$ (M+H)$^+$: m/z=473.1. Found: 473.2.

Step 5. 1-{5-Chloro-2-ethoxy-4-fluoro-3-[5-(methylsulfonyl)pyridin-3-yl]phenyl}ethanamine dihydrochloride The desired compound was prepared according to the procedure of Example 179, step 5, using tert-butyl (1-{5-chloro-2-ethoxy-4-fluoro-3-[5-(methylsulfonyl)pyridin-3-yl]phenyl}ethyl)carbamate as the starting material in quantitative yield. LCMS for $C_{16}H_{19}ClFN_2O_3S$ (M+H)$^+$: m/z=373.1. Found: 373.1.

Step 6. N-(1-{5-chloro-2-ethoxy-4-fluoro-3-[5-(methylsulfonyl)pyridin-3-yl]phenyl}ethyl)-9H-purin-6-amine The desired compound was prepared according to the procedure of Example 194, step 8, using 1-{5-chloro-2-ethoxy-4-fluoro-3-[5-(methylsulfonyl)pyridin-3-yl]phenyl}ethanamine dihydrochloride as the starting material in 60% yield. LCMS for $C_{21}H_{21}ClFN_6O_3S$ (M+H)$^+$: m/z=491.1. Found: 491.1.

Step 7. 4-Ethoxy-2-fluoro-3-[5-(methylsulfonyl)pyridin-3-yl]-5-[1-(9H-purin-6-ylamino)ethyl]benzonitrile bis(trifluoroacetate)

The desired racemic compound was prepared according to the procedure of Example 211, step 8, using N-(1-{5-chloro-2-ethoxy-4-fluoro-3-[5-(methylsulfonyl)pyridin-3-yl]phenyl}ethyl)-9H-purin-6-amine as the starting material in 82% yield. $^1$H NMR (300 MHz, DMSO-d$_6$) δ 9.17 (d, J=2.2 Hz, 1H), 9.09-9.05 (m, 1H), 8.82-8.67 (m, 1H), 8.57-8.52 (m, 1H), 8.38-8.31 (m, 2H), 8.17 (d, J=7.5 Hz, 1H), 5.92-5.70 (m, 1H), 3.97-3.84 (m, 1H), 3.54-3.44 (m, 1H), 3.40 (s, 3H), 1.58 (d, J=6.9 Hz, 3H), 1.04 (t, J=6.9 Hz, 3H). LCMS for $C_{22}H_{21}FN_7O_3S$ (M+H)$^+$: m/z=482.1. Found: 482.2.

Example 213

6-Chloro-3-ethoxy-2-(1-ethylazetidin-3-yl)-4-[1-(9H-purin-6-ylamino)ethyl]benzonitrile bis(trifluoroacetate)

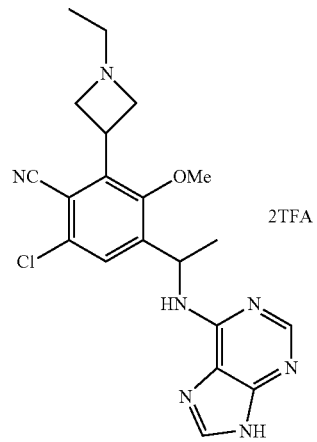 [SMILES: CCN1CC(c2c(C#N)c(Cl)cc(C(C)Nc3ncnc4[nH]cnc34)c2OC)C1]

Step 1.
4-Acetyl-6-chloro-3-ethoxy-2-iodobenzonitrile

A solution of 1-(5-chloro-2-ethoxy-4-fluoro-3-iodophenyl)ethanone (1.0 g, 2.9 mmol, from Example 211, Step 1) and potassium cyanide (0.29 g, 4.4 mmol) in DMF (11 mL) was stirred at 40° C. for 3 hours. The reaction mixture was diluted with water (100 mL) and extracted with EtOAc (2×75 mL). The combined organic layers were washed with brine, dried over sodium sulfate, filtered, and concentrated to a crude orange oil. The crude material was dissolved in 1:1 hexane/dichloromethane and purified by flash column chromatography using EtOAc in hexanes (0%-30% over 30 min) to give the desired product (0.79 g, 77%). LCMS for $C_{11}H_{10}ClINO_2$ $(M+H)^+$: m/z=349.9. Found: 349.9.

Step 2. tert-Butyl 3-(3-acetyl-5-chloro-6-cyano-2-ethoxyphenyl)azetidine-1-carboxylate The desired compound was prepared according to the procedure of Example 165, step 1, using 4-acetyl-6-chloro-3-ethoxy-2-iodobenzonitrile as the starting material in 82% yield. LCMS for $C_{19}H_{23}ClN_2O_4Na$ $(M+Na)^+$: m/z=401.1. Found: 401.0.

Step 3. tert-Butyl 3-[3-(1-aminoethyl)-5-chloro-6-cyano-2-ethoxyphenyl]azetidine-1-carboxylate The desired compound was prepared according to the procedure of Example 179, step 2, using tert-butyl 3-(3-acetyl-5-chloro-6-cyano-2-ethoxyphenyl)azetidine-1-carboxylate as the starting material in quantitative yield. LCMS for $C_{19}H_{26}ClN_3O_3Na$ $(M+Na)^+$: m/z=402.2. Found: 402.1.

Step 4. 2-Azetidin-3-yl-6-chloro-3-ethoxy-4-[1-(9H-purin-6-ylamino)ethyl]benzonitrile The desired compound was prepared according to the procedure of Example 194, step 8, using tert-butyl 3-[3-(1-amino ethyl)-5-chloro-6-cyano-2-ethoxyphenyl]azetidine-1-carboxylate as the starting material in 90% yield. LCMS for $C_{19}H_{21}ClN_7O$ $(M+H)^+$: m/z=398.1. Found: 398.1.

Step 5. 6-Chloro-3-ethoxy-2-(1-ethylazetidin-3-yl)-4-[1-(9H-purin-6-ylamino)ethyl]benzonitrile bis(trifluoroacetate)

A solution of 2-azetidin-3-yl-6-chloro-3-ethoxy-4-[1-(9H-purin-6-ylamino)ethyl]benzonitrile (45 mg, 0.11 mmol) in methanol (1.5 mL) was treated with sodium cyanoborohydride (0.022 g, 0.35 mmol) followed by acetaldehyde (0.079 mL, 1.4 mmol) and stirred at room temperature for 16 hours. The reaction mixture was diluted with methanol and purified by preparative LCMS (XBridge C18 Column, eluting with a gradient of acetonitrile in water with 0.1% trifluoroacetic acid, at flow rate of 60 mL/min) to give the desired product (27 mg, 40%). $^1$H NMR (400 MHz, DMSO-$d_6$) δ 10.02 (br s, 1H), 8.50 (br s, 1H), 8.26 (s, 1H), 8.19 (s, 1H), 7.79 (s, 1H), 5.80-5.61 (m, 1H), 4.69-4.47 (m, 3H), 4.42-4.31 (m, 1H), 4.30-4.15 (m, 2H), 3.95-3.84 (m, 1H), 3.21-3.07 (m, 1H), 1.49 (d, J=6.9 Hz, 3H), 1.43 (t, J=6.9 Hz, 3H), 1.23 (s, 1H), 1.08 (t, J=7.2 Hz, 3H). LCMS for $C_{21}H_{25}ClN_7O$ $(M+H)^+$: m/z=426.2. Found: 426.2.

Example 214

6-Chloro-3-ethoxy-2-(1-isopropylazetidin-3-yl)-4-[1-(9H-purin-6-ylamino)ethyl]benzonitrile bis(trifluoroacetate)

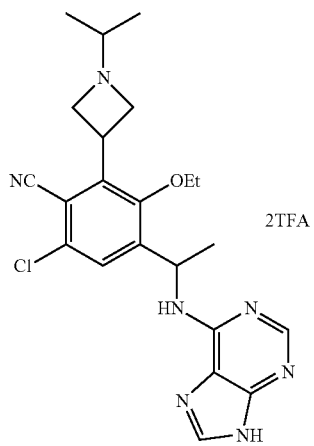 [SMILES: CCOc1c(C(C)Nc2ncnc3[nH]cnc23)cc(Cl)c(C#N)c1C1CN(C(C)C)C1]

The desired racemic compound was prepared according to the procedure of Example 213, step 5, using acetone as the starting material in 37% yield. This racemic material was separated by chiral HPLC (ChiralPak AD-H column, 20×250 mm, 5 micron particle size, eluting with 30% ethanol in hexanes at 12 mL/min) to give the desired peak 1 isomer (retention time: 13.6 min). $^1$H NMR (400 MHz, DMSO-$d_6$) δ 10.16 (br s, 1H), 8.50 (br s, 1H), 8.26 (s, 1H), 8.20 (s, 1H), 7.80 (s, 1H), 5.86-5.58 (m, 1H), 4.60-4.46 (m, 3H), 4.45-4.37 (m, 1H), 4.35-4.17 (m, 2H), 3.95-3.87 (m, 1H), 3.50-3.31 (m, 1H), 1.49 (d, J=6.9 Hz, 3H), 1.44 (t, J=6.9 Hz, 3H), 1.24 (d, J=6.4 Hz, 2H), 1.13 (dd, J=6.4, 3.0 Hz, 3H). LCMS for $C_{22}H_{27}ClN_7O$ $(M+H)^+$: m/z=440.2. Found: 440.2.

Experimental procedures for further compounds are summarized in Table 10 below.

TABLE 10

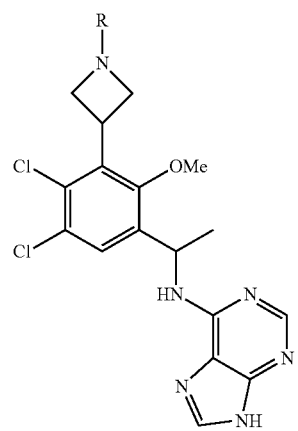

| Ex. No. Name | R | Salt | Proc.[a] |
|---|---|---|---|
| 197 N-(1-{4,5-Dichloro-2-methoxy-3-[1-(tetrahydrofuran-3-yl)azetidin-3-yl]phenyl}ethyl)-9H-purin-6-amine bistrifluoroacetate | 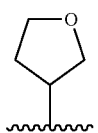 [SMILES: *C1CCOC1] | 2TFA | 194 |
| 198 N-(1-{4,5-Dichloro-2-methoxy-3-[1-(2,2,2-trifluoro-1-methylethyl)azetidin-3-yl]phenyl}ethyl)-9H-purin-6-amine bistrifluoroacetate | 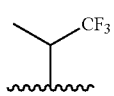 | 2TFA | 194 |
| 199 N-{1-[4,5-Dichloro-2-methoxy-3-(1-methylazetidin-3-yl)phenyl]ethyl}-9H-purin-6-amine | —CH₃ | — | 194 |
| 200 N-(1-{4,5-Dichloro-2-methoxy-3-[1-(2-methoxyethyl)azetidin-3-yl]phenyl}ethyl)-9H-purin-6-amine | 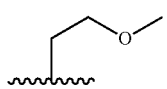 [SMILES: *CCOC] | — | 194 |
| 201 N-(1-{4,5-Dichloro-3-[1-(cyclopropylmethyl)azetidin-3-yl]-2-methoxyphenyl}ethyl)-9H-purin-6-amine | 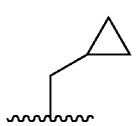 [SMILES: *CC1CC1] | — | 194 |
| 202 N-(1-{4,5-dichloro-2-methoxy-3-[1-(tetrahydrofuran-3-ylmethyl)azetidin-3-yl]phenyl}ethyl)-9H-purin-6-amine | 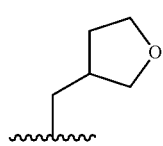 [SMILES: *CC1CCOC1] | — | 194 |
| 203 N-(1-{4,5-Dichloro-2-methoxy-3-[1-(4,4,4-trifluorobutyl)azetidin-3-yl]phenyl}ethyl)-9H-purin-6-amine | 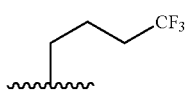 | — | 194 |
| 204 N-(1-{4,5-Dichloro-2-methoxy-3-[1-(1,3-thiazol-2-ylmethyl)azetidin-3-yl]phenyl}ethyl)-9H-purin-6-amine | 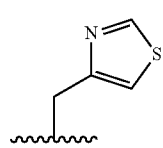 [SMILES: *Cc1cscn1] | — | 194 |
| 205 N-(1-{4,5-Dichloro-2-methoxy-3-[1-(3,3,3-trifluoropropyl)azetidin-3-yl]phenyl}ethyl)-9H-purin-6-amine | 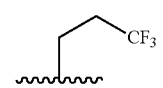 | — | 194 |

TABLE 10-continued

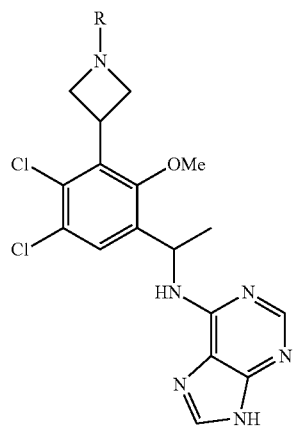

| Ex. No. | Name | R | Salt | Proc.[a] |
|---|---|---|---|---|
| 208 | 2-(3-{2,3-Dichloro-6-methoxy-5-[1-(9H-purin-6-ylamino)ethyl]phenyl}azetidin-1-yl)propan-1-ol bistrifluoroacetate | 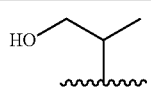 | 2TFA | 194 |
| 209 | N-{1-[4,5-Dichloro-3-(1-cyclobutylazetidin-3-yl)-2-methoxyphenyl]ethyl}-9H-purin-6-amine bistrifluoroacetate | 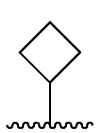 [SMILES: *C1CCC1] | 2TFA | 194 |

[a] $^1$H NMR data (Varian Inova 500 spectrometer, a Mercury 400 spectrometer, or a Varian (or Mercury) 300 spectrometer) and LCMS mass spectral data (MS) for the compounds above is provided below in Table 11.

TABLE 11

$^1$H NMR data for compounds in Table 10

| Ex. No. | MS [M + H]$^+$ | Solvent | MHz | $^1$H NMR Spectra |
|---|---|---|---|---|
| 197 | 463.0, 465.0 | DMSO-d$_6$ | 300 | δ 10.44 (br s, 1H), 9.93 (br s, 0.5H), 8.78-8.65 (m, 1H), 8.37-8.25 (m, 2H), 7.75 (s, 1H), 5.97-5.53 (m, 1H), 4.70-4.57 (m, 2H), 4.43-4.20 (m, 3H), 4.12-4.01 (m, 0.5H), 3.94-3.86 (m, 1.5H), 3.83 (s, 3H), 3.69-3.53 (m, 2H), 2.24-2.05 (m, 1H), 1.98-1.81 (m, 1H), 1.49 (d, J = 6.7Hz, 3H). |
| 198 | 489.0, 491.0 | DMSO-d$_6$ | 300 | δ 8.64 (br s, 1H), 8.34-8.20 (m, 2H), 7.68 (s, 1H), 5.83-5.57 (m, 1H), 4.29-4.04 (m, 4H), 3.81 (s, 3H), 3.74-3.38 (m, 3H), 1.48 (d, J = 6.9Hz, 3H), 1.14 (d, J = 6.2Hz, 3H). |
| 199 | 407.0, 409.0 | DMSO-d$_6$ | 300 | δ 8.30-7.94 (m, 3H), 7.62 (s, 1H), 5.97-5.53 (m, 1H), 3.99-3.81 (m, 3H), 3.79 (s, 3H), 2.95 (dd, J = 8.9, 6.5Hz, 1H), 2.81 (dd, J = 8.8, 6.4Hz, 1H), 2.15 (s, 3H), 1.44 (d, J = 6.9Hz, 3H). |
| 200 | 451.0, 453.0 | DMSO-d$_6$ | 300 | δ 8.16-7.97 (m, 3H), 7.63 (s, 1H), 5.87-5.54 (m, 1H), 4.00-3.83 (m, 3H), 3.79 (s, 3H), 3.31-3.26 (m, 4H), 3.21 (s, 3H), 3.07-2.94 (m, 1H), 2.94-2.82 (m, 1H), 1.44 (d, J = 6.9Hz, 3H). |
| 201 | 447.0 | DMSO-d$_6$ | 300 | δ 8.30-7.97 (m, 3H), 7.62 (s, 1H), 5.88-5.53 (m, 1H), 4.01-3.84 (m, 3H), 3.80 (s, 3H), 3.00-2.91 (m, 1H), 2.87-2.77 (m, 1H), 2.16 (d, J = 6.6Hz, 2H), 1.44 (d, J = 6.9Hz, 3H), 0.81-0.63 (m, 1H), 0.49-0.25 (m, 2H), 0.09--0.02 (m, 2H). |
| 202 | 477.1 | DMSO-d$_6$ | 300 | δ 8.19-8.07 (m, 3H), 7.62 (s, 1H), 5.86-5.48 (m, 1H), 4.04-3.83 (m, 3H), 3.80 (s, 3H), 3.77-3.53 (m, 3H), 3.04-2.92 (m, 1H), 2.90-2.77 (m, 1H), 2.35-2.26 (m, 2H), 2.24-2.10 (m, 1H), 2.00-1.80 (m, 1H), 1.44 (d, J = 6.9Hz, 3H). |
| 203 | 503.1 | DMSO-d$_6$ | 300 | δ 8.22-8.03 (m, 3H), 7.63 (s, 1H), 5.91-5.50 (m, 1H), 4.03-3.85 (m, 3H), 3.80 (s, 3H), 3.04-2.90 (m, 1H), 2.90-2.77 (m, 1H), 2.40-2.15 (m, 4H), 1.56-1.36 (m, 4H). |

TABLE 11-continued

¹H NMR data for compounds in Table 10

| Ex. No. | MS [M + H]⁺ | Solvent | MHz | ¹H NMR Spectra |
|---|---|---|---|---|
| 204 | 490.0 | DMSO-$d_6$ | 300 | δ 9.03 (d, J = 2.0 Hz, 1H), 8.25-8.03 (m, 3H), 7.63 (s, 1H), 7.47 (d, J = 1.9Hz, 1H), 5.97-5.50 (m, 1H), 4.08-3.85 (m, 3H), 3.80 (s, 3H), 3.66 (s, 2H), 3.20-3.11 (m, 1H), 3.09-2.97 (m, 1H), 1.44 (d, J = 6.9Hz, 3H). |
| 205 | 489.0 | DMSO-$d_6$ | 300 | δ 8.25-7.97 (m, 3H), 7.63 (s, 1H), 5.97-5.45 (m, 1H), 4.02-3.84 (m, 3H), 3.80 (s, 3H), 3.01 (dd, J = 8.5, 6.3Hz, 1H), 2.93-2.86 (m, 1H), 2.41-2.18 (m, 2H), 1.44 (d, J = 6.9Hz, 3H). |
| 208 | 451.0, 453.0 | DMSO-$d_6$ | 300 | δ 10.01 (br s, 1H), 8.63-8.44 (m, 1H), 8.36-8.14 (m, 2H), 7.76 (s, 1H), 5.86-5.60 (m, 1H), 4.59-4.45 (m, 2H), 4.43-4.22 (m, 3H), 3.84 (d, J = 3.0 Hz, 3H), 3.70-3.55 (m, 1H), 3.50-3.31 (m, 2H), 1.49 (d, J = 6.8Hz, 3H), 1.28-1.17 (m, 0.5H), 1.16-1.02 (m, 2.5H). |
| 209 | 447.1, 449.1 | DMSO-$d_6$ | 300 | δ 10.54 (br s, 1H), 9.83 (br s, 0.5H), 8.57 (br s, 1H), 8.39-8.16 (m, 2H), 7.75 (s, 1H), 5.71 (m, 1H), 4.60-4.47 (m, 2H), 4.45-4.21 (m, 2H), 4.19-4.06 (m, 2H), 3.89-3.80 (m, 3H), 2.19-1.97 (m, 4H), 1.87-1.63 (m, 1H), 1.48 (d, J = 6.9Hz, 3H), 1.23 (s, 1H). |

Example A

PI3Kδ Scintillation Proximity Assay

Materials:

[γ-³³P]ATP (10 mCi/mL) was purchased from Perkin-Elmer (Waltham, Mass.). Lipid kinase substrate, D-myo-Phosphatidylinositol 4,5-bisphosphate (PtdIns(4,5)P2)D (+)-sn-1,2-di-O-octanoylglyceryl, 3-O-phospho linked (PIP2), CAS 204858-53-7, was purchased from Echelon Biosciences (Salt Lake City, Utah). PI3Kδ (p110δ/p85α) was purchased from Millipore (Bedford, Mass.). ATP, MgCl₂, DTT, EDTA, MOPS and CHAPS were purchased from Sigma-Aldrich (St. Louis, Mo.). Wheat Germ Agglutinin (WGA) YSi SPA Scintillation Beads was purchased from GE healthcare life sciences (Piscataway, N.J.).

Assay:

The kinase reaction was conducted in polystyrene 384-well matrix white plate from Thermo Fisher Scientific in a final volume of 25 μL. Inhibitors were first diluted serially in DMSO and added to the plate wells before the addition of other reaction components. The final concentration of DMSO in the assay was 0.5%. The PI3K assays were carried out at room temperature in 20 mM MOPS, pH 6.7, 10 mM MgCl₂, 5 mM DTT and CHAPS 0.03%. Reactions were initiated by the addition of ATP, the final reaction mixture consisted of 20 μM PIP2, 20 μM ATP, 0.2 μCi [γ-³³P]ATP, 4 nM PI3Kδ. Reactions were incubated for 210 minutes and terminated by the addition of 40 μL SPA beads suspended in quench buffer: 150 mM potassium phosphate pH 8.0, 20% glycerol. 25 mM EDTA, 400 μM ATP. The final concentration of SPA beads is 1.0 mg/mL. After the plate sealing, plates were shaken overnight at room temperature and centrifuged at 1800 rpm for 10 minutes, the radioactivity of the product was determined by scintillation counting on Topcount (Perkin-Elmer). IC₅₀ determination was performed by fitting the curve of percent control activity versus the log of the inhibitor concentration using the GraphPad Prism 3.0 software. Table 12 shows PI3Kδ scintillation proximity assay data for certain compounds described herein.

TABLE 12

IC₅₀ data for PI3Kδ scintillation proximity assay

| Example | IC₅₀ (nM) |
|---|---|
| 1 | B |
| 2 | A |
| 3 | C |
| 4 | E |
| 5 | A |
| 6 | A |
| 7 | A |
| 8 | A |
| 9 | B |
| 10 | A |
| 11 | A |
| 12 | A |
| 13 | A |
| 14 | A |
| 15 | A |
| 16 | A |
| 17 | A |
| 18 | D |
| 19 | A |
| 20 | A |
| 21 | A |
| 22 | A |
| 23 | A |
| 24 | A |
| 25 | A |
| 26 | A |
| 27 | A |
| 28 | A |
| 29 | A |
| 30 | A |
| 31 | A |
| 32 | A |
| 33 | A |
| 34 | A |
| 35 | B |
| 36 | A |
| 37 | A |
| 38 | C |
| 39 | C |
| 40 | A |
| 41 | A |
| 42 | A |
| 43 | A |
| 44 | A |
| 45 | A |
| 46 | A |
| 47 | C |

TABLE 12-continued

IC$_{50}$ data for PI3Kδ scintillation proximity assay

| Example | IC$_{50}$ (nM) |
|---|---|
| 48 | A |
| 49 | A |
| 50[a] | A/B |
| 51 | A |
| 52 | A |
| 53 | A |
| 54[a] | A/A |
| 55 | A |
| 56 | A |
| 57 | A |
| 58 | B |
| 59 | C |
| 60 | A |
| 61 | A |
| 62 | A |
| 63 | A |
| 64 | A |
| 65 | A |
| 66 | A |
| 67 | A |
| 68 | A |
| 69 | A |
| 70 | A |
| 71 | A |
| 72 | A |
| 73 | A |
| 74[a] | A/A |
| 75[a] | A/A |
| 76 | A |
| 77 | A |
| 78 | A |
| 79 | C |
| 80 | A |
| 81 | A |
| 82 | A |
| 83 | A |
| 84 | A |
| 85 | D |
| 86[a] | B/C |
| 87 | A |
| 88 | A |
| 89 | B |
| 90 | D |
| 91 | B |
| 92 | C |
| 93 | B |
| 94 | A |
| 95 | A |
| 96 | A |
| 97 | B |
| 98 | A |
| 99 | D |
| 100 | A |
| 101 | C |
| 102 | C |
| 103 | A |
| 104 | A |
| 105 | A |
| 106 | A |
| 107 | A |
| 108 | A |
| 109 | A |
| 110 | A |
| 111 | A |
| 112 | A |
| 113 | A |
| 114 | A |
| 115 | A |
| 116 | A |
| 117 | A |
| 118 | B |
| 119 | C |
| 120 | B |
| 121 | A |
| 122 | D |
| 123 | B |
| 124 | A |
| 125 | B |
| 126 | A |
| 127 | A |
| 128 | A |
| 129 | A |
| 130 | A |
| 131 | A |
| 132 | A |
| 133 | B |
| 134 | A |
| 135 | A |
| 136 | C |
| 137 | B |
| 138 | B |
| 139 | B |
| 140 | B |
| 141 | D |
| 142 | B |
| 143 | C |
| 144 | A |
| 145 | A |
| 146 | B |
| 147 | A |
| 148 | B |
| 149 | A |
| 150 | A |
| 151 | A |
| 152 | A |
| 153 | A |
| 154 | A |
| 155 | A |
| 156 | A |
| 157 | A |
| 158 | A |
| 159 | A |
| 160 | A |
| 161 | A |
| 162 | A |
| 163 | A |
| 164 | A |
| 165 | A |
| 166 | A |
| 167 | A |
| 168 | A |
| 169 | A |
| 170 | A |
| 171 | A |
| 172 | A |
| 173 | A |
| 174 | A |
| 175 | A |
| 176 | A |
| 177 | A |
| 178 | A |
| 179 | A |
| 180 | A |
| 181 | A |
| 182 | A |
| 183 | A |
| 184 | A |
| 185 | A |
| 186 | A |
| 187 | A |
| 188 | A |
| 189 | A |
| 190 | A |
| 191 | A |
| 192[a] | A/A |
| 193[a] | A/A |
| 194 | A |
| 195 | A |
| 196 | A |
| 197 | A |
| 198 | A |
| 199 | A |

TABLE 12-continued

IC$_{50}$ data for PI3Kδ scintillation proximity assay

| Example | IC$_{50}$ (nM) |
|---|---|
| 200 | A |
| 201 | A |
| 202 | A |
| 203 | A |
| 204 | A |
| 205 | A |
| 206 | A |
| 207 | A |
| 208 | A |
| 209 | A |
| 210 | A |
| 211 | A |
| 212 | A |
| 213 | A |
| 214 | A |

* "A" = <50 nM; "B" = 50 nM-100 nM; "C" = >100 nM to 250 nM; "D" = >250 nM to 500 nM; "E" = >500 nM to 1 μM; and "F" = >1 μM;
nt = not tested
[a] two isomers were isolated in the corresponding experiments and they were tested respectively

Example B

B cell proliferation assay

To acquire B cells, human PBMC are isolated from the peripheral blood of normal, drug free donors by standard density gradient centrifugation on Ficoll-Hypague (GE Healthcare, Piscataway, N.J.) and incubated with anti-CD19 microbeads (Miltenyi Biotech, Auburn, Calif.). The B cells are then purified by positive immunosorting using an autoMacs (Miltenyi Biotech) according to the manufacture's instruction.

The purified B cells ($2\times10^5$/well/200 μL) are cultured in 96-well ultra-low binding plates (Corning, Corning, N.Y.) in RPMI1640, 10% FBS and goat F(ab')2 anti-human IgM (10 μg/ml) (Invitrogen, Carlsbad, Calif.) in the presence of different amount of test compounds for three days. [$^3$H]-thymidine (1 μCi/well) (PerkinElmer, Boston, Mass.) in PBS is then added to the B cell cultures for an additional 12 hours before the incorporated radioactivity is separated by filtration with water through GF/B filters (Packard Bioscience, Meriden, Conn.) and measured by liquid scintillation counting with a TopCount (Packard Bioscience).

Example C

Pfeiffer cell proliferation assay

Pfeiffer cell line (diffuse large B cell lymphoma) was purchased from ATCC (Manassas, Va.) and maintained in the culture medium recommended (RPMI and 10% FBS). To measure the anti-proliferation activity of the compounds, the Pfeiffer cells were plated with the culture medium ($2\times10^3$ cells/well/per 200 μl) into 96-well ultra-low binding plates (Corning, Corning, N.Y.), in the presence or absence of a concentration range of test compounds. After 3-4 days, [$^3$H]-thymidine (1 μCi/well) (PerkinElmer, Boston, Mass.) in PBS was then added to the cell culture for an additional 12 hours before the incorporated radioactivity was separated by filtration with water through GF/B filters (Packard Bioscience, Meridenj, Conn.) and measured by liquid scintillation counting with a TopCount (Packard Bioscience). Table 13 shows Pfeiffer cell proliferation data for certain compounds described herein.

TABLE 13:

IC$_{50}$ data for Pfeiffer cell proliferation assay*

| Example | IC$_{50}$ (nM) |
|---|---|
| 1 | C |
| 2 | A |
| 3 | D |
| 5 | A |
| 6 | A |
| 7 | A |
| 8 | D |
| 9 | B |
| 10 | B |
| 11 | A |
| 12 | A |
| 13 | A |
| 14 | A |
| 15 | A |
| 16 | A |
| 17 | A |
| 18 | B |
| 19 | A |
| 20 | B |
| 21 | A |
| 22 | A |
| 23 | A |
| 24 | B |
| 25 | A |
| 26 | A |
| 27 | B |
| 28 | B |
| 29 | B |
| 30 | B |
| 31 | A |
| 32 | A |
| 33 | A |
| 34 | A |
| 35 | D |
| 36 | A |
| 37 | A |
| 38 | D |
| 39 | D |
| 40 | A |
| 41 | D |
| 42 | B |
| 43 | B |
| 44 | B |
| 45 | B |
| 46 | A |
| 47 | D |
| 48 | A |
| 49 | A |
| 50[a] | D/C |
| 51 | A |
| 52 | A |
| 53 | A |
| 60 | D |
| 71 | A |
| 72 | A |
| 73 | A |
| 74[a] | A/A |
| 75[a] | A/B |
| 76 | A |
| 77 | A |
| 78 | A |
| 79 | B |
| 80 | A |
| 81 | A |
| 82 | A |
| 83 | A |
| 84 | A |
| 86[a] | D/D |
| 87 | A |
| 88 | A |
| 89 | C |
| 91 | D |
| 92 | B |
| 93 | D |
| 94 | A |
| 95 | C |

TABLE 13:-continued

IC$_{50}$ data for Pfeiffer cell proliferation assay*

| Example | IC$_{50}$ (nM) |
|---|---|
| 96 | A |
| 97 | B |
| 98 | A |
| 100 | D |
| 106 | A |
| 107 | B |
| 109 | A |
| 110 | B |
| 111 | A |
| 112 | A |
| 124 | A |
| 166 | A |
| 170 | A |
| 174 | A |
| 176 | A |
| 177 | A |
| 178 | A |
| 179 | A |
| 180 | A |
| 187 | A |
| 194 | A |
| 195 | A |
| 196 | A |
| 197 | A |
| 199 | A |
| 200 | A |
| 201 | A |
| 202 | A |
| 203 | A |
| 204 | A |
| 205 | A |
| 208 | A |
| 212 | B |
| 213 | A |

*"A" = <100 nM; "B" = 100 nM-500 nM; "C" = >500 nM to 1 µM; "D" = 1 µM

[a] two isomers were isolated in the corresponding experiments and they were tested respectively

Example D

Akt Phosphorylation Assay

Ramos cells (B lymphocyte from Burkitts lymphoma) are obtained from ATCC (Manassas, Va.) and maintained in RPMI1640 and 10% FBS. The cells (3×10$^7$ cells/tube/3 mL in RPMI) are incubated with different amounts of test compounds for 2 h at 37° C. and then stimulated with goat F(ab')2 anti-human IgM (5 µg/mL) (Invitrogen) for 17 minutes in a 37° C. water bath. The stimulated cells are spun down at 4° C. with centrifugation and whole cell extracts are prepared using 300 µL lysis buffer (Cell Signaling Technology, Danvers, Mass.). The resulting lysates are sonicated and supernatants are collected. The phosphorylation level of Akt in the supernatants are analyzed by using PathScan phospho-Akt1 (Ser473) sandwich ELISA kits (Cell Signaling Technology) according to the manufacturer's instruction.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A compound of Formula IIa:

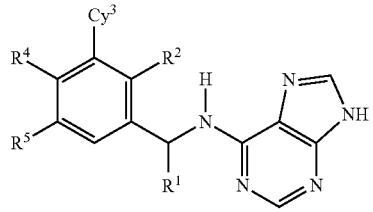

IIa or a pharmaceutically acceptable salt thereof; wherein:
$R^1$ is methyl or ethyl;
$R^2$ is selected from $C_{1-6}$ alkyl, —O—($C_{1-6}$ alkyl), —O—($C_{1-4}$ alkylene)$_n$-(4-7 membered heterocycloalkyl), and phenyl; wherein said phenyl is optionally substituted by 1, 2, 3, or 4 independently selected halo groups;
$Cy^3$ is selected from phenyl, a piperidine ring, a pyrrolidin-2-one ring, a 1,3-oxazolidin-2-one ring, an isoxazole ring, a pyrazole ring, a tetrazole ring, a triazole ring, a pyridine ring, a pyrimidine ring, an azetidine ring, a pyrrole ring, a tetrahydrofuran ring, and a morpholin-2-one ring; each of which is optionally substituted with 1, 2, 3, or 4 independently selected $R^{3a}$ groups;
$R^4$ is selected from H, halo, $C_{1-3}$ alkyl, CN, cyano-$C_{1-6}$ alkyl, and $C_{1-6}$ haloalkyl;
$R^5$ is selected from $C_{1-3}$ alkyl, halo, and CN;
each $R^{3a}$ is independently selected from halo, CN, NO$_2$, $C_{1-6}$ alkyl, $C_{1-6}$ haloalkyl, $C_{3-7}$ cycloalkyl, 4-7 membered heterocycloalkyl, (4-7 membered heterocycloalkyl)-$C_{1-3}$ alkyl, (5-6 membered heteroaryl)-$C_{1-3}$ alkyl, OR$^a$, C(O)R$^b$, C(O)OR$^a$, C(O)NR$^c$R$^d$, NR$^c$R$^d$, NR$^c$C(O)R$^b$, and S(O)$_2$R$^b$; wherein said $C_{1-6}$ alkyl, $C_{3-7}$ cycloalkyl, and 4-7 membered heterocycloalkyl are each optionally substituted by 1, 2, 3, or 4 groups independently selected from OH, CN, halo, $C_{1-6}$ alkyl, $C_{1-6}$ haloalkyl, cyano-$C_{1-6}$ alkyl, HO—$C_{1-6}$ alkyl, $C_{1-4}$ alkoxy-$C_{1-6}$ alkyl, $C_{1-6}$ alkoxy, $C_{1-6}$ haloalkoxy, amino, $C_{1-6}$ alkylamino, di($C_{1-6}$ alkyl)amino, and $C_{3-7}$ cycloalkyl;
each R$^a$, R$^c$, and R$^d$ is independently selected from H, $C_{1-6}$ alkyl, $C_{1-6}$ haloalkyl, $C_{3-7}$ cycloalkyl, and 4-7 membered heterocycloalkyl; wherein said $C_{1-6}$ alkyl, $C_{3-7}$ cycloalkyl, and 4-7 membered heterocycloalkyl are each optionally substituted with 1, 2, 3, 4, or 5 substituents independently selected from OH, CN, halo, $C_{1-6}$ alkyl, $C_{1-6}$ haloalkyl, $C_{1-6}$ alkoxy, $C_{1-6}$ haloalkoxy, and amino;
each R$^b$ is independently selected from $C_{1-6}$ alkyl, $C_{1-6}$ haloalkyl, $C_{3-7}$ cycloalkyl, 4-7 membered heterocycloalkyl; each of which is optionally substituted with 1, 2, 3, 4, or 5 substituents independently selected from OH, CN, halo, $C_{1-6}$ alkyl, $C_{1-6}$ haloalkyl, $C_{1-6}$ alkoxy, $C_{1-6}$ haloalkoxy, and amino; and
n is 0 or 1.

2. The compound of claim 1, which is 4-{3-chloro-6-methoxy-2-methyl-5-[1-(9H-purin-6-ylamino)ethyl]phenyl}pyrrolidin-2-one, or a pharmaceutically acceptable salt thereof.

3. A composition comprising a compound according to claim 1, or a pharmaceutically acceptable salt thereof, and at least one pharmaceutically acceptable carrier.

4. A composition comprising a compound according to claim 2, or a pharmaceutically acceptable salt thereof, and at least one pharmaceutically acceptable carrier.

5. A method of treating asthma in a patient, comprising administering to said patient a therapeutically effective amount of a compound of claim 1, or a pharmaceutically acceptable salt thereof, wherein said treating refers to inhibiting or ameliorating.

6. A method of treating brain cancer in a patient, comprising administering to said patient a therapeutically effective amount of a compound of claim 1, or a pharmaceutically acceptable salt thereof, wherein said treating refers to inhibiting or ameliorating.

7. A method of treating colon cancer in a patient, comprising administering to said patient a therapeutically effective amount of a compound of claim 1, or a pharmaceutically acceptable salt thereof, wherein said treating refers to inhibiting or ameliorating.

8. A method of treating bladder cancer in a patient, comprising administering to said patient a therapeutically effective amount of a compound of claim 1, or a pharmaceutically acceptable salt thereof, wherein said treating refers to inhibiting or ameliorating.

9. A method of treating asthma in a patient, comprising administering to said patient a therapeutically effective amount of a compound of claim 2, or a pharmaceutically acceptable salt thereof, wherein said treating refers to inhibiting or ameliorating.

10. A method of treating brain cancer in a patient, comprising administering to said patient a therapeutically effective amount of a compound of claim 2, or a pharmaceutically acceptable salt thereof, wherein said treating refers to inhibiting or ameliorating.

11. A method of treating colon cancer in a patient, comprising administering to said patient a therapeutically effective amount of a compound of claim 2, or a pharmaceutically acceptable salt thereof, wherein said treating refers to inhibiting or ameliorating.

12. A method of treating bladder cancer in a patient, comprising administering to said patient a therapeutically effective amount of a compound of claim 2, or a pharmaceutically acceptable salt thereof, wherein said treating refers to inhibiting or ameliorating.

\* \* \* \* \*